US008828406B2

(12) United States Patent
Garcia-Sastre et al.

(10) Patent No.: US 8,828,406 B2
(45) Date of Patent: Sep. 9, 2014

(54) INFLUENZA VIRUSES AND USES THEREOF

(75) Inventors: Adolfo Garcia-Sastre, New York, NY (US); Peter Palese, Leonia, NJ (US); Qinshan Gao, New York, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 0 days.

(21) Appl. No.: 13/387,485

(22) PCT Filed: Jul. 29, 2010

(86) PCT No.: PCT/US2010/043697
§ 371 (c)(1),
(2), (4) Date: Jun. 1, 2012

(87) PCT Pub. No.: WO2011/014645
PCT Pub. Date: Feb. 3, 2011

(65) Prior Publication Data
US 2012/0244183 A1   Sep. 27, 2012

Related U.S. Application Data

(60) Provisional application No. 61/229,858, filed on Jul. 30, 2009.

(51) Int. Cl.
| A61K 39/145 | (2006.01) |
| C12N 7/04 | (2006.01) |
| C12N 7/02 | (2006.01) |
| A61P 37/04 | (2006.01) |
| C12N 7/01 | (2006.01) |
| C12N 15/44 | (2006.01) |
| C07K 14/005 | (2006.01) |
| C12N 7/00 | (2006.01) |
| A61K 39/00 | (2006.01) |

(52) U.S. Cl.
CPC ......... *C07K 14/005* (2013.01); *A61K 2039/525* (2013.01); *C12N 2760/16122* (2013.01); *C12N 7/00* (2013.01); *C12N 2760/16162* (2013.01); *C12N 2760/16262* (2013.01); *C12N 2760/16222* (2013.01); *A61K 2039/5254* (2013.01)
USPC ................. 424/209.1; 424/184.1; 435/235.1; 435/236; 435/239; 536/23.72

(58) Field of Classification Search
CPC ...... C12N 15/86; C12N 2840/44; C12N 7/00; C12N 15/102; C12N 2760/16122; C12N 2760/16121; C12N 2760/16143; C12N 2760/16162; C12N 2760/16222; C12N 2760/16262; A61K 2039/53; A61K 39/145; A61K 2039/5254; A61K 39/12; C07K 14/005; C07K 16/1018; C07K 2319/00
USPC ......... 424/209.1, 184.1; 435/235.1, 236, 239; 536/23.72

See application file for complete search history.

(56) References Cited

U.S. PATENT DOCUMENTS

| 6,022,726 | A | | 2/2000 | Palese et al. | |
| 6,146,642 | A | * | 11/2000 | Garcia-Sastre et al. | ... 424/214.1 |
| 6,544,785 | B1 | * | 4/2003 | Palese et al. | ................... 435/325 |
| 6,649,372 | B1 | * | 11/2003 | Palese et al. | ................. 435/69.1 |
| 7,384,774 | B2 | * | 6/2008 | Palese et al. | ............... 435/235.1 |
| 7,968,101 | B2 | * | 6/2011 | Kawaoka et al. | ........... 424/206.1 |
| 2006/0019350 | A1 | * | 1/2006 | Palese et al. | ................. 435/69.1 |
| 2008/0254060 | A1 | * | 10/2008 | Palese et al. | ............... 424/199.1 |
| 2009/0246830 | A1 | * | 10/2009 | Kawaoka et al. | ............. 435/69.3 |
| 2011/0300604 | A1 | * | 12/2011 | Kawaoka et al. | ........... 435/235.1 |
| 2012/0058538 | A1 | * | 3/2012 | Palese et al. | ............... 435/235.1 |
| 2012/0122185 | A1 | * | 5/2012 | Palese et al. | ............... 435/235.1 |

FOREIGN PATENT DOCUMENTS

WO   WO 03/068923 A2   8/2003

OTHER PUBLICATIONS

Flandorfer A, Garcia-Sastre A, Basler CF, Palese P. Chimeric influenza A viruses with a functional influenza B virus neuraminidase or hemagglutinin. J Virol. Sep. 2003;77(17):9116-23.*
Chiang C, Chen GW, Shih SR. Mutations at alternative 5' splice sites of M1 mRNA negatively affect influenza A virus viability and growth rate. J Virol. Nov. 2008;82(21):10873-86. doi: 10.1128/JVI.00506-08. Epub Sep. 3, 2008.*
Robb NC, Jackson D, Vreede FT, Fodor E. Splicing of influenza A virus NS1 mRNA is independent of the viral NS1 protein. J Gen Virol. Sep. 2010;91(Pt 9):2331-40. Epub Jun. 2, 2010*
Garaigorta U, Ortín J. Mutation analysis of a recombinant NS replicon shows that influenza virus NS1 protein blocks the splicing and nucleo-cytoplasmic transport of its own viral mRNA. Nucleic Acids Res. 2007;35(14):4573-82. Epub May 8, 2007*
Hale BG, Randall RE, Ortín J, Jackson D. The multifunctional NS1 protein of influenza A viruses. J Gen Virol. Oct. 2008;89(Pt 10):2359-76.*
Ghate AA, Air GM. Influenza type B neuraminidase can replace the function of type A neuraminidase. Virology. Nov. 25, 1999;264(2):265-77. Teaches that influenza A and B do not reassort, but neuraminidase from B can replace NA from A.*

(Continued)

*Primary Examiner* — Benjamin P Blumel
*Assistant Examiner* — Rachel Gill
(74) *Attorney, Agent, or Firm* — Jones Day

(57) ABSTRACT

Described herein are chimeric influenza virus gene segments and nucleic acid sequences encoding such chimeric influenza virus gene segments. A chimeric influenza virus gene segment described herein comprises packaging signals found in the non-coding and coding regions of one type of influenza virus gene segment and an open reading frame of a different type of influenza virus gene segment or fragment thereof. Also described herein are recombinant influenza viruses comprising two or more chimeric influenza virus gene segments and the use of such viruses in the prevention and/or treatment of influenza virus disease.

15 Claims, 51 Drawing Sheets

(56) References Cited

OTHER PUBLICATIONS

Figures 9A, 9B, 9C, 9D:
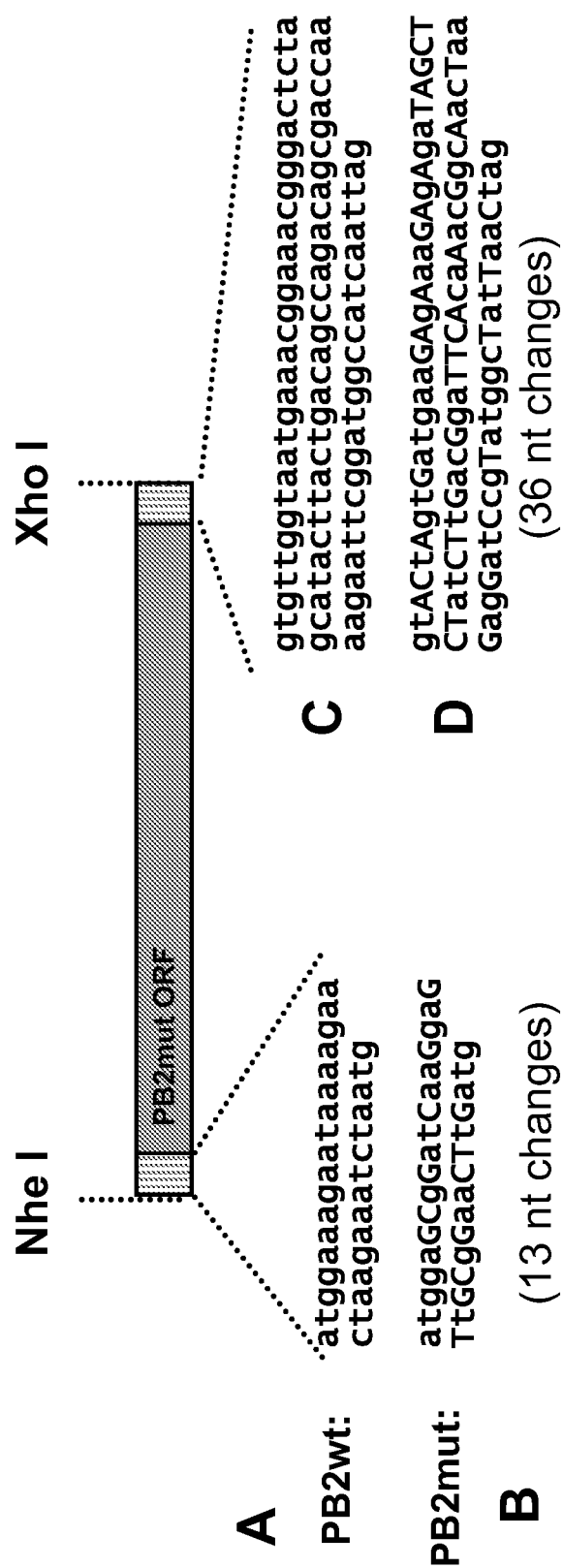

Ng SS, Li OT, Cheung TK, Malik Peiris JS, Poon LL. Heterologous influenza vRNA segments with identical non-coding sequences stimulate viral RNA replication in trans. Virol J. Jan. 11, 2008;5:2.*
Horimoto T, Takada A, Iwatsuki-Horimoto K, Hatta M, Goto H, Kawaoka Y. Generation of influenza A viruses with chimeric (type A/B) hemagglutinins. J Virol. Jul. 2003;77(14):8031-8.*
Li C, Hatta M, Watanabe S, Neumann G, Kawaoka Y. Compatibility among polymerase subunit proteins is a restricting factor in reassortment between equine H7N7 and human H3N2 influenza viruses. J Virol. Dec. 2008;82(23):11880-8. Epub Sep. 24, 2008.*
Enami et al., 1991, "An influenza virus containing nine different RNA segments", Virology; 185:291-298.
Flandorfer et al., 2003, "Chimeric influenza A viruses with a functional influenza B virus neuraminidase or hemagglutinin", J Virol; 77(17):9116-9123.
Fodor, et al., 1999, "Rescue of influenza A virus from recombinant DNA", J Virol 73:9679-9682.
Fujii et al., 2003, "Selective incorporation of influenza virus RNA segments into virions", Proc Natl Acad Sci USA; 100(4):2002-2007.
Fujii et al., 2005, "Importance of both the coding and the segment-specific noncoding regions of the influenza A virus NS segment for its efficient incorporation into virions", J Virol 79:3766-3774.
Gao et al., 2008, "A seven-segmented influenza A virus expressing the influenza C virus glycoprotein HEF", J Virol; 82(13):6419-6426.
Gao et al., 2009, "Rewiring the RNAs of influenza virus to prevent reassortment", Proc Natl Acad Sci USA; 106(37):15891-15896.
Gao et al., 2010, "A nine-segment influenza A virus carrying subtype H1 and H3 hemagglutinins", J Virol; 84(16):8062-8071.
Gog et al., 2007, "Codon conservation in the influenza A virus genome defines RNA packaging signals", Nucleic Acids Research; 35(6):1897-1907.
International Preliminary Report on Patentability of International application No. PCT/US2010/043697, dated Jan. 31, 2012.
International Search Report of International application No. PCT/US2010/043697, dated Nov. 17, 2010.
Liang et al., 2005, "cis-acting packaging signals in the influenza virus PB1, PB2, and PA genomic RNA segments", J Virol; 79(16):10348-10355.
Liang et al., 2008, "Mutational analyses of packaging signals in influenza virus PA, PB1, and PB2 genomic RNA segments", J Virol; 82(1):229-236.
Marsh et al., 2007, "Specific residues of the influenza A virus hemagglutinin viral RNA are important for efficient packaging into budding virions", J Virol; 81:9727-9736.
Marsh et al., 2007, "Specific residues of the influenza A virus hemagglutinin viral RNA are important for efficient packaging into budding virions", J Virol; 81(18):9727-9736.
Muramoto et al., 2006, "Hierarchy among viral RNA (vRNA) segments in their role in vRNA incorporation into influenza A virions", J Virol; 80(5):2318-2325.
Quinlivan, 2005, "Attenuation of equine influenza viruses through truncations of the NS1 protein", J Virol; 79:8431-8439.
Watanabe et al., 2003, "Exploitation of nucleic acid packaging signals to generate a novel influenza virus-based vector stably expressing two foreign genes", J Virol; 77:10575-10583.
Written Opinion of International application No. PCT/US2010/043697, dated Nov. 17, 2010.
Wu et al., 2010, "A live bivalent influenza vaccine based on a H9N2 virus strain", Vaccine; 28(3):673-680.

* cited by examiner

A
```
     1 agcgaaagca ggtcaattat attcaattg gaaagaataa aagaactaag aaatctattg
    61 tcgcagtctc gcaccgcga gatactcaca aaaccaccg tggaccattt ggccataatc
   121 aagaagtaca catcaggaag acaggagaag acagagaag aaCCTagc
                                                    Nhe I
```

B
```
  2161             ctCgagaa aggagagaag gctaatgtgc taattgggca aggagacgtg
  2221 gtgttggtaa tgaaacggaa acggactct agcatactta ctgacagcca gacagcgacc
  2281 aaagaattc ggatggccat caattagtgt cgaatagttt aaaaacgacc ttgttttctac
  2341 t
```
Xho I

Fig. 1A-1B

A
```
     1 agcgaaagca ggcaaaccat ttgattggtt gtcaatccga ccttactttt cttaaagtg
    61 ccagcacaaa Ttgctataag cttcaactttc ccttatactg gagaccctcc ttacagcct
   121 gggacaggaa caggatacac ctggTtcct AGc
                                      Nhe I
```

B
```
  2161             ctCgagcc cgaattgatg atcatgaaga tctgttccac cattgaagag
  2221 ggaaggataa agaaagaaga gttcactgag atcatgaaga tctgttccac cattgaagag
  2281 ctcagacgc aaaaatagtt aatttagctt gtcccttcatg aaaaatgcc ttgttttctac
  2341 t
```
Xho I

Fig. 2A-2B

A

```
   1 agcgaaagca ggtactgatc caaattgaaa gattttgtgc gacaatgctt caatccgttg
  61 attgtcgagc ttgcggaaaa aacaatgaaa gagttTggg aggacctgaa aatcgaaaca
 121 aacaaatttg cagcaatttg ctaGc
                          NheI
        XhoI
```

B

```
2041              c tcgaGcctgg gaccttttgat cttgggggc tatatgaagc aattgaggag
2101 tgcctgatta atgatccctg ggttttgctt aatgcttctt ggttcaactc cttccttaca
2161 catgcattga gttagttgtg gcagtgctac tatttgctat ccatactgtc caaaaagta
2221 ccttgttttct act
```

Fig. 3A-3B

A

```
   1 agcaaaagca ggggaaaata aaaacaacca aaTtgaaggc aaacctactg gtcctgttaa
  61 gtgcacttgc agctgcagTt gcagacacaa tttgtatagg ctaGc
                                                  NheI
```

B

```
1561     XhoI
1621 tCgaGatcta ctcaactgtc gccagttcac ggatcttttgc agtcatctga gggcaatca    c
1681 gtttctggat gtgttctaat ggttctttgc agtctttgc agtcatctga gattagaatt
1741 tcagaaaatat gaggaaaaaac acccttgttt ctact
```

Fig. 4A-4B

A
```
   1 agcaaaagca gggtagataa tcactcactg agtgacatca aaatcTtggc gtcccaaggc
  61 accaaacggt cttacgaaca gTtggagact gTtggagaac gccagaTtgc cactgaaatc
 121 agagcatccg tcggaaaaTt gattggtgga attggacgat tctacatcca aGCTAgc
                                                         Nhe I
```

B
```
1381                                              CtcG aggggcgggg agtctttcag
1441 ctctcggacg aaaaggcagc gagcccgatc gtgccttcct ttgacatgag taatgaagga
1501 tcttattcct tcggagacaa tgcagaggag tacgacaatt aaagaaaaat acccttgttt
1561 ctact
```
                            Xho I

Fig. 5A-5B

A
```
   1 agcgaaagca ggggttttaaa Ttgaatccaa atcagaaaat aacaaccatt ggatcaatct
  61 gtctggtagt cggactaatt agcctaatat tgcaaatagg gaatataatc tcaatTtgga
 121 ttagccattc aGCTAGC
              Nhe I
```

B
```
1201                                         ctCGaGga ggccgtgctt ctgggttgaa ttaatcaggg
1261 gacgacctaa agaaaaaaca atctggacta gtgcgagcag cattctttt tgtggcgtga
1321 atagtgatac tgtagattgg tcttggccag acggtgctga gttgccattc agcattgaca
1381 agtagtctgt tcaaaaaact cctgttct act
```
                              Xho I

Fig. 6A-6B

A
```
   1 agcgaaagca ggtagatatt gaaagTtgag tcttctaacc gaggtcgaaa cCtacgtact
  61 ctctatcatc ccgtcaggcc ccctcaaagc cgagatcgca cagagacttg aagTtgtctt
 121 tgcagggaag aacactgatc ttgaggttct cTtggaTtgg ctaaagacaa gaccaatcct
 181 gtcacctctg actaagggga ttttaggatt tgtgttcacg ctcaccgtgc ccagtgagcg
 241 aggactgcag cgtagacgct ttgtccaaaT tgccctTaTt gCTaGc
                                                   Nhe I
```

B
```
 781          ctcG Agctattgcc gcaaatatca ttgggatctt gcacttgaca ttgtggattc
 841 ttgatcgtct ttttttcaaa tgcatttacc gtcgctttaa atacggactg aaaggagggc
 901 cttctacgga aggagtgcca aagtctatga gggaagaata tcgaaaggaa cagcagagtg
 961 ctgtggatgc tgacgatggt catttTgtca gcatagagct ggagtaaaaa actacctTgt
1021 ttctact
```

Fig. 7A-7B

A
```
   1 agcaaaagca gggtgacaaa gacataTattgg atccaaacac tgtgtcaagc tttcagCtag
  61 attgcttTct ttggCTgtc cgcaaacgag ttgcagacca agaCctagC
                                                      Nhe I
```

B
```
 721                                                        ctCG agataacaga gaatagttttt
 781 gagcaaataa catttatgca agccttacat ctattgcttg aagtgggagca agagataaga
 841 actttctcgt ttcagcttat ttaataataa aaaacacccT tgtttctact
```

Fig. 8A-8B

```
   1 agcaaaagca ggggaaaata aaaacaacca aaatgaaggc aaactactg gtctgttat
  61 atgaattgt agctacagat gcagacacaa tatgtatagg ctaccatgcg aacaattcaa
 121 ccgacactgt tgacacaata ttgagaaga atgtgtagt gcacattct gttaccctgc
 181 tcgagacag acataacggg aaactatgta aattaaagg aatagcccc ctacaattgg
 241 ggaaatgtaa catcactgga tgtctttgg gaaatctaga atgcgactca ctgcttccag
 301 cgagatcatg tgctacatt gtagaaatac caactctga gaatggagca tgttatccag
 361 gagattcat cgactatgag gaactgagg agtaattgag ctctgtatca tcattagaaa
 421 gattcgaaat attcccaag gaaagttcat ggcccaatca tacattcaac ggagtaacag
 481 tatgatgctc ccatagggga aaagcagtt tttacagaaa tttgttatgg ctgacgaaga
 541 aggggattc ataccccaag ctgaccaatt cctatgttaa caataaaggg aaagaagtcc
 601 ttgtactatg gggtgtcat caccctgtcca gaagtgatga gtaacagagt ctctatagta
 661 atggaaatgc ttatgtctct gtagtgttt caaattataa caggagatt accccgaaa
 721 tagctgcag gcctaaagta aagatcaac atgggaggat gaacattac tggacttgc
 781 tagaatcgg agacacaata atattgagg caattgttaa tctaatagca ccatggatg
 841 cttcgcact tagtagaggg tttgagttcc gcatcatcac ttcaaacgcg tcaattgatg
 901 agtgtaacac gaagtgttca acaccccagg gatctataaa caggcaatctc ccttccaga
 961 atatacactc agtcaccata gagagtgcc caaatatgt caggagtacc aaattgagga
1021 tggttacagg actaagaaat atcccatcca ttcaatscag aggtctattt ggagccattg
1081 ccggttttat tgaggggga tggactggaa tgatagattg gtggtatggt tatcatcatc
1141 agaatgaaca gggatcaggc tatgcagctg atcaaaaag cactcagaat gccattaacg
1201 ggattacaaa caaggtgaac tctgttatcg agaaaataa cactcaattc acagctgtgg
1261 gtaaagaatt caacaacttg gaaaaagga tggaaatttt aaataaaaaa gttgatgatg
1321 ggtttttgga catttggaca tatsaagcag aattgttagt tctactggaa aatgaaagaa
1391 cttggattt tcatgactta aatgtgaaga acttgtacga gaaagtaaaa agccaattaa
1441 agaataatgc caaagaaatc ggaaatgggt gttttgagtt ctaccaaaag tgtgacaatg
1501 aatgcatgga aagtgtaaga aatggaactt atgattatcc aaaatattca gaagaatcaa
1561 agttgaacag ggaaaaata gatggagtga aattggaatc aatggggtg tatcagattt
1621 tggcatttta ctcaactgtc gccagttcac tggtgttttt gctctctctg gggttaatcca
1681 gttttggat gtgtttaat gggtccttgc agtgcagaat atgcatctga gattaggatt
1741 tcagaaatat aaggaaaaac accttgtttt ctact
```

FIG. 17

```
   1 agcgaaagca ggagtttaaa tgaatccaaa ccagaaaata ataaccattg ggtcaatctg
  61 tatggtagtc ggaataatta gcctaatatt gaaatagga aatataact caatatggat
 121 tagtaatcca attcaaaccg gaaatcaaaa ctataccgga atatgcaatc aagcagcat
 181 tacctataaa gtgtgtgcag ggcaggaatc aacttcagtg atatttaaccg gtaattcatc
 241 tctttgtccc atccgtgggt gggcatataca catgaaagac aatgcataa gaatggttc
 301 caaggagac gttttgttca taagagagcc ttttatttca tgtctcact tggaatgcag
 361 gacttttttt ctgatcaag gcgccatact gaatgacaag cattcaaggg ggaccttaa
 421 ggacagaagc ccttataggg tcttaatgag ctgtcctgtc ggtgaagctc cgtcccgta
 481 caattcaagg tttgaatcgg ttgcttggtc agccagcgcc tgtcatgatg gagtgggtg
 541 gctaacaatc ggaatttctg gtctcagatga tggagcagtg gctgtatcaa aatacccg
 601 tatattaact gaaaacaaa aaagttggag gaagcatata ttgagaacac aagagtctga
 661 atgtactgt gtaaatggtt tatgtttac cataatgcc gatggcctaa gtgacgggt
 721 ggcctcgtac aaaatttca agatcgagaa ggggaaggtt actaaatcaa tagagttgaa
 781 tgcaccaat tctcactacg aggagtgttc ctgttaccct gatacggta aagcatgtg
 841 tgtgtcaga gacaattggc actgttcgaa ccgactatgg gagtccttcg attaaaaact
 901 atattataaa ataggataca tctgcagtgg gtttttcggt gacagcctct gtcccaaaga
 961 tggacaggc agcggggct caatgtctgc tcatggagta aacggagtaa agggattttc
1021 atataagcat ggcaatggtg ttcggatagg aaggactaaa agtgacagtt ccagactatgg
1081 gtttgatatg attcgggatc ctaatggagg gacagagact gatagtaggt tctctatgag
1141 acacagatgtt gtgccaataa ctaatcggtc aggtacagc ggaagttccg ttcaatatcc
1201 tgagtaaaca gggctagact gtatgaggcc ttgcttctgg ggtgaattaa tcaggggct
1261 actgaggag gatgaaact ggactagtgg gagcatcatt tattttgtg gtgtgaatag
1321 tgatacgta gattggtctt gcccagacgg tgctgagtg ccgttcacta tgcaagta
1391 gtttgttcaa aaactccctt gtttctact
```

FIG. 18

```
   1 agcaaaagca ggtagatatt gaaag????? ????????? ????????? ?????????
  61 ????????? ????????? ????????? ????????? ????????? ?????????
 121 ????????? ????????? ????????? ????????? ????????? ?????????
 181 ????????? ????????? ????????? ????????? ????????? ?????????
 241 ????????? ????????? ????????? ????????? ????????? ?????????
 301 ????????? ????????? ????????? ????????? ????????? ?????????
 361 ????????? ????????? ????????? ????????? ????????? ?????????
 421 ????????? ????????? ????????? ????????? ????????? ?????????
 481 ????????? ????????? ????????? ????????? ????????? ?????????
 541 ????????? ????????? ????????? ????????? ????????? ?????????
 601 ????????? ????????? ????????? ????????? ????????? ?????????
 661 ????????? ????????? ????????? ????????? ????????? ?????????
 721 ????????? ????????? ????????? ????????? ????????? ?????????
 781 ????????? ????????? ????????? ????????? ????????? ?????????
 841 ????????? ????????? ????????? ????????? ????????? ?????????
 901 ????????? ????????? ????????? ????????? ????????? ?????????
 961 ????????? ????????? ????????? ????????? ?????aaa actaccttgt
1021 ttctact
```

FIG. 19

```
  1 agcaaaagca gggtgacaaa gacata....
 61 ...........................
121 ...........................
181 ...........................
241 ...........................
301 ...........................
361 ...........................
421 ...........................
481 ...........................
541 ...........................
601 ...........................
661 ...........................
721 ...........................
781 ...........................
841 ..........  ........taataa aaaacaccct tgtttctact
```

FIG. 20

```
   1 agcgaaagca ggtactgatt caaaaggaa gatttttgtgc gacaatgctt caatccgatg
  61 aatgtcgagc ttgtggaaaa ggcaatgaaa gagtatggag aggaccgtga aatcgaaata
 121 aacaaattgg cagcaatatg cactcactg gaagtgtgct tcatgtattc agaatttcac
 181 ttcatcgatg aagaggcga gtcaatagtc gtagaactty ggaccaaa tgcactttg
 241 aagtatagat ttgaaataat cgaggaaga gatccacaa tagcttggac agtaataaac
 301 agatatttgca anactacagg ggctgagaaa ccttgtttc tacagaett gtatgattac
 361 aagaagaaa gattatcga aatggactta acaagcagag aagttacat atactatctg
 421 gaaaagtcta ataaaatta atctgagaag accacactcc acattttctc attaacggg
 481 gaggaatgg ccataagt cgactactct ctgatgaag aagtaggc gaggatcaaa
 541 accaggtat tcaccataag ataagcctg gtagtagag gcctctgga ttccttcgt
 601 cagtccgaga gagtgaaga gaccattgaa gaaagattg aaatcacagg aacaatgcg
 661 aagcttgcg accaaagtct tcgcaaaac ttctccagcc ttgaaatt tagagcctat
 721 gtggatggat ttgaaccgaa cggctacatt gagggcaagt ttcccaat gtcaaagaa
 781 gtaaatgcta gaattgacc ttttgaaa tcaataccac gaccacttay aatccggat
 841 gggcctcct gttccagcg gtccaaatc ctgctgatgg atgcctaaa attaagcatt
 901 gaggaccaaa gtatgaggg agagggata ttgtatang atgaatcaa atgcatgaga
 961 acattctttg gaggaagga accatgtt gtaaactac acgaaaggg aataatcca
1021 aattatctc tgtcatggaa gcagtactg gagacctgc aggacattga gaatgaggag
1081 aaaattcaa ggactaaaa tatgaagaaa acgagtcagt taaagtggc actggtgag
1141 aaatggcat cagaaaagt agacttgac gctgtaaag atgtagcgb ttgaagcaa
1201 tatgatagtg aagaaccaga attgaggtcg cttgcaagtt ggattcagaa tgagttcaac
1261 aaggcatgtg aactgacycg ttcagctgg atagagctcg atgagatgg agaagatgg
1321 gttcaatcg aaccattgc aagcatgaga aggaattatt tctcagtaga gtgtctcat
1381 tgcagagtca cagaatacat aatgaaggca gtgtacatca ataccccct gttaatgca
1441 tcctgtgcag caatggatga ttccaattta attgaaga taagtaaght aagaactaag
1501 gaggaaggt gaaagaccaa tttgtacggt ttcatcataa aaggaagatc ctacttaagg
1561 aatgacacg atgtgtaaaa cttgtgago atgagttc cctactyga cccaagactt
1621 gaaccacaca aatgggagaa gtactgtgt cttgagtag gagatactgct tctaagaagt
1681 tgcataggc atgtttaaag gctatgttc tggtaggtga ggataaaag aacttaaaa
1741 attaaaatga aatggggat gaaaataggg cgttgccttc cttcagtcact tcaaacaatc
1801 gagagtatga ttgaagctga gtcctctgtc aaggagaaag acatgaccaa agagttctttg
1861 gaaatatgat cagaaacatg gtcgntgga gagtcccaca gaggagtgga ggaagttcc
1921 atgggaagy tctgcagac tttattgca aagtcggtat tcaacagctt gtatgcatct
1981 ctaaacggg aaggattttc agcggatca agaaaatgc ttcttatgt tcaggctctt
2041 agggacaaac tggaactgg gacttttgat ctggggggtc tatatgaagc aattgaggag
2101 tgctgaata atgatcctg ggttttgctt aatgcttctt ggttaactc ctcctcaca
2161 cagcattga gagttgtgtg gcaatgctac tatttgctat ccatactgtc caaaaagta
2221 ccttgttttct act
```

FIG. 21

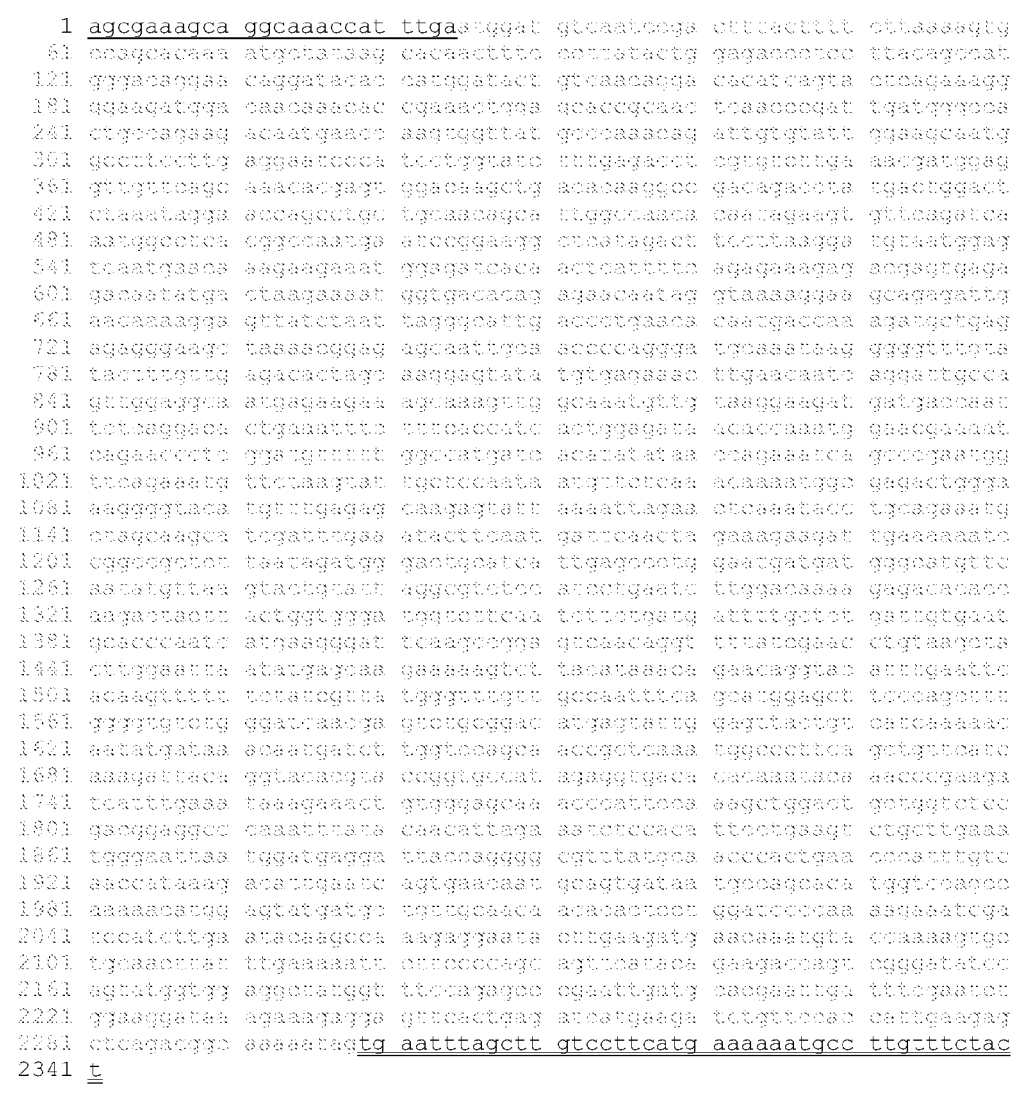

```
   1 agcgaaagca ggcaaaccat ttga......... .......... .......... ..........
  61 .......... .......... .......... .......... .......... ..........
 121 .......... .......... .......... .......... .......... ..........
 181 .......... .......... .......... .......... .......... ..........
 241 .......... .......... .......... .......... .......... ..........
 301 .......... .......... .......... .......... .......... ..........
 361 .......... .......... .......... .......... .......... ..........
 421 .......... .......... .......... .......... .......... ..........
 481 .......... .......... .......... .......... .......... ..........
 541 .......... .......... .......... .......... .......... ..........
 601 .......... .......... .......... .......... .......... ..........
 661 .......... .......... .......... .......... .......... ..........
 721 .......... .......... .......... .......... .......... ..........
 781 .......... .......... .......... .......... .......... ..........
 841 .......... .......... .......... .......... .......... ..........
 901 .......... .......... .......... .......... .......... ..........
 961 .......... .......... .......... .......... .......... ..........
1021 .......... .......... .......... .......... .......... ..........
1081 .......... .......... .......... .......... .......... ..........
1141 .......... .......... .......... .......... .......... ..........
1201 .......... .......... .......... .......... .......... ..........
1261 .......... .......... .......... .......... .......... ..........
1321 .......... .......... .......... .......... .......... ..........
1381 .......... .......... .......... .......... .......... ..........
1441 .......... .......... .......... .......... .......... ..........
1501 .......... .......... .......... .......... .......... ..........
1561 .......... .......... .......... .......... .......... ..........
1621 .......... .......... .......... .......... .......... ..........
1681 .......... .......... .......... .......... .......... ..........
1741 .......... .......... .......... .......... .......... ..........
1801 .......... .......... .......... .......... .......... ..........
1861 .......... .......... .......... .......... .......... ..........
1921 .......... .......... .......... .......... .......... ..........
1981 .......... .......... .......... .......... .......... ..........
2041 .......... .......... .......... .......... .......... ..........
2101 .......... .......... .......... .......... .......... ..........
2161 .......... .......... .......... .......... .......... ..........
2221 .......... .......... .......... .......... .......... ..........
2281 .......... .......tg aatttagctt gtccttcatg aaaaaatgcc ttgtttctac
2341 t
```

FIG. 22

```
   1 agcgaaagca ggtcaattat attcaatgtg gaagaataaa aagaactaag gaatcaatg
  61 ...
 121 ...
```

FIG. 23

```
   1 agcaaaagca gggtagataa tcactcacag agtgacatcg aaatcatgga gaccaaggga
  61 ...
 121 ...
 181 gaacttaaac ...
 241 ...
 301 ...
 361 ...
 421 ...
 481 ...
 541 ...
 601 ...
 661 ...
 721 ...
 781 ...
 841 ...
 901 ...
 961 ...
1021 ...
1081 ...
1141 ...
1201 ...
1261 ...
1321 ...
1381 ...
1441 ...
1501 ...                                          agaaaaat accttgttt
1561 ctact
```

FIG. 24

NS-HAmut-NS construct (1941nt):

(22 nt changes) ... (45 nt changes)

77nt ↱ ↓ 102nt
26nt [NS | HAmut ORF | NS] 26nt
3' NCR ................................................ 5' NCR

HA-NSmut-HA construct (1099nt):

67nt ↱ ↓ 105nt
32nt [HA | NSmut ORF | HA] 45nt
3' NCR ................................................ 5' NCR (12 nt changes) ... (15 nt changes)

▨/▤ mut: Mutation    ↱ : Translation start   ↓ : Translation stop

Fig. 26A

Swap(mut) virus:

- ⊣ A/PR/8/34 PB2 ⊢
- ⊣ A/PR/8/34 PB1 ⊢
- ⊣ A/PR/8/34 PA ⊢
- ⊣ [NS | HAmut ORF | NS] ⊢
- ⊣ A/PR/8/34 NP ⊢
- ⊣ A/PR/8/34 NA ⊢
- ⊣ A/PR/8/34 M ⊢
- ⊣ [HA | NSmut ORF | HA] ⊢

Fig. 26B

NS-HAwt-NS:
NS-HAmut-NS:
PR/8 HA:
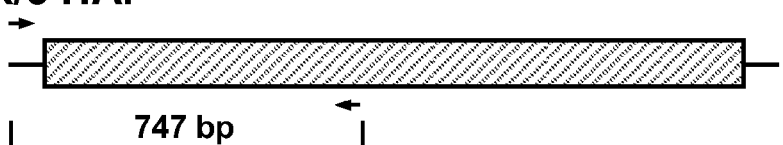
Fig. 28B
HA-NSwt-HA:
HA-NSmut-HA:
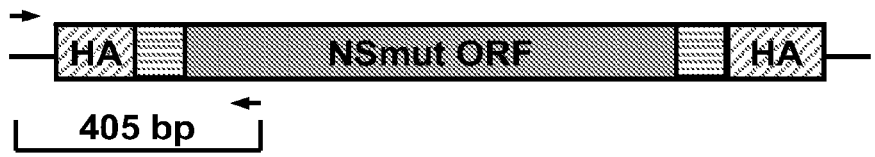
PR/8 NS:
Fig. 28C

Fig. 29A

NA-PB1mut-NA:

AGCGAAAGCAGGGGTTTAAATTGAATCCAAATCAGAAAATAACAACCATTGGATCAATCTGTC
TGGTAGTCGGACTAATTAGCCTAATATTGCAAATAGGGAATATAATCTCAATTTGGATTAGCC
ATTCAATTCAAACTGGAAGTCAAAACCATACTGGAATTTGCAACCAAGCTAGCATGGACGTTA
ACCCAACTCTGTTATTTCTGAAGGTACCGGCGCAGAACGCCATCAGTACGACCTTTCCTTATA
CTGGAGACCCTCCTTACAGCCATGGGACAGGAACAGGATACACCATGGATACTGTCAACAGGA
CACATCAGTACTCAGAAAAGGGAAGATGGACAACAAACACCGAAACTGGAGCACCGCAACTCA
ACCCGATTGATGGGCCACTGCCAGAAGACAATGAACCAAGTGGTTATGCCCAAACAGATTGTG
TATTGGAAGCAATGGCTTTCCTTGAGGAATCCCATCCTGGTATTTTTGAAAACTCGTGTATTG
AAACGATGGAGGTTGTTCAGCAAACACGAGTAGACAAGCTGACACAAGGCCGACAGACCTATG
ACTGGACTCTAAATAGAAACCAACCTGCTGCAACAGCATTGGCCAACACAATAGAAGTGTTCA
GATCAAATGGCCTCACGGCCAATGAGTCTGGAAGGCTCATAGACTTCCTTAAGGATGTAATGG
AGTCAATGAAAAAAGAAGAAATGGGGATCACAACTCATTTTCAGAGAAAGAGACGGGTGAGAG
ACAATATGACTAAGAAAATGATAACACAGAGAACAATAGGTAAAAAGAAGCAGAGATTGAACA
AAAGGAGTTATCTAATTAGAGCATTGACCCTGAACACAATGACCAAAGATGCTGAGAGAGGGA
AGCTAAAACGGAGAGCAATTGCAACCCCAGGGATGCAAATAAGGGGGTTTGTATACTTTGTTG
AGACACTGGCAAGGAGTATATGTGAGAAACTTGAACAATCAGGGTTGCCAGTTGGAGGCAATG
AGAAGAAAGCAAAGTTGGCAAATGTTGTAAGGAAGATGATGACCAATTCTCAGGACACCGAAC
TTTCTTTCACCATCACTGGAGATAACACCAAATGGAACGAAAATCAGAATCCTCGGATGTTTT
TGGCCATGATCACATATATGACAAGAAATCAGCCCGAATGGTTCAGAAATGTTCTAAGTATTG
CTCCAATAATGTTCTCAAACAAAATGGCGAGACTGGGAAAAGGGTATATGTTTGAGAGCAAGA
GTATGAAACTTAGAACTCAAATACCTGCAGAAATGCTAGCAAGCATCGATTTGAAATATTTCA
ATGATTCAACAAGAAAGAAGATTGAAAAAATCCGACCGCTCTTAATAGAGGGGACTGCATCAT
TGAGCCCTGGAATGATGATGGGCATGTTCAATATGTTAAGCACTGTATTAGGCGTCTCCATCC
TGAATCTTGGACAAAAGAGATACACCAAGACTACTTACTGGTGGGATGGTCTTCAATCCTCTG
ACGATTTTGCTCTGATTGTGAATGCACCCAATCATGAAGGGATTCAAGCCGGAGTCGACAGGT
TTTATCGAACCTGTAAGCTACTTGGAATCAATATGAGCAAGAAAAAGTCTTACATAAACAGAA
CAGGTACATTTGAATTCACAAGTTTTTTCTATCGTTATGGGTTTGTTGCCAATTTCAGCATGG
AGCTCCCCAGTTTTGGGGTGTCTGGGATCAACGAGTCAGCGGACATGAGTATTGGAGTTACTG
TCATCAAAAACAATATGATAAACAATGATCTTGGTCCAGCAACAGCTCAAATGGCCCTTCAGT
TGTTCATCAAAGATTACAGGTACACGTACCGATGCCATAGAGGTGACACACAAATACAAACCC
GAAGATCATTTGAAATAAAGAAACTGTGGGAGCAAACCCGTTCCAAAGCTGGACTGCTGGTCT
CCGACGGAGGCCCAAATTTATACAACATTAGAAATCTCCACATTCCTGAAGTCTGCCTAAAAT
GGGAATTGATGGATGAGGATTACCAGGGGCGTTTATGCAACCCACTGAACCCATTTGTCAGCC
ATAAAGAAATTGAATCAATGAACAATGCAGTGATGATGCCAGCACATGGTCCAGCCAAAAACA
TGGAGTATGATGCTGTTGCAACAACACACTCCTGGATCCCCAAAAGAAATCGATCCATCTTGA
ATACAAGTCAAAGAGGAGTACTTGAAGATGAACAAATGTACCAAAGGTGCTGCAATTTATTTG
AAAAATTCTTCCCCAGCAGTTCATACAGAAGACCAGTCGGGATATCCAGTATGGTGGAGGCTA
TGGTTTCCAGAGCCCGAATTGATGCACGGATTGATTTCGAATCTGGAAGGATAAAGAAAGAAG
AGTTCACTGAGATCATGAAAATTTGCAGTACAATCGAGGAACTTCGGAGACAGAAGTAGCTCG
AGTGAGCTAACAGGGCTAGACTGTATGAGGCCGTGCTTCTGGGTTGAATTAATCAGGGGACGA
CCTAAAGAAAAAACAATCTGGACTAGTGCGAGCAGCATTTCTTTTTGTGGCGTGAATAGTGAT
ACTGTAGATTGGTCTTGGCCAGACGGTGCTGAGTTGCCATTCAGCATTGACAAGTAGTCTGTT
CAAAAAACTCCTTGTTTCTACT

Fig. 32A

NA-PB2MUT-NA:

```
AGCGAAAGCAGGGGTTTAAATTGAATCCAAATCAGAAAATAACAACCATTGGATCAATCTGTC
TGGTAGTCGGACTAATTAGCCTAATATTGCAAATAGGGAATATAATCTCAATTTGGATTAGCC
ATTCAATTCAAACTGGAAGTCAAAACCATACTGGAATTTGCAACCAAGCTAGCATGGAGCGGA
TCAAGGAGTTGCGGAACTTGATGTCGCAGTCTCGCACCCGCGAGATACTCACAAAAACCACCG
TGGACCATATGGCCATAATCAAGAAGTACACATCAGGAAGACAGGAGAAGAACCCAGCACTTA
GGATGAAATGGATGATGGCAATGAAATATCCAATTACAGCAGACAAGAGGATAACGGAAATGA
TTCCTGAGAGAAATGAGCAAGGACAAACTTTATGGAGTAAAATGAATGATGCAGGATCAGACC
GAGTGATGGTATCACCTCTGGCTGTGACATGGTGGAATAGGAATGGACCAATAACAAATACAG
TTCATTATCCAAAAATCTACAAAACTTATTTTGAAAGAGTCGAAAGGCTAAAGCATGGAACCT
TTGGCCCTGTCCATTTTAGAAACCAAGTCAAAATACGTCGGAGAGTTGACATAAATCCTGGTC
ATGCAGATCTCAGTGCCAAGGAGGCACAGGATGTAATCATGGAAGTTGTTTTCCCTAACGAAG
TGGGAGCCAGGATACTAACATCGGAATCGCAACTAACGATAACCAAAGAGAAGAAAGAAGAAC
TCCAGGATTGCAAAATTTCTCCTTTGATGGTTGCATACATGTTGGAGAGAGAACTGGTCCGCA
AAACGAGATTCCTCCCAGTGGCTGGTGGAACAAGCAGTGTGTACATTGAAGTGTTGCATTTGA
CTCAAGGAACATGCTGGGAACAGATGTATACTCCAGGAGGGGAAGTGAGGAATGATGATGTTG
ATCAAAGCTTGATTATTGCTGCTAGGAACATAGTGAGAAGAGCTGCAGTATCAGCAGATCCAC
TAGCATCTTTATTGGAGATGTGCCACAGCACACAGATTGGTGGAATTAGGATGGTAGACATCC
TTAGGCAGAACCCAACAGAAGAGCAAGCCGTGGATATATGCAAGGCTGCAATGGGACTGAGAA
TTAGCTCATCCTTCAGTTTTGGTGGATTCACATTTAAGAGAACAAGCGGATCATCAGTCAAGA
GAGAGGAAGAGGTGCTTACGGCAATCTTCAAACATTGAAGATAAGAGTGCATGAGGGATATG
AAGAGTTCACAATGGTTGGGAGAAGAGCAACAGCCATACTCAGAAAAGCAACCAGGAGATTGA
TTCAGCTGATAGTGAGTGGGAGAGACGAACAGTCGATTGCCGAAGCAATAATTGTGGCCATGG
TATTTTCACAAGAGGATTGTATGATAAAAGCAGTCAGAGGTGATCTGAATTTCGTCAATAGGG
CGAATCAGCGATTGAATCCTATGCATCAACTTTTAAGACATTTTCAGAAGGATGCGAAAGTGC
TTTTTCAAAATTGGGGAGTTGAACCTATCGACAATGTGATGGGAATGATTGGGATATTGCCAG
ACATGACTCCAAGCATCGAGATGTCAATGAGAGGAGTGAGAATCAGCAAAATGGGTGTAGATG
AGTACTCCAGCACGGAGAGGGTAGTGGTGAGCATTGACCGTTTTTTGAGAATCCGGGACCAAC
GAGGAAATGTACTACTGTCTCCCGAGGAGGTCAGTGAAACACAGGGAACAGAGAAACTGACAA
TAACTTACTCATCGTCAATGATGTGGGAGATTAATGGTCCTGAATCAGTGTTGGTCAATACCT
ATCAATGGATCATCAGAAACTGGGAAACTGTTAAAATTCAGTGGTCCCAGAACCCTACAATGC
TATACAATAAAATGGAATTTGAACCATTTCAGTCTTTAGTACCTAAGGCCATTAGAGGCCAAT
ACAGTGGGTTTGTAAGAACTCTGTTCCAACAAATGAGGGATGTGCTTGGGACATTTGATACCG
CACAGATAATAAAACTTCTTCCCTTCGCAGCCGCTCCACCAAAGCAAAGTAGAATGCAGTTCT
CCTCATTTACTGTGAATGTGAGGGGATCAGGAATGAGAATACTTGTAAGGGGCAATTCTCCTG
TATTCAACTATAACAAGGCCACGAAGAGACTCACAGTTCTCGGAAAGGATGCTGGCACTTTAA
CTGAAGACCCAGATGAAGGCACAGCTGGAGTGGAGTCCGCTGTTCTGAGGGGATTCCTCATTC
TGGGCAAAGAAGACAAGAGATATGGGCCAGCACTAAGCATCAATGAACTGAGCAACCTTGCGA
AAGGAGAGAAGGCTAATGTGCTAATTGGGCAAGGAGACGTGGTACTAGTGATGAAGAGAAAGA
GAGATAGCTCTATCTTGACGGATTCACAAACGGCAACTAAGAGGATCCGTATGGCTATTAACT
AGCTCGAGTGAGCTAACAGGGCTAGACTGTATGAGGCCGTGCTTCTGGGTTGAATTAATCAGG
GGACGACCTAAAGAAAAACAATCTGGACTAGTGCGAGCAGCATTTCTTTTTGTGGCGTGAAT
AGTGATACTGTAGATTGGTCTTGGCCAGACGGTGCTGAGTTGCCATTCAGCATTGACAAGTAG
TCTGTTCAAAAAACTCCTTGTTTCTACT
```

Fig. 32B

NA-PAmut-NA:

AGCGAAAGCAGGGGTTTAAATTGAATCCAAATCAGAAAATAACAACCATTGGATCAATCTGTC
TGGTAGTCGGACTAATTAGCCTAATATTGCAAATAGGGAATATAATCTCAATTTGGATTAGCC
ATTCAATTCAAACTGGAAGTCAAAACCATACTGGAATTTGCAACCAAGCTAGCATGGAGGACT
TCGTAAGGCAGTGTTTTAACCCAATGATCGTTGAACTCGCAGAGAAGACGATGAAGGAGTATG
GGGAGGACCTGAAAATCGAAACAAACAAATTTGCAGCAATATGCACTCACTTGGAAGTATGCT
TCATGTATTCAGATTTTCACTTCATCAATGAGCAAGGCGAGTCAATAATCGTAGAACTTGGTG
ATCCAAATGCACTTTTGAAGCACAGATTTGAAATAATCGAGGGAAGAGATCGCACAATGGCCT
GGACAGTAGTAAACAGTATTTGCAACACTACAGGGGCTGAGAAACCAAAGTTTCTACCAGATT
TGTATGATTACAAGGAGAATAGATTCATCGAAATTGGAGTAACAAGGAGAGAAGTTCACATAT
ACTATCTGGAAAAGGCCAATAAAATTAAATCTGAGAAAACACACATCCACATTTTCTCGTTCA
CTGGGGAAGAAATGGCCACAAAGGCAGACTACACTCTCGATGAAGAAAGCAGGGCTAGGATCA
AAACCAGACTATTCACCATAAGACAAGAAATGGCCAGCAGAGGCCTCTGGGATTCCTTTCGTC
AGTCCGAGAGAGGAGAAGAGACAATTGAAGAAAGGTTTGAAATCACAGGAACAATGCGCAAGC
TTGCCGACCAAAGTCTCCCGCCGAACTTCTCCAGCCTTGAAAATTTTAGAGCCTATGTGGATG
GATTCGAACCGAACGGCTACATTGAGGGCAAGCTGTCTCAAATGTCCAAAGAAGTAAATGCTA
GAATTGAACCTTTTTTGAAAACAACACCACGACCACTTAGACTTCCGAATGGGCCTCCCTGTT
CTCAGCGGTCCAAATTCCTGCTGATGGATGCCTTAAAATTAAGCATTGAGGACCCAAGTCATG
AAGGAGAGGGAATACCGCTATATGATGCAATCAAATGCATGAGAACATTCTTTGGATGGAAGG
AACCCAATGTTGTTAAACCACACGAAAAGGGAATAAATCCAAATTATCTTCTGTCATGGAAGC
AAGTACTGGCAGAACTGCAGGACATTGAGAATGAGGAGAAAATTCCAAAGACTAAAAATATGA
AGAAAACAAGTCAGCTAAAGTGGGCACTTGGTGAGAACATGGCACCAGAAAAGGTAGACTTTG
ACGACTGTAAAGATGTAGGTGATTTGAAGCAATATGATAGTGATGAACCAGAATTGAGGTCGC
TAGCAAGTTGGATTCAGAATGAGTTTAACAAGGCATGCGAACTGACAGATTCAAGCTGGATAG
AGCTCGATGAGATTGGAGAAGATGTGGCTCCAATTGAACACATTGCAAGCATGAGAAGGAATT
ATTTCACATCAGAGGTGTCTCACTGCAGAGCCACAGAATACATAATGAAGGGGGTGTACATCA
ATACTGCCTTGCTTAATGCATCTTGTGCAGCAATGGATGATTTCCAATTAATTCCAATGATAA
GCAAGTGTAGAACTAAGGAGGGAAGGCGAAAGACCAACTTGTATGGTTTCATCATAAAAGGAA
GATCCCACTTAAGGAATGACACCGACGTGGTAAACTTTGTGAGCATGGAGTTTTCTCTCACTG
ACCCAAGACTTGAACCACATAAATGGGAGAAGTACTGTGTTCTTGAGATAGGAGATATGCTTA
TAAGAAGTGCCATAGGCCAGGTTTCAAGGCCCATGTTCTTGTATGTGAGAACAAATGGAACCT
CAAAAATTAAAATGAAATGGGGAATGGAGATGAGGCGTTGCCTCCTCCAGTCACTTCAACAAA
TTGAGAGTATGATTGAAGCTGAGTCCTCTGTCAAAGAGAAAGACATGACCAAAGAGTTCTTTG
AGAACAAATCAGAAACATGGCCCATTGGAGAGTCCCCCAAAGGAGTGGAGGAAAGTTCCATTG
GGAAGGTCTGCAGGACTTTATTAGCAAAGTCGGTATTCAACAGCTTGTATGCATCTCCACAAC
TAGAAGGATTTTCAGCTGAATCAAGAAAACTGCTTCTTATCGTTCAGGCTCTTAGGGACAACC
TTGAACCTGGGACCTTTGATCTTGGGGGGCTATATGAAGCAATTGAGGAGTGCCTGATTAATG
ATCCCTGGGTTTTGCTTAACGCCAGCTGGTTTAATTCTTTTTTGACGCACGCGCTATCATAGC
TCGAGTGAGCTAACAGGGCTAGACTGTATGAGGCCGTGCTTCTGGGTTGAATTAATCAGGGGA
CGACCTAAAGAAAAACAATCTGGACTAGTGCGAGCAGCATTTCTTTTTGTGGCGTGAATAGT
GATACTGTAGATTGGTCTTGGCCAGACGGTGCTGAGTTGCCATTCAGCATTGACAAGTAGTCT
GTTCAAAAAACTCCTTGTTTCTACT

Fig. 32C

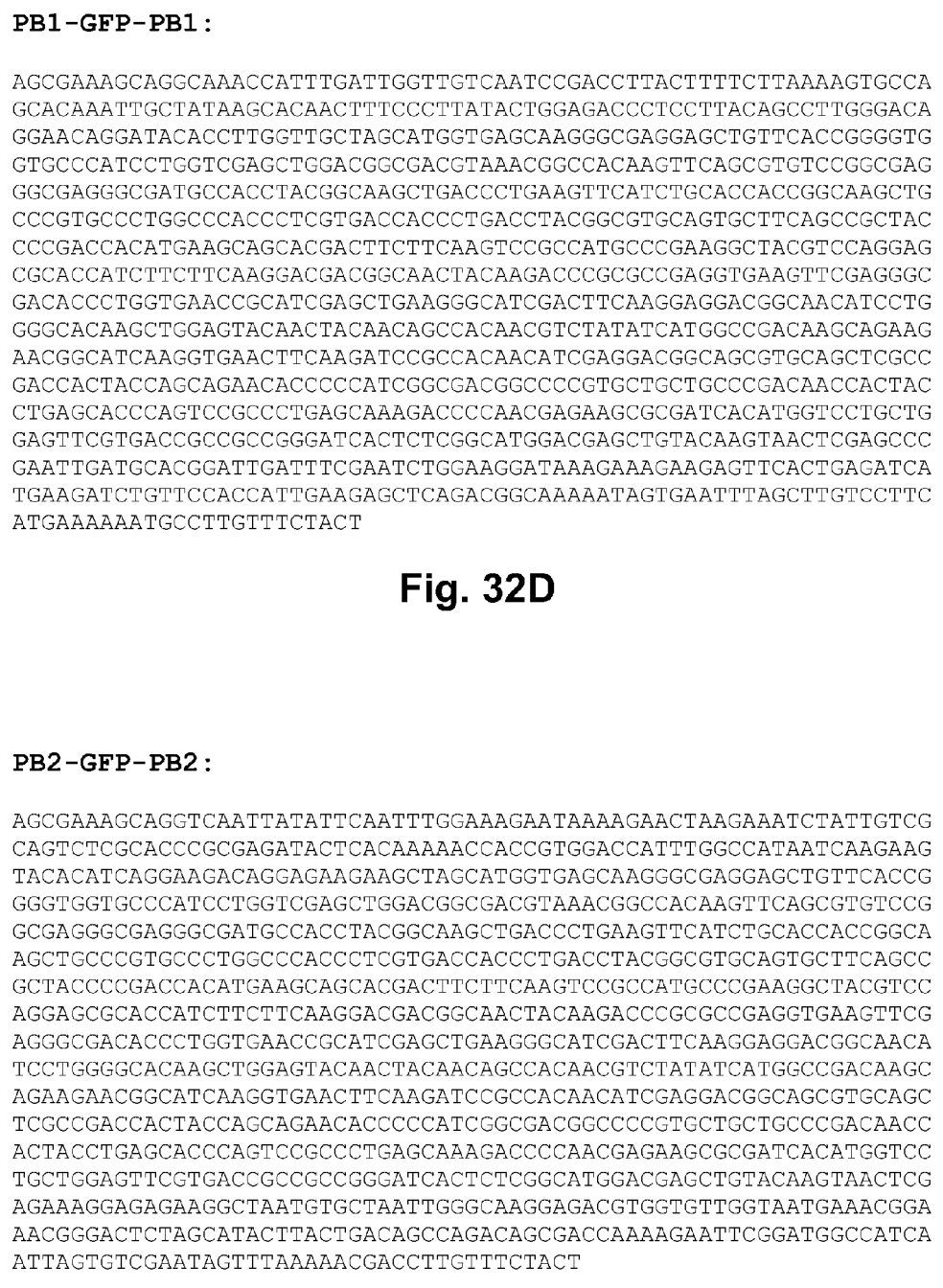

PB1-GFP-PB1:

AGCGAAAGCAGGCAAACCATTTGATTGGTTGTCAATCCGACCTTACTTTTCTTAAAAGTGCCA
GCACAAATTGCTATAAGCACAACTTTCCCTTATACTGGAGACCCTCCTTACAGCCTTGGGACA
GGAACAGGATACACCTTGGTTGCTAGCATGGTGAGCAAGGGCGAGGAGCTGTTCACCGGGGTG
GTGCCCATCCTGGTCGAGCTGGACGGCGACGTAAACGGCCACAAGTTCAGCGTGTCCGGCGAG
GGCGAGGGCGATGCCACCTACGGCAAGCTGACCCTGAAGTTCATCTGCACCACCGGCAAGCTG
CCCGTGCCCTGGCCCACCCTCGTGACCACCCTGACCTACGGCGTGCAGTGCTTCAGCCGCTAC
CCCGACCACATGAAGCAGCACGACTTCTTCAAGTCCGCCATGCCCGAAGGCTACGTCCAGGAG
CGCACCATCTTCTTCAAGGACGACGGCAACTACAAGACCCGCGCCGAGGTGAAGTTCGAGGGC
GACACCCTGGTGAACCGCATCGAGCTGAAGGGCATCGACTTCAAGGAGGACGGCAACATCCTG
GGGCACAAGCTGGAGTACAACTACAACAGCCACAACGTCTATATCATGGCCGACAAGCAGAAG
AACGGCATCAAGGTGAACTTCAAGATCCGCCACAACATCGAGGACGGCAGCGTGCAGCTCGCC
GACCACTACCAGCAGAACACCCCCATCGGCGACGGCCCCGTGCTGCTGCCCGACAACCACTAC
CTGAGCACCCAGTCCGCCCTGAGCAAAGACCCCAACGAGAAGCGCGATCACATGGTCCTGCTG
GAGTTCGTGACCGCCGCCGGGATCACTCTCGGCATGGACGAGCTGTACAAGTAACTCGAGCCC
GAATTGATGCACGGATTGATTTCGAATCTGGAAGGATAAAGAAAGAAGAGTTCACTGAGATCA
TGAAGATCTGTTCCACCATTGAAGAGCTCAGACGGCAAAAATAGTGAATTTAGCTTGTCCTTC
ATGAAAAAATGCCTTGTTTCTACT

Fig. 32D

PB2-GFP-PB2:

AGCGAAAGCAGGTCAATTATATTCAATTTGGAAAGAATAAAAGAACTAAGAAATCTATTGTCG
CAGTCTCGCACCCGCGAGATACTCACAAAAACCACCGTGGACCATTTGGCCATAATCAAGAAG
TACACATCAGGAAGACAGGAGAAGAAGCTAGCATGGTGAGCAAGGGCGAGGAGCTGTTCACCG
GGGTGGTGCCCATCCTGGTCGAGCTGGACGGCGACGTAAACGGCCACAAGTTCAGCGTGTCCG
GCGAGGGCGAGGGCGATGCCACCTACGGCAAGCTGACCCTGAAGTTCATCTGCACCACCGGCA
AGCTGCCCGTGCCCTGGCCCACCCTCGTGACCACCCTGACCTACGGCGTGCAGTGCTTCAGCC
GCTACCCCGACCACATGAAGCAGCACGACTTCTTCAAGTCCGCCATGCCCGAAGGCTACGTCC
AGGAGCGCACCATCTTCTTCAAGGACGACGGCAACTACAAGACCCGCGCCGAGGTGAAGTTCG
AGGGCGACACCCTGGTGAACCGCATCGAGCTGAAGGGCATCGACTTCAAGGAGGACGGCAACA
TCCTGGGGCACAAGCTGGAGTACAACTACAACAGCCACAACGTCTATATCATGGCCGACAAGC
AGAAGAACGGCATCAAGGTGAACTTCAAGATCCGCCACAACATCGAGGACGGCAGCGTGCAGC
TCGCCGACCACTACCAGCAGAACACCCCCATCGGCGACGGCCCCGTGCTGCTGCCCGACAACC
ACTACCTGAGCACCCAGTCCGCCCTGAGCAAAGACCCCAACGAGAAGCGCGATCACATGGTCC
TGCTGGAGTTCGTGACCGCCGCCGGGATCACTCTCGGCATGGACGAGCTGTACAAGTAACTCG
AGAAAGGAGAGAAGGCTAATGTGCTAATTGGGCAAGGAGACGTGGTGTTGGTAATGAAACGGA
AACGGGACTCTAGCATACTTACTGACAGCCAGACAGCGACCAAAAGAATTCGGATGGCCATCA
ATTAGTGTCGAATAGTTTAAAAACGACCTTGTTTCTACT

Fig. 32E

PA-GFP-PA:

```
AGCGAAAGCAGGTACTGATCCAAATTGGAAGATTTTGTGCGACATTGCTTCAATCCGTTGATT
GTCGAGCTTGCGGAAAAAACATTGAAAGAGTTTGGGGAGGACCTGAAAATCGAAACAAACAAA
TTTGCAGCAATTTGCTAGCATGGTGAGCAAGGGCGAGGAGCTGTTCACCGGGGTGGTGCCCAT
CCTGGTCGAGCTGGACGGCGACGTAAACGGCCACAAGTTCAGCGTGTCCGGCGAGGGCGAGGG
CGATGCCACCTACGGCAAGCTGACCCTGAAGTTCATCTGCACCACCGGCAAGCTGCCCGTGCC
CTGGCCCACCCTCGTGACCACCCTGACCTACGGCGTGCAGTGCTTCAGCCGCTACCCCGACCA
CATGAAGCAGCACGACTTCTTCAAGTCCGCCATGCCCGAAGGCTACGTCCAGGAGCGCACCAT
CTTCTTCAAGGACGACGGCAACTACAAGACCCGCGCCGAGGTGAAGTTCGAGGGCGACACCCT
GGTGAACCGCATCGAGCTGAAGGGCATCGACTTCAAGGAGGACGGCAACATCCTGGGGCACAA
GCTGGAGTACAACTACAACAGCCACAACGTCTATATCATGGCCGACAAGCAGAAGAACGGCAT
CAAGGTGAACTTCAAGATCCGCCACAACATCGAGGACGGCAGCGTGCAGCTCGCCGACCACTA
CCAGCAGAACACCCCCATCGGCGACGGCCCCGTGCTGCTGCCCGACAACCACTACCTGAGCAC
CCAGTCCGCCCTGAGCAAAGACCCCAACGAGAAGCGCGATCACATGGTCCTGCTGGAGTTCGT
GACCGCCGCCGGGATCACTCTCGGCATGGACGAGCTGTACAAGTAACTCGAGCCTGGGACCTT
TGATCTTGGGGGGCTATATGAAGCAATTGAGGAGTGCCTGATTAATGATCCCTGGGTTTTGCT
TAATGCTTCTTGGTTCAACTCCTTCCTTACACATGCATTGAGTTAGTTGTGGCAGTGCTACTA
TTTGCTATCCATACTGTCCAAAAAAGTACCTTGTTTCTACT
```

Fig. 32F

PB1-HA(HK)-PB1:

AGCGAAAGCAGGCAAACCATTTGATTGGTTGTCAATCCGACCTTACTTTTCTTAAAAGTGCCA
GCACAAATTGCTATAAGCACAACTTTCCCTTATACTGGAGACCCTCCTTACAGCCTTGGGACA
GGAACAGGATACACCTTGGTTGCTAGCATGAAGACCATCATTGCTTTGAGCTACATTTTCTGT
CTGGCTCTCGGCCAAGACCTTCCAGGAAATGACAACAGCACAGCAACGCTGTGCCTGGGACAT
CATGCGGTGCCAAACGGAACACTAGTGAAAACAATCACAGATGATCAGATTGAAGTGACTAAT
GCTACTGAGCTAGTTCAGAGCTCCTCAACGGGGAAAATATGCAACAATCCTCATCGAATCCTT
GATGGAATAGACTGCACACTGATAGATGCTCTATTGGGGGACCCTCATTGTGATGTTTTTCAA
AATGAGACATGGGACCTTTTCGTTGAACGCAGCAAAGCTTTCAGCAACTGTTACCCTTATGAT
GTGCCAGATTATGCCTCCCTTAGGTCACTAGTTGCCTCGTCAGGCACTCTGGAGTTTATCACT
GAGGGTTTCACTTGGACTGGGGTCACTCAGAATGGGGGAAGCAATGCTTGCAAAAGGGGACCT
GGTAGCGGTTTTTTCAGTAGACTGAACTGGTTGACCAAATCAGGAAGCACATATCCAGTGCTG
AACGTGACTATGCCAAACAATGACAATTTTGACAAACTATACATTTGGGGGGTTCACCACCCG
AGCACGAACCAAGAACAAACCAGCCTGTATGTTCAAGCATCAGGGAGAGTCACAGTCTCTACC
AGGAGAAGCCAGCAAACTATAATCCCGAATATCGGGTCCAGACCCTGGGTAAGGGGTCTGTCT
AGTAGAATAAGCATCTATTGGACAATAGTTAAGCCGGGAGACGTACTGGTAATTAATAGTAAT
GGGAACCTAATCGCTCCTCGGGGTTATTTCAAAATGCGCACTGGGAAAAGCTCAATAATGAGG
TCAGATGCACCTATTGATACCTGTATTTCTGAATGCATCACTCCAAATGGAAGCATTCCCAAT
GACAAGCCCTTTCAAAACGTAAACAAGATCACATATGGAGCATGCCCCAAGTATGTTAAGCAA
AACACCCTGAAGTTGGCAACAGGGATGCGGAATGTACCAGAGAAACAAACTAGAGGCCTATTC
GGCGCAATAGCAGGTTTCATAGAAAATGGTTGGGAGGGAATGATAGACGGTTGGTACGGTTTC
AGGCATCAAAATTCTGAGGGCACAGGACAAGCAGCAGATCTTAAAAGCACTCAAGCAGCCATC
GACCAAATCAATGGAAATTGAACAGGGTAATCGAGAAGACGAACGAGAAATTCCATCAAATC
GAAAAGGAATTCTCAGAAGTAGAAGGGAGAATTCAGGACCTCGAGAAATACGTTGAAGACACT
AAAATAGATCTCTGGTCTTACAATGCGGAGCTTCTTGTCGCTCTGGAGAATCAACATACAATT
GACCTGACTGACTCGGAAATGAACAAGCTGTTTGAAAAAACAGGGAGGCAACTGAGGGAAAAT
GCTGAAGACATGGGCAATGGTTGCTTCAAAATATACCACAAATGTGACAACGCTTGCATAGAG
TCAATCAGAAATGGGACTTATGACCATGATGTATACAGAGACGAAGCATTAAACAACCGGTTT
CAGATCAAAGGTGTTGAACTGAAGTCTGGATACAAAGACTGGATCCTGTGGATTTCCTTTGCC
ATATCATGCTTTTTGCTTTGTGTTGTTTTGCTGGGGTTCATCATGTGGGCCTGCCAGAGAGGC
AACATTAGGTGCAACATTTGCATTTGACTCGAGCCCGAATTGATGCACGGATTGATTTCGAAT
CTGGAAGGATAAAGAAAGAAGAGTTCACTGAGATCATGAAGATCTGTTCCACCATTGAAGAGT
CAGACGGCAAAAATAGTGAATTTAGCTTGTCCTTCATGAAAAAATGCCTTGTTTCTACT

Fig. 32G

PB2-HA(HK)-PB2:

```
AGCGAAAGCAGGTCAATTATATTCAATTTGGAAAGAATAAAAGAACTAAGAAATCTATTGTCG
CAGTCTCGCACCCGCGAGATACTCACAAAAACCACCGTGGACCATTTGGCCATAATCAAGAAG
TACACATCAGGAAGACAGGAGAAGAAGCTAGCATGAAGACCATCATTGCTTTGAGCTACATTT
TCTGTCTGGCTCTCGGCCAAGACCTTCCAGGAAATGACAACAGCACAGCAACGCTGTGCCTGG
GACATCATGCGGTGCCAAACGGAACACTAGTGAAAACAATCACAGATGATCAGATTGAAGTGA
CTAATGCTACTGAGCTAGTTCAGAGCTCCTCAACGGGGAAAATATGCAACAATCCTCATCGAA
TCCTTGATGGAATAGACTGCACACTGATAGATGCTCTATTGGGGGACCCTCATTGTGATGTTT
TTCAAAATGAGACATGGGACCTTTTCGTTGAACGCAGCAAAGCTTTCAGCAACTGTTACCCTT
ATGATGTGCCAGATTATGCCTCCCTTAGGTCACTAGTTGCCTCGTCAGGCACTCTGGAGTTTA
TCACTGAGGGTTTCACTTGGACTGGGGTCACTCAGAATGGGGGAAGCAATGCTTGCAAAAGGG
GACCTGGTAGCGGTTTTTTCAGTAGACTGAACTGGTTGACCAAATCAGGAAGCACATATCCAG
TGCTGAACGTGACTATGCCAAACAATGACAATTTTGACAAACTATACATTTGGGGGGTTCACC
ACCCGAGCACGAACCAAGAACAAACCAGCCTGTATGTTCAAGCATCAGGGAGAGTCACAGTCT
CTACCAGGAGAAGCCAGCAAACTATAATCCCGAATATCGGGTCCAGACCCTGGGTAAGGGGTC
TGTCTAGTAGAATAAGCATCTATTGGACAATAGTTAAGCCGGGAGACGTACTGGTAATTAATA
GTAATGGGAACCTAATCGCTCCTCGGGGTTATTTCAAAATGCGCACTGGGAAAAGCTCAATAA
TGAGGTCAGATGCACCTATTGATACCTGTATTTCTGAATGCATCACTCCAAATGGAAGCATTC
CCAATGACAAGCCCTTTCAAAACGTAAACAAGATCACATATGGAGCATGCCCCAAGTATGTTA
AGCAAAACACCCTGAAGTTGGCAACAGGGATGCGGAATGTACCAGAGAAACAAACTAGAGGCC
TATTCGGCGCAATAGCAGGTTTCATAGAAAATGGTTGGGAGGGAATGATAGACGGTTGGTACG
GTTTCAGGCATCAAAATTCTGAGGGCACAGGACAAGCAGCAGATCTTAAAAGCACTCAAGCAG
CCATCGACCAAATCAATGGGAAATTGAACAGGGTAATCGAGAAGACGAACGAGAAATTCCATC
AAATCGAAAAGGAATTCTCAGAAGTAGAAGGGAGAATTCAGGACCTCGAGAAATACGTTGAAG
ACACTAAAATAGATCTCTGGTCTTACAATGCGGAGCTTCTTGTCGCTCTGGAGAATCAACATA
CAATTGACCTGACTGACTCGGAAATGAACAAGCTGTTTGAAAAAACAGGGAGGCAACTGAGGG
AAAATGCTGAAGACATGGGCAATGGTTGCTTCAAAATATACCACAAATGTGACAACGCTTGCA
TAGAGTCAATCAGAAATGGGACTTATGACCATGATGTATACAGAGACGAAGCATTAAACAACC
GGTTTCAGATCAAAGGTGTTGAACTGAAGTCTGGATACAAAGACTGGATCCTGTGGATTTCCT
TTGCCATATCATGCTTTTTGCTTTGTGTTGTTTTGCTGGGGTTCATCATGTGGGCCTGCCAGA
GAGGCAACATTAGGTGCAACATTTGCATTTGACTCGAGAAAGGAGAGAAGGCTAATGTGCTAA
TTGGGCAAGGAGACGTGGTGTTGGTAATGAAACGGAAACGGGACTCTAGCATACTTACTGACA
GCCAGACAGCGACCAAAAGAATTCGGATGGCCATCAATTAGTGTCGAATAGTTTAAAAACGAC
CTTGTTTCTACT
```

Fig. 32H

PB1-Luc-PB1:

AGCGAAAGCAGGCAAACCATTTGATTGGTTGTCAATCCGACCTTACTTTTCTTAAAAGTGCCA
GCACAAATTGCTATAAGCACAACTTTCCCTTATACTGGAGACCCTCCTTACAGCCTTGGGACA
GGAACAGGATACACCTTGGTTGCTAGCATGACTTCGAAAGTTTATGATCCAGAACAAAGGAAA
CGGATGATAACTGGTCCGCAGTGGTGGGCCAGATGTAAACAAATGAATGTTCTTGATTCATTT
ATTAATTATTATGATTCAGAAAAACATGCAGAAAATGCTGTTATTTTTTACATGGTAACGCG
GCCTCTTCTTATTTATGGCGACATGTTGTGCCACATATTGAGCCAGTAGCGCGGTGTATTATA
CCAGACCTTATTGGTATGGGCAAATCAGGCAAATCTGGTAATGGTTCTTATAGGTTACTTGAT
CATTACAAATATCTTACTGCATGGTTTGAACTTCTTAATTTACCAAAGAAGATCATTTTTGTC
GGCCATGATTGGGGTGCTTGTTTGGCATTTCATTATAGCTATGAGCATCAAGATAAGATCAAA
GCAATAGTTCACGCTGAAAGTGTAGTAGATGTGATTGAATCATGGGATGAATGGCCTGATATT
GAAGAAGATATTGCGTTGATCAAATCTGAAGAAGGAGAAAAAATGGTTTTGGAGAATAACTTC
TTCGTGGAAACCATGTTGCCATCAAAAATCATGAGAAAGTTAGAACCAGAAGAATTTGCAGCA
TATCTTGAACCATTCAAAGAGAAAGGTGAAGTTCGTCGTCCAACATTATCATGGCCTCGTGAA
ATCCCGTTAGTAAAAGGTGGTAAACCTGACGTTGTACAAATTGTTAGGAATTATAATGCTTAT
CTACGTGCAAGTGATGATTTACCAAAAATGTTTATTGAATCGGACCCAGGATTCTTTTCCAAT
GCTATTGTTGAAGGTGCCAAGAAGTTTCCTAATACTGAATTTGTCAAAGTAAAAGGTCTTCAT
TTTTCGCAAGAAGATGCACCTGATGAAATGGGAAAATATATCAAATCGTTCGTTGAGCGAGTT
CTCAAAAATGAACAATAACTCGAGCCCGAATTGATGCACGGATTGATTTCGAATCTGGAAGGA
TAAAGAAGAAGAGTTCACTGAGATCATGAAGATCTGTTCCACCATTGAAGAGCTCAGACGGC
AAAAATAGTGAATTTAGCTTGTCCTTCATGAAAAAATGCCTTGTTTCTACT

Fig. 32 I

A better growing 9-segment virus (~$10^8$ pfu/ml in eggs):

-NA(ps)+GFP:
or
-NA(ps)+HK HA:

PB2 | PB1 | PA | HA | NP | NAmut (PA) | M | NS | GFP ORF or HK HA ORF (NA)

Fig. 38

INFLUENZA VIRUSES AND USES THEREOF

This application is the national stage entry of international patent application No. PCT/US2010/043697, filed Jul. 29, 2010, which claims priority benefit of U.S. provisional application No. 61/229,858, filed Jul. 30, 2009, each of which is incorporated herein by reference in its entirety.

This invention was made with United States Government support under award numbers U01 AI070469, 1RC1 AI086061-01, HHSN2662000700010C and U54 AI057158-06 from the National Institutes of Health. The United States Government has certain rights in this invention.

1. INTRODUCTION

Described herein are chimeric influenza virus gene segments and nucleic acid sequences encoding such chimeric influenza virus gene segments. A chimeric influenza virus gene segment described herein comprises packaging signals found in the non-coding and coding regions of one type of influenza virus gene segment and an open reading frame of a different type of influenza virus gene segment or fragment thereof. Also described herein are recombinant influenza viruses comprising two or more chimeric influenza virus gene segments and the use of such viruses in the prevention and/or treatment of influenza virus disease.

2. BACKGROUND

Influenza viruses are enveloped RNA viruses that belong to the family of Orthomyxoviridae (Palese and Shaw (2007) Orthomyxoviridae: The Viruses and Their Replication, 5th ed. Fields' Virology, edited by B. N. Fields, D. M. Knipe and P. M. Howley. Wolters Kluwer Health/Lippincott Williams & Wilkins, Philadelphia, USA, p 1647-1689). The natural host of influenza viruses are avians, but influenza viruses (including those of avian origin) also can infect and cause illness in humans and other animal hosts (canines, pigs, horses, sea mammals, and mustelids). For example, the H5N1 avian influenza virus circulating in Asia has been found in pigs in China and Indonesia and has also expanded its host range to include cats, leopards, and tigers, which generally have not been considered susceptible to influenza A (CIDRAP—Avian influenza: Agricultural and Wildlife Considerations). The occurrence of influenza virus infections in animals could potentially give rise to human pandemic influenza strains.

Influenza A and B viruses are major human pathogens, causing a respiratory disease that ranges in severity from sub-clinical infection to primary viral pneumonia which can result in death. The clinical effects of infection vary with the virulence of the influenza strain and the exposure, history, age, and immune status of the host. The cumulative morbidity and mortality caused by seasonal influenza is substantial due to the relatively high rate of infection. In a normal season, influenza can cause between 3-5 million cases of severe illness and up to 500,000 deaths worldwide (World Health Organization (2003) Influenza: Overview; who.int/mediacentre/factsheets/fs211/en/website; March 2003). In the United States, influenza viruses infect an estimated 10-15% of the population (Glezen and Couch R B (1978) Interpandemic Influenza in the Houston area, 1974-76. N Engl J Med 298: 587-592; Fox et al. (1982) Influenza virus infections in Seattle families, 1975-1979. II. Pattern of infection in invaded households and relation of age and prior antibody to occurrence of infection and related illness. Am J Epidemiol 116: 228-242) and are associated with approximately 30,000 deaths each year (Thompson W W et al. (2003) Mortality Associated With Influenza and Respiratory Syncytial Virus in the United States. JAMA 289: 179-186; Belshe (2007) Translational research on vaccines: Influenza as an example. Clin Pharmacol Ther 82: 745-749).

In addition to annual epidemics, influenza viruses are the cause of infrequent pandemics. For example, influenza A viruses can cause pandemics such as those that occurred in 1918, 1957 and 1968. Due to the lack of pre-formed immunity against the major viral antigen, hemagglutinin (HA), pandemic influenza viruses can affect greater than 50% of the population in a single year and often cause more severe disease than seasonal influenza viruses. A stark example is the pandemic of 1918, in which an estimated 50-100 million people were killed (Johnson and Mueller (2002) Updating the Accounts: Global Mortality of the 1918-1920 "Spanish" Influenza Pandemic Bulletin of the History of Medicine 76: 105-115). Since the emergence of the highly pathogenic avian H5N1 influenza virus in the late 1990s (Claas et al. (1998) Human Influenza A H5N1 virus related to a highly pathogenic avian Influenza virus. Lancet 351: 472-7), there have been concerns that the virus may become transmissible between humans and cause a major pandemic. Recently, the World Health Organization has declared the H1N1 2009 swine influenza virus a pandemic virus.

An effective way to protect against influenza virus infection is through vaccination with attenuated influenza virus. However, due to reassortment, co-infection of an individual with a live attenuated vaccine strain and a wild-type strain of influenza could allow the formation of replication-competent virus carrying, e.g., the vaccine-derived hemagglutinin, to which the infected person would likely to be naive. Accordingly, there is a need to develop methods of preventing the reassortment of vaccine strains of influenza virus with wild-type influenza viruses.

3. SUMMARY

Described herein are chimeric influenza virus gene segments and nucleic acid sequences encoding such chimeric influenza virus gene segments or the complement thereof which are useful in the production of recombinant influenza viruses. Two or more chimeric influenza virus gene segments or complements thereof, or nucleic acid sequences encoding such gene segments or the complements thereof may be used in the production of recombinant influenza viruses. Without being bound by any theory, the two or more chimeric influenza virus gene segments segregate together (i.e., cosegregate) during replication of the recombinant influenza viruses such that the recombinant influenza viruses have a reduced ability to reassort with other influenza viruses (e.g., wild-type influenza viruses) or are unable to reassort with other influenza viruses as determined by techniques known to one skilled in the art. The reduced ability or inability of such recombinant influenza viruses to reassort with other influenza viruses may improve the safety of the recombinant influenza viruses as a live attenuated vaccine. Accordingly, such recombinant influenza viruses may be useful in either the prevention of influenza virus disease, the treatment of influenza virus disease or influenza virus infection, or both.

In certain aspects, a chimeric influenza virus gene segment comprises: (a) packaging signals found in the 3' and the 5' non-coding regions of a first type of influenza virus gene segment, (b) packaging signals found in the 3' proximal coding region sequence of the first type of influenza virus gene segment, the 5' proximal coding region sequence of the first type of influenza virus gene segment, or both the 3' and the 5' proximal coding region sequences of the first type of influenza virus gene segment, and (c) an open reading frame or a fragment thereof from a second, different type of influenza virus gene segment, wherein the open reading frame contains one, two, three or more mutations in the influenza virus packaging signals found in the open reading frame. In certain embodiments, the 3' and/or the 5' proximal coding regions sequences flank the open reading frame and are translated in frame with the open reading frame. In other embodiments, the 3' and/or the 5' proximal coding region sequences flank the open reading frame and are not translated. In some embodiments, the 3' proximal coding region sequence has been mutated so as to eliminate any start codons and preclude the translation of the 3' proximal coding region sequence. In certain embodiments, the 3' proximal coding region is derived from an influenza virus NS or M gene segment. In a specific embodiment, the 3' proximal coding region is derived from an influenza virus NS gene segment and the 3' proximal coding region has been mutated to eliminate the mRNA 5' splice site. In another specific embodiment, the 3' proximal coding region is derived from an influenza virus M gene segment and the 3' proximal coding region has been mutated to eliminate the distal 5' splice site. In some embodiments, the 5' proximal coding region sequence has one or more mutations so as to ensure that the 5' proximal coding region sequence is not translated. In a specific embodiment, the mutations introduced into the open reading frame of the influenza virus gene segment or a fragment are silent mutations.

In one embodiment, a chimeric influenza virus gene segment comprises: (i) the 3' non-coding region of a first type of influenza virus gene segment; (ii) a 3' proximal coding region of the first type of influenza virus gene segment, wherein any start codon in the 3' proximal coding region of the first type of influenza virus gene segment is mutated; (iii) at least the 3' proximal 20 nucleotides from an open reading frame of a second type of influenza virus gene segment, wherein the at least 20 nucleotides carry one or more mutations; (iv) a 5' proximal coding region of the first type of influenza virus gene segment; and (v) the 5' non-coding region of the first type of influenza virus gene segment, wherein the nucleic acid is engineered such that an open reading frame may be inserted following in frame with the at least 20 nucleotides of the open reading frame of the second type of influenza virus gene segment. In another embodiment, a chimeric influenza virus gene segment comprises: (i) the 3' non-coding region of a first type of influenza virus gene segment; (ii) a 3' proximal coding region of the first type of influenza virus gene segment, wherein any start codon in the 3' proximal coding region of the first type of influenza virus gene segment is mutated; (iii) at least the 5' proximal 30 nucleotides of an open reading frame of a second type of influenza virus gene segment, wherein the at least 30 nucleotides carry one or more mutations; (iv) a 5' proximal coding region of the first type of influenza virus gene segment; and (v) the 5' non-coding region of the first type of influenza virus gene segment, wherein the nucleic acid is engineered such that an open reading frame may be inserted preceding in frame with the at least 30 nucleotides of the open reading frame of the second type of influenza virus gene segment. In another embodiment, a chimeric influenza virus gene segment comprises: (i) the 3' non-coding region of a first type of influenza virus gene segment; (ii) a 3' proximal coding region of the first type of influenza virus gene segment, wherein any start codon in the 3' proximal coding region of the first type of influenza virus gene segment is mutated; (iii) at least the 3' proximal 20 nucleotides of an open reading frame of a second type of influenza virus gene segment, wherein the at least 20 nucleotides carry one or more mutations; (iv) at least the 5' proximal 30 nucleotides of the open reading frame of the second type of influenza virus gene segment, wherein the at least 30 nucleotides carry one or more mutations; (v) a 5' proximal coding region of the first type of influenza virus gene segment; and (vi) the 5' non-coding region of the first type of influenza virus gene segment, wherein the nucleic acid is engineered such that an open reading frame may be inserted in frame between the at least 20 nucleotides from the open reading frame of the second type of influenza virus gene segment and the at least 30 nucleotides of the open reading frame of the second type of influenza virus gene segment. In certain embodiments, the 3' proximal coding region sequence is derived from an influenza virus NS or M gene segment. In a specific embodiment, the 3' proximal coding region sequence is derived from an influenza virus NS gene segment and the 3' proximal coding region has been mutated so as to eliminate the mRNA 5' splice site. In another specific embodiment, the 3' proximal coding region sequence is derived from an influenza virus M gene segment and the 3' proximal coding region has been mutated so as to eliminate the distal 5' splice site.

In a specific embodiment, a chimeric influenza virus gene segment provided herein comprises: (i) the 3' non-coding region of a first type of influenza virus gene segment; (ii) a 3' proximal coding region of the first type of influenza virus gene segment, wherein any start codon in the 3' proximal coding region of the first type of influenza virus gene segment is mutated; (iii) an open reading frame of a second type of influenza virus gene segment, wherein the 3' proximal nucleotides and the 5' proximal nucleotides of the open reading frame are mutated; (iv) a 5' proximal coding region of the first type of influenza virus gene segment; and (v) the 5' non-coding region of the first type of influenza virus gene segment.

In certain aspects, provided herein are nucleic acid sequences comprising the complement of a chimeric influenza virus gene segment which may be useful in the production of recombinant influenza viruses. In specific embodiments, a nucleic acid sequence provided herein comprises the complement of a chimeric influenza virus gene segment, wherein the chimeric influenza virus gene segment comprises: (a) packaging signals found in the 3' and the 5' non-coding regions of a first type of influenza virus gene segment, (b) packaging signals found in the 3' proximal coding region sequence of the first type of influenza virus gene segment, the 5' proximal coding region sequence of the first type of influenza virus gene segment, or both the 3' and the 5' proximal coding region sequences of the first type of influenza virus gene segment, and (c) an open reading frame or a fragment thereof from a second, different type of influenza virus gene segment, wherein the open reading frame contains one, two, three or more mutations in the influenza virus packaging signals found in the open reading frame. In certain embodiments, the 3' and/or the 5' proximal coding regions sequences flank the open reading frame and are translated in frame with the open reading frame. In other embodiments, the 3' and/or the 5' proximal coding region sequences flank the open reading frame and are not translated. In some embodiments, the 3' proximal coding region sequence has been mutated so as to eliminate any start codons and preclude the translation of the 3' proximal coding region sequence. In certain embodiments, the 3' proximal coding region sequence is derived from an influenza virus NS or M gene segment. In a specific embodiment, the 3' proximal coding region sequence is derived from an influenza virus NS gene segment and the 3' proximal coding region has been mutated so as to eliminate the mRNA 5' splice site. In another specific embodiment, the 3' proximal coding region sequence is derived from an influenza virus M gene segment and the 3' proximal coding region has been mutated so as to eliminate the distal 5' splice site. In some embodiments, the 5' proximal coding region sequence has one or more mutations so as to ensure that the 5' proximal coding region sequence is not translated. In a specific embodiment, the mutations introduced into the open reading frame of the influenza virus gene segment or a fragment are silent mutations.

In one embodiment, a nucleic acid sequence provided herein comprises the complement of a chimeric influenza virus gene segment, wherein the chimeric influenza virus gene segment comprises: (i) the 3' non-coding region of a first type of influenza virus gene segment; (ii) a 3' proximal coding region of the first type of influenza virus gene segment, wherein any start codon in the 3' proximal coding region of the first type of influenza virus gene segment is mutated; (iii) at least the 3' proximal 20 nucleotides from an open reading frame of a second type of influenza virus gene segment, wherein the at least 20 nucleotides carry one or more mutations; (iv) a 5' proximal coding region of the first type of influenza virus gene segment; and (v) the 5' non-coding region of the first type of influenza virus gene segment, wherein the nucleic acid is engineered such that an open reading frame may be inserted following in frame with the at least 20 nucleotides of the open reading frame of the second type of influenza virus gene segment. In another embodiment, a nucleic acid sequence provided herein comprises the complement of a chimeric influenza virus gene segment, wherein the chimeric influenza virus gene segment comprises: (i) the 3' non-coding region of a first type of influenza virus gene segment; (ii) a 3' proximal coding region of the first type of influenza virus gene segment, wherein any start codon in the 3' proximal coding region of the first type of influenza virus gene segment is mutated; (iii) at least the 5' proximal 30 nucleotides of an open reading frame of a second type of influenza virus gene segment, wherein the at least 30 nucleotides carry one or more mutations; (iv) a 5' proximal coding region of the first type of influenza virus gene segment; and (v) the 5' non-coding region of the first type of influenza virus gene segment, wherein the nucleic acid is engineered such that an open reading frame may be inserted preceding in frame with the at least 30 nucleotides of the open reading frame of the second type of influenza virus gene segment. In another embodiment, a nucleic acid sequence provided herein comprises the complement of a chimeric influenza virus gene segment, wherein the chimeric influenza virus gene segment comprises: (i) the 3' non-coding region of a first type of influenza virus gene segment; (ii) a 3' proximal coding region of the first type of influenza virus gene segment, wherein any start codon in the 3' proximal coding region of the first type of influenza virus gene segment is mutated; (iii) at least the 3' proximal 20 nucleotides of an open reading frame of a second type of influenza virus gene segment, wherein the at least 20 nucleotides carry one or more mutations; (iv) at least the 5' proximal 30 nucleotides of the open reading frame of the second type of influenza virus gene segment, wherein the at least 30 nucleotides carry one or more mutations; (v) a 5' proximal coding region of the first type of influenza virus gene segment; and (vi) the 5' non-coding region of the first type of influenza virus gene segment, wherein the nucleic acid is engineered such that an open reading frame may be inserted in frame between the at least 20 nucleotides from the open reading frame of the second type of influenza virus gene segment and the at least 30 nucleotides of the open reading frame of the second type of influenza virus gene segment. In certain embodiments, the 3' proximal coding region sequence is derived from an influenza virus NS or M gene segment. In a specific embodiment, the 3' proximal coding region sequence is derived from an influenza virus NS gene segment and the 3' proximal coding region has been mutated so as to eliminate the mRNA 5' splice site. In another specific embodiment, the 3' proximal coding region sequence is derived from an influenza virus M gene segment and the 3' proximal coding region has been mutated so as to eliminate the distal 5' splice site.

In a specific embodiment, a nucleic acid sequence provided herein comprises the complement of a chimeric influenza virus gene segment, wherein the chimeric influenza virus gene segment comprises: (i) the 3' non-coding region of a first type of influenza virus gene segment; (ii) a 3' proximal coding region of the first type of influenza virus gene segment, wherein any start codon in the 3' proximal coding region of the first type of influenza virus gene segment is mutated; (iii) an open reading frame of a second type of influenza virus gene segment, wherein the 3' proximal nucleotides and the 5' proximal nucleotides of the open reading frame are mutated; (iv) a 5' proximal coding region of the first type of influenza virus gene segment; and (v) the 5' non-coding region of the first type of influenza virus gene segment. In certain embodiments, the 3' proximal coding region sequence is derived from an influenza virus NS or M gene segment. In a specific embodiment, the 3' proximal coding region sequence is derived from an influenza virus NS gene segment and the 3' proximal coding region has been mutated so as to eliminate the mRNA 5' splice site. In another specific embodiment, the 3' proximal coding region sequence is derived from an influenza virus M gene segment and the 3' proximal coding region has been mutated so as to eliminate the distal 5' splice site.

In certain aspects, provided herein are nucleic acid sequences comprising a nucleotide sequence encoding a chimeric influenza virus gene segment or the complement thereof which may be useful in the production of recombinant influenza viruses. In specific embodiments, a nucleic acid sequence provided herein comprises a nucleotide sequence encoding a chimeric influenza virus gene segment or the complement thereof, wherein the chimeric influenza virus gene segment comprises: (a) packaging signals found in the 3' and the 5' non-coding regions of a first type of influenza virus gene segment, (b) packaging signals found in the 3' proximal coding region sequence of the first type of influenza virus gene segment, the 5' proximal coding region sequence of the first type of influenza virus gene segment, or both the 3' and the 5' proximal coding region sequences of the first type of influenza virus gene segment, and (c) an open reading frame or a fragment thereof from a second, different type of influenza virus gene segment, wherein the open reading frame contains one, two, three or more mutations in the influenza virus packaging signals found in the open reading frame. In certain embodiments, the 3' and/or the 5' proximal coding regions sequences flank the open reading frame and are translated in frame with the open reading frame. In other embodiments, the 3' and/or the 5' proximal coding region sequences flank the open reading frame and are not translated. In some embodiments, the 3' proximal coding region sequence has been mutated so as to eliminate any start codons and preclude the translation of the 3' proximal coding region sequence. In certain embodiments, the 3' proximal coding region sequence is derived from an influenza virus NS or M gene segment. In a specific embodiment, the 3' proximal coding region sequence is derived from an influenza virus NS gene segment and the 3' proximal coding region has been mutated so as to eliminate the mRNA 5' splice site. In another specific embodiment, the 3' proximal coding region sequence is derived from an influenza virus M gene segment and the 3' proximal coding region has been mutated so as to eliminate the distal 5' splice site. In some embodiments, the 5' proximal coding region sequence has one or more mutations so as to ensure that the 5' proximal coding region sequence is not translated. In a specific embodiment, the mutations introduced into the open reading frame of the influenza virus gene segment or a fragment are silent mutations.

In one embodiment, a nucleic acid sequence provided herein comprises a nucleotide sequence encoding a chimeric influenza virus gene segment or the complement thereof, wherein the chimeric influenza virus gene segment comprises: (i) the 3' non-coding region of a first type of influenza virus gene segment; (ii) a 3' proximal coding region of the first type of influenza virus gene segment, wherein any start codon in the 3' proximal coding region of the first type of influenza virus gene segment is mutated; (iii) at least the 3' proximal 20 nucleotides from an open reading frame of a second type of influenza virus gene segment, wherein the at least 20 nucleotides carry one or more mutations; (iv) a 5' proximal coding region of the first type of influenza virus gene segment; and (v) the 5' non-coding region of the first type of influenza virus gene segment, wherein the nucleic acid is engineered such that an open reading frame may be inserted following in frame with the at least 20 nucleotides of the open reading frame of the second type of influenza virus gene segment. In another embodiment, a nucleic acid sequence provided herein comprises a nucleotide sequence encoding a chimeric influenza virus gene segment or the complement thereof, wherein the chimeric influenza virus gene segment comprises: (i) the 3' non-coding region of a first type of influenza virus gene segment; (ii) a 3' proximal coding region of the first type of influenza virus gene segment, wherein any start codon in the 3' proximal coding region of the first type of influenza virus gene segment is mutated; (iii) at least the 5' proximal 30 nucleotides of an open reading frame of a second type of influenza virus gene segment, wherein the at least 30 nucleotides carry one or more mutations; (iv) a 5' proximal coding region of the first type of influenza virus gene segment; and (v) the 5' non-coding region of the first type of influenza virus gene segment, wherein the nucleic acid is engineered such that an open reading frame may be inserted preceding in frame with the at least 30 nucleotides of the open reading frame of the second type of influenza virus gene segment. In another embodiment, a nucleic acid sequence provided herein comprises a nucleotide sequence encoding a chimeric influenza virus gene segment or the complement thereof, wherein the chimeric influenza virus gene segment comprises: (i) the 3' non-coding region of a first type of influenza virus gene segment; (ii) a 3' proximal coding region of the first type of influenza virus gene segment, wherein any start codon in the 3' proximal coding region of the first type of influenza virus gene segment is mutated; (iii) at least the 3' proximal 20 nucleotides of an open reading frame of a second type of influenza virus gene segment, wherein the at least 20 nucleotides carry one or more mutations; (iv) at least the 5' proximal 30 nucleotides of the open reading frame of the second type of influenza virus gene segment, wherein the at least 30 nucleotides carry one or more mutations; (v) a 5' proximal coding region of the first type of influenza virus gene segment; and (vi) the 5' non-coding region of the first type of influenza virus gene segment, wherein the nucleic acid is engineered such that an open reading frame may be inserted in frame between the at least 20 nucleotides from the open reading frame of the second type of influenza virus gene segment and the at least 30 nucleotides of the open reading frame of the second type of influenza virus gene segment. In certain embodiments, the 3' proximal coding region sequence is derived from an influenza virus NS or M gene segment. In a specific embodiment, the 3' proximal coding region sequence is derived from an influenza virus NS gene segment and the 3' proximal coding region has been mutated so as to eliminate the mRNA 5' splice site. In another specific embodiment, the 3' proximal coding region sequence is derived from an influenza virus M gene segment and the 3' proximal coding region has been mutated so as to eliminate the distal 5' splice site.

In a specific embodiment, a nucleic acid sequence provided herein comprises a nucleotide sequence encoding a chimeric influenza virus gene segment or the complement thereof, wherein the chimeric influenza virus gene segment comprises: (i) the 3' non-coding region of a first type of influenza virus gene segment; (ii) a 3' proximal coding region of the first type of influenza virus gene segment, wherein any start codon in the 3' proximal coding region of the first type of influenza virus gene segment is mutated; (iii) an open reading frame of a second type of influenza virus gene segment, wherein the 3' proximal nucleotides and the 5' proximal nucleotides of the open reading frame are mutated; (iv) a 5' proximal coding region of the first type of influenza virus gene segment; and (v) the 5' non-coding region of the first type of influenza virus gene segment. In certain embodiments, the 3' proximal coding region sequence is derived from an influenza virus NS or M gene segment. In a specific embodiment, the 3' proximal coding region sequence is derived from an influenza virus NS gene segment and the 3' proximal coding region has been mutated so as to eliminate the mRNA 5' splice site. In another specific embodiment, the 3' proximal coding region sequence is derived from an influenza virus M gene segment and the 3' proximal coding region has been mutated so as to eliminate the distal 5' splice site.

In another aspect, provided herein are recombinant influenza viruses comprising one, two, three, four, five, six, seven or eight chimeric influenza virus gene segments described herein. In a specific embodiment, provided herein are recombinant influenza viruses comprising two or more chimeric influenza virus gene segments described herein, wherein the two or more chimeric influenza virus gene segments cosegregate. Without being bound by theory, the chimeric influenza virus gene segments have a reduced ability to reassort independently of each other with other influenza virus gene segments, and thus, the reassortment of the recombinant influenza virus with other influenza viruses (e.g., wild-type influenza viruses) is reduced or inhibited. Recombinant influenza viruses that are unable to reassort will produce fewer viral plaques that contain viruses with one or more chimeric influenza virus gene segments that has reassorted independently of one or more other chimeric influenza virus gene segments. In certain embodiments, a recombinant influenza virus described herein comprises an attenuating mutation.

In one embodiment, a recombinant influenza virus comprising a first chimeric influenza virus gene segment and a second chimeric influenza virus gene segment, wherein (a) the first chimeric influenza virus gene segment comprises: (i) the 3' non-coding region of a first type of influenza virus gene segment; (ii) a 3' proximal coding region of the first type of influenza virus gene segment, wherein any start codon in the 3' proximal coding region of the first type of influenza virus gene segment is mutated; (iii) the open reading frame of a second type of influenza virus gene segment, wherein 3' and the 5' proximal nucleotides in the open reading frame are mutated; (iv) a 5' proximal coding region of the first type of influenza virus gene segment; and (v) the 5' non-coding region of the first type of influenza virus gene segment; and wherein (b) the second chimeric influenza virus gene segment comprises: (i) the 3' non-coding region of a second type of influenza virus gene segment; (ii) a 3' proximal coding region of the second type of influenza virus gene segment, wherein any start codon in the 3' proximal coding region of the second type of influenza virus gene segment is mutated; (iii) the open reading frame of a first type of influenza virus gene segment, wherein 3' and the 5' proximal nucleotides in the open reading frame are mutated; (iv) a 5' proximal coding region of the second type of influenza virus gene segment; and (v) the 5' non-coding region of the second type of influenza virus influenza gene segment.

In another embodiment, a recombinant influenza virus comprises a first chimeric influenza virus gene segment; a second chimeric influenza virus gene segment; and a third chimeric influenza virus gene segment, wherein (a) the first chimeric influenza virus gene segment comprises: (i) the 3' non-coding region of a third type of influenza virus gene segment; (ii) a 3' proximal coding region of the third type of influenza virus gene segment, wherein any start codon in the 3' proximal coding region of the third influenza virus gene segment is mutated; (iii) the open reading frame of a first type of influenza virus gene segment, wherein 3' and the 5' proximal nucleotides in the open reading frame are mutated; (iv) a 5' proximal coding region of the third type of influenza virus gene segment; and (v) the 5' non-coding region of the third type of influenza virus gene segment; and wherein (b) the second chimeric influenza virus gene segment comprises: (i) the 3' non-coding region of the first type of influenza virus gene segment; (ii) a 3' proximal coding region of the first type of influenza virus gene segment, wherein any start codon in the 3' proximal coding region of the first type of influenza virus gene segment is mutated; (iii) the open reading frame of a second type of influenza virus gene segment, wherein 3' and the 5' proximal nucleotides in the open reading frame are mutated; (iv) a 5' proximal coding region of the first type of influenza virus gene segment; and (v) the 5' non-coding region of the first type of influenza virus gene segment; and wherein (c) the third chimeric influenza virus gene segment comprises: (i) the 3' non-coding region of the second type of influenza virus gene segment; (ii) a 3' proximal coding region of the second type of influenza virus gene segment, wherein any start codon in the 3' proximal coding region of the second type of influenza virus gene segment is mutated; (iii) the open reading frame of the third type of influenza virus gene segment, wherein 3' and the 5' proximal nucleotides in the open reading frame are mutated; (iv) a 5' proximal coding region of the second type of influenza virus gene segment; and (v) the 5' non-coding region of the second type of influenza virus gene segment. In certain embodiments, the 3' proximal coding region sequence is derived from an influenza virus NS or M gene segment. In a specific embodiment, the 3' proximal coding region sequence is derived from an influenza virus NS gene segment and the 3' proximal coding region has been mutated so as to eliminate the mRNA 5' splice site. In another specific embodiment, the 3' proximal coding region sequence is derived from an influenza virus M gene segment and the 3' proximal coding region has been mutated so as to eliminate the distal 5' splice site.

In another aspect, provided herein are recombinant influenza viruses containing nine gene segments, wherein at least two of the gene segments are chimeric influenza virus gene segments such as described herein. In certain embodiments, a recombinant influenza virus comprises nine gene segments, wherein (a) at least one gene segment comprises: (i) the packaging signals found in the 3' non-coding region of a first type of influenza virus gene segment or a derivative thereof; (ii) the packaging signals found in the 3' proximal coding region of the first type of influenza virus gene segment or a derivative thereof, wherein any start codon in the 3' proximal coding region of the first type of influenza virus gene segment is mutated; (iii) an open reading frame of a second type of influenza virus gene segment or a fragment or a derivative thereof, wherein the 3' and 5' proximal nucleotides in the open reading frame are mutated; (iv) the packaging signals found in the 5' proximal coding region of the first type of influenza virus gene segment or a derivative thereof; and (v) the packaging signals found in the 5' non-coding region of the first type of influenza virus gene segment or a derivative thereof; and (b) at least one gene segment comprises: (i) the packaging signals found in the 3' non-coding region of the second type of influenza virus gene segment or a derivative thereof; (ii) the packaging signals found in the 3' proximal coding region of the second type of influenza virus gene segment or a derivative thereof, wherein any start codon in the 3' proximal coding region of the first type of influenza virus gene segment is mutated; (iii) an open reading frame heterologous to 1, 2, 3, 4, 5, 6, 7 or 8 of the influenza virus gene segment; (iv) the packaging signals found in the 5' proximal coding region of the second type of influenza virus gene segment or a derivative thereof; and (v) the packaging signals found in the 5' non-coding region of the second type of influenza virus gene segment or a derivative thereof. In certain embodiments, the 3' proximal coding region sequence is derived from an influenza virus NS or M gene segment. In a specific embodiment, the 3' proximal coding region sequence is derived from an influenza virus NS gene segment and the 3' proximal coding region has been mutated so as to eliminate the mRNA 5' splice site. In another specific embodiment, the 3' proximal coding region sequence is derived from an influenza virus M gene segment and the 3' proximal coding region has been mutated so as to eliminate the distal 5' splice site. In certain embodiments, the recombinant influenza virus is attenuated. In some embodiments, the recombinant influenza virus encodes and/or expresses influenza virus antigens from two different types, subtypes or strains of influenza virus. In a specific embodiment, the recombinant influenza virus encodes and/or expresses HA antigens from two different types, subtypes or strains of influenza virus. For example the recombinant influenza virus encodes and/or expresses an H1 HA and an H3 HA antigen. In some embodiments, the one HA antigens is from a seasonal influenza virus and the other HA antigen is from a pandemic influenza virus. In specific embodiments, each of the two HA antigens comprise an attenuating mutation. In certain embodiments, the recombinant influenza virus encodes and/or expresses influenza virus antigens and at least one, two, three or four, or 1 to 3, 1 to 4, or 2 to 4 non-influenza virus antigens (e.g., antigens from bacterial pathogens, or viral pathogens other an influenza virus). In accordance with these embodiments, in some embodiments, the heterologous open reading frame of the one gene segment can encode an influenza virus antigen from a different type, subtype or strain of influenza virus than the influenza virus antigens encoded by the other gene segments. In other embodiments, the heterologous open reading frame of the one gene segment can encode a non-influenza virus antigen (e.g., a bacterial antigen, tumor antigen, or viral antigen other than an influenza virus antigen).

In specific embodiments, the nine-segmented recombinant influenza viruses described herein more stably incorporate the ninth segment than those previously described. In certain embodiments, the nine-segmented recombinant influenza viruses described herein maintain the ninth segment over at least 4, 5, 6, 7, 8 or more passages, or 4 to 6, 4 to 8, or 5 to 8 passages in embryonated eggs or tissue culture as assessed by techniques known in the art (including, e.g., the limiting dilution technique described in the examples infra).

In another aspect, provided herein are substrates (e.g., host cells and eggs) comprising a nucleic acid sequence described herein. In one embodiment, provided herein are substrates comprising a chimeric influenza virus gene segment or a complement thereof. In another embodiment, provided herein are substrates comprising a nucleic acid sequence comprising a nucleotide sequence encoding a chimeric influenza virus gene segment or a complement thereof.

In another aspect, provided herein are substrates comprising a recombinant influenza virus comprising one, two or more chimeric influenza virus gene segments described herein. In another aspect, provided herein are compositions comprising a recombinant influenza virus comprising one, two or more chimeric influenza virus gene segments described herein.

In anther aspect, provided herein are kits comprising a nucleic acid sequence or recombinant influenza virus described herein. In one embodiment, a kit provided herein comprises, in one or more containers, a nucleic acid sequence described herein. In another embodiment, a kit provided herein, comprises, in one or more containers, a recombinant influenza virus described herein.

In yet another aspect, provided herein are methods of using a recombinant influenza virus comprising one, two or more chimeric influenza virus gene segments. In one embodiment, provided herein is a method for eliciting an immune response against an influenza virus in a subject, wherein the method comprises administering a recombinant influenza virus described herein or a composition thereof to the subject. In another embodiment, provided herein is a method of preventing and/or treating an influenza virus infection in a subject, wherein the method comprises administering a recombinant influenza virus described herein or a composition thereof to the subject. In another embodiment, provided herein is a method for preventing and/or treating an influenza virus disease in a subject, wherein the method comprises administering a recombinant influenza virus described herein or a composition thereof to the subject. In another embodiment, provided herein are methods for generating or identifying antibodies that bind to an influenza virus utilizing a recombinant influenza virus described herein or a composition thereof.

3.1 Terminology

As used herein, the phrase "ability to reassort" in the context of an influenza virus gene segment or a chimeric influenza virus gene segment is used to describe the ability of the influenza virus gene segment or the chimeric influenza virus gene segment to segregate independently from other influenza virus gene segments or chimeric influenza virus gene segments through at least one life cycle of the influenza virus and to encode a replication competent virus in combination with the remainder of the influenza virus gene segments in an influenza virus genome. In the context of an influenza virus, the phrase "ability to reassort" is used herein to describe the ability of the influenza virus to combine any one of its gene segments with the gene segments of a different influenza virus such that the progeny influenza virus with the combined gene segments is replication competent. An influenza virus has a reduced ability to reassort if certain combinations of the mixed gene segments do not yield replication competent virus or a virus with reduced replication competence. In certain embodiments, an influenza virus with reduced replication competence is a virus that produces at least 1 log, 1.5 logs, 2 logs, 25 logs, 3 logs, 3.5 logs, 4 logs, 4.5 logs, 5 logs, 5.5 logs, 6 logs, 6.5 logs, 7 logs, 7.5 logs, 8 logs, 8.5 logs, 9 logs or 10 logs lower titers of replicating progeny than the replicating progeny produced by a wild-type influenza virus of the same type.

As used herein, the term "about" or "approximately" when used in conjunction with a number refers to any number within 1, 5 or 10% of the referenced number.

As used herein, the term "derivative" in the context of an influenza virus gene segment refers to a nucleotide sequence that is at least 50%, 55%, 60%, 65%, 70%, 75%, 80%, 85%, 90%, 95% or 98% identical to a particular nucleotide sequence of an influenza virus, or a nucleotide sequence that hybridizes under stringent conditions to a particular nucleotide sequence of an influenza virus.

As used herein, the term "effective amount" in the context of administering a therapy to a subject refers to the amount of a therapy which has a prophylactic and/or therapeutic effect(s). In certain embodiments, an "effective amount" in the context of administration of a therapy to a subject refers to the amount of a therapy which is sufficient to achieve one, two, three, four, or more of the following effects: (i) reduction or amelioration in the severity of an influenza virus infection, an influenza virus disease or symptom associated therewith; (ii) reduction in the duration of an influenza virus infection, an influenza virus disease or symptom associated therewith; (iii) prevention of the progression of an influenza virus infection, an influenza virus disease or symptom associated therewith; (iv) regression of an influenza virus infection, an influenza virus disease or symptom associated therewith; (v) prevention of the development or onset of an influenza virus infection, an influenza virus disease or symptom associated therewith; (vi) prevention of the recurrence of an influenza virus infection, an influenza virus disease or symptom associated therewith; (vii) reduction or prevention of the spread of an influenza virus from one cell to another cell, one tissue to another tissue, or one organ to another organ; (viii) prevention or reduction of the spread/transmission of an influenza virus from one subject to another subject; (ix) reduction in organ failure associated with an influenza virus infection or influenza virus disease; (x) reduction in the hospitalization of a subject; (xi) reduction in the hospitalization length; (xii) an increase in the survival of a subject with an influenza virus infection or a disease associated therewith; (xiii) elimination of an influenza virus infection or a disease associated therewith; (xiv) inhibition or reduction in influenza virus replication; (xv) inhibition or reduction in the binding or fusion of influenza virus to a host cell(s); (xvi) inhibition or reduction in the entry of an influenza virus into a host cell(s); (xvii) inhibition or reduction of the replication of the influenza virus genome; (xviii) inhibition or reduction in the synthesis of influenza virus proteins; (xix) inhibition or reduction in the assembly of influenza virus particles; (xx) inhibition or reduction in the release of influenza virus particles from a host cell(s); (xxi) reduction in influenza virus titer; (xxii) reduction in the number of symptoms associated with an influenza virus infection or an influenza virus disease; (xxiii) enhancement, improvement, supplementation, complementation, or augmentation of the prophylactic or therapeutic effect(s) of another therapy; (xxiv) prevention of the onset or progression of a secondary infection associated with an influenza virus infection; and/or (xxv) prevention of the onset or diminution of disease severity of bacterial pneumonias occurring secondary to influenza virus infections. Exemplary doses of an effective amount are provided in Section 5.7.2, infra.

In certain embodiments, the effective amount of a therapy does not result in complete protection from an influenza virus disease, but results in a lower titer or reduced number of influenza viruses compared to an untreated subject. In certain embodiments, the effective amount of a therapy results in a 0.5 fold, 1 fold, 2 fold, 4 fold, 6 fold, 8 fold, 10 fold, 15 fold, 20 fold, 25 fold, 50 fold, 75 fold, 100 fold, 125 fold, 150 fold, 175 fold, 200 fold, 300 fold, 400 fold, 500 fold, 750 fold, or 1,000 fold or greater reduction in titer of Influenza virus relative to an untreated subject. In some embodiments, the effective amount of a therapy results in a reduction in titer of influenza virus relative to an untreated subject of approximately 1 log or more, approximately 2 logs or more, approximately 3 logs or more, approximately 4 logs or more, approximately 5 logs or more, approximately 6 logs or more, approximately 7 logs or more, approximately 8 logs or more, approximately 9 logs or more, approximately 10 logs or more, 1 to 5 logs, 2 to 10 logs, 2 to 5 logs, or 2 to 8 logs. Benefits of a reduction in the titer, number or total burden of influenza virus include, but are not limited to, less severe symptoms of the infection, fewer symptoms of the infection, reduction in the length of the disease associated with the infection, and prevention of the onset or diminution of disease severity of bacterial pneumonias occurring secondary to influenza virus infections.

As used herein, the term "elderly human" refers to a human 65 years or older.

As used herein, the term "fragment" in the context of a nucleic acid sequence refers to a nucleotide sequence comprising at least 2 or at least 3 consecutive nucleotides from a parent sequence. In a specific embodiment, the term refers to a nucleotide sequence of 2 to 30, 5 to 30, 10 to 60, 25 to 100, 150 to 300 or more consecutive nucleotides from a parent sequence. In another embodiment, the term refers to a nucleotide sequence of at least 5, 10, 15, 20, 25, 30, 35, 40, 45, 50, 55, 60, 65, 70, 75, 80, 85, 90, 95, 100, 110, 125, 150, 175, 200, 250, 275, 300, 325, 350, 375, 400, 425, 450 or 475 consecutive nucleotides of a parent sequence.

As used herein, the term "fragment" in the context of an amino acid sequence refers to an amino acid sequence comprising at least 2 consecutive amino acid residues from a parent sequence. In a specific embodiment, the term refers to an amino acid sequence of 2 to 30, 5 to 30, 10 to 60, 25 to 100, 150 to 300 or more consecutive amino acid residues from a parent sequence. In another embodiment, the term refers to an amino acid sequence of at least 5, 10, 15, 20, 25, 30, 35, 40, 45, 50, 55, 60, 65, 70, 75, 80, 85, 90, 95, 100, 110, 125, 150, 175, 200, 250, 275, 300, 325, 350, 375, 400, 425, 450 or 475 consecutive amino acid residues of a parent sequence.

As used herein, the term "heterologous" refers to a unit that is not found naturally be associated with another unit. For example, a first nucleotide sequence is said be a heterologous to a second nucleotide sequence if the two nucleotide sequences are not found in nature to be associated with each other.

As used herein, the term "host cell" refers to any type of cell, e.g., a primary cell or a cell from a cell line. In specific embodiments, the term "host cell" refers a cell transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

As used herein, the term "human adult" refers to a human that is 18 years or older.

As used herein, the term "human child" refers to a human that is 1 year to 18 years old.

As used herein, the term "human infant" refers to a newborn to 1 year old human.

As used herein, the term "hybridizes under stringent conditions" describes conditions for hybridization and washing under which nucleotide sequences at least 50% (preferably, 55%, 60%, 65%, 70%, 75%, 80%, 85%, 90%, 95% or 98%) identical to each other typically remain hybridized to each other. Such stringent conditions are known to those skilled in the art and can be found in Current Protocols in Molecular Biology, John Wiley & Sons, N.Y. (1989), 6.3.1-6.3.6.

Generally, stringent conditions are selected to be about 5 to 10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (for example, 10 to 50 nucleotides) and at least 60° C. for long probes (for example, greater than 50 nucleotides). Stringent conditions may also be achieved with the addition of destabilizing agents, for example, formamide. For selective or specific hybridization, a positive signal is at least two times background, preferably 10 times background hybridization.

In one, non-limiting example stringent hybridization conditions are hybridization at 6× sodium chloride/sodium citrate (SSC) at about 45° C., followed by one or more washes in 0.1×SSC, 0.2% SDS at about 68° C. In a specific, non-limiting example stringent hybridization conditions are hybridization in 6×SSC at about 45° C., followed by one or more washes in 0.2×SSC, 0.1% SDS at 50-65° C. (i.e., one or more washes at 50° C., 55° C., 60° C. or 65° C.). It is understood that the nucleic acids described herein do not include nucleic acid molecules that hybridize under these conditions solely to a nucleotide sequence consisting of only A or T nucleotides.

As used herein, the term "in combination" in the context of the administration of a therapy(ies) to a subject, refers to the use of more than one therapy. The use of the term "in combination" does not restrict the order in which therapies are administered to a subject. A first therapy can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

As used herein, the term "infection" means the invasion by, multiplication and/or presence of a virus in a cell or a subject. In one embodiment, an infection is an "active" infection, i.e., one in which the virus is replicating in a cell or a subject. Such an infection is characterized by the spread of the virus to other cells, tissues, and/or organs, from the cells, tissues, and/or organs initially infected by the virus. An infection may also be a latent infection, i.e., one in which the virus is not replicating. In certain embodiments, an infection refers to the pathological state resulting from the presence of the virus in a cell or a subject, or by the invasion of a cell or subject by the virus.

As used herein, the term "influenza virus disease" and phrases referring to a disease associated with an influenza virus infection refer to the pathological state resulting from the presence of an influenza virus (e.g., influenza A or B virus)

in a cell or subject or the invasion of a cell or subject by an influenza virus. In specific embodiments, the term refers to a respiratory illness caused by an influenza virus.

As used herein, the phrases "IFN-deficient systems" or "IFN-deficient substrates" refer to systems, e.g., cells, cell lines and animals, such as mice, chickens, turkeys, rabbits, rats, horses etc., which (a) do not produce one, two or more types of IFN, or do not produce any type of IFN, or produce low levels of one, two or more types of IFN, or produce low levels of any IFN (i.e., a reduction in any IFN expression of 5-10%, 10-20%, 20-30%, 30-40%, 40-50%, 50-60%, 60-70%, 70-80%, 80-90% or more when compared to IFN-competent systems under the same conditions), (b) do not respond or respond less efficiently to one, two or more types of IFN, or do not respond to any type of IFN, and/or (c) are deficient in the activity of antiviral genes induced by one, two or more types of IFN, or induced by any type of IFN.

An "isolated" protein (e.g., an antibody) is substantially free of cellular material or heterologous proteins (also referred to herein as contaminating proteins) from the cell or tissue source from which the protein is derived, or substantially free of chemical precursors or other chemicals when chemically synthesized. The language "substantially free of cellular material" includes preparations of a protein (e.g., an antibody) in which the protein is separated from cellular components of the cells from which it is isolated or recombinantly produced. Thus, a protein (e.g., an antibody) that is substantially free of cellular material includes preparations of protein having less than about 30%, 20%, 10%, or 5% (by dry weight) of heterologous protein. When the protein is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the protein of interest. In another specific embodiment, antibodies described herein are isolated.

As used herein, the term "isolated" in the context of nucleic acids refers to a nucleic acid molecule which is separated from other nucleic acid molecules which are present in the natural source of the nucleic acid molecule or substantially free of chemical precursors or other chemicals when chemically synthesized. Moreover, an "isolated" nucleic acid molecule, such as a cDNA molecule, can be substantially free of other cellular material, or culture medium when produced by recombinant techniques, or substantially free of chemical precursors or other chemicals when chemically synthesized; however, "isolated" excludes members of a library of clones such as a cDNA library. In a specific embodiment, a nucleic acid described herein is isolated.

As used herein, the terms "manage," "managing," and "management" refer to the beneficial effects that a subject derives from a therapy (e.g., a prophylactic or therapeutic agent), which does not result in a cure of the infection or disease associated therewith. In certain embodiments, a subject is administered one or more therapies (e.g., prophylactic or therapeutic agents) to "manage" an influenza virus disease, or one or more symptoms thereof, so as to prevent the progression or worsening of the disease.

As used herein, the phrase "multiplicity of infection" or "MOI" is the average number of virus per infected cell. The MOI is determined by dividing the number of virus added (ml added×plaque forming units (pfu)) by the number of cells added (ml added×cells/ml).

As used herein, the term "nucleic acid" refers to deoxyribonucleotides, deoxyribonucleic acids, ribonucleotides, and ribonucleic acids, and polymeric forms thereof, and includes either single- or double-stranded forms. Nucleic acids include naturally occurring nucleic acids, such as deoxyribonucleic acid ("DNA") and ribonucleic acid ("RNA") as well as nucleic acid analogs. Nucleic acid analogs include those which include non-naturally occurring bases, nucleotides that engage in linkages with other nucleotides other than the naturally occurring phosphodiester bond or which include bases attached through linkages other than phosphodiester bonds. Thus, nucleic acid analogs include, for example and without limitation, phosphorothioates, phosphorodithioates, phosphorotriesters, phosphoramidates, boranophosphates, methylphosphonates, chiral-methyl phosphonates, 2-O-methyl ribonucleotides, peptide-nucleic acids (PNAs), locked-nucleic acids (LNAs), and the like.

"Percent identity:" To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/ total number of positions ×100%). In one embodiment, the two sequences are the same length.

The determination of percent identity between two sequences can also be accomplished using a mathematical algorithm. One non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acids described herein. BLAST protein searches can be performed with the XBLAST program parameters set, e.g., to score-50, wordlength=3 to obtain amino acid sequences homologous to a protein described herein. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website). Another non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM 120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

As used herein, the terms "prevent," "preventing" and "prevention" in the context of the administration of a therapy(ies) to a subject refer to a prophylactic effect that results from the administration of a therapy or a combination of therapies. In a specific embodiment, the terms "prevent," "preventing" and "prevention" in the context of the administration of a therapy (ies) to a subject to prevent an influenza virus disease refer to one or more of the following effects resulting from the administration of a therapy or a combination of therapies: (i) the inhibition or reduction in the development or onset of an influenza virus disease or a symptom thereof (e.g., fever, myalgia, edema, inflammatory infiltrates); (ii) the inhibition or reduction in the recurrence of an influenza virus disease or a symptom associated therewith; and (iii) the reduction or inhibition in influenza virus infection and/or replication.

In another specific embodiment, the terms "prevent", "preventing" and "prevention" in the context of the administration of a therapy(ies) to a subject to prevent an influenza virus infection refer to one or more of the following effects resulting from the administration of a therapy or a combination of therapies: (i) the reduction or inhibition of the spread of influenza virus from one cell to another cell; (ii) the reduction or inhibition of the spread of influenza virus from one organ or tissue to another organ or tissue; and/or (iii) the reduction or inhibition of the spread of influenza virus from one region of an organ or tissue to another region of the organ or tissue (e.g., the reduction in the spread of influenza virus from the upper to the lower respiratory tract).

As used herein, the term "3' proximal" in the context of an open reading frame of an influenza virus gene segment refers to the nucleotides beginning from the start codon of the open reading frame towards the 5' end of the open reading frame. In certain embodiments, the term "3' proximal nucleotides" refers to 1, 2, 3, 4, 5, 6, 7, 8, 9, 10, 11, 12, 13, 14, 15, 16, 17, 18, 19, 20 or more nucleotides within the first 20 to 250 nucleotides of an open reading frame beginning from the start codon towards the 5' end of the open reading frame.

As used herein, the term "3' proximal coding region" in context of an influenza virus gene segment refers to the first 5 to 450 nucleotides from the 3' end of the coding region of an influenza virus gene segment, or any integer between 5 and 450. In a specific embodiment, the 3' proximal coding region sequence refers to the first 5 to 25 nucleotides from the 3' end of the coding region of an influenza virus gene segment, or any integer between 5 and 25. In another embodiment, the 3' proximal coding region sequence refers to the first 25 to 50 nucleotides from the 3' end of the coding region of an influenza virus gene segment, or any integer between 25 and 50. In another embodiment, the 3' proximal coding region sequence refers to the first 50 to 100 nucleotides from the 3' end of the coding region of an influenza virus gene segment, or any integer between 50 and 100. In another embodiment, the 3' proximal coding region sequence refers to the first 50 to 150 nucleotides from the 3' end of the coding region of an influenza virus gene segment, or any integer between 50 and 150. In another embodiment, the 3' proximal coding region sequence refers to the first 100 to 250 nucleotides from the 3' end of the coding region of an influenza virus gene segment, or any integer between 100 and 250.

As used herein, the term "3' termini" in the context of an open reading of an influenza virus gene segment refers to the first 20 to 250 nucleotides beginning from the start codon of the open reading frame towards the 5' end of the open reading frame.

As used herein, the term "5' proximal" in the context of an open reading frame of an influenza virus gene segment refers to the nucleotides beginning from the stop codon of the open reading frame towards the 3' end of the open reading frame. In certain embodiments, the term "5' proximal nucleotides" refers to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more nucleotides within the first 30 to 250 nucleotides of an open reading frame beginning from the stop codon towards the 3' end of the open reading frame.

As used herein, the term "5' proximal coding region" in context of an influenza virus gene segment refers to the first 5 to 450 nucleotides from the 5' end of the coding region of an influenza virus gene segment, or any integer between 5 and 450. In a specific embodiment, the 5' proximal coding region sequence refers to the first 5 to 25 nucleotides from the 5' end of the coding region of an influenza virus gene segment, or any integer between 5 and 25. In another embodiment, the 5' proximal coding region sequence refers to the first 25 to 50 nucleotides from the 5' end of the coding region of an influenza virus gene segment, or any integer between 25 and 50. In another embodiment, the 5' proximal coding region sequence refers to the first 50 to 100 nucleotides from the 5' end of the coding region of an influenza virus gene segment, or any integer between 50 and 100. In another embodiment, the 5' proximal coding region sequence refers to the first 50 to 150 nucleotides from the 5' end of the coding region of an influenza virus gene segment, or any integer between 50 and 150. In another embodiment, the 5' proximal coding region sequence refers to the first 100 to 250 nucleotides from the 5' end of the coding region of an influenza virus gene segment, or any integer between 100 and 250.

As used herein, the term "5' termini" in the context of an open reading frame of an influenza virus gene segment refers to the first 30 to 250 nucleotides beginning from the stop codon of the open reading frame towards the 3' end of the open reading frame.

As used herein, the terms "subject" and "patient" are used interchangeably to refer to an animal (e.g., birds, reptiles, and mammals). In a specific embodiment, a subject is a bird. In another embodiment, a subject is a mammal including a non-primate (e.g., a camel, donkey, zebra, cow, pig, horse, goat, sheep, cat, dog, rat, and mouse) and a primate (e.g., a monkey, chimpanzee, and a human). In another embodiment, a subject is a human. In another embodiment, a subject is a human infant. In another embodiment, a subject is a human child. In another embodiment, the subject is a human adult. In another embodiment, a subject is an elderly human. In another embodiment, a subject is a non-human animal (e.g., a non-human mammal or a bird).

As used herein, the terms "therapies" and "therapy" can refer to any protocol(s), method(s), compound(s), composition(s), formulation(s), and/or agent(s) that can be used in the prevention or treatment of a viral infection or a disease or symptom associated therewith. In certain embodiments, the terms "therapies" and "therapy" refer to biological therapy, supportive therapy, and/or other therapies useful in treatment or prevention of a viral infection or a disease or symptom associated therewith known to one of skill in the art. In some embodiments, the term "therapy" refers to an immunogenic composition (e.g., an influenza virus vaccine).

As used herein, the terms "treat," "treatment," and "treating" in the context of the administration of a therapy(ies) to a subject refer a beneficial or therapeutic effect resulting from the administration of a therapy or a combination of therapies. In specific embodiments, such terms refer to one, two, three, four, five or more of the following effects resulting from the administration of a therapy or a combination of therapies: (i) reduction or amelioration in the severity of an influenza virus infection, an influenza virus disease or symptom associated therewith; (ii) reduction in the duration of an influenza virus infection, an influenza virus disease or symptom associated therewith; (iii) prevention of the progression of an influenza virus infection, an influenza virus disease or symptom associated therewith; (iv) regression of an influenza virus infection, an influenza virus disease or symptom associated therewith; (v) prevention of the development or onset of an influenza virus infection, an influenza virus disease or symptom associated therewith; (vi) prevention of the recurrence of an influenza virus infection, an influenza virus disease or symptom associated therewith; (vii) reduction or prevention of the spread of an influenza virus from one cell to another cell, one tissue to another tissue, or one organ to another organ; (viii) prevention or reduction of the spread/transmission of an influenza virus from one subject to another subject; (ix) reduction in organ failure associated with an influenza virus infection or influenza virus disease; (x) reduction in the hospitalization of a subject; (xi) reduction in the hospitalization length; (xii) an increase in the survival of a subject with an influenza virus infection or a disease associated therewith; (xiii) elimination of an influenza virus infection or a disease associated therewith; (xiv) inhibition or reduction in influenza virus replication; (xv) inhibition or reduction in the binding or fusion of influenza virus to a host cell(s); (xvi) inhibition or reduction in the entry of an influenza virus into a host cell(s); (xvii) inhibition or reduction of replication of the influenza virus genome; (xviii) inhibition or reduction in the synthesis of influenza virus proteins; (xix) inhibition or reduction in the assembly of influenza virus particles; (xx) inhibition or reduction in the release of influenza virus particles from a host cell(s); (xxi) reduction in influenza virus titer; (xxii) the reduction in the number of symptoms associated with an influenza virus infection or an influenza virus disease; (xxiii) enhancement, improvement, supplementation, complementation, or augmentation of the prophylactic or therapeutic effect(s) of another therapy; (xxiv) prevention of the onset or progression of a secondary infection associated with an influenza virus infection; and/or (xxv) prevention of the onset or diminution of disease severity of bacterial pneumonias occurring secondary to influenza virus infections.

As used herein, the term "type of influenza virus gene segment(s)" refers to an HA, NA, NS, PB1, PB2, PA, M, or NP gene segment from an influenza virus.

As used herein, in some embodiments, the term "wildtype" in the context of a virus refers to the types of viruses that are prevalent, circulating and naturally producing typical outbreaks of disease.

4. BRIEF DESCRIPTION OF THE FIGURES

FIGS. 1A-1B. PB2 Packaging Sequences of PR8. (A) Nucleotide sequence of 3' non-coding region (NCR) (SEQ ID NO:1) and 3' proximal coding region sequence (SEQ ID NO:2) of influenza PR8 virus with an NheI restriction enzyme recognition site (SEQ ID NO:3). The 3' NCR is shaded and the 3' proximal coding region sequence is underlined. (B) Nucleotide sequence of 5' NCR (SEQ ID NO:4) and 5' proximal coding region sequence (SEQ ID NO:5) of influenza PR8 virus with an XhoI restriction enzyme recognition site (SEQ ID NO:6). The 5' NCR is shaded and the 5' proximal coding region sequence is underlined. Certain capitalized letters represent mutations introduced into the sequence to delete to ATG initiation codon. Additional capitalized letters are found within the XhoI and NheI restriction enzyme recognition sites.

FIGS. 2A-2B. PB1 Packaging Sequences of PR8. (A) Nucleotide sequence of 3' NCR (SEQ ID NO:7) and 3' proximal coding region sequence (SEQ ID NO:8) of influenza PR8 virus with an NheI restriction enzyme recognition site (SEQ ID NO:9). The 3' NCR is shaded and the 3' proximal coding region sequence is underlined. (B) Nucleotide sequence of 5' NCR (SEQ ID NO:10) and 5' proximal coding region sequence (SEQ ID NO:11) of influenza PR8 virus with an XhoI restriction enzyme recognition site (SEQ ID NO:12). The 5' NCR is shaded and the 5' proximal coding region sequence is underlined. Certain capitalized letters represent mutations introduced into the sequence to delete to ATG initiation codon. Additional capitalized letters are found within the XhoI and NheI restriction enzyme recognition sites.

FIGS. 3A-3B. PA Packaging Sequences of PR8. (A) Nucleotide sequence of 3' NCR (SEQ ID NO:13) and 3' proximal coding region sequence (SEQ ID NO:14) of influenza PR8 virus with an NheI restriction enzyme recognition site (SEQ ID NO:15). The 3' NCR is shaded and the 3' proximal coding region sequence is underlined. (B) Nucleotide sequence of 5' NCR (SEQ ID NO:16) and 5' proximal coding region sequence (SEQ ID NO:17) of influenza PR8 virus with an XhoI restriction enzyme recognition site (SEQ ID NO:18). The 5' NCR is shaded and the 5' proximal coding region sequence is underlined. Certain capitalized letters represent mutations introduced into the sequence to delete to ATG initiation codon. Additional capitalized letters are found within the XhoI and NheI restriction enzyme recognition sites.

FIGS. 4A-4B. HA Packaging Sequences of PR8. (A) Nucleotide sequence of 3' NCR (SEQ ID NO:19) and 3' proximal coding region sequence (SEQ ID NO:20) of influenza PR8 virus with an NheI restriction enzyme recognition site (SEQ ID NO:21). The 3' NCR is shaded and the 3' proximal coding region sequence is underlined. (B) Nucleotide sequence of 5' NCR (SEQ ID NO:22) and 5' proximal coding region sequence (SEQ ID NO:23) of influenza PR8 virus with an XhoI restriction enzyme recognition site (SEQ ID NO:24). The 5' NCR is shaded and the 5' proximal coding region sequence is underlined. Certain capitalized letters represent mutations introduced into the sequence to delete to ATG initiation codon. Additional capitalized letters are found within the XhoI and NheI restriction enzyme recognition sites.

FIGS. 5A-5B. NP Packaging Sequences of PR8. (A) Nucleotide sequence of 3' NCR (SEQ ID NO:25) and 3' proximal coding region sequence (SEQ ID NO:26) of influenza PR8 virus with an NheI restriction enzyme recognition site (SEQ ID NO:27). The 3' NCR is shaded and the 3' proximal coding region sequence is underlined. (B) Nucleotide sequence of 5' non-coding region NCR (SEQ ID NO:28) and 5' proximal coding region sequence (SEQ ID NO:29) of influenza PR8 virus with an XhoI restriction enzyme recognition site (SEQ ID NO:30). The 5' NCR is shaded and the 5' proximal coding region sequence is underlined. Certain capitalized letters represent mutations introduced into the sequence to delete to ATG initiation codon. Additional capitalized letters are found within the XhoI and NheI restriction enzyme recognition sites.

FIGS. 6A-6B. NA Packaging Sequences of PR8. (A) Nucleotide sequence of 3' NCR (SEQ ID NO:31) and 3' proximal coding region sequence (SEQ ID NO:32) of influenza PR8 virus with an NheI restriction enzyme recognition site (SEQ ID NO:33). The 3' NCR is shaded and the 3' proximal coding region sequence is underlined. (B) Nucleotide sequence of 5' NCR (SEQ ID NO:34) and 5' proximal coding region sequence (SEQ ID NO:35) of influenza PR8 virus with an XhoI restriction enzyme recognition site (SEQ ID NO:36). The 5' NCR is shaded and the 5' proximal coding region sequence is underlined. Certain capitalized letters represent mutations introduced into the sequence to delete to ATG initiation codon. Additional capitalized letters are found within the XhoI and NheI restriction enzyme recognition sites.

FIGS. 7A-7B. M Packaging Sequences of PR8. (A) Nucleotide sequence of 3' NCR (SEQ ID NO:37) and 3' proximal coding region sequence (SEQ ID NO:38) of influenza PR8 virus with an NheI restriction enzyme recognition site (SEQ ID NO:39). The 3' NCR is shaded and the 3' proximal coding region sequence is underlined. (B) Nucleotide sequence of 5' NCR (SEQ ID NO:40) and 5' proximal coding region sequence (SEQ ID NO:41) of influenza PR8 virus with an XhoI restriction enzyme recognition site (SEQ ID NO:42). The 5' NCR is shaded and the 5' proximal coding region sequence is underlined. In FIG. 7A, the capitalized letter at position 52 represents the mutation introduced into the sequence in order to eliminate the mRNA 5' splice site. Other capitalized letters represent mutations introduced into the sequence to delete to ATG initiation codon or are found within the XhoI and NheI restriction enzyme recognition sites.

FIGS. 8A-8B. NS Packaging Sequences of PR8. (A) Nucleotide sequence of 3' NCR (SEQ ID NO:43) and 3' proximal coding region sequence (SEQ ID NO:44) of influenza PR8 virus with an NheI restriction enzyme recognition site (SEQ ID NO:45). The 3' NCR is shaded and the 3' proximal coding region sequence is underlined. (B) Nucleotide sequence of 5' NCR (SEQ ID NO:46) and 5' proximal coding region sequence (SEQ ID NO:47) of influenza PR8 virus with an XhoI restriction enzyme recognition site (SEQ ID NO:48). The 5' NCR is shaded and the 5' proximal coding region sequence is underlined. In FIG. 8A, the capitalized letter at position 57 represents the mutation introduced into the sequencer in order to eliminate the distal 5' splice site. Other capitalized letters represent mutations introduced into the sequence to delete to ATG initiation codon or are found within the XhoI and NheI restriction enzyme recognition sites.

FIGS. 9A-9B. Serial silent mutations introduced into the open reading frame region (ORF) packaging sequences for PB2. (A) Wild-type ORF 3' termini sequence (SEQ ID NO:49). (B) Mutated ORF 3' termini sequence (SEQ ID NO:50). (C) Wild-type ORF 5' termini sequence (SEQ ID NO:51). (D) Mutated ORF 5' termini sequence (SEQ ID NO:52).

Figures 10A, 10B, 10C, 10D:
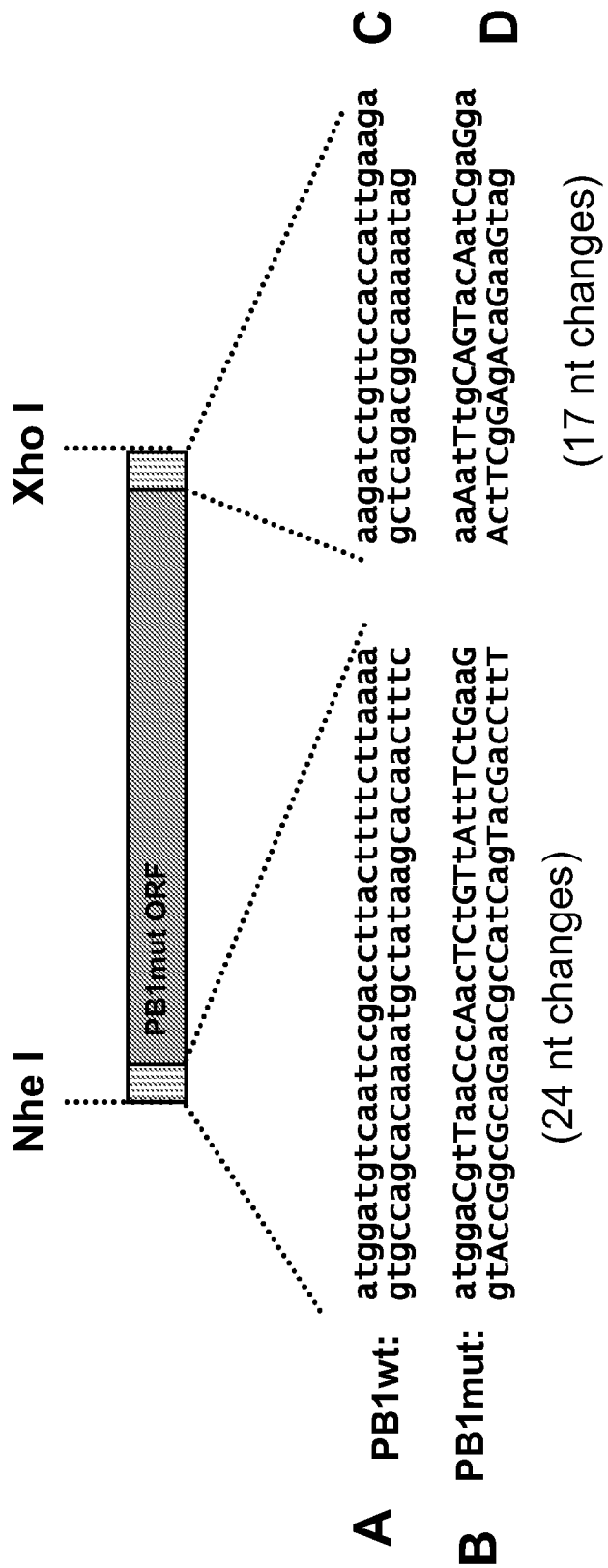

FIGS. 10A-10B. Serial silent mutations introduced into the open reading frame region (ORF) packaging sequences for PB1. (A) Wild-type ORF 3' termini sequence (SEQ ID NO:53). (B) Mutated ORF 3' termini sequence (SEQ ID NO:54). (C) Wild-type ORF 5' termini sequence (SEQ ID NO:55). (D) Mutated ORF 5' termini sequence (SEQ ID NO:56).

Figures 11A, 11B, 11C, 11D:
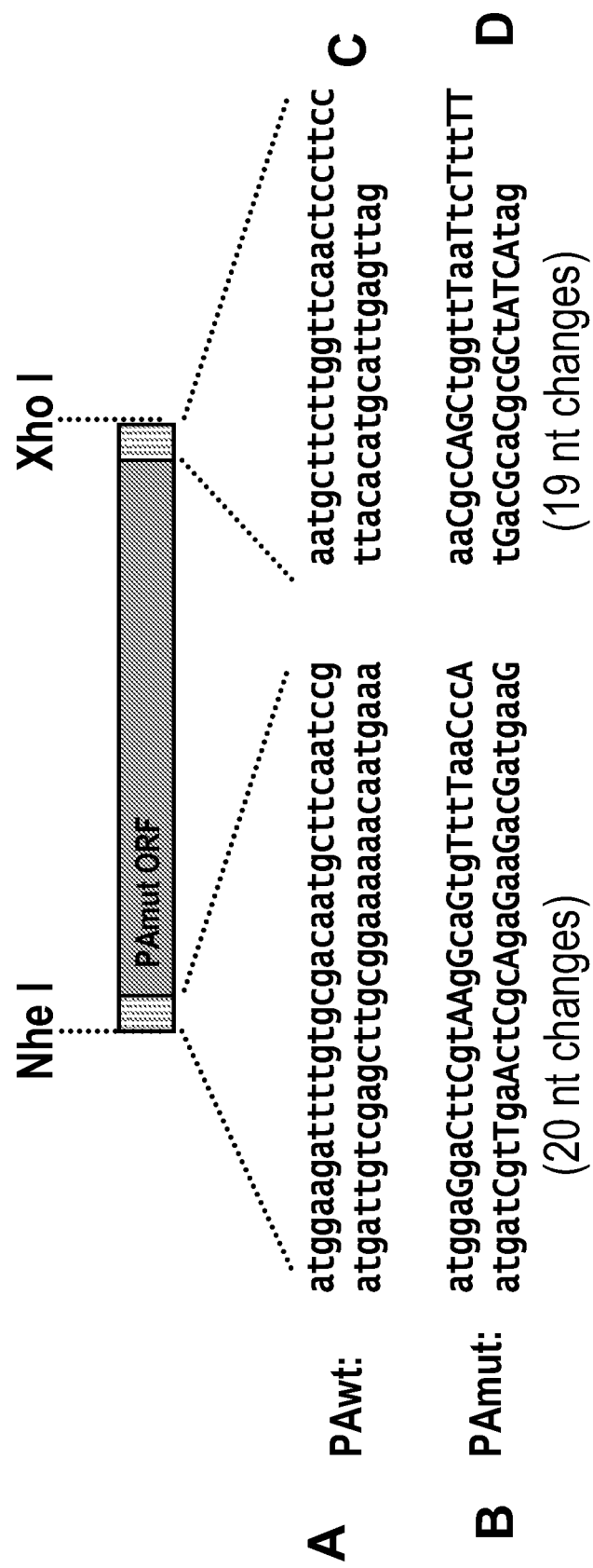

FIGS. 11A-11B. Serial silent mutations introduced into the open reading frame region (ORF) packaging sequences for PA. (A) Wild-type ORF 3' termini sequence (SEQ ID NO:57). (B) Mutated ORF 3' termini sequence (SEQ ID NO:58). (C) Wild-type ORF 5' termini sequence (SEQ ID NO:59). (D) Mutated ORF 5' termini sequence (SEQ ID NO:60).

Figures 12A, 12B, 12C, 12D:
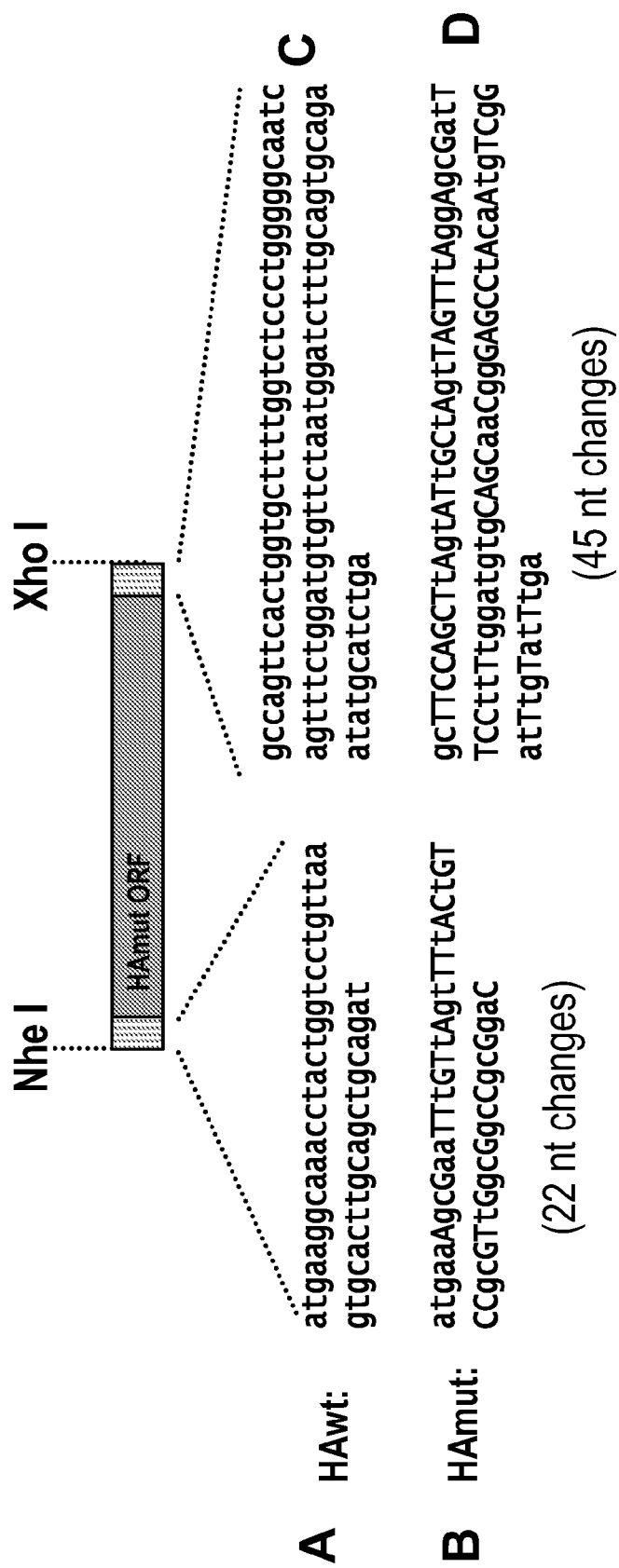

FIGS. 12A-12B. Serial silent mutations introduced into the open reading frame region (ORF) packaging sequences for HA. (A) Wild-type ORF 3' termini sequence (SEQ ID NO:61). (B) Mutated ORF 3' termini sequence (SEQ ID NO:62). (C) Wild-type ORF 5' termini sequence (SEQ ID NO:63). (D) Mutated ORF 5' termini sequence (SEQ ID NO:64).

Figures 13A, 13B, 13C, 13D:
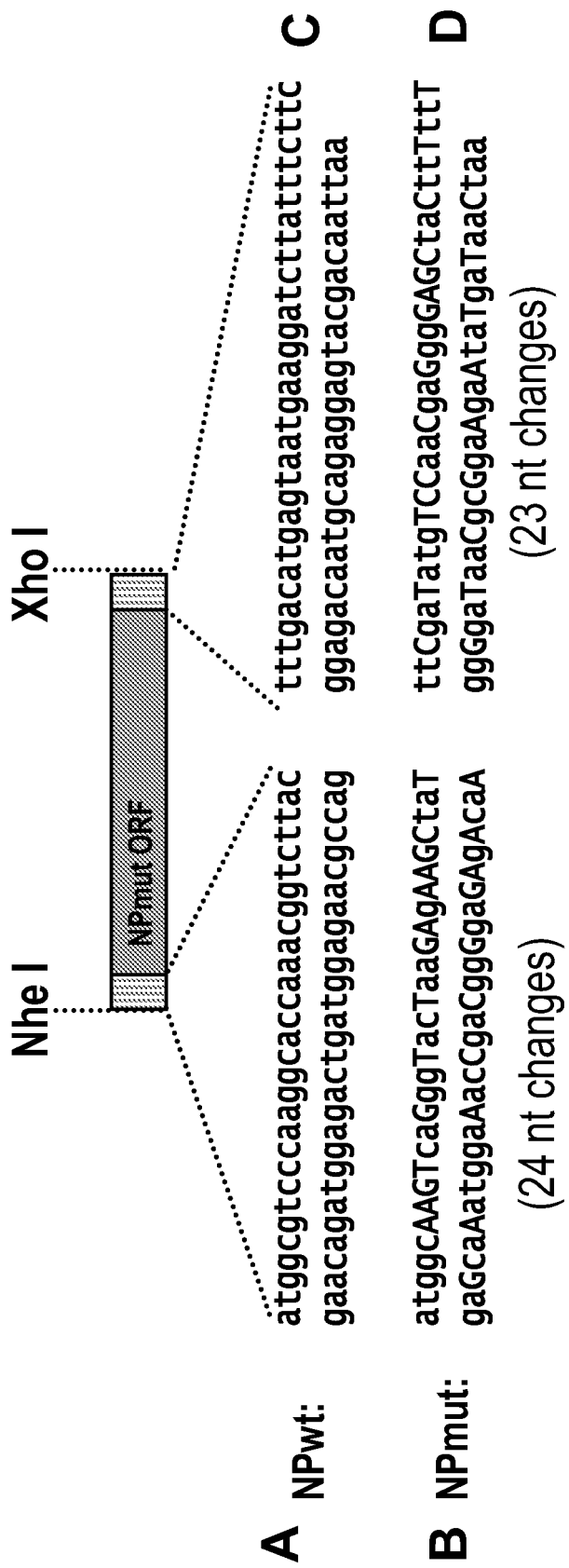

FIGS. 13A-13B. Serial silent mutations introduced into the open reading frame region (ORF) packaging sequences for NP. (A) Wild-type ORF 3' termini sequence (SEQ ID NO:65). (B) Mutated ORF 3' termini sequence (SEQ ID NO:66). (C) Wild-type ORF 5' termini sequence (SEQ ID NO:67). (D) Mutated ORF 5' termini sequence (SEQ ID NO:68).

Figures 14A, 14B, 14C, 14D:
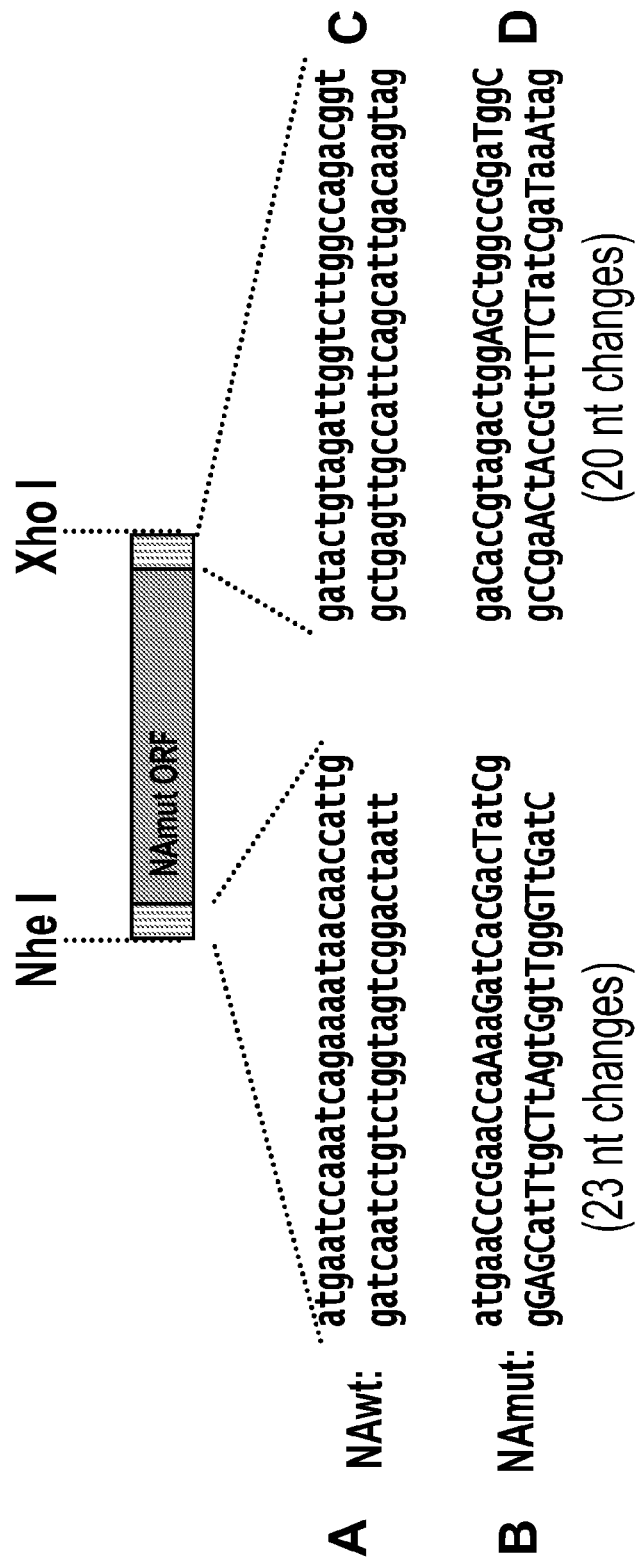

FIGS. 14A-14B. Serial silent mutations introduced into the open reading frame region (ORF) packaging sequences for NA. (A) Wild-type ORF 3' termini sequence (SEQ ID NO:69). (B) Mutated ORF 3' termini sequence (SEQ ID NO:70). (C) Wild-type ORF 5' termini sequence (SEQ ID NO:71). (D) Mutated ORF 5' termini sequence (SEQ ID NO:72).

Figures 15A, 15B, 15C, 15D:
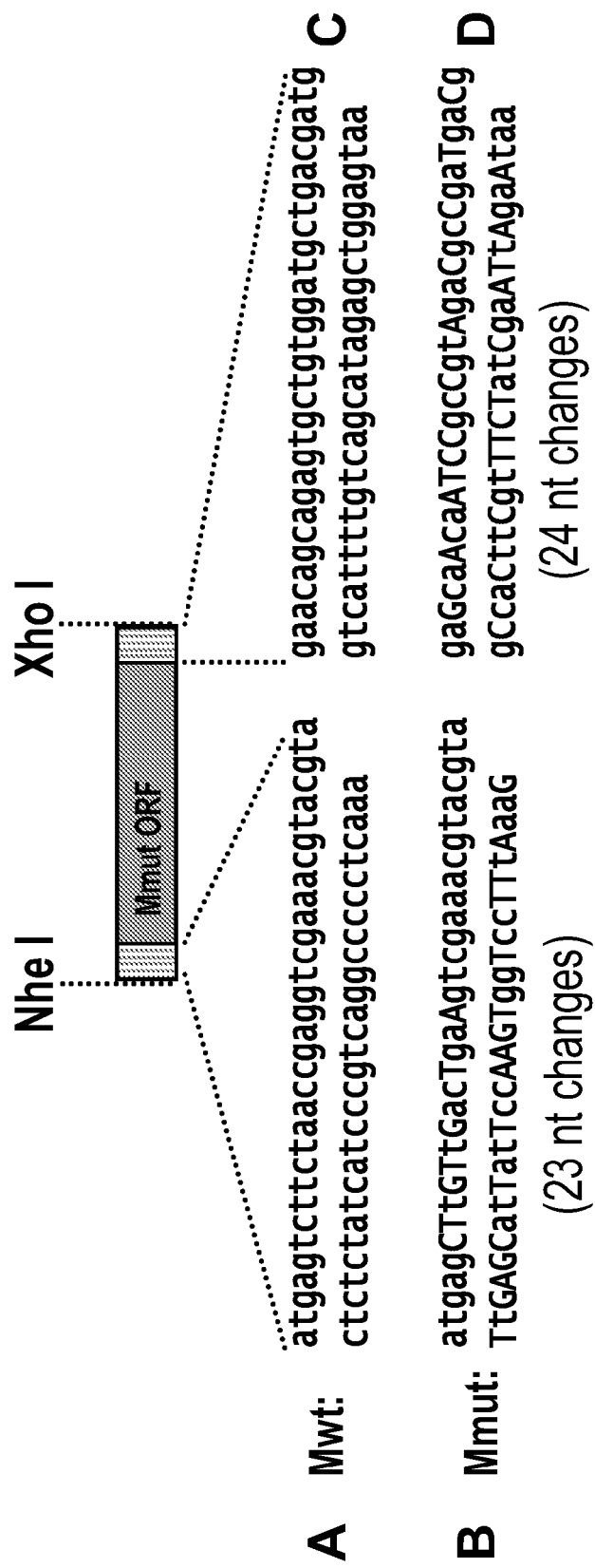

FIGS. 15A-15B. Serial silent mutations introduced into the open reading frame region (ORF) packaging sequences for M. (A) Wild-type ORF 3' termini sequence (SEQ ID NO:73). (B) Mutated ORF 3' termini sequence (SEQ ID NO:74). (C) Wild-type ORF 5' termini sequence (SEQ ID NO:75). (D) Mutated ORF 5' termini sequence (SEQ ID NO:76).

Figures 16A, 16B, 16C, 16D:
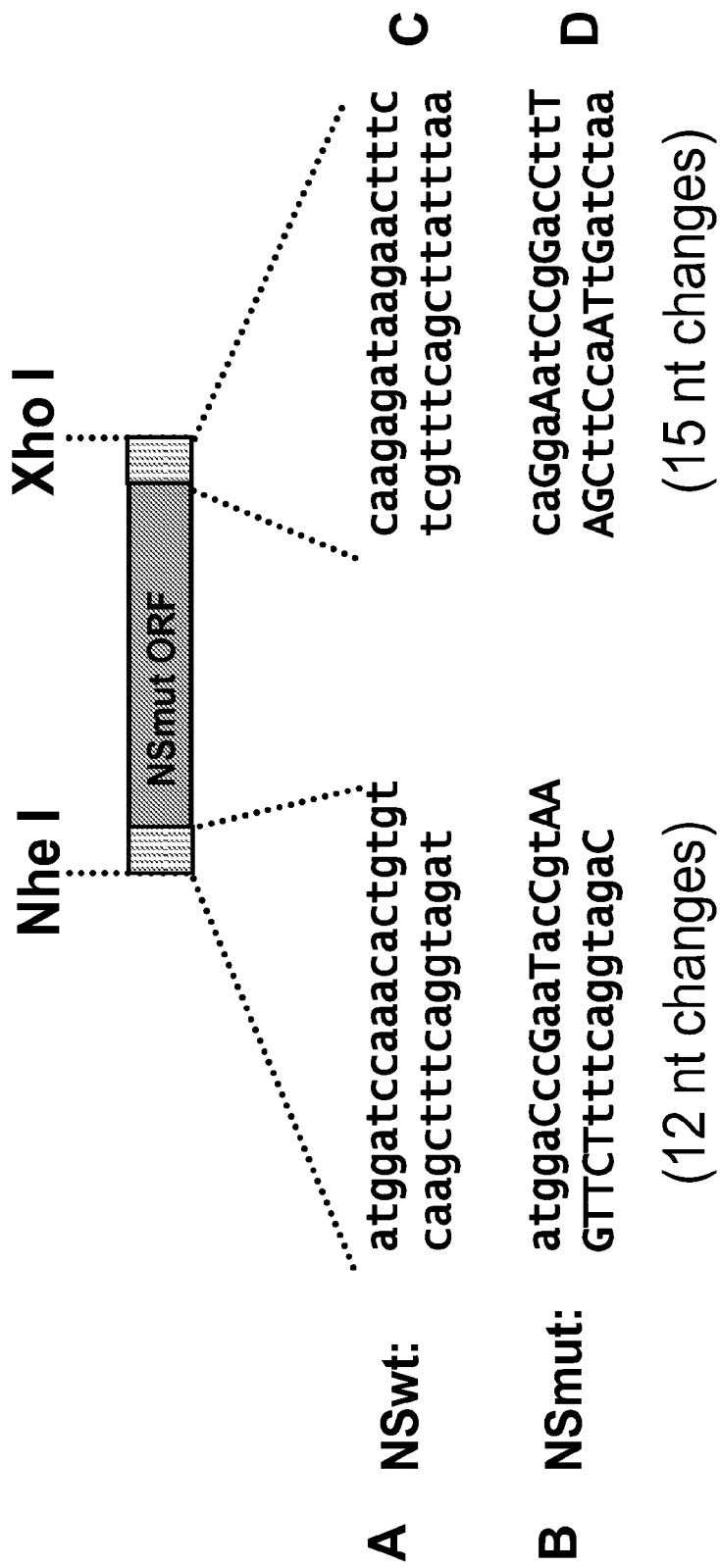

FIGS. 16A-16B. Serial silent mutations introduced into the open reading frame region (ORF) packaging sequences for NS. (A) Wild-type ORF 3' termini sequence (SEQ ID NO:77). (B) Mutated ORF 3' termini sequence (SEQ ID NO:78). (C) Wild-type ORF 5' termini sequence (SEQ ID NO:79). (D) Mutated ORF 5' termini sequence (SEQ ID NO:80).

FIG. 17. Influenza virus A/WSN/33 HA gene segment (GenBank No. J02176; GI: 324199; SEQ ID NO:84). The nucleotide sequence of the 3' NCR (SEQ ID NO:81) is underlined, the nucleotide sequence of the HA open reading frame (SEQ ID NO:82) is in plain text, and the nucleotide sequence of the 5' NCR (SEQ ID NO:83) is double underlined.

FIG. 18. Influenza virus A/WSN/33 NA gene segment (GenBank No. J02177; GI: 324481; SEQ ID NO:88). The nucleotide sequence of the 3' NCR (SEQ ID NO:85) is underlined, the nucleotide sequence of the NA open reading frame (SEQ ID NO:86) is in plain text, and the nucleotide sequence of the 5' NCR (SEQ ID NO:87) is double underlined.

FIG. 19. Influenza virus A/WSN/33 M gene segment (GenBank No. L25814; GI: 414302; SEQ ID NO:92). The nucleotide sequence of the 3' NCR (SEQ ID NO:89) is underlined, the nucleotide sequence of the M1/M2 open reading frame (SEQ ID NO:90) is in plain text, and the nucleotide sequence of the 5' NCR (SEQ ID NO:91) is double underlined. The open reading frame for M1 is from nucleotides 26 to 784. The open reading frame for M2 is from nucleotides 26 to 51 of exon 1 and nucleotides 740 to 1007 of exon 2.

Figure 20:
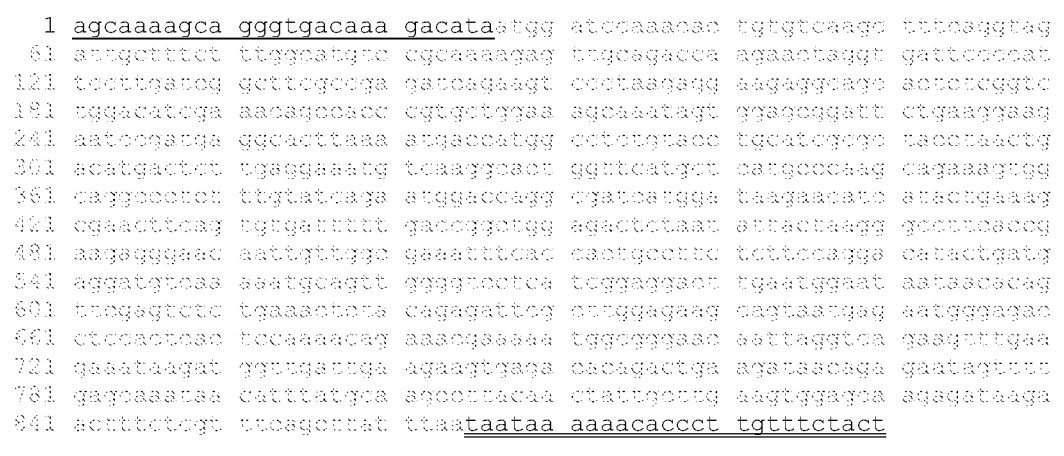

FIG. 20. Influenza virus A/WSN/33 NS gene segment (GenBank No. Z21498; GI: 296585; SEQ ID NO:96). The nucleotide sequence of the 3' NCR (SEQ ID NO:93) is underlined, the nucleotide sequence of the NS1/NS2 open reading frame (SEQ ID NO:94) is in plain text, and the nucleotide sequence of the 5' NCR (SEQ ID NO:95) is double underlined. The open reading frame for NS1 is from nucleotides 27 to 719. The open reading frame for NS2 is from nucleotides 27 to 56 of exon 1 and nucleotides 529 to 864.

FIG. 21. Influenza virus A/WSN/33 PA gene segment (GenBank No. X17336; GI: 60812; SEQ ID NO:100). The nucleotide sequence of the 3' NCR (SEQ ID NO:97) is underlined, the nucleotide sequence of the PA open reading frame (SEQ ID NO:98) is in plain text, and the nucleotide sequence of the 5' NCR (SEQ ID NO:99) is double underlined.

FIG. 22. Influenza virus A/WSN/33 PB1 gene segment (GenBank No. J02178; GI: 324899; SEQ ID NO:104). The nucleotide sequence of the 3' NCR (SEQ ID NO:101) is underlined, the nucleotide sequence of the PB1 open reading frame (SEQ ID NO:102) is in plain text, and the nucleotide sequence of the 5' NCR (SEQ ID NO:103) is double underlined.

FIG. 23. Influenza virus A/WSN/33 PB2 gene segment (GenBank No. J02179; GI: 324913; SEQ ID NO:108). The nucleotide sequence of the 3' NCR (SEQ ID NO:105) is underlined, the nucleotide sequence of the PB2 open reading frame (SEQ ID NO:106) is in plain text, and the nucleotide sequence of the 5' NCR (SEQ ID NO:107) is double underlined.

FIG. 24. Influenza virus A/WSN/33 NP gene segment (GenBank No. M30746; GI: 324676; SEQ ID NO:112). The nucleotide sequence of the 3' NCR (SEQ ID NO:109) is underlined, the nucleotide sequence of the NP open reading frame (SEQ ID NO:110) is in plain text, and the nucleotide sequence of the 5' NCR (SEQ ID NO:111) is double underlined.

FIGS. 25A-25F. Generation of the recombinant Swap(wt) virus carrying HA and NS chimeric segments which can independently reassort. (A) NS-HAwt-NS and HA-NSwt-HA constructs. The A/PR/8/34 HA wild type (HAwt) ORF (hatched) was flanked by the NS 3', 5' NCRs and the 77 nt, 102 nt of NS ORF packaging signals (in red), generating the 1941 nt long NS-HAwt-NS construct; likewise, the NS wild type (NSwt) ORF (straight lines) was flanked by the HA 3', 5' NCRs and the 67 nt, 105 nt of HA ORF packaging signals (hatched), generating the 1099 nt long HA-NSwt-HA construct. The ATGs (in positive sense) upstream of the HA and NS translation start codons were all mutated to TTGs (in positive sense). The 5' splice on the 77 nt part of NS packaging signals in the NS-HAwt-NS construct was also mutated. (B) Genome structure of the Swap(wt) virus. Six A/PR/8/34 ambisense plasmids (Gao Q, Brydon E W, Palese P (2008) A seven-segmented influenza A virus expressing the influenza C virus glycoprotein HEF. *J Virol* 82:6419-6426, Quinlivan M, et al. (2005) Attenuation of equine influenza viruses through truncations of the NS1 protein. *J Virol* 79:8431-8439, Kopecky-Bromberg S A, et al. (2009) Alpha-C-galactosylceramide as an adjuvant for a live attenuated influenza virus vaccine. *Vaccine* 27:3766-3774), and the NS-HAwt-NS and HA-NSwt-HA constructs were used to generate the Swap(wt) virus. (Sequencing of the NS-HAwt-NS RNA segment revealed one G81U mutation in the 3' end. No nucleotide changes were identified for the HA-NSwt-HA RNA segment). (C) Genome structure of the Reassortant(NS) virus which contains seven A/PR/8/34 RNAs and the HA-NSwt-HA RNA. (D) Genome structure of the Reassortant (HA) virus which contains seven A/PR/8/34 RNAs and the NS-HAwt-NS segment. (E) Immunostaining of the plaques formed in MDCK cells by the recombinant viruses. (F) Growth rates of the recombinant viruses in eggs at 37° C.

FIGS. 26A-26E. Generation of the recombinant Swap (mut) virus carrying HA and NS chimeric segments which can not independently reassort. (A) NS-HAmut-NS and HA-NSmut-HA constructs. The strategy was the same as that described in FIG. 17A, except that the ORF region contained serial synonymous mutations: the NS-HAmut-NS construct carried 22 and 45 nt changes at the 3' and 5' ends, respectively; the HA-NSmut-HA construct had 12 and 15 nt changes in the NS ORF. (B) Genome structure of the Swap(mut) virus. The genomic composition is similar to that of the Swap(wt) virus (FIG. 17B), except that the NS-HAmut-NS and HA-NSmut-HA constructs were substituted for rescue. [Sequencing the NS-HAmut-NS RNA of the Swap(mut) virus revealed eight A to G mutations in the 3' end. The sequence of the 3' end 130 nt of the NS-HAmut-NS RNA is: 3'-ucguuuucgucccacuguuucu-guauGaccuagguuugugacacag-uucgGGagucgaucuaacgGGagaaaccga acaggcguuugcu-caacgucugguucucgGucguacuuucgcuuGGacaaucaa (SEQ ID NO:113; capitalized Gs designate the changes observed in virus RNA). For the HA-NSmut-HA RNA segment, two conversions on the NS 3' ORF region were observed: A122G, which results in a Val to Ala amino acid change; and U318C, which is silent.] (C) Plaque phenotype of the Swap(mut) virus in MDCK cells. (D) Growth rates of the recombinant viruses in 10-day-old embryonated chicken eggs at 37° C. (E) Failure to rescue two hypothetical reassortant viruses. The experiment on the left used seven A/PR/8/34 plasmids (Gao Q, Brydon E W, Palese P (2008) A seven-segmented influenza A virus expressing the influenza C virus glycoprotein HEF. *J Virol* 82:6419-6426, Quinlivan M, et al. (2005) Attenuation of equine influenza viruses through truncations of the NS1 protein. *J Virol* 79:8431-8439, Kopecky-Bromberg S A, et al. (2009) Alpha-C-galactosylceramide as an adjuvant for a live attenuated influenza virus vaccine. *Vaccine* 27:3766-3774) and the HA-NSmut-HA construct, and the one on the right used seven A/PR/8/34 plasmids (Gao Q, Brydon E W, Palese P (2008) A seven-segmented influenza A virus expressing the influenza C virus glycoprotein HEF. *J Virol* 82:6419-6426, Quinlivan M, et al. (2005) Attenuation of equine influenza viruses through truncations of the NS1 protein. *J Virol* 79:8431-8439, Kopecky-Bromberg S A, et al. (2009) Alpha-C-galactosylceramide as an adjuvant for a live attenuated influenza virus vaccine. *Vaccine* 27:3766-3774) and the NS-HAmut-NS.

FIGS. 27A-27E. Analyzing the vRNA genome packaging efficiency of the recombinant viruses. Five recombinant viruses [rA/PR/8/34 (A), Swap(wt) (B), Reassortant(NS) (C), Reassortant(HA) (D) and Swap(mut) (E)] were grown in eggs at 37° C. and purified viral RNA was separated (0.5 µg/lane) on a 2.8% acrylamide gel and visualized by silver staining. The RNA from the rA/PR/8/34 (A) and Swap(mut) (E) viruses was separated on one gel, and the RNA from the other three viruses [Swap(wt) (B), Reassortant(NS) (C) and Reassortant(HA) (D)] was separated on another gel.

FIGS. 28A-28E. The chimeric NS segment of the Swap (wt), but not of Swap(mut), virus can reassort in infected cells. (A) Diagram of the co-infection experiments. (B) RT-PCR primer design to detect the chimeric and wild type HA segments. The RT-PCR products are 824 bp in length for the NS-HAwt-NS or NS-HAmut-NS segments and 747 bp for the wild type HA. (C) RT-PCR primer design to detect the chimeric and wild type NS segments. The RT-PCR products for the chimeric and wild type NS segments are 405 and 326 bp long, respectively. (D) The Swap(wt) and rA/PR/8/34 viruses co-infection experiment. 24 single plaques were characterized by RT-PCR (10 shown in the gel) using primers indicated in (B) and (C). The rA/PR/8/34 and Swap(wt) viruses were used for RT-PCR control (2nd and 3rd lane). M, marker. (E) The Swap(mut) and rA/PR/8/34 co-infection experiment. 48 single plaques were characterized by RT-PCR (10 shown in the gel). The bands below the wild type or chimeric NS PCR products were artificial by-products of the PCR reaction.

FIGS. 29A-29H. Generation of influenza viruses with a ninth GFP segment. (A) Generation of NA-PB1mut-NA, NA-PB2mut-NA, NA-PAmut-NA, PB1-GFP-PB1, PB2-GFP-PB2 and PA-GFP-PA constructs. To generate NA-PB1mut-NA, NA-PB2mut-NA, NA-PAmut-NA constructs, the PB1mut, PB2mut or PAmut ORF regions were obtained by PCR and serial silent mutations were introduced into the 3' and 5' proximal regions: 24 and 17 nt for PB1mut; 13 and 36 nt for PB2mut; and 19 and 19 nt for PAmut (see Section 7.1). The PB1mut, PB2mut or PAmut ORFs were then flanked by 179 nt of NA packaging sequences in the 3' end and 215 nt of NA packaging sequences in the 5' end. The ATGs located on the 179 nt of NA packaging sequences were all mutated to TTGs. To generate the PB1-GFP-PB1, PB2-GFP-PB2 and PA-GFP-PA constructs, the GFP ORF region was flanked by the PB1, PB2 and PA packaging sequences, respectively. The PB1 packaging sequences included 153 nt of PB1 3' end and 159 nt of PB1 5' end; The PB2 packaging sequences included 158 nt of PB2 3' end and 169 nt of PB2 5' end; and the PA packaging sequences included 129 nt of PA 3' end and 184 nt of PA 5' end. The ATGs located on the 3' ends of PB1, PB2 and PA packaging sequences were all mutated to TTGs. The translation start and stop codons of each construct are indicated by arrows. (B) Genome structure of -PB1(ps) and -PB1(ps)+GFP viruses. Seven A/PR/8/34 ambisense plasmids (pDZ-PB2, pDZ-PA, pDZ-HA, pDZ-NP, pDZ-NA, pDZ-M, pDZ-NS), and one chimeric construct NA-PB1mut-NA were used to generate the -PB1(ps) virus by using reverse genetics (Fodor et al., 1999, J Virol 73:9679-82; Quinlivan et al., 2005, J Virol 79:8431-9). For the rescue of -PB1(ps)+GFP virus, a ninth PB1-GFP-PB1 construct was included. (C) Genome structure of -PB2(ps)+GFP virus. Similar to the -PB1(ps)+GFP virus in B, the virus contained a chimeric NA-PB2mut-NA segment instead of a wild type PB2, seven A/PR/8/34 segments (PB1, PA, HA, NP, NA, M, NS) and a ninth PB2-GFP-PB2 chimeric segment. The virus lacking a ninth PB2-GFP-PB2 segment was not rescued. (D) Genome structure of -PA(ps) and -PA(ps)+GFP viruses. Similar to -PB1(ps) in B, the -PA(ps) virus contained a chimeric NA-PAmut-NA segment instead of a wild type PA and seven A/PR/8/34 segments (PB2, PB1, HA, NP, NA, M, NS). The -PA(ps)+GFP virus contained a ninth PA-GFP-PA chimeric segment. (E) Growth curves of viruses in 10-day-old embryonated chicken eggs at 37° C. The error bars represent standard deviations. (F) Immunostaining of the plaques formed in MDCK cells by the recombinant viruses two days post infection. (G) GFP expression of recombinant viruses in 293T cells one day post infection (MOI 0.5). The viruses used for infection had been passaged five to ten times in eggs. (H) Hemagglutination assay of viruses grown in 10-day-old embryonated chicken eggs at 37° C.

FIGS. 30A-30H. Generation of nine-segmented influenza viruses carrying both H1 and H3 subtype HAs. (A) Generation of PB1-HA(HK)-PB1 and PB2-HA(HK)-PB2 constructs. The A/HK/1/68 HA ORF was amplified from a pCAGGS-HK HA plasmid (Wang et al., 2009, PLoS Pathog 6:e1000796) by PCR and used to replace the GFP ORF of PB1-GFP-PB1 and PB2-GFP-PB2 constructs in FIG. 29A, generating the PB1-HA(HK)-PB1 and PB2-HA(HK)-PB2 constructs. (B) Genome structure of -PB1(ps)+HK HA virus. Similar to -PB1(ps)+GFP virus in FIG. 29B, the virus contained a chimeric NA-PB1mut-NA segment instead of a wild type PB1, seven A/PR/8/34 segments (PB2, PA, HA, NP, NA, M, NS) and a ninth PB1-HA(HK)-PB1 chimeric segment. (C) Genome structure of -PB2(ps)+HK HA virus. The chimeric PB2-HA(HK)-PB2 segment was used to replace the PB2-GFP-PB2 of the -PB2(ps)+GFP virus in FIG. 29C, generating the -PB2(ps)+HK HA virus. (D) Growth curves of viruses in 10-day-old embryonated chicken eggs at 37° C. The error bars represent standard deviations. (E) Western blot to detect the A/PR/8/34 and A/HK/1/68 HAs in purified virions. Viruses [rA/PR/8/34, X31, -PB2(ps)+HK HA and -PB1(ps)+HK HA] were grown in eggs at 37° C. and purified through a 30% sucrose cushion. A Western blot was performed to detect the presence of NP and HA proteins using specific mouse monoclonal antibodies: PY102 for A/PR/8/34 HA0 and HA1 (Reale et al., 1986, J Immunol 137:1352-8), HT103 for A/PR/8/34 NP (O'Neill et al., 1998, Embo J 17:288-96), 66A6 for A/HK/1/68 HA0 and HAL and 12D1 for A/HK/1/68 HA0 and HA2 (Wang et al., 2009, PLoS Pathog 6:e1000796). (F) Western blot to detect the A/PR/8/34 and A/HK/1/68 HAs in virus infected MDCK cells. MDCK monolayers were infected by viruses [rA/PR/8/34, X31, -PB1(ps)+HK HA and -PB2(ps)+HK HA] at an MOI of 10 to 0.0001. One day post infection, the cells were washed with PBS and harvested using 2× protein loading buffer [100 mM This -HCl (PH 6.8), 4% sodium dodecyl sulfate, 20% glycerol, 5% β-mercaptoethanol and 0.2% bromophenol blue] and run on a 10% SDS PAGE gel. The A/PR/8/34 HA0, NP, and A/HK/1/68 HA0 were detected by monoclonal antibodies PY102, HT103 and 66A6, respectively (O'Neill et al., 1998, Embo J 17:288-96; Wang et al., 2009, PLoS Pathog 6:e1000796; Wang et al., 2009, PLoS Pathog 6:e1000796). (G) H1/H3 sandwich ELISA to determine whether both H1 and H3 subtype HA proteins were incorporated into the same particles of the -PB1(ps)+HK HA and -PB2(ps)+HK HA viruses (see Section 7.1). The error bars represent standard deviations. (H) Analyzing the vRNA genome packaging efficiency of the recombinant viruses. Four recombinant viruses [rA/PR/8/34, X31, -PB1(ps)+HK HA and -PB2(ps)+HK HA] were grown in eggs at 37° C. and purified viral RNA was separated (0.5 μg/lane) on a 2.8% acrylamide gel and visualized by silver staining. The rRNA band was confirmed based on size and previously reported findings. The identity of an additional band marked with a "?" is unknown.

FIGS. 31A-31D. Immunization of mice with -PB1(ps)+HK HA virus conferred complete protection from lethal challenges of rA/PR/8/34 and X31 viruses. (A) Growth curves of viruses in 10-day-old embryonated chicken eggs at 37° C. (B) Pathogenicity of -PB1(ps)+HK HA and -PB1(ps)+Luc viruses. Groups of C57BL/6 mice were given PBS, -PB1(ps)+HK HA virus, or the -PB1(ps)+Luc virus, at $10^3$ or $10^4$ PFU through the intranasal route and observed for two weeks for weight loss and signs of disease. The average body weights of animals in each group are indicated as percentages of the original body weights. (C) rA/PR/8/34 virus challenge experiment. Three weeks after the infection, the groups of mice that received PBS, $10^3$ PFU -PB1(ps)+HK HA virus, and $10^3$ PFU -PB1(ps)+Luc virus, were challenged intranasally with 100 $MLD_{50}$ of rA/PR/8/34 virus. The mice were then observed daily for two weeks for body weight loss and signs of disease. (D) X31 virus challenge experiment. X31 virus challenge was performed as in (C) except that the groups of mice were challenged by using 33 $MLD_{50}$ of X31 virus instead of rA/PR/8/34 virus. The error bars in A-D represent standard deviations.

FIG. 32. Nucleic acid sequences of chimeric gene segments. (A) Nucleic acid sequence of NA-PB1mut-NA (SEQ ID NO:119). (B) Nucleic acid sequence of NA-PB2mut-NA (SEQ ID NO:120). (C) Nucleic acid sequence of NA-PAmut-NA (SEQ ID NO:121). (D) Nucleic acid sequence of PB1-GFP-PB1 (SEQ ID NO:122). (E) Nucleic acid sequence of PB2-GFP-PB2 (SEQ ID NO:123). (F) Nucleic acid sequence of PA-GFP-PA (SEQ ID NO:124). (G) Nucleic acid sequence of PB1-HA(HK)-PB1 (SEQ ID NO:125). (H) Nucleic acid sequence of PB2-HA(HK)-PB2 (SEQ ID NO:126). (I) Nucleic acid sequence of PB1-Luc-PB1 (SEQ ID NO:127).

Figure 33:
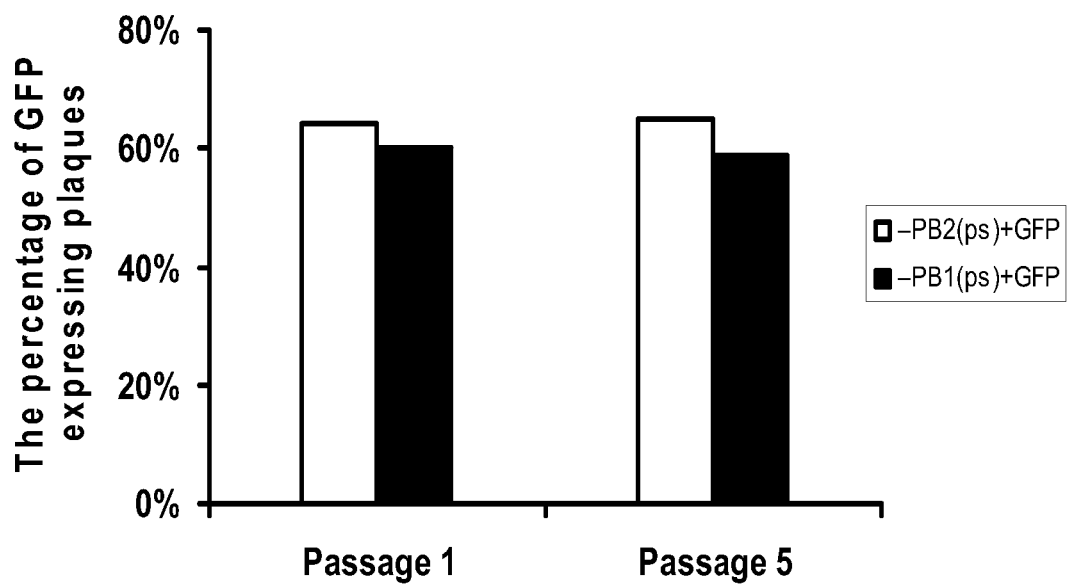

FIG. 33. The percentage of GFP expressing plaques formed by the -PB2(ps)+GFP and -PB1(ps)+GFP viruses in MDCK cells. Regular plaque assay was performed and immunostaining of the plaques was used to measure the titers of both viruses at passages 1 and 5 in 10-day-old eggs. Mab HT103 (anti-A/PR/8/34 NP) was used in this procedure.

Figure 34:
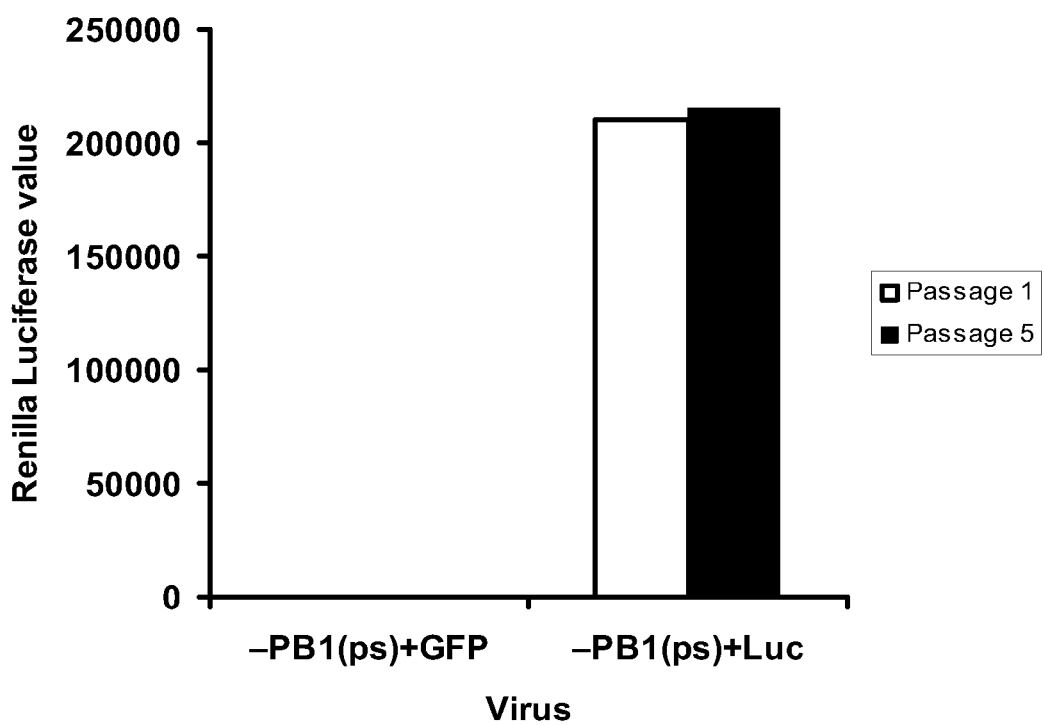

FIG. 34. Expression of *Renilla* luciferase by the -PB1(ps)+Luc virus in MDCK cells. MDCK cells in a 6-well plate were infected by the -PB1(ps)+GFP or -PB1(ps)+Luc virus at an moi of 5. Sixteen hours later, the *Renilla* luciferase activity was measured using a *Renilla* luciferase assay system (Promega).

Figure 35:

FIG. 35. Chimeric gene segments of recombinant influenza virus generated by transfecting 293T cells with chimeric plasmids carrying NA-PB2mut-NA, PB2-PB1mut-PB2, PB1-PAmut-PB1, M-NPmut-M, PA-NAmut-PA, NP-Mmut-NP and 2 plasmids carrying the wild type A/PR/8/34 HA and NS segments.

Figure 36:

FIG. 36. Chimeric gene segments of recombinant influenza virus generated by transfecting 293T cells with chimeric plasmids carrying NA-PB2mut-NA, PB2-PB1mut-PB2, PB1-PAmut-PB1, NS-HAmut-NS, PA-NAmut-PA, HA-NSmut-HA and 2 wild type A/PR/8/34 NP and M segments.

Figure 37:

FIG. 37. Chimeric gene segments of recombinant influenza virus generated by transfecting 293T cells with chimeric plasmids carrying NA-PB2mut-NA, PB2-PB1mut-PB2, PB1-PAmut-PB1, NP-HAmut-NP, NS-NPmut-NS, PA-NAmut-PA, HA-NSmut-HA), and 1 wild type A/PR/8/34 M segments.

FIG. 38. Chimeric gene segments of recombinant influenza virus generated by transfecting 293T cells with chimeric plasmids carrying PB2, PB1, PA, HA, NP, PA-NAmut-PA, M, NS segments as well as an NA-GFP ORF-NA or NA-HK HA ORF-NA segment.

5. DETAILED DESCRIPTION

Described herein are chimeric influenza virus gene segments and nucleic acid sequences encoding such chimeric influenza virus gene segments which are useful in the production of recombinant influenza viruses. In particular, two or more chimeric influenza virus gene segments or complements thereof, or nucleic acid sequences encoding such gene segments or the complements thereof may be used in the production of recombinant influenza viruses. Without being bound by any theory, the two or more chimeric influenza virus gene segments segregate together (i.e., cosegregate) during replication of the recombinant influenza viruses such that the recombinant influenza viruses have a reduced ability to reassort with other influenza viruses (e.g., wild-type influenza viruses) or are unable to reassort with other influenza viruses as determined by techniques known to one skilled in the art. The reduced ability or inability of such recombinant influenza viruses to reassort with other influenza viruses may improve the safety of the recombinant influenza viruses as a live attenuated vaccine. Accordingly, such recombinant influenza viruses may be useful in either the prevention of influenza virus disease, the treatment of influenza virus disease or influenza virus infection, or both.

5.1 Nucleic Acids

Provided herein are nucleic acid sequences that are a chimera of coding and non-coding regions of two influenza virus gene segments or derivatives thereof, or the complement thereof. Also provided herein are nucleic acid sequences that encode a chimera of coding and non-coding regions of two influenza virus gene segments or derivatives thereof, or the complement thereof. In certain aspects, a nucleic acid sequence provided herein comprises or encodes: (a) packaging signals found in the 3' and the 5' non-coding regions of a first type of influenza virus gene segment or the complements thereof, (b) packaging signals found in the 3' proximal coding region sequence of the first type of influenza virus gene segment or the complement thereof, the 5' proximal coding region sequence of the first type of influenza virus gene segment or the complement thereof, or both the 3' and the 5' proximal coding region sequences of the first type of influenza virus gene segment or the complements thereof, and (c) an open reading frame or a fragment thereof from a second, different type of influenza virus gene segment, or a complement thereof, wherein the open reading frame contains one, two, three or more mutations in the influenza virus packaging signals found in the open reading frame. The first and second types of influenza virus gene segments refer to two different influenza virus gene segments. For example, the first type of influenza virus gene segment may be a hemagglutinin (HA) influenza virus gene segment and the second type of influenza virus gene segment may be an NS influenza virus gene segment. In certain embodiments, the 3' and/or the 5' proximal coding regions sequences flank the open reading frame and are translated in frame with the open reading frame. In other embodiments, the 3' and/or the 5' proximal coding region sequences flank the open reading frame and are not translated. In some embodiments, the 3' proximal coding region sequence has been mutated so as to eliminate any start codons and preclude the translation of the 3' proximal coding region sequence. In certain embodiments, the 3' proximal coding region sequence is derived from an influenza virus NS or M gene segment. In a specific embodiment, the 3' proximal coding region sequence is derived from an influenza virus NS gene segment and the 3' proximal coding region has been mutated so as to eliminate the mRNA 5' splice site. In another specific embodiment, the 3' proximal coding region sequence is derived from an influenza virus M gene segment and the 3' proximal coding region has been mutated so as to eliminate the distal 5' splice site. In some embodiments, the 5' proximal coding region sequence has one or more mutations so as to ensure that the 5' proximal coding region sequence is not translated. In a specific embodiment, the mutations introduced into the open reading frame of the influenza virus gene segment or a fragment thereof are silent mutations.

Influenza virus gene segment packaging signals are known. In addition, techniques for identifying influenza virus gene segment packaging signals are well known and examples are described in Section 5.8, infra. In certain embodiments, a chimeric influenza virus gene segment comprises packaging signals found in the non-coding and coding regions of one type of influenza virus segment that are sufficient to achieve packaging of the chimeric influenza virus gene segment at an efficiency of at least 10%, 15%, 20%, 25%, 30%, 35%, 40%, 45%, 50%, 55%, 60%, 65%, 70%, 75%, 80%, 85%, 90%, 95%, 98%, or 99% relative to the packaging of the wild-type influenza virus gene segment that the packaging signals are obtained or derived from. In a specific embodiment, a chimeric influenza virus gene segment comprises packaging signals found in the non-coding and coding regions of one type of influenza virus segment that are sufficient to achieve packaging of the chimeric influenza virus gene segment at an efficiency of at least 10%, 15%, 20%, 25%, 30%, 35%, 40%, 45%, 50%, 55%, 60%, 65%, 70%, 75%, 80%, 85%, 90%, 95%, 98%, or 99% relative to the packaging of the wild-type influenza virus gene segment that the packaging signals are obtained or derived from as determined by acrylamide gel electrophoresis of purified vRNA under the same type of assay conditions. In some embodiments, a chimeric influenza virus gene segment comprises packaging signals found in the non-coding and coding regions of one type of influenza virus segment that are sufficient to achieve packaging of the chimeric influenza virus gene segment at an efficiency of 10% to 50%, 10% to 75%, 10% to 90%, 10% to 95%, 10% to 99.5%, 25% to 50%, 25% to 75%, 25% to 90%, 25% to 99.5%, 50% to 75%, 50% to 90%, or 50% to 99.5% relative to the packaging of the wild-type influenza virus gene segment that the packaging signals are obtained or derived from. In a specific embodiment, a chimeric influenza virus gene segment comprises packaging signals found in the non-coding and coding regions of one type of influenza virus segment that are sufficient to achieve packaging of the chimeric influenza virus gene segment at an efficiency of 10% to 50%, 10% to 75%, 10% to 90%, 10% to 95%, 10% to 99.5%, 25% to 50%, 25% to 75%, 25% to 90%, 25% to 99.5%, 50% to 75%, 50% to 90%, or 50% to 99.5% relative to the packaging of the wild-type influenza virus gene segment that the packaging signals are obtained or derived from as determined by acrylamide gel electrophoresis of purified vRNA under the same type of assay conditions. In other embodiments, a chimeric influenza virus gene segment comprises packaging signals found in the non-coding and coding regions of one type of influenza virus segment that are sufficient to achieve packaging of the chimeric influenza virus gene segment at the same efficiency as the packaging of the wild-type influenza virus gene segment that the packaging signals are obtained or derived from. In a specific embodiment, a chimeric influenza virus gene segment comprises packaging signals found in the non-coding and coding regions of one type of influenza virus segment that are sufficient to achieve packaging of the chimeric influenza virus gene segment at the same efficiency as the packaging of the wild-type influenza virus gene segment that the packaging signals are obtained or derived from as determined by acrylamide gel electrophoresis of purified vRNA under the same type of assay conditions. With respect to the acrylamide gel electrophoreis referenced, virus may be purified and RNA isolated and run on a 2.8% denaturing polyacrylamide gel which may then be stained with a silver staining kit (Invitrogen) (see, e.g., Gao et al., 2008 J. Virol. 82: 6419-6426; Gao et al., 2009 PNAS USA 106(37):15891-6; and Example 1 herein for a description of such an assay).

In a specific embodiment, a nucleic acid sequence provided herein comprises or encodes, in the order presented: (a) packaging signals found in the 3' non-coding region of a first type of influenza virus gene segment or a derivative thereof (referred to herein as the "3' NCR1"), or a complement thereof, (b) packaging signals found in the 3' proximal coding region sequence of the first type of influenza virus gene segment or a derivative thereof (referred to herein as the "3' CRS1"), or a complement thereof, (c) an open reading frame or a fragment thereof from a second, different type of influenza virus gene segment or a derivative thereof, wherein the open reading frame contains one, two, three or more mutations in the influenza virus packaging signals found in the open reading frame (referred to herein as the "mORF"), or a complement thereof, (d) packaging signals found in the 5' proximal coding region sequence of the first type of influenza virus gene segment or a derivative thereof (referred to herein as the "5' CRS1"), or a complement thereof, and (e) packaging signals found in the 5' non-coding region of the first type of influenza virus gene segment or a derivative thereof (referred to herein as the 5' NCR1"), or a complement thereof. The first and second types of influenza virus gene segments refer to two different influenza virus gene segments. In certain embodiments, the 3' and/or the 5' proximal coding region sequences are translated in frame with the open reading frame. In other embodiments, the 3' and the 5' proximal coding region sequences flank the open reading frame and are not translated. In some embodiments, the 3' proximal coding region sequence has been mutated so as to eliminate any start codons and preclude the translation of the 3' proximal coding region sequence. In certain embodiments, the 3' proximal coding region sequence is derived from an influenza virus NS or M gene segment. In a specific embodiment, the 3' proximal coding region sequence is derived from an influenza virus NS gene segment and the 3' proximal coding region has been mutated so as to eliminate the mRNA 5' splice site. In another specific embodiment, the 3' proximal coding region sequence is derived from an influenza virus M gene segment and the 3' proximal coding region has been mutated so as to eliminate the distal 5' splice site. In some embodiments, the 5' proximal coding region sequence has one or more mutations so as to ensure that the 5' proximal coding region sequence is not translated. In a specific embodiment, the mutations introduced into the open reading frame of the influenza virus gene segment are silent mutations.

In one aspect, nucleic acid sequences provided herein may comprise or encode a combination of: (i) the following or the complement thereof from one type of influenza virus gene segment: 5' and 3' non-coding regions and either a 3' proximal coding region sequence with any start codon eliminated so that it is not translated, a 5' proximal coding region sequence that is not translated, or both a 3' proximal coding region sequence with any start codon eliminated so that it is not translated and a 5' proximal coding region sequence that is not translated; and (ii) either at least the 3' proximal 20 nucleotides of an open reading frame from a different type of influenza virus gene segment or the complement thereof with one, two three or more mutations, at least the 5' proximal 30 nucleotides of an open reading frame from a different type of influenza virus gene segment or the complement thereof with one, two, three or more mutations, or both the at least 3' proximal 20 nucleotides of an open reading frame and at least the 5' proximal 30 nucleotides of an open reading frame from a different type of influenza virus gene segment or the complement thereof with one, two, three or more mutations. In certain embodiments, the 3' proximal coding region sequence is derived from an influenza virus NS or M gene segment. In a specific embodiment, the 3' proximal coding region sequence is derived from an influenza virus NS gene segment and the 3' proximal coding region has been mutated so as to eliminate the mRNA 5' splice site. In another specific embodiment, the 3' proximal coding region sequence is derived from an influenza virus M gene segment and the 3' proximal coding region has been mutated so as to eliminate the distal 5' splice site. In some embodiments, such nucleic acid sequences may be used as a template to engineer in a nucleotide sequence (e.g., a heterologous nucleotide sequence) which is in frame with the 3' proximal 20 nucleotides and/or the 5' proximal 30 nucleotides of the open reading frame from the different type of influenza virus gene segment. In other words, a template chimeric influenza virus gene segment or complement thereof, or a nucleic acid encoding the gene segment or complement thereof may be used as a basis to incorporate a nucleotide sequence (e.g., a heterologous nucleotide sequence) in frame with the 3' and/or 5' proximal nucleotides of the open reading frame of the different type of influenza virus gene segment so that the entire chimeric influenza virus gene segment or complement thereof, or nucleic acid encoding the same does not need to be generated each and every time. The chimeric influenza virus gene segment or complement thereof, or a nucleic acid encoding the gene segment or complement thereof may contain one, two or more restriction enzyme sites that would enable the incorporation of a heterologous nucleotide sequence in frame with the 3' and/or 5' proximal nucleotides of the open reading frame of the different type of influenza virus gene segment. In a specific embodiment, the heterologous nucleotide sequence comprises or encodes coding sequence from a different influenza virus type or strain, or the complement thereof.

In one embodiment, a nucleic acid sequence provided herein is a chimeric influenza virus gene segment that comprises:
- a 3' NCR1 which comprises or consists of a 3' non-coding region (NCR) of a first type of influenza virus gene segment or a fragment thereof, or a nucleotide sequence that is at least 50% (in some embodiments, at least 60%, at least 65%, at least 70%, at least 75%, at least 80%, at least 85%, at least 90%, at least 95%, or at least 98%) identical to a 3' NCR of a first type of influenza virus gene segment or a fragment thereof, or a nucleotide sequence that hybridizes under stringent conditions to a 3' NCR of a first of type influenza virus gene segment or a fragment thereof;
- (ii) a 3' CRS1 which comprises or consists of a 3' proximal coding region sequence of the first type of influenza virus gene segment, or a nucleotide sequence that is at least 50% (in some embodiments, at least 60%, at least 65%, at least 70%, at least 75%, at least 80%, at least 85%, at least 90%, at least 95%, or at least 98%) identical to a 3' proximal coding region sequence of the first type of influenza virus gene segment, or a nucleotide sequence that hybridizes under stringent conditions to a 3' proximal coding region sequence of the first type of influenza virus gene segment, wherein any start codon present in the sequence in (ii) has been eliminated;
- (iii) a mORF which comprises or consists of (a) at least the 3' proximal 20 nucleotides of an open reading frame of a second type of influenza virus gene segment, or an open reading frame comprising at least the 3' proximal 20 nucleotides of an open reading frame of a second type of influenza virus gene segment and a heterologous nucleotide sequence, wherein at least 1, 2, 3, 4, 5, 6, 7, 8, 9, 10, 11, 12, 13, 14, 15, 16, 17, 18, 19 or 20 of the 3' proximal nucleotides of the open reading frame of the second type of influenza virus gene segment have been mutated, and/or (b) at least the 5' proximal 30 nucleotides of an open reading frame of a second type of influenza virus gene segment, or an open reading frame comprising at least the 5' proximal 30 nucleotides of an open reading frame of a second type of influenza virus gene segment and a heterologous nucleotide sequence, wherein at least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 of the 5' proximal nucleotides of the open reading frame of the second type of influenza virus gene segment have been mutated; and
- (iv) a 5' NCR1 which comprises or consists of a 5' NCR of the first type of influenza virus gene segment or a fragment thereof, or a nucleotide sequence that is at least 50% (in some embodiments, at least 60%, at least 65%, at least 70%, at least 75%, at least 80%, at least 85%, at least 90%, at least 95%, or at least 98%) identical to a 5' NCR of the first type of influenza virus gene segment or a fragment thereof, or a nucleotide sequence that hybridizes under stringent conditions to a 5' NCR of the first type of influenza virus gene segment or a fragment thereof.

The first and second types of influenza virus gene segments may refer to any two influenza virus gene segments of hemagglutinin (HA), neuraminidase (NA; for influenza A and B viruses), M, NS, PA, PB1, PB2, and NP. For example, the first type of influenza virus gene segment may be an influenza virus HA gene segment and the second type of influenza virus gene segment may be an influenza virus NS gene segment. In a specific embodiment, the mutations introduced into the 3' and/or 5' proximal nucleotides of the open reading frame of the second influenza virus gene segment are silent mutations. In certain embodiments, no additional nucleotides are inserted between (i) to (v). In certain embodiments, the 3'CRS1 is derived from an influenza virus NS or M gene segment. In a specific embodiment, the 3'CRS1 is derived from an influenza virus NS gene segment and the 3'CRS1 has been mutated so as to eliminate the mRNA 5' splice site. In another specific embodiment, the 3'CRS1 is derived from an influenza virus M gene segment and the 3'CRS1 has been mutated so as to eliminate the distal 5' splice site.

In another embodiment, a nucleic acid sequence provided herein is a chimeric influenza virus gene segment that comprises:
- (i) a 3' NCR1 which comprises or consists of a 3' NCR of a first type of influenza virus gene segment or a fragment thereof, or a nucleotide sequence that is at least 50% (in some embodiments, at least 60%, at least 65%, at least 70%, at least 75%, at least 80%, at least 85%, at least 90%, at least 95%, or at least 98%) identical to a 3' NCR of a first type of influenza virus gene segment or a fragment thereof, or a nucleotide sequence that hybridizes under stringent conditions to a 3' NCR of a first type of influenza virus gene segment or a fragment thereof;
- (ii) a mORF which comprises or consists of (a) at least the 3' proximal 20 nucleotides of an open reading frame of a second type of influenza virus gene segment, or an open reading frame comprising at least the 3' proximal 20 nucleotides of an open reading frame of a second type of influenza virus gene segment and a heterologous nucleotide sequence, wherein at least 1, 2, 3, 4, 5, 6, 7, 8, 9, 10, 11, 12, 13, 14, 15, 16, 17, 18, 19 or 20 of the 3' proximal nucleotides of the open reading frame of the second type of influenza virus gene segment have been mutated, and/or (b) at least the 5' proximal 30 nucleotides of an open reading frame of a second type of influenza virus gene segment, or an open reading frame comprising at least the 5' proximal 30 nucleotides of an open reading frame of a second type of influenza virus gene segment and a heterologous nucleotide sequence, wherein at least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 of the 5' proximal nucleotides of the open reading frame of the second type of influenza virus gene segment have been mutated;
- (iii) a 5' CRS1 which comprises or consists of a 5' proximal coding region sequence of the first type of influenza virus gene segment, or a nucleotide sequence that is at least 50% (in some embodiments, at least 60%, at least 65%, at least 70%, at least 75%, at least 80%, at least 85%, at least 90%, at least 95%, or at least 98%) identical to a 5' proximal coding region sequence of the first type of influenza virus gene segment, or a nucleotide sequence that hybridizes under stringent conditions to a 5' proximal coding region sequence of the first type of influenza virus gene segment, wherein the sequence in (iv) is not translated; and (iv) a 5' NCR1 which comprises or consists of a 5' NCR of the first type of influenza virus gene segment or a fragment thereof, or a nucleotide sequence that is at least 50% (in some embodiments, at least 60%, at least 65%, at least 70%, at least 75%, at least 80%, at least 85%, at least 90%, at least 95%, or at least 98%) identical to a 5' NCR of the first type of influenza virus gene segment or a fragment thereof, or a nucleotide sequence that hybridizes under stringent conditions to a 5' NCR of the first type of influenza virus gene segment or a fragment thereof.

The first and second types of influenza virus gene segments may refer to any two influenza virus gene segments of HA, NA (for influenza A and B viruses), M, NS, PA, PB1, PB2, and NP. For example, the first type of influenza virus gene segment may be an influenza virus HA gene segment and the second type of influenza virus gene segment may be an influenza virus NS gene segment. In a specific embodiment, the mutations introduced into the 3' and 5' proximal nucleotides of the open reading frame of the second influenza virus gene segment are silent mutations. In certain embodiments, no additional nucleotides are inserted between (i) to (v). In certain embodiments, the 3'CRS1 is derived from an influenza virus NS or M gene segment. In a specific embodiment, the 3'CRS1 is derived from an influenza virus NS gene segment and the 3'CRS1 has been mutated so as to eliminate the mRNA 5' splice site. In another specific embodiment, the 3'CRS1 is derived from an influenza virus M gene segment and the 3'CRS1 has been mutated so as to eliminate the distal 5' splice site.

In a specific embodiment, a nucleic acid sequence provided herein is a chimeric influenza virus gene segment that comprises:

(i) a 3' NCR1 which comprises or consists of a 3' NCR of a first type of influenza virus gene segment or a fragment thereof, or a nucleotide sequence that is at least 50% (in some embodiments, at least 60%, at least 65%, at least 70%, at least 75%, at least 80%, at least 85%, at least 90%, at least 95%, or at least 98%) identical to a 3' NCR of a first type of influenza virus gene segment or a fragment thereof, or a nucleotide sequence that hybridizes under stringent conditions to a 3' NCR of a first type of influenza virus gene segment or a fragment thereof;

(ii) a 3' CRS1 which comprises or consists of a 3' proximal coding region sequence of the first type of influenza virus gene segment, or a nucleotide sequence that is at least 50% (in some embodiments, at least 60%, at least 65%, at least 70%, at least 75%, at least 80%, at least 85%, at least 90%, at least 95%, or at least 98%) identical to a 3' proximal coding region sequence of the first type of influenza virus gene segment, or a nucleotide sequence that hybridizes under stringent conditions to a 3' proximal coding region sequence of the first type of influenza virus gene segment, wherein any start codon present in the sequence in (ii) has been eliminated;

(iii) a mORF which comprises or consists of (a) at least the 3' proximal 20 nucleotides of an open reading frame of a second type of influenza virus gene segment, or an open reading frame comprising at least the 3' proximal 20 nucleotides of an open reading frame of a second type of influenza virus gene segment and a heterologous nucleotide sequence, wherein the at least 1, 2, 3, 4, 5, 6, 7, 8, 9, 10, 11, 12, 13, 14, 15, 16, 17, 18, 19 or 20 of the 3' proximal nucleotides of the open reading frame of the second type of influenza virus gene segment have been mutated, and/or (b) at least the 5' proximal 30 nucleotides of an open reading frame of a second type of influenza virus gene segment, or an open reading frame comprising at least the 5' proximal 30 nucleotides of an open reading frame of a second type of influenza virus gene segment and a heterologous nucleotide sequence, wherein the at least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 of the 5' proximal nucleotides of the open reading frame of the second type of influenza virus gene segment have been mutated;

(iv) a 5' CRS1 which comprises or consists of a 5' proximal coding region sequence of the first type of influenza virus gene segment, or a nucleotide sequence that is at least 50% (in some embodiments, at least 60%, at least 65%, at least 70%, at least 75%, at least 80%, at least 85%, at least 90%, at least 95%, or at least 98%) identical to a 5' proximal coding region sequence of the first type of influenza virus gene segment, or a nucleotide sequence that hybridizes under stringent conditions to a 5' proximal coding region sequence of the first type of influenza virus gene segment, wherein the sequence in (iv) is not translated; and (v) a 5' NCR1 which comprises or consists of a 5' NCR of the first type of influenza virus gene segment or a fragment thereof, or a nucleotide sequence that is at least 50% (in some embodiments, at least 60%, at least 65%, at least 70%, at least 75%, at least 80%, at least 85%, at least 90%, at least 95%, or at least 98%) identical to a 5' NCR of the first type of influenza virus gene segment or a fragment thereof, or a nucleotide sequence that hybridizes under stringent conditions to a 5' NCR of the first type of influenza virus gene segment or a fragment thereof.

The first and second types of influenza virus gene segments may refer to any two influenza virus gene segments of HA, NA (for influenza A and B viruses), M, NS, PA, PB1, PB2, and NP. For example, the first type of influenza virus gene segment may be an influenza virus HA gene segment and the second type of influenza virus gene segment may be an influenza virus NS gene segment. In a specific embodiment, the mutations introduced into the 3' and 5' proximal nucleotides of the open reading frame of the second influenza virus gene segment are silent mutations. In certain embodiments, no additional nucleotides are inserted between (i) to (v). In certain embodiments, the 3'CRS1 is derived from an influenza virus NS or M gene segment. In a specific embodiment, the 3'CRS1 is derived from an influenza virus NS gene segment and the 3'CRS1 has been mutated so as to eliminate the mRNA 5' splice site. In another specific embodiment, the 3'CRS1 is derived from an influenza virus M gene segment and the 3'CRS1 has been mutated so as to eliminate the distal 5' splice site.

In another embodiment, a nucleic acid sequence provided herein is a chimeric influenza virus gene segment that comprises:

(i) a 3' NCR1 which comprises or consists of a 3' NCR of a first type of influenza virus gene segment or a fragment thereof, or a nucleotide sequence that is at least 50% (in some embodiments, at least 60%, at least 65%, at least 70%, at least 75%, at least 80%, at least 85%, at least 90%, at least 95%, or at least 98%) identical to a 3' NCR of a first type of influenza virus gene segment or a fragment thereof, or a nucleotide sequence that hybridizes under stringent conditions to a 3' NCR of a first type of influenza virus gene segment or a fragment thereof;

(ii) a 3' CRS1 which comprises or consists of a 3' proximal coding region sequence of the first type of influenza virus gene segment, or a nucleotide sequence that is at least 50% (in some embodiments, at least 60%, at least 65%, at least 70%, at least 75%, at least 80%, at least 85%, at least 90%, at least 95%, or at least 98%) identical to a 3' proximal coding region sequence of the first type of influenza virus gene segment, or a nucleotide sequence that hybridizes under stringent conditions to a 3' proximal coding region sequence of the first type of influenza virus gene segment, wherein any start codon present in the sequence in (ii) has been eliminated;

(iii) a mORF which comprises or consists of an open reading frame of a second type of influenza virus gene segment, or an open reading frame comprising an open reading frame of a second type of influenza virus gene segment and a heterologous nucleotide sequence, wherein 3' and 5' proximal nucleotides of the open reading frame of the second type of influenza virus gene segment have been mutated; and (iv) a 5' NCR1 which comprises or consists of a 5' NCR of the first type of influenza virus gene segment or a fragment thereof, or a nucleotide sequence that is at least 50% (in some embodiments, at least 60%, at least 65%, at least 70%, at least 75%, at least 80%, at least 85%, at least 90%, at least 95%, or at least 98%) identical to a 5' NCR of the first type of influenza virus gene segment or a fragment thereof, or a nucleotide sequence that hybridizes under stringent conditions to a 5' NCR of the first type of influenza virus gene segment or a fragment thereof.

The first and second types of influenza virus gene segments may refer to any two influenza virus gene segments of HA, NA (for influenza A and B viruses), M, NS, PA, PB1, PB2, and NP. For example, the first type of influenza virus gene segment may be an influenza virus HA gene segment and the second type of influenza virus gene segment may be an influenza virus NS gene segment. In a specific embodiment, the mutations introduced into the 3' and 5' proximal nucleotides of the open reading frame of the second influenza virus gene segment are silent mutations. In certain embodiments, no additional nucleotides are inserted between (i) to (v). In certain embodiments, the 3'CRS1 is derived from an influenza virus NS or M gene segment. In a specific embodiment, the 3'CRS1 is derived from an influenza virus NS gene segment and the 3'CRS1 has been mutated so as to eliminate the mRNA 5' splice site. In another specific embodiment, the 3'CRS1 is derived from an influenza virus M gene segment and the 3'CRS1 has been mutated so as to eliminate the distal 5' splice site.

In another embodiment, a nucleic acid sequence provided herein is a chimeric influenza virus gene segment that comprises:

(i) a 3' NCR1 which comprises or consists of a 3' non-coding region (NCR) of a first type of influenza virus gene segment or a fragment thereof, or a nucleotide sequence that is at least 50% (in some embodiments, at least 60%, at least 65%, at least 70%, at least 75%, at least 80%, at least 85%, at least 90%, at least 95%, or at least 98%) identical to a 3' NCR of a first type of influenza virus gene segment or a fragment thereof, or a nucleotide sequence that hybridizes under stringent conditions to a 3' NCR of a first type of influenza virus gene segment or a fragment thereof;

(ii) a mORF which comprises or consists of an open reading frame of a second type of influenza virus gene segment, or an open reading frame comprising an open reading frame of a second type of influenza virus gene segment and a heterologous nucleotide sequence, wherein 3' and 5' proximal nucleotides of the open reading frame of the second type of influenza virus gene segment have been mutated;

(iii) a 5' CRS1 which comprises or consists of a 5' proximal coding region sequence of the first type of influenza virus gene segment, or a nucleotide sequence that is at least 50% (in some embodiments, at least 60%, at least 65%, at least 70%, at least 75%, at least 80%, at least 85%, at least 90%, at least 95%, or at least 98%) identical to a 5' proximal coding region sequence of the first type of influenza virus gene segment, or a nucleotide sequence that hybridizes under stringent conditions to a 5' proximal coding region sequence of the first type of influenza virus gene segment, wherein the sequence in (iv) is not translated; and (iv) a 5' NCR1 which comprises or consists of a 5' NCR of the first type of influenza virus gene segment or a fragment thereof, or a nucleotide sequence that is at least 50% (in some embodiments, at least 60%, at least 65%, at least 70%, at least 75%, at least 80%, at least 85%, at least 90%, at least 95%, or at least 98%) identical to a 5' NCR of the first type of influenza virus gene segment or a fragment thereof, or a nucleotide sequence that hybridizes under stringent conditions to a 5' NCR of the first type of influenza virus gene segment or a fragment thereof.

The first and second types of influenza virus gene segments may refer to any two influenza virus gene segments of HA, NA (for influenza A and B viruses), M, NS, PA, PB1, PB2, and NP. For example, the first type of influenza virus gene segment may be an influenza virus HA gene segment and the second type of influenza virus gene segment may be an influenza virus NS gene segment. In a specific embodiment, the mutations introduced into the 3' and 5' proximal nucleotides of the open reading frame of the second influenza virus gene segment are silent mutations. In certain embodiments, no additional nucleotides are inserted between (i) to (v). In certain embodiments, the 3'CRS1 is derived from an influenza virus NS or M gene segment. In a specific embodiment, the 3'CRS1 is derived from an influenza virus NS gene segment and the 3'CRS1 has been mutated so as to eliminate the mRNA 5' splice site. In another specific embodiment, the 3'CRS1 is derived from an influenza virus M gene segment and the 3'CRS1 has been mutated so as to eliminate the distal 5' splice site.

In a specific embodiment, a nucleic acid sequence provided herein is a chimeric influenza virus gene segment that comprises:

(i) a 3' NCR1 which comprises or consists of a 3' NCR of a first type of influenza virus gene segment or a fragment thereof, or a nucleotide sequence that is at least 50% (in some embodiments, at least 60%, at least 65%, at least 70%, at least 75%, at least 80%, at least 85%, at least 90%, at least 95%, or at least 98%) identical to a 3' NCR of a first type of influenza virus gene segment or a fragment thereof, or a nucleotide sequence that hybridizes under stringent conditions to a 3' NCR of a first type of influenza virus gene segment or a fragment thereof;

(ii) a 3' CRS1 which comprises or consists of a 3' proximal coding region sequence of the first type of influenza virus gene segment, or a nucleotide sequence that is at least 50% (in some embodiments, at least 60%, at least 65%, at least 70%, at least 75%, at least 80%, at least 85%, at least 90%, at least 95%, or at least 98%) identical to a 3' proximal coding region sequence of the first type of influenza virus gene segment, or a nucleotide sequence that hybridizes under stringent conditions to a 3' proximal coding region sequence of the first type of influenza virus gene segment, wherein any start codon present in the sequence in (ii) has been eliminated;

(iii) a mORF which comprises or consists of an open reading frame of a second type of influenza virus gene segment, or an open reading frame comprising an open reading frame of a second type of influenza virus gene segment and a heterologous nucleotide sequence, wherein 3' and 5' proximal nucleotides of the open reading frame of the second type of influenza virus gene segment have been mutated;

(iv) a 5' CRS1 which comprises or consists of a 5' proximal coding region sequence of the first type of influenza virus gene segment, or a nucleotide sequence that is at least 50% (in some embodiments, at least 60%, at least 65%, at least 70%, at least 75%, at least 80%, at least 85%, at least 90%, at least 95%, or at least 98%) identical to a 5' proximal coding region sequence of the first type of influenza virus gene segment, or a nucleotide sequence that hybridizes under stringent conditions to a 5' proximal coding region sequence of the first type of influenza virus gene segment, wherein the sequence in (iv) is not translated; and (v) a 5' NCR1 which comprises or consists of a 5' NCR of the first type of influenza virus gene segment or a fragment thereof, or a nucleotide sequence that is at least 50% (in some embodiments, at least 60%, at least 65%, at least 70%, at least 75%, at least 80%, at least 85%, at least 90%, at least 95%, or at least 98%) identical to a 5' NCR of the first type of influenza virus gene segment or a fragment thereof, or a nucleotide sequence that hybridizes under stringent conditions to a 5' NCR of the first type of influenza virus gene segment or a fragment thereof.

The first and second types of influenza virus gene segments may refer to any two influenza virus gene segments of HA, NA (for influenza A and B viruses), M, NS, PA, PB1, PB2, and NP. For example, the first type of influenza virus gene segment may be an influenza virus HA gene segment and the second type of influenza virus gene segment may be an influenza virus NS gene segment. In a specific embodiment, the mutations introduced into the 3' and 5' proximal nucleotides of the open reading frame of the second influenza virus gene segment are silent mutations. In certain embodiments, no additional nucleotides are inserted between (i) to (v). In certain embodiments, the 3'CRS1 is derived from an influenza virus NS or M gene segment. In a specific embodiment, the 3'CRS1 is derived from an influenza virus NS gene segment and the 3'CRS1 has been mutated so as to eliminate the mRNA 5' splice site. In another specific embodiment, the 3'CRS1 is derived from an influenza virus M gene segment and the 3'CRS1 has been mutated so as to eliminate the distal 5' splice site.

The chimeric influenza virus gene segments described herein may be a chimeric of coding and non-coding regions of any two influenza virus gene segments of HA, NA (for influenza A and B viruses), M, NS, PA, PB1, PB2, and NP or derivatives thereof. The coding and non-coding regions that make up a chimeric influenza virus gene segment may be obtained or derived from the same type of influenza virus or the same strain of influenza virus. The coding and non-coding regions that make up a chimeric influenza virus gene segment may also be obtained or derived from different types of influenza viruses, different subtypes of influenza viruses or different strains of influenza virus. The coding and non-coding regions that make up a chimeric influenza virus gene segment may be obtained or derived from a seasonal or pandemic strain of influenza virus.

In one embodiment, the coding and non-coding regions that make up a chimeric influenza virus gene segment are obtained or derived from an influenza A virus (see Section 5.2, infra, for examples of influenza A viruses). In another embodiment, the coding and non-regions that make up a chimeric influenza virus gene segment are obtained or derived from the same strain of an influenza A virus. In another embodiment, the coding and non-coding regions that make up a chimeric influenza virus gene segment are obtained or derived from the same HA and/or NA subtype. For example, the coding and non-coding regions may be from an influenza A virus of the H1N1 subtype.

In a specific embodiment, the 3' and/or 5' NCR from an influenza A virus, influenza B virus, or influenza C virus is of the same strain or subtype; and/or the 3' and/or 5' proximal coding region sequence from an influenza A virus, influenza B virus, or influenza C virus is of the same strain or subtype.

In another embodiment, the coding and non-coding regions that make up a chimeric influenza virus gene segment are obtained or derived from an influenza B virus (see Section 5.2, infra, for examples of influenza B viruses). In another embodiment, the coding and non-regions that make up a chimeric influenza virus gene segment are obtained or derived from the same strain of an influenza B virus. In another embodiment, the coding and non-coding regions that make up a chimeric influenza virus gene segment are obtained or derived from an influenza C virus (see Section 5.2, infra, for examples of influenza C viruses). In another embodiment, the coding and non-regions that make up a chimeric influenza virus gene segment are obtained derived from the same strain of an influenza C virus.

The nucleic acid sequences provided herein may be in the form of a genomic (i.e., negative sense RNA) or antigenomic (i.e., positive sense RNA) segment. The nucleic acid sequences provided herein may also encode a chimeric influenza virus gene segment or the complement thereof. In one embodiment, a nucleic acid sequence provided herein is a chimeric influenza virus gene segment. In another embodiment, a nucleic acid sequence provided herein comprises the complement of a chimeric influenza virus gene segment described herein. In another embodiment, a nucleic acid sequence provided herein encodes a chimeric influenza virus gene segment described herein or the complement thereof.

In certain embodiments, a nucleic acid sequence that encodes a chimeric influenza virus gene segment described herein or the complement thereof is bicistronic and permits the expression of two sequences. In other words, the nucleic acid sequence encodes for an mORF and another open reading frame (e.g., an open reading frame encoding a heterologous protein). In one embodiment, such a nucleic acid sequence comprises an internal ribosomal entry site (IRES) after the mORF and before the other open reading frame.

In certain embodiments, a nucleic acid sequence that encodes a chimeric influenza virus gene segment described herein or the complement thereof comprises a promoter. Specific examples of promoters include an RNA polymerase I promoter, an RNA polymerase II promoter, an RNA polymerase III promoter, a T7 promoter and a T3 promoter. In a specific embodiment, a nucleic acid sequence that encodes a chimeric influenza virus gene segment or the complement thereof comprises a human RNA polymerase I promoter. In certain embodiments, a nucleic acid sequence that encodes a chimeric influenza virus gene segment described herein or the complement thereof comprises a transcription termination sequence. Specific examples of transcription termination sequences include an RNA polymerase I terminator sequence, an RNA polymerase II terminator sequence, or an RNA polymerase III terminator sequence. In some embodiments, a nucleic acid sequence that encodes a chimeric influenza virus gene segment described herein or the complement thereof comprises a ribozyme recognition sequence. In a specific embodiment, a nucleic acid sequence that encodes a chimeric influenza virus gene segment described herein or the complement thereof comprises an RNA polymerase I promoter sequence and an RNA polymerase I terminator sequence. In certain embodiments, a nucleic acid sequence that encodes a chimeric influenza virus gene segment or the complement thereof comprises an RNA polymerase I promoter, an RNA polymerase I termination sequence, an RNA polymerase II promoter, and a polyadenylation signal.

In certain embodiments, a nucleic acid sequence described herein is part of or incorporated into a vector. In a specific embodiment, a nucleic acid sequence described herein is part of or incorporated into a vector that facilitates the production of a chimeric influenza virus gene segment or the complement thereof. In one embodiment, a nucleic acid sequence described herein is part of or incorporated into the pDZ vector (see, e.g., Quinlivan et al., 2005, J. of Virology 79: 8431-8439 for information relating to the pDZ vector). In another embodiment, a nucleic acid sequence described herein is part of or incorporated into the pHW2000 vector (see, e.g., Hoffmann et al., 2000, Proc Natl Acad Sci USA. 97(11):6108-13 for information relating to the pHW2000 vector). In another embodiment, a nucleic acid sequence described herein is part of or incorporated into the pAD3000 vector (see, e.g., Hoffmann et al., 2000, Proc Natl Acad Sci USA. 97(11):6108-13 for information relating to the pAD3000 vector). In another embodiment, a nucleic acid sequence described herein is part of or incorporated into the pAD4000 vector (see, e.g., Wang et al., 2007, J. of Virology 4: 102 for information relating to the pAD4000 vector).

In some embodiments, a nucleic acid sequence described herein is introduced (e.g., transfected) into a substrate, such as a host cell or an embryonated egg. Thus, in some embodiments, provided herein is a substrate (e.g., host cells or eggs) comprising a nucleic acid sequence described herein. In other embodiments, a nucleic acid sequence described herein is part of or incorporated into a vector is introduced (e.g., transfected) into a substrate, such as a host cell or an embryonated egg. Thus, in some embodiments, provided herein is a substrate (e.g., host cells or eggs) comprising a nucleic acid sequence described herein that is part of or incorporated into a vector. Host cells and embryonated eggs are known in the art and examples are provided herein, e.g., in Section 5.4, infra.

In certain embodiments, a nucleic acid described herein is propagated in an influenza virus. In certain embodiments, a group of cosegregating chimeric influenza virus gene segments (see Section 5.2, entitled Influenza Virus Comprising Chimeric Influenza Virus Gene Segment) is propagated in an influenza virus.

In specific aspects, multiple chimeric influenza virus gene segments may be produced. Influenza A virus has a total of eight (8) gene segments and a chimeric of two, three, four, five, six, seven or all eight gene segments may be produced. Influenza B virus has a total of eight (8) gene segments and a chimeric of two, three, four, five, six, seven or all eight gene segments may be produced. Influenza C virus has a total of seven (7) gene segments and a chimeric of two, three, four, five, six or all seven gene segments may be produced. In a specific embodiment, two or more chimeric influenza virus gene segments are produced. By way of example and not limitation, two chimeric influenza virus gene segments may be produced, wherein (a) the first chimeric influenza virus gene segment comprises:
  (i) a 3' NCR of a first type of influenza virus gene segment or a fragment thereof, or a nucleotide sequence that is at least 50% (in some embodiments, at least 60%, at least 65%, at least 70%, at least 75%, at least 80%, at least 85%, at least 90%, at least 95%, or at least 98%) identical to a 3' NCR of a first type of influenza virus gene segment or a fragment thereof, or a nucleotide sequence that hybridizes under stringent conditions to a 3' NCR of a first type of influenza virus gene segment or a fragment thereof;
  (ii) a 3' proximal coding region sequence of the first type of influenza virus gene segment, or a nucleotide sequence that is at least 50% (in some embodiments, at least 60%, at least 65%, at least 70%, at least 75%, at least 80%, at least 85%, at least 90%, at least 95%, or at least 98%) identical to a 3' proximal coding region sequence of the first type of influenza virus gene segment, or a nucleotide sequence that hybridizes under stringent conditions to a 3' proximal coding region sequence of the first type of influenza virus gene segment, wherein any start codon present in the sequence in (ii) has been eliminated;
  (iii) an open reading frame of a second influenza virus gene segment, or an open reading frame comprising an open reading frame of a second type of influenza virus gene segment and a heterologous nucleotide sequence, wherein 3' and 5' proximal nucleotides of the open reading frame of the second type of influenza virus gene segment have been mutated;
  (iv) a 5' proximal coding region sequence of the first type of influenza virus gene segment, or a nucleotide sequence that is at least 50% (in some embodiments, at least 60%, at least 65%, at least 70%, at least 75%, at least 80%, at least 85%, at least 90%, at least 95%, or at least 98%) identical to a 5' proximal coding region sequence of the first type of influenza virus gene segment, or a nucleotide sequence that hybridizes under stringent conditions to a 5' proximal coding region sequence of the first type of influenza virus gene segment, wherein the sequence in (iv) is not translated; and
  (v) a 5' NCR of the first type of influenza virus gene segment or a fragment thereof, or a nucleotide sequence that is at least 50% (in some embodiments, at least 60%, at least 65%, at least 70%, at least 75%, at least 80%, at least 85%, at least 90%, at least 95%, or at least 98%) identical to a 5' NCR of the first type of influenza virus gene segment or a fragment thereof, or a nucleotide sequence that hybridizes under stringent conditions to a 5' NCR of the first type of influenza virus gene segment or a fragment thereof; and wherein (b) the second chimeric influenza virus gene segment comprises:
  (i) a 3' NCR of the second type of influenza virus gene segment or a fragment thereof, or a nucleotide sequence that is at least 50% (in some embodiments, at least 60%, at least 65%, at least 70%, at least 75%, at least 80%, at least 85%, at least 90%, at least 95%, or at least 98%) identical to a 3' NCR of the second type of influenza virus gene segment or a fragment thereof, or a nucleotide sequence that hybridizes under stringent conditions to a 3' NCR of the second type of influenza virus gene segment or a fragment thereof;

(ii) a 3' proximal coding region sequence of the second type of influenza virus gene segment, or a nucleotide sequence that is at least 50% (in some embodiments, at least 60%, at least 65%, at least 70%, at least 75%, at least 80%, at least 85%, at least 90%, at least 95%, or at least 98%) identical to a 3' proximal coding region sequence of the second type of influenza virus gene segment, or a nucleotide sequence that hybridizes under stringent conditions to a 3' proximal coding region sequence of the second type of influenza virus gene segment, wherein any start codon present in the sequence in (ii) has been eliminated;

(iii) an open reading frame of the first type of influenza virus gene segment, or an open reading frame comprising an open reading frame of the first type of influenza virus gene segment and a heterologous nucleotide sequence, wherein 3' and 5' proximal nucleotides of the open reading frame of the first type of influenza virus gene segment have been mutated;

(iv) a 5' proximal coding region sequence of the second type of influenza virus gene segment, or a nucleotide sequence that is at least 50% (in some embodiments, at least 60%, at least 65%, at least 70%, at least 75%, at least 80%, at least 85%, at least 90%, at least 95%, or at least 98%) identical to a 5' proximal coding region sequence of the second type of influenza virus gene segment, or a nucleotide sequence that hybridizes under stringent conditions to a 5' proximal coding region sequence of the second type of influenza virus gene segment, wherein the sequence in (iv) is not translated; and (v) a 5' NCR of the second type of influenza virus gene segment or a fragment thereof, or a nucleotide sequence that is at least 50% (in some embodiments, at least 60%, at least 65%, at least 70%, at least 75%, at least 80%, at least 85%, at least 90%, at least 95%, or at least 98%) identical to a 5' NCR of the second type of influenza virus gene segment or a fragment thereof, or a nucleotide sequence that hybridizes under stringent conditions to a 5' NCR of the second type of influenza virus gene segment or a fragment thereof.

In certain embodiments, the 3' proximal coding region sequence is derived from an influenza virus NS or M gene segment. In a specific embodiment, the 3' proximal coding region sequence is derived from an influenza virus NS gene segment and the 3' proximal coding region has been mutated so as to eliminate the mRNA 5' splice site. In another specific embodiment, the 3' proximal coding region sequence is derived from an influenza virus M gene segment and the 3' proximal coding region has been mutated so as to eliminate the distal 5' splice site.

In another specific embodiment, three or more chimeric influenza virus gene segments are produced. By way of example and not limitation, three chimeric influenza virus gene segments may be produced, wherein (a) the first chimeric influenza virus gene segment comprises:

(i) a 3' NCR of a first type of influenza virus gene segment or a fragment thereof, or a nucleotide sequence that is at least 50% (in some embodiments, at least 60%, at least 65%, at least 70%, at least 75%, at least 80%, at least 85%, at least 90%, at least 95%, or at least 98%) identical to a 3' NCR of a first type of influenza virus gene segment or a fragment thereof, or a nucleotide sequence that hybridizes under stringent conditions to a 3' NCR of a first type of influenza virus gene segment or a fragment thereof;

(ii) a 3' proximal coding region sequence of the first type of influenza virus gene segment, or a nucleotide sequence that is at least 50% (in some embodiments, at least 60%, at least 65%, at least 70%, at least 75%, at least 80%, at least 85%, at least 90%, at least 95%, or at least 98%) identical to a 3' proximal coding region sequence of the first type of influenza virus gene segment, or a nucleotide sequence that hybridizes under stringent conditions to a 3' proximal coding region sequence of the first type of influenza virus gene segment, wherein any start codon present in the sequence in (ii) has been eliminated;

(iii) an open reading frame of a third type of influenza virus gene segment, or an open reading frame comprising an open reading frame of a third type of influenza virus gene segment and a heterologous nucleotide sequence, wherein 3' and 5' proximal nucleotides of the open reading frame of the third type of influenza virus gene segment have been mutated;

(iv) a 5' proximal coding region sequence of the first type of influenza virus gene segment, or a nucleotide sequence that is at least 50% (in some embodiments, at least 60%, at least 65%, at least 70%, at least 75%, at least 80%, at least 85%, at least 90%, at least 95%, or at least 98%) identical to a 5' proximal coding region sequence of the first type of influenza virus gene segment, or a nucleotide sequence that hybridizes under stringent conditions to a 5' proximal coding region sequence of the first type of influenza virus gene segment, wherein the sequence in (iv) is not translated; and (v) a 5' NCR of the first type of influenza virus gene segment or a fragment thereof, or a nucleotide sequence that is at least 50% (in some embodiments, at least 60%, at least 65%, at least 70%, at least 75%, at least 80%, at least 85%, at least 90%, at least 95%, or at least 98%) identical to a 5' NCR of the first type of influenza virus gene segment or a fragment thereof, or a nucleotide sequence that hybridizes under stringent conditions to a 5' NCR of the first type of influenza virus gene segment or a fragment thereof; and wherein (b) the second chimeric influenza virus gene segment comprises:

(i) a 3' NCR of the second type of influenza virus gene segment or a fragment thereof, or a nucleotide sequence that is at least 50% (in some embodiments, at least 60%, at least 65%, at least 70%, at least 75%, at least 80%, at least 85%, at least 90%, at least 95%, or at least 98%) identical to a 3' NCR of the second type of influenza virus gene segment or a fragment thereof, or a nucleotide sequence that hybridizes under stringent conditions to a 3' NCR of the second type of influenza virus gene segment or a fragment thereof;

(ii) a 3' proximal coding region sequence of the second type of influenza virus gene segment, or a nucleotide sequence that is at least 50% (in some embodiments, at least 60%, at least 65%, at least 70%, at least 75%, at least 80%, at least 85%, at least 90%, at least 95%, or at least 98%) identical to a 3' proximal coding region sequence of the second type of influenza virus gene segment, or a nucleotide sequence that hybridizes under stringent conditions to a 3' proximal coding region sequence of the second type of influenza virus gene segment, wherein any start codon present in the sequence in (ii) has been eliminated;

(iii) an open reading frame of the first type of influenza virus gene segment, or an open reading frame comprising an open reading frame of the first type of influenza virus gene segment and a heterologous nucleotide sequence, wherein 3' and 5' proximal nucleotides of the open reading frame of the first type of influenza virus gene segment have been mutated;

(iv) a 5' proximal coding region sequence of the second type of influenza virus gene segment, or a nucleotide sequence that is at least 50% (in some embodiments, at least 60%, at least 65%, at least 70%, at least 75%, at least 80%, at least 85%, at least 90%, at least 95%, or at least 98%) identical to a 5' proximal coding region sequence of the second type of influenza virus gene segment, or a nucleotide sequence that hybridizes under stringent conditions to a 5' proximal coding region sequence of the second type of influenza virus gene segment, wherein the sequence in (iv) is not translated; and (v) a 5' NCR of the second type of influenza virus gene segment or a fragment thereof, or a nucleotide sequence that is at least 50% (in some embodiments, at least 60%, at least 65%, at least 70%, at least 75%, at least 80%, at least 85%, at least 90%, at least 95%, or at least 98%) identical to a 5' NCR of the second type of influenza virus gene segment or a fragment thereof, or a nucleotide sequence that hybridizes under stringent conditions to a 5' NCR of the second type of influenza virus gene segment or a fragment thereof; wherein (c) the third chimeric influenza virus gene segment comprises:

(i) a 3' NCR of the third type of influenza virus gene segment or a fragment thereof, or a nucleotide sequence that is at least 50% (in some embodiments, at least 60%, at least 65%, at least 70%, at least 75%, at least 80%, at least 85%, at least 90%, at least 95%, or at least 98%) identical to a 3' NCR of the third type of influenza virus gene segment or a fragment thereof, or a nucleotide sequence that hybridizes under stringent conditions to a 3' NCR of the third type of influenza virus gene segment or a fragment thereof;

(ii) a 3' proximal coding region sequence of the third type of influenza virus gene segment, or a nucleotide sequence that is at least 50% (in some embodiments, at least 60%, at least 65%, at least 70%, at least 75%, at least 80%, at least 85%, at least 90%, at least 95%, or at least 98%) identical to a 3' proximal coding region sequence of the third type of influenza virus gene segment, or a nucleotide sequence that hybridizes under stringent conditions to a 3' proximal coding region sequence of the third type of influenza virus gene segment, wherein any start codon present in the sequence in (ii) has been eliminated;

(iii) an open reading frame of the second type of influenza virus gene segment, or an open reading frame comprising an open reading frame of the second type of influenza virus gene segment and a heterologous nucleotide sequence, wherein 3' and 5' proximal nucleotides of the open reading frame of the second type of influenza virus gene segment have been mutated;

(iv) a 5' proximal coding region sequence of the third type of influenza virus gene segment, or a nucleotide sequence that is at least 50% (in some embodiments, at least 60%, at least 65%, at least 70%, at least 75%, at least 80%, at least 85%, at least 90%, at least 95%, or at least 98%) identical to a 5' proximal coding region sequence of the third type of influenza virus gene segment, or a nucleotide sequence that hybridizes under stringent conditions to a 5' proximal coding region sequence of the third type of influenza virus gene segment, wherein the sequence in (iv) is not translated; and (v) a 5' NCR of the third type of influenza virus gene segment or a fragment thereof, or a nucleotide sequence that is at least 50% (in some embodiments, at least 60%, at least 65%, at least 70%, at least 75%, at least 80%, at least 85%, at least 90%, at least 95%, or at least 98%) identical to a 5' NCR of the third type of influenza virus gene segment or a fragment thereof, or a nucleotide sequence that hybridizes under stringent conditions to a 5' NCR of the third type of influenza virus gene segment or a fragment thereof.

In certain embodiments, the 3' proximal coding region sequence is derived from an influenza virus NS or M gene segment. In a specific embodiment, the 3' proximal coding region sequence is derived from an influenza virus NS gene segment and the 3' proximal coding region has been mutated so as to eliminate the mRNA 5' splice site. In another specific embodiment, the 3' proximal coding region sequence is derived from an influenza virus M gene segment and the 3' proximal coding region has been mutated so as to eliminate the distal 5' splice site.

Techniques for the production or use of the nucleic acids will employ, unless otherwise indicated, routine conventional techniques of molecular biology and recombinant DNA manipulation and production. Any cloning technique known to the skilled artisan can be used to assemble the nucleic acids described herein and to mutate nucleotides where necessary. Such techniques are well-known and are available to the skilled artisan in laboratory manuals such as Sambrook and Russell, Molecular Cloning: A Laboratory Manual, $3^{rd}$ edition, Cold Spring Harbor Laboratory Press, Cold Spring Harbor, N.Y. (2001). In particular, polymerase chain reaction, restriction enzymes, ligase enzyme, mutagenic primers, and amplification of nucleic acid fragments in vectors can be used to generate the individual elements of the nucleic acids described herein and then to assemble them.

5.1.1. Influenza Virus Noncoding Regions

The chimeric influenza virus gene segments described herein comprise a 3' NCR1 and a 5' NCR1. A 3' NCR1 comprises or consists of packaging signals found in the 3' non-coding region an influenza virus gene segment or a derivative thereof. In a specific embodiment, a 3' NCR1 comprises or consists of a 3' NCR of an influenza virus gene segment or a fragment thereof, or a nucleotide sequence that is at least 50% (in some embodiments, at least 60%, at least 65%, at least 70%, at least 75%, at least 80%, at least 85%, at least 90%, at least 95%, or at least 98%) identical to a 3' NCR of an influenza virus gene segment or a fragment thereof, or a nucleotide sequence that hybridizes under stringent conditions to a 3' NCR of an influenza virus gene segment or a fragment thereof. A 5' NCR1 comprises or consists of packaging signals found in the 5' non-coding region an influenza virus gene segment or a derivative thereof. In a specific embodiment, a 5' NCR1 comprises or consists of a 5' NCR of an influenza virus gene segment or a fragment thereof, or a nucleotide sequence that is at least 50% (in some embodiments, at least 60%, at least 65%, at least 70%, at least 75%, at least 80%, at least 85%, at least 90%, at least 95%, or at least 98%) identical to a 5' NCR of an influenza virus gene segment or a fragment thereof, or a nucleotide sequence that hybridizes under stringent conditions to a 5' NCR of an influenza virus gene segment or a fragment thereof. In a specific embodiment, the 3' NCR1 and the 5' NCR1 are from the same type of influenza virus gene segment. In other words, the 3' NCR1 and the 5' NCR1 are both from an HA, NA (for influenza A and B viruses), M, NS, PA, PB1, PB2, or NP influenza virus gene segment. The 3' NCR1 and the 5' NCR1 may be from the same type of influenza virus gene segment (HA, NA (for influenza A and B viruses), M, NS, PA, PB1, PB2, or NP) from the same influenza virus strain. For example, the 3' NCR1 and 5' NCR1 may both be from an HA influenza virus gene segment of the same influenza virus strain. Alternatively, the 3' NCR1 and the 5' NCR1 may be from the same type of influenza virus gene segment from two different strains of influenza virus. For example, the 3' NCR1 may be from an HA gene segment of one influenza virus strain and the 5' NCR1 may be from an HA gene segment of a different influenza virus strain.

In a specific embodiment, a 3' NCR1 and a 5' NCR1 are from the same type of influenza virus gene segment from an influenza A virus (see Section 5.2, infra, for examples of influenza A viruses). In other embodiments, a 3' NCR1 and a 5' NCR1 are from the same type of influenza virus gene segment from an influenza B virus (see Section 5.2, infra, for examples of influenza B viruses). In other embodiments, a 3' NCR1 and a 5' NCR1 are from the same type of influenza virus gene segment from an influenza C virus (see Section 5.2, infra, for examples of influenza C viruses). In some embodiments, a 3' NCR1 and a 5' NCR1 are from an influenza virus gene segment from a pandemic influenza virus. In other embodiments, a 3' NCR1 and a 5' NCR1 are from an influenza virus gene segment from a seasonal influenza virus.

In certain embodiments, a 3' NCR1 comprises or consists of the entire 3' NCR of an influenza virus gene segment. The 3' NCRs for influenza viruses are known in the art or can readily be determined using standard molecular biology and virology techniques. For example, the 3' NCR for each segment of the influenza A/WSN/33 (WSN) virus is provided in Table 1, infra.

TABLE 1

| WSN Gene Segment | Length of 3' NCR | FIG./SEQ ID NO: |
|---|---|---|
| HA | 32 | FIG. 17/SEQ ID NO: 81 |
| NA | 19 | FIG. 18/SEQ ID NO: 85 |
| M | 25 | FIG. 19/SEQ ID NO: 89 |
| NS | 26 | FIG. 20/SEQ ID NO: 93 |
| PA | 24 | FIG. 21/SEQ ID NO: 97 |
| PB1 | 24 | FIG. 22/SEQ ID NO: 101 |
| PB2 | 27 | FIG. 23/SEQ ID NO: 105 |
| NP | 45 | FIG. 24/SEQ ID NO: 109 |

By way of example and not by limitation, provided in Table 2, infra, are nucleotide sequences of the 3' NCR for each segment of the influenza A/PR/8/34 (PR8) virus.

TABLE 2

| PR8 Gene Segment | Length of Sequence | FIG./SEQ ID NO: |
|---|---|---|
| HA | 32 | FIG. 4/SEQ ID NO: 19 |
| NA | 20 | FIG. 6/SEQ ID NO: 31 |
| M | 25 | FIG. 7/SEQ ID NO: 37 |
| NS | 26 | FIG. 8/SEQ ID NO: 43 |
| PA | 24 | FIG. 3/SEQ ID NO: 13 |
| PB1 | 24 | FIG. 2/SEQ ID NO: 7 |
| PB2 | 27 | FIG. 1/SEQ ID NO: 1 |
| NP | 45 | FIG. 5/SEQ ID NO: 25 |

In some embodiments, a 3' NCR1 comprises or consists of a fragment of the 3' NCR of an influenza virus gene segment. In certain embodiments, a 3' NCR1 comprises or consists of 35, 30, 25, 20, 15, 10 or 5 nucleotides or 5 to 10, 5 to 15, 5 to 20, 5 to 25, 5 to 30, 5 to 35, 10 to 15, 10 to 20, 10 to 25, 10 to 30, 10 to 35, 15 to 20, 15 to 25, 15 to 30, 15 to 35, 20 to 25, 20 to 30, 20 to 35, 25 to 30, or 25 to 35 nucleotides of the 3' NCR of an influenza virus gene segment. In some embodiments, a 3' NCR1 comprises or consists of a nucleotide sequence that is at least 50%, at least 55%, at least 60%, at least 65%, at least 70%, at least 75%, at least 80%, at least 85%, at least 90%, at least 95%, at least 98% or at least 99% identical to the 3' NCR of an influenza virus gene segment. In certain embodiments, a 3' NCR1 comprises or consists of a nucleotide sequence that is 50% to 65%, 60% to 80%, 65% to 90%, 70% to 95%, 80% to 95%, 90% to 99%, 95% to 99% identical to the 3' NCR of an influenza virus gene segment.

In some embodiments, a 3' NCR1 comprises or consists of a nucleotide sequence that is at least 50%, at least 55%, at least 60%, at least 65%, at least 70%, at least 75%, at least 80%, at least 85%, at least 90%, at least 95%, at least 98% or at least 99% identical to 35, 30, 25, 20, 15, 10 or 5 contiguous nucleotides or 5 to 10, 5 to 15, 5 to 20, 5 to 25, 5 to 30, 5 to 35, 10 to 15, 10 to 20, 10 to 25, 10 to 30, 10 to 35, 15 to 20, 15 to 25, 15 to 30, 15 to 35, 20 to 25, 20 to 30, 20 to 35, 25 to 30, or 25 to 35 contiguous nucleotides of the 3' NCR of an influenza virus gene segment. In certain embodiments, a 3' NCR1 comprises or consists of a nucleotide sequence that is 50% to 65%, 60% to 80%, 65% to 90%, 70% to 95%, 80% to 95%, 90% to 99%, 95% to 99% identical to 35, 30, 25, 20, 15, 10 or 5 contiguous nucleotides or 5 to 10, 5 to 15, 5 to 20, 5 to 25, 5 to 30, 5 to 35, 10 to 15, 10 to 20, 10 to 25, 10 to 30, 10 to 35, 15 to 20, 15 to 25, 15 to 30, 15 to 35, 20 to 25, 20 to 30, 20 to 35, 25 to 30, or 25 to 35 contiguous nucleotides of the 3' NCR of an influenza virus gene segment In some embodiments, a 3' NCR1 comprises or consists of a nucleotide sequence that hybridizes under stringent conditions to the 3' NCR of an influenza virus gene segment. In certain embodiments, a 3' NCR1 comprises or consists of a nucleotide sequence that hybridizes under stringent conditions to a fragment of the 3' NCR of an influenza virus gene segment. In some embodiments, a 3' NCR1 comprises of consists of a nucleotide sequence that hybridizes under stringent conditions to a sequence consisting of 35, 30, 25, 20, 15, 10 or 5 contiguous nucleotides or 5 to 10, 5 to 15, 5 to 20, 5 to 25, 5 to 30, 5 to 35, 10 to 15, 10 to 20, 10 to 25, 10 to 30, 10 to 35, 15 to 20, 15 to 25, 15 to 30, 15 to 35, 20 to 25, 20 to 30, 20 to 35, 25 to 30, or 25 to 35 contiguous nucleotides of the 3' NCR of an influenza virus gene segment.

In certain embodiments, a 5' NCR1 comprises or consists of the entire 5' NCR of an influenza virus gene segment. The 5' NCRs for influenza viruses are known in the art or can readily be determined using standard molecular biology and virology techniques. For example, the 5' NCR for each segment of the influenza A/WSN/33 (WSN) virus is provided in Table 3, infra.

TABLE 3

| WSN Gene Segment | Length of 5' NCR | SEQ ID NO: |
|---|---|---|
| HA | 45 | FIG. 17/SEQ ID NO: 83 |
| NA | 28 | FIG. 18/SEQ ID NO: 87 |
| M | 20 | FIG. 19/SEQ ID NO: 91 |
| NS | 26 | FIG. 20/SEQ ID NO: 95 |
| PA | 58 | FIG. 21/SEQ ID NO: 99 |
| PB1 | 43 | FIG. 22/SEQ ID NO: 103 |
| PB2 | 34 | FIG. 23/SEQ ID NO: 107 |
| NP | 23 | FIG. 24/SEQ ID NO: 111 |

By way of example and not by limitation, provided in Table 4, infra, are nucleotide sequences of the 5' NCR for each segment of the influenza A/PR/8/34 (PR8) virus.

TABLE 4

| PR8 Gene Segment | Length of Sequence | FIG./SEQ ID NO: |
|---|---|---|
| HA | 45 | FIG. 4/SEQ ID NO: 22 |
| NA | 28 | FIG. 6/SEQ ID NO: 34 |
| M | 20 | FIG. 7/SEQ ID NO: 40 |
| NS | 26 | FIG. 8/SEQ ID NO: 46 |
| PA | 58 | FIG. 3/SEQ ID NO: 16 |
| PB1 | 43 | FIG. 2/SEQ ID NO: 10 |
| PB2 | 34 | FIG. 1/SEQ ID NO: 4 |
| NP | 23 | FIG. 5/SEQ ID NO: 28 |

In some embodiments, a 5' NCR1 comprises or consists of a fragment of the 5' NCR of an influenza virus gene segment. In certain embodiments, a 5' NCR1 comprises or consists of 35, 30, 25, 20, 15, 10 or 5 nucleotides or 5 to 10, 5 to 15, 5 to 20, 5 to 25, 5 to 30, 5 to 35, 10 to 15, 10 to 20, 10 to 25, 10 to 30, 10 to 35, 15 to 20, 15 to 25, 15 to 30, 15 to 35, 20 to 25, 20 to 30, 20 to 35, 25 to 30, or 25 to 35 nucleotides of the 5' NCR of an influenza virus gene segment. In some embodiments, a 5' NCR1 comprises or consists of a nucleotide sequence that is at least 50%, at least 55%, at least 60%, at least 65%, at least 70%, at least 75%, at least 80%, at least 85%, at least 90%, at least 95%, at least 98% or at least 99% identical to the 5' NCR of an influenza virus gene segment. In certain embodiments, a 5' NCR1 comprises or consists of a nucleotide sequence that is 50% to 65%, 60% to 80%, 65% to 90%, 70% to 95%, 80% to 95%, 90% to 99%, 95% to 99% identical to the 5' NCR of an influenza virus gene segment.

In some embodiments, a 5' NCR1 comprises or consists of a nucleotide sequence that is at least 50%, at least 55%, at least 60%, at least 65%, at least 70%, at least 75%, at least 80%, at least 85%, at least 90%, at least 95%, at least 98% or at least 99% identical to 35, 30, 25, 20, 15, 10 or 5 contiguous nucleotides or 5 to 10, 5 to 15, 5 to 20, 5 to 25, 5 to 30, 5 to 35, 10 to 15, 10 to 20, 10 to 25, 10 to 30, 10 to 35, 15 to 20, 15 to 25, 15 to 30, 15 to 35, 20 to 25, 20 to 30, 20 to 35, 25 to 30, or 25 to 35 contiguous nucleotides of the 5' NCR of an influenza virus gene segment. In certain embodiments, a 5' NCR1 comprises or consists of a nucleotide sequence that is 50% to 65%, 60% to 80%, 65% to 90%, 70% to 95%, 80% to 95%, 90% to 99%, 95% to 99% identical to 35, 30, 25, 20, 15, 10 or 5 contiguous nucleotides or 5 to 10, 5 to 15, 5 to 20, 5 to 25, 5 to 30, 5 to 35, 10 to 15, 10 to 20, 10 to 25, 10 to 30, 10 to 35, 15 to 20, 15 to 25, 15 to 30, 15 to 35, 20 to 25, 20 to 30, 20 to 35, 25 to 30, or 25 to 35 contiguous nucleotides of the 5' NCR of an influenza virus gene segment.

In some embodiments, a 5' NCR1 comprises or consists of a nucleotide sequence that hybridizes under stringent conditions to the 5' NCR of an influenza virus gene segment. In certain embodiments, a 5' NCR1 comprises or consists of a nucleotide sequence that hybridizes under stringent conditions to a fragment of the 5' NCR of an influenza virus gene segment. In some embodiments, a 5' NCR1 comprises or consists of a nucleotide sequence that hybridizes under stringent conditions to a sequence consisting of 35, 30, 25, 20, 15, 10 or 5 contiguous nucleotides or 5 to 10, 5 to 15, 5 to 20, 5 to 25, 5 to 30, 5 to 35, 10 to 15, 10 to 20, 10 to 25, 10 to 30, 10 to 35, 15 to 20, 15 to 25, 15 to 30, 15 to 35, 20 to 25, 20 to 30, 20 to 35, 25 to 30, or 25 to 35 contiguous nucleotides of the 5' NCR of an influenza virus gene segment.

5.1.2. Influenza Virus Terminal Coding Region that is not Translated

The chimeric influenza virus gene segments described herein may comprise either a 3' CRS1, a 5' CRS1, or both a 3' CRS1 and a 5' CRS1. A 3' CRS1 comprises or consists of packaging signals found in the 3' proximal coding region sequence of an influenza virus gene segment or a derivative thereof. In a specific embodiment, a 3' CRS1 comprises or consists of a 3' proximal coding region sequence of an influenza virus gene segment, or a nucleotide sequence that is at least 50% (in some embodiments, at least 60%, at least 65%, at least 70%, at least 75%, at least 80%, at least 85%, at least 90%, at least 95%, or at least 98%) identical to a 3' proximal coding region sequence of an influenza virus gene segment, or a nucleotide sequence that hybridizes under stringent conditions to a 3' proximal coding region sequence of an influenza virus gene segment. In certain embodiments, the 3' proximal coding region sequence is translated. In other embodiments, the 3' proximal coding region sequence is not translated. In some embodiments, the 3' proximal coding region sequence has been mutated so as to eliminate any start codons and preclude the translation of the 3' proximal coding region sequence. In certain embodiments, the 3' proximal coding region sequence of an influenza virus gene segment is from an influenza virus NS or M gene segment. In a specific embodiment, the 3' proximal coding region sequence of an influenza virus gene segment is from an influenza virus NS gene segment and the mRNA 5' splice site has been mutated to prevent splicing from occurring. In another specific embodiment, the 3' proximal coding region sequence of an influenza virus gene segment is from an influenza virus M gene segment and the mRNA distal 5' splice site has been mutated to prevent splicing from occurring.

A 5' CRS1 comprises or consists of packaging signals found in the 5' proximal coding region sequence of an influenza virus gene segment or a derivative thereof. In a specific embodiment, 5' CRS1 comprises or consists of a 5' proximal coding region sequence of an influenza virus gene segment, or a nucleotide sequence that is at least 50% (in some embodiments, at least 60%, at least 65%, at least 70%, at least 75%, at least 80%, at least 85%, at least 90%, at least 95%, or at least 98%) identical to a 5' proximal coding region sequence of an influenza virus gene segment, or a nucleotide sequence that hybridizes under stringent conditions to a 5' proximal coding region sequence of an influenza virus gene segment. In certain embodiments, the 5' proximal coding region sequence is translated. In other embodiments, the 5' proximal coding region sequence is not translated. In some embodiments, the 5' proximal coding region sequence has one or more mutations so as to ensure that the 5' proximal coding region sequence is not translated.

In a specific embodiment, the 3' CRS1 and the 5' CRS1 are from the same type of influenza virus gene segment. In other words, the 3' CRS1 and the 5' CRS1 are both from an HA, NA (for influenza A and B viruses), M, NS, PA, PB1, PB2, or NP influenza virus gene segment. The 5' CRS1 and the 5' CRS1 may be from the same type of influenza virus gene segment (HA, NA (for influenza A and B viruses), M, NS, PA, PB1, PB2, or NP) from the same influenza virus strain. For example, the 3' CRS1 and 5' CRS1 may both be from an HA influenza virus gene segment of the same influenza virus strain. Alternatively, the 3' CRS1 and the 5' CRS1 may be from the same type of influenza virus gene segment from two different strains of influenza virus. For example, the 3' CRS1 may be from an HA gene segment of one influenza virus strain and the 5' CRS1 may be from an HA gene segment of a different influenza virus strain.

In a specific embodiment, a 3' CRS1 and a 5' CRS1 are from the same type of influenza virus gene segment from an influenza A virus (see Section 5.2, infra, for examples of influenza A viruses). In other embodiments, a 3′ CRS1 and a 5′ CRS1 are from the same type of influenza virus gene segment from an influenza B virus (see Section 5.2, infra, for examples of influenza B viruses). In other embodiments, a 3′ CRS1 and a 5′ CRS1 are from the same type of influenza virus gene segment from an influenza C virus (see Section 5.2, infra, for examples of influenza C viruses). In certain embodiments, a 3′ CRS1 and a 5′ CRS1 are from an influenza virus gene segment from a pandemic influenza virus. In other embodiments, a 3′ CRS1 and a 5′ CRS1 are from an influenza virus gene segment from a seasonal influenza virus.

In certain embodiments, a 3′ CRS1 and/or a 5′ CRS1 are from the same strain of the same type of influenza virus gene segment as a 3′ NCR1 and/or a 5′ NCR1. In other embodiments, a 3′ CRS1 and/or a 5′ CRS1 are from a first strain of a type of influenza virus gene segment and a 3′ NCR1 and/or a 5′ NCR1 are from a different strain of the same type of influenza virus gene segment.

In certain embodiments, a 3′ CRS1 comprises or consists of the 3′ proximal coding region sequence of an influenza virus gene segment. The coding regions for influenza virus gene segments are known in the art or can readily be determined using standard molecular biology and virology techniques. In a specific embodiment, a 3′ CRS1 comprises or consists of the 3′ most 50 to 150 nucleotide, 75 to 150 nucleotides, 100 to 150 nucleotides, or 120 nucleotides of an influenza virus PB2 gene segment. In another embodiment, a 3' CRS1 comprises or consists of the 3' most 25 to 150 nucleotides, 50 to 150 nucleotides, 75 to 150 nucleotides, 100 to 150 nucleotides or 60 nucleotides of an influenza virus PB1 gene segment. In another embodiment, a 3' CRS1 comprises or consists of the 3' most 2 to 25 nucleotides, 2 to 15 nucleotides, 2 to 10 nucleotides, 5 to 150 nucleotides 25 to 150 nucleotides, 50 to 150 nucleotides, 75 to 150 nucleotides, 100 to 150 nucleotides or 9 nucleotides of an influenza virus HA gene segment. In another embodiment, a 3' CRS1 comprises or consists of the 3' most 25 to 150 nucleotides, 50 to 150 nucleotides, 75 to 150 nucleotides, 100 to 150 nucleotides or 60 nucleotides of an influenza virus NP gene segment. In another embodiment, a 3' CRS1 comprises or consists of the 3' most 25 to 250 nucleotides, 50 to 250 nucleotides, 75 to 250 nucleotides, 100 to 250 nucleotides, 125 to 250 nucleotides, 150 to 250 nucleotides, 175 to 250 nucleotides, 150 to 200 nucleotides, or 183 nucleotides of an influenza virus NA gene segment. In another embodiment, a 3' CRS1 comprises or consists of the 3' most 25 to 250 nucleotides, 50 to 250 nucleotides, 75 to 250 nucleotides, 100 to 250 nucleotides, 125 to 250 nucleotides, 150 to 250 nucleotides, 175 to 250 nucleotides, 200 to 250 nucleotides, or 222 nucleotides of an influenza virus M gene segment. In another embodiment, a 3' CRS1 comprises or consists of the 3' most 10 to 150 nucleotides, 25 to 150 nucleotides, 50 to 150 nucleotides, 75 to 150 nucleotides, 100 to 150 nucleotides, or 35 nucleotides of an influenza virus NS gene segment. In another embodiment, a 3' CRS1 comprises or consist of the 3' most 25 to 200 nucleotides, 50 to 200 nucleotides, 50 to 150 nucleotides, 50 to 125 nucleotides, 75 to 200 nucleotides, 75 to 150 nucleotides, 100 to 200 nucleotides, 100 to 150 nucleotides, or 100 to 125 nucleotides of an influenza PA gene segment.

By way of example and not by limitation, provided in Table 5, infra, are examples of nucleotide sequences of a 3' proximal coding region for each segment of the influenza A/PR/8/34 (PR8) virus.

TABLE 5

| PR8 Gene Segment | Length of Sequence | FIG./SEQ ID NO: |
|---|---|---|
| HA | 67 | FIG. 4/SEQ ID NO: 20 |
| NA | 111 | FIG. 6/SEQ ID NO: 32 |
| M | 255 | FIG. 7/SEQ ID NO: 38 |
| NS | 77 | FIG. 8/SEQ ID NO: 44 |
| PA | 115 | FIG. 3/SEQ ID NO: 14 |
| PB1 | 123 | FIG. 2/SEQ ID NO: 8 |
| PB2 | 125 | FIG. 1/SEQ ID NO: 2 |
| NP | 126 | FIG. 5/SEQ ID NO: 26 |

Any start codon present in the 3' proximal coding region sequence of an influenza virus gene segment may be eliminated using any technique known to one of skill in the art. A start codon may be eliminated by nucleotide substitutions, deletions and/or insertions. In specific embodiments, one or more start codons present in the 3' proximal coding region of an influenza virus gene segment are eliminated by one or more nucleotide substitutions. In some embodiments, one or more start codons present in the 3' proximal coding region of an influenza virus gene segment are eliminated by one or more insertions and/or deletions. The elimination of any start codons present in the 3' proximal coding region sequence of an influenza virus gene segment should prevent the translation of the sequence.

The mRNA 5' splice site present in the 3' proximal coding region sequence of an influenza virus NS gene segment and/or the distal 5' splice site present in the 3' proximal coding region sequence of an influenza virus M gene segment may be eliminated using any technique known to one of skill in the art. Such splice sites may be eliminated by nucleotide substitutions, deletions and/or insertions. In specific embodiments, such splice sites are eliminated by nucleotide substitutions. The elimination of such splice sites such prevent unwanted alternative splicing from occurring.

In some embodiments, a 3' CRS1 comprises or consists of a nucleotide sequence that is at least 50%, at least 55%, at least 60%, at least 65%, at least 70%, at least 75%, at least 80%, at least 85%, at least 90%, at least 95%, at least 98% or at least 99% identical to the 3' proximal coding region sequence of an influenza virus gene segment. In certain embodiments, a 3' CRS1 comprises or consists of a nucleotide sequence that is 50% to 65%, 60% to 80%, 65% to 90%, 70% to 95%, 80% to 95%, 90% to 99%, 95% to 99% identical to the 3' proximal coding region sequence of an influenza virus gene segment. In some embodiments, a 3' CRS1 comprises or consists of a nucleotide sequence that hybridizes under stringent conditions to the 3' proximal coding region sequence of an influenza virus gene segment.

In certain embodiments, a 5' CRS1 comprises or consists of the 5' proximal coding region sequence of an influenza virus gene segment. The coding regions for influenza viruses are known in the art or can readily be determined using standard molecular biology and virology techniques. In a specific embodiment, a 5' CRS1 comprises or consists of the 5' most 50 to 150 nucleotide, 75 to 150 nucleotides, 100 to 150 nucleotides, or 120 nucleotides of an influenza virus PB2 gene segment. In another embodiment, a 5' CRS1 comprises or consists of the 5' most 25 to 150 nucleotides, 50 to 150 nucleotides, 75 to 150 nucleotides, 100 to 150 nucleotides or 60 nucleotides of an influenza virus PB1 gene segment. In another embodiment, a 5' CRS1 comprises or consists of the 3' most 5 to 150 nucleotides 25 to 150 nucleotides, 50 to 150 nucleotides, 75 to 100 nucleotides, 75 to 150 nucleotides, 100 to 150 nucleotides, or 80 nucleotides of an influenza virus HA gene segment. In another embodiment, a 5' CRS1 comprises or consists of the 5' most 25 to 200 nucleotides, 50 to 200 nucleotides, 75 to 200 nucleotides, 100 to 200 nucleotides, 120 to 175 nucleotides, 120 to 150 nucleotides, or 120 nucleotides of an influenza virus NP gene segment. In another embodiment, a 5' CRS1 comprises or consists of the 5' most 25 to 250 nucleotides, 50 to 250 nucleotides, 75 to 250 nucleotides, 100 to 250 nucleotides, 125 to 250 nucleotides, 150 to 250 nucleotides, 175 to 250 nucleotides, 150 to 200 nucleotides, or 157 nucleotides of an influenza virus NA gene segment. In another embodiment, a 5' CRS1 comprises or consists of the 3' most 25 to 250 nucleotides, 50 to 250 nucleotides, 75 to 250 nucleotides, 100 to 250 nucleotides, 125 to 250 nucleotides, 150 to 250 nucleotides, 175 to 250 nucleotides, 200 to 250 nucleotides, or 220 nucleotides of an influenza virus M gene segment. In another embodiment, a 5' CRS1 comprises or consists of the 5' most 10 to 150 nucleotides, 25 to 150 nucleotides, 50 to 150 nucleotides, 75 to 150 nucleotides, 100 to 150 nucleotides, or 35 nucleotides of an influenza virus NS gene segment. In another embodiment, a 3' CRS1 comprises or consist of the 3' most 25 to 200 nucleotides, 50 to 200 nucleotides, 50 to 150 nucleotides, 50 to 125 nucleotides, 75 to 200 nucleotides, 75 to 150 nucleotides, 100 to 200 nucleotides, 100 to 150 nucleotides, or 100 to 125 nucleotides of an influenza PA gene segment.

By way of example and not by limitation, provided in Table 6, infra, are examples of nucleotide sequences of a 5' proximal coding region for each segment of the influenza A/PR/8/34 (PR8) virus.

TABLE 6

| PR8 Gene Segment | Length of Sequence | FIG./SEQ ID NO: |
|---|---|---|
| HA | 105 | FIG. 4/SEQ ID NO: 23 |
| NA | 157 | FIG. 6/SEQ ID NO: 35 |
| M | 215 | FIG. 7/SEQ ID NO: 41 |
| NS | 102 | FIG. 8/SEQ ID NO: 47 |
| PA | 120 | FIG. 3/SEQ ID NO: 17 |
| PB1 | 110 | FIG. 2/SEQ ID NO: 11 |
| PB2 | 129 | FIG. 1/SEQ ID NO: 5 |
| NP | 120 | FIG. 5/SEQ ID NO: 29 |

In some embodiments, a 5' CRS1 comprises or consists of a nucleotide sequence that is at least 50%, at least 55%, at least 60%, at least 65%, at least 70%, at least 75%, at least 80%, at least 85%, at least 90%, at least 95%, at least 98% or at least 99% identical to the 5' proximal coding region sequence of an influenza virus gene segment. In certain embodiments, a 5' CRS1 comprises or consists of a nucleotide sequence that is 50% to 65%, 60% to 80%, 65% to 90%, 70% to 95%, 80% to 95%, 90% to 99%, 95% to 99% identical to the 5' proximal coding region sequence of an influenza virus gene segment. In some embodiments, a 5' CRS1 comprises or consists of a nucleotide sequence that hybridizes under stringent conditions to the 5' proximal coding region sequence of an influenza virus gene segment.

5.1.3. Open Reading Frame of an Influenza Virus Gene Segment

The chimeric influenza virus gene segments described herein comprise a mORF. A mORF comprises or consists of an open reading frame or a fragment thereof from an influenza virus gene segment or a derivative thereof, wherein the open reading frame contains one, two, three or more mutations in the influenza virus packaging signals found in the open reading frame. In a specific embodiment, a mORF comprises or consists of: either (a) at least the 3' proximal 20 nucleotides of an open reading frame of an influenza virus gene segment, or an open reading frame comprising at least the 3' proximal 20 nucleotides of an open reading frame of an influenza virus gene segment and a heterologous nucleotide sequence, wherein at least 1, 2, 3, 4, 5, 6, 7, 8, 9, 10, 11, 12, 13, 14, 15, 16, 17, 18, 19, or 20 of the 3' proximal nucleotides of the open reading frame of the influenza virus gene segment have been mutated; (b) at least the 5' proximal 30 nucleotides of an open reading frame of an influenza virus gene segment, or an open reading frame comprising at least the 5' proximal 30 nucleotides of an open reading frame of an influenza virus gene segment and a heterologous nucleotide sequence, wherein at least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 of the 5' proximal nucleotides of the open reading frame of the influenza virus gene segment have been mutated; or (c) both (a) and (b). In a specific embodiment, the at least 3' proximal 20 nucleotides of an open reading frame of an influenza virus gene segment and the at least 5' proximal 30 nucleotides of an open reading frame of an influenza virus gene segment are from the same type of influenza virus gene segment. In other words, the at least 3' proximal 20 nucleotides of an open reading frame of an influenza virus gene segment and the at least 5' proximal 30 nucleotides of an open reading frame of an influenza virus gene segment are both from an HA, NA (for influenza A and B viruses), M, NS, PA, PB1, PB2, or NP influenza virus gene segment. The at least 3' proximal 20 nucleotides of an open reading frame of an influenza virus gene segment and the at least 5' proximal 30 nucleotides of an open reading frame of an influenza virus gene segment may be from the same type of influenza virus gene segment (HA, NA (for influenza A and B viruses), M, NS, PA, PB1, PB2, or NP) from the same influenza virus strain. For example, the at least 3' proximal 20 nucleotides of an open reading frame of an influenza virus gene segment and the at least 5' proximal 30 nucleotides of an open reading frame of an influenza virus gene segment may both be from an HA influenza virus gene segment of the same influenza virus strain. Alternatively, the at least 3' proximal 20 nucleotides of an open reading frame of an influenza virus gene segment and the at least 5' proximal 30 nucleotides of an open reading frame of an influenza virus gene segment may be from the same type of influenza virus gene segment from two different strains of influenza virus. For example, the at least 3' proximal 20 nucleotides of an open reading frame of an influenza virus gene segment and the at least 5' proximal 30 nucleotides of an open reading frame of an influenza virus gene segment may be from an HA gene segment of a different influenza virus strain.

In a specific embodiment, the at least 3' proximal 20 nucleotides of an open reading frame of an influenza virus gene segment and the at least 5' proximal 30 nucleotides of an open reading frame of an influenza virus gene segment are from the same type of influenza virus gene segment from an influenza A virus (see Section 5.2, infra, for examples of influenza A viruses). In other embodiments, the at least 3' proximal 20 nucleotides of an open reading frame of an influenza virus gene segment and the at least 5' proximal 30 nucleotides of an open reading frame of an influenza virus gene segment are from the same type of influenza virus gene segment from an influenza B virus (see Section 5.2, infra, for examples of influenza B viruses). In other embodiments, the at least 3' proximal 20 nucleotides of an open reading frame of an influenza virus gene segment and the at least 5' proximal 30 nucleotides of an open reading frame of an influenza virus gene segment are from the same type of influenza virus gene segment from an influenza C virus (see Section 5.2, infra, for examples of influenza C viruses). In certain embodiments, the at least 3' proximal 20 nucleotides of an open reading frame of an influenza virus gene segment and the at least 5' proximal 30 nucleotides of an open reading frame of an influenza virus gene segment are from the same pandemic influenza virus. In other embodiments, the at least 3' proximal 20 nucleotides of an open reading frame of an influenza virus gene segment and the at least 5' proximal 30 nucleotides of an open reading frame of an influenza virus gene segment are from the same seasonal influenza virus.

In one embodiment, a mORF comprises or consists of at least the 3' proximal 20 nucleotides of an open reading frame of an influenza virus gene segment, wherein at least 1, 2, 3, 4, 5, 6, 7, 8, 9, 10, 11, 12, 13, 14, 15, 16, 17, 18, 19, or 20 of the 3' proximal nucleotides of the open reading frame of the influenza virus gene segment have been mutated. In certain embodiments, a mORF comprises or consists of the 3' most 20 to 200 nucleotides, 20 to 175 nucleotides, 20 to 150 nucleotides, 20 to 125 nucleotides, 20 to 100 nucleotides, 20 to 100 nucleotides, 20 to 75 nucleotides, 20 to 50 nucleotides, or any integer in between of an open reading frame of an influenza virus gene segment, wherein at least 1, 2, 3, 4, 5, 6, 7, 8, 9, 10, 11, 12, 13, 14, 15, 16, 17, 18, 19, 20 or more nucleotides have been mutated. In a specific embodiment, a mORF comprises or consists of the 3' most 20 to 200 nucleotides, or any integer in between of an open reading frame of an influenza virus gene segment, wherein 1 to 200 nucleotides, 10 to 200 nucleotides, 20 to 200 nucleotides, 20 to 175 nucleotides, 20 to 150 nucleotides, 20 to 125 nucleotides, 20 to 100 nucleotides, 20 to 75 nucleotides, 20 to 50 nucleotides, or any integer in between have been mutated.

In one embodiment, a mORF comprises or consists of at least the 3' proximal 20 nucleotides of an open reading frame of an influenza virus gene segment and a heterologous nucleotide sequence, wherein at least 1, 2, 3, 4, 5, 6, 7, 8, 9, 10, 11, 12, 13, 14, 15, 16, 17, 18, 19, or 20 of the 3' proximal nucleotides of the open reading frame of the influenza virus gene segment have been mutated. In certain embodiments, a mORF comprises or consists of the 3' most 20 to 200 nucleotides, 20 to 175 nucleotides, 20 to 150 nucleotides, 20 to 125 nucleotides, 20 to 100 nucleotides, 20 to 100 nucleotides, 20 to 75 nucleotides, 20 to 50 nucleotides, or any integer in between of an open reading frame of an influenza virus gene segment and a heterologous nucleotide sequence, wherein at least 1, 2, 3, 4, 5, 6, 7, 8, 9, 10, 11, 12, 13, 14, 15, 16, 17, 18, 19, or more nucleotides have been mutated. In a specific embodiment, a mORF comprises or consists of the 3' most 20 to 200 nucleotides, or any integer in between of an open reading frame of an influenza virus gene segment and a heterologous nucleotide sequence, wherein the 1 to 200 nucleotides, 10 to 200 nucleotides, 20 to 200 nucleotides, 20 to 175 nucleotides, 20 to 150 nucleotides, 20 to 125 nucleotides, 20 to 100 nucleotides, 20 to 75 nucleotides, 20 to 50 nucleotides, or any integer in between have been mutated.

In another embodiment, a mORF comprises or consists of at least the 5' proximal 20 or 30 nucleotides of an open reading frame of an influenza virus gene segment, wherein at least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 of the 5' proximal nucleotides of the open reading frame of the influenza virus gene segment have been mutated. In certain embodiments, a mORF comprises or consists of the 5' most 30 to 200 nucleotides, 30 to 175 nucleotides, 30 to 150 nucleotides, 30 to 125 nucleotides, 30 to 100 nucleotides, 30 to 100 nucleotides, 30 to 75 nucleotides, 230 to 50 nucleotides, or any integer in between of an open reading frame of an influenza virus gene segment, wherein 1, 2, 3, 4, 5, 6, 7, 8, 9, 10, 11, 12, 13, 14, 15, 16, 17, 18, 19, or more nucleotides have been mutated. In a specific embodiment, a mORF comprises or consists of the 5' most 30 to 200 nucleotides, or any integer in between 30 and 200 of an open reading frame of an influenza virus gene segment, wherein the 1 to 200 nucleotides, 10 to 200 nucleotides, 20 to 200 nucleotides, 20 to 175 nucleotides, 20 to 150 nucleotides, 20 to 125 nucleotides, 20 to 100 nucleotides, 20 to 75 nucleotides, 20 to 50 nucleotides, or any integer in between have been mutated.

In one embodiment, a mORF comprises or consists of at least the 5' proximal 30 nucleotides of an open reading frame of an influenza virus gene segment and a heterologous nucleotide sequence, wherein at least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 of the 5' proximal nucleotides of the open reading frame of the influenza virus gene segment have been mutated. In certain embodiments, a mORF comprises or consists of the 5' most 30 to 200 nucleotides, 30 to 175 nucleotides, 30 to 150 nucleotides, 30 to 125 nucleotides, 30 to 100 nucleotides, 30 to 100 nucleotides, 30 to 75 nucleotides, 30 to 50 nucleotides, or any integer in between of an open reading frame of an influenza virus gene segment and a heterologous nucleotide sequence, wherein 1, 2, 3, 4, 5, 6, 7, 8, 9, 10, 11, 12, 13, 14, 15, 16, 17, 18, 19, 20 or more nucleotides have been mutated. In a specific embodiment, a mORF comprises or consists of the 5' most 30 to 200 nucleotides, or any integer in between 30 and 200 of an open reading frame of an influenza virus gene segment and a heterologous nucleotide sequence, wherein the 1 to 200 nucleotides, 10 to 200 nucleotides, 20 to 200 nucleotides, 20 to 175 nucleotides, 20 to 150 nucleotides, 20 to 125 nucleotides, 20 to 100 nucleotides, 20 to 75 nucleotides, 20 to 50 nucleotides, or any integer in between have been mutated. In certain embodiments, when the mORF includes a heterologous nucleotide sequence, any stop codon in the open reading frame of the influenza virus gene segment is eliminated so that one open reading frame remains that allows the translation of a fusion protein.

In another embodiment, a mORF comprises or consists of at least the 3' proximal 20 nucleotides and at least the 5' proximal 30 nucleotides of an open reading frame of an influenza virus gene segment, wherein at least 1, 2, 3, 4, 5, 6, 7, 8, 9, 10, 11, 12, 13, 14, 15, 16, 17, 18, 19 or 20 of the 3' proximal nucleotides and/or at least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 of the 5' proximal nucleotides of the open reading frame of the influenza virus gene segment have been mutated. In certain embodiments, a mORF comprises or consists of the 3' most 20 to 200 nucleotides, 20 to 175 nucleotides, 20 to 150 nucleotides, 20 to 125 nucleotides, 20 to 100 nucleotides, 20 to 100 nucleotides, 20 to 75 nucleotides, 20 to 50 nucleotides, or any integer in between of an open reading frame of an influenza virus gene segment and 5' most 30 to 200 nucleotides, 30 to 175 nucleotides, 30 to 150 nucleotides, 30 to 125 nucleotides, 30 to 100 nucleotides, 30 to 100 nucleotides, 30 to 75 nucleotides, 30 to 50 nucleotides, or any integer in between of an open reading frame of an influenza virus gene segment, wherein 1, 2, 3, 4, 5, 6, 7, 8, 9, 10, 11, 12, 13, 14, 15, 16, 17, 18, 19, 20 or more nucleotides in the 3' termini and/or 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 or more nucleotides in the 5' termini have been mutated. In certain embodiments, when the mORF includes a heterologous nucleotide sequence, any stop codon in the open reading frame of the influenza virus gene segment is eliminated so that one open reading frame remains that allows the translation of a fusion protein.

In another embodiment, a mORF comprises or consists of (a) at least the 3' proximal 20 nucleotides and at least the 5' proximal 30 nucleotides of an open reading frame of an influenza virus gene segment, wherein 1, 2, 3, 4, 5, 6, 7, 8, 9, 10, 11, 12, 13, 14, 15, 16, 17, 18, 19, 20 or more of the 3' proximal nucleotides and/or 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 or more of the 5' proximal nucleotides of the open reading frame of the influenza virus gene segment have been mutated, and (b) a heterologous nucleotide sequence. In certain embodiments, a mORF comprises or consists of (a) the 3' most 20 to 200 nucleotides, 20 to 175 nucleotides, 20 to 150 nucleotides, 20 to 125 nucleotides, 20 to 100 nucleotides, 20 to 100 nucleotides, 20 to 75 nucleotides, 20 to 50 nucleotides, or any integer in between of an open reading frame of an influenza virus gene segment and/or 5' most 30 to 200 nucleotides, 30 to 175 nucleotides, 30 to 150 nucleotides, 30 to 125 nucleotides, 30 to 100 nucleotides, 30 to 100 nucleotides, 30 to 75 nucleotides, 30 to 50 nucleotides, or any integer in between of an open reading frame of an influenza virus gene segment, wherein 1, 2, 3, 4, 5, 6, 7, 8, 9, 10, 11, 12, 13, 14, 15, 16, 17, 18, 19, 20 or more nucleotides in the 3' termini and/or 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 or more nucleotides in the 5' termini have been mutated, and (b) a heterologous nucleotide sequence. In certain embodiments, when the mORF includes a heterologous nucleotide sequence, any stop codon in the open reading frame of the influenza virus gene segment is eliminated so that one open reading frame remains that allows the translation of a fusion protein.

In certain embodiments, a mORF comprises or consists of the entire open reading frame of an influenza virus gene segment, wherein the open reading frame of the influenza virus gene segment contains 1 to 200, 1 to 175, 1 to 150, 1 to 125, 1 to 100, 1 to 75, 1 to 50, 1 to 25, 20 to 200, 20 to 175, 20 to 150, 20 to 150, 20 to 125, 20 to 100, 20 to 75 or 20 to 50 mutations, or an integer in between. In a specific embodiments, a mORF comprises or consists of the entire open reading frame of an influenza virus gene segment, wherein the open reading frame of the influenza virus gene segment contains 1 to 200, 1 to 175, 1 to 150, 1 to 125, 1 to 100, 1 to 75, 1 to 50, 1 to 25, 20 to 200, 20 to 175, 20 to 150, 20 to 150, 20 to 125, 20 to 100, 20 to 75 or 20 to 50 mutations (or an integer in between) at the 3' termini and/or 1 to 200, 1 to 175, 1 to 150, 1 to 125, 1 to 100, 1 to 75, 1 to 50, 1 to 25, 20 to 200, 20 to 175, 20 to 150, 20 to 125, 20 to 100, 20 to 75 or 20 to 50 mutations (or an integer in between) at the 5' termini. For example, a mORF may comprise or consist of the entire open reading frame of the influenza virus gene segment HA, NA, PA, PB1, PB2, NP, NS or M, wherein the open reading frame of the influenza virus gene segment contains 1 to 200, 1 to 175, 1 to 150, 1 to 125, 1 to 100, 1 to 75, 1 to 50, or 1 to 25 mutations (or an integer in between) at the 3' termini and/or 1 to 200, 1 to 175, 1 to 150, 1 to 125, 1 to 100, 1 to 75, 1 to 50, or 1 to 25 mutations (or an integer in between) at the 5' termini. In certain embodiments, a mORF comprises or consists of the entire open reading frame of an influenza virus gene segment, wherein the open reading frame of the influenza virus gene segment contains 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mutations at the 3' termini and/or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mutations at the 5' termini.

In a specific embodiments, a mORF comprises or consists of the entire open reading frame of an influenza virus gene segment and a heterologous nucleotide sequence, wherein the open reading frame of the influenza virus gene segment contains 1 to 200, 1 to 175, 1 to 150, 1 to 125, 1 to 100, 1 to 75, 1 to 50, or 1 to 25 mutations (or an integer in between) at the 3' termini and/or 1 to 200, 1 to 175, 1 to 150, 1 to 125, 1 to 100, 1 to 75, 1 to 50, or 1 to 25 mutations (or an integer in between) at the 5' termini. In certain embodiments, a mORF comprises or consists of the entire open reading frame of an influenza virus gene segment and a heterolgous nucleotide sequence, wherein the open reading frame of the influenza virus gene segment contains 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mutations at the 3' termini and/or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mutations at the 5' termini. In certain embodiments, when the mORF includes a heterologous nucleotide sequence, any stop codon in the open reading frame of the influenza virus gene segment is eliminated so that one open reading frame remains that allows the translation of a fusion protein.

The open reading frames of influenza virus gene segments are known in the art or can readily be determined using standard molecular biology and virology techniques. For example and not by limitation, the open reading frames for each gene product of influenza WSN virus is provided below in Table 7, infra.

TABLE 7

| WSN ORF | Length of Sequence | FIG./SEQ ID NO: |
|---|---|---|
| HA | 1698 | FIG. 17/SEQ ID NO: 182 |
| NA | 1362 | FIG. 18/SEQ ID NO: 86 |
| M1/M2 | 759/294 | FIG. 19/SEQ ID NO: 90 |
| NS1/NS2 | 693/366 | FIG. 20/SEQ ID NO: 84 |
| PA | 2151 | FIG. 21/SEQ ID NO: 98 |
| PB1 | 2274 | FIG. 22/SEQ ID NO: 102 |
| PB2 | 2280 | FIG. 23/SEQ ID NO: 106 |
| NP | 1497 | FIG. 24/SEQ ID NO: 110 |

In specific embodiments, mutations in the open reading frame of an influenza virus gene segment or a fragment thereof mutate or eliminate one or more or all of the packaging signals found in the open reading frame. In particular embodiments, such packaging signals are found in the 3' and 5' ends of the sequence. In certain embodiments, mutations in the open reading frame of an influenza virus gene segment or a fragment thereof are silent mutations, i.e., mutations that alter the nucleotide sequence of the open reading frame but do not alter the amino acid sequence encoded by the open reading frame. Most naturally occurring amino acids are encoded by multiple different codons (methionine and tryptophan are the exception)—a phenomenon that has been termed degeneracy of the genetic code. Thus, certain mutations of a codon can result in a different nucleotide sequence while encoding the same amino acid.

In certain embodiments, mutations in the open reading frame of an influenza virus gene segment or a fragment thereof result in a conservative amino acid exchange in the protein, i.e., a mutation that results in an amino acid exchange where the new amino acid has very similar chemical properties as the original, wild type amino acid. Such conservative amino acid exchanges include amino acid exchanges such as acidic amino acid for acidic amino acid; basic amino acid for basic amino acid; aliphatic amino acid for aliphatic amino acid; and aromatic amino acid for aromatic amino acid.

By way of example and not by limitation, examples of silent mutations that may be introduced into the open reading frame of each gene segment of the influenza PR8 virus are provided below in Table 8, infra.

TABLE 8

| PR8 Gene Segment | Wild-Type - 3' Termini (FIG.; SEQ ID NO:) | Mutated - 3' Termini (FIG.; SEQ ID NO:) | Wild-Type - 5' Termini (FIG.; SEQ ID NO:) | Mutated - 5' Termini (FIG.; SEQ ID NO:) |
|---|---|---|---|---|
| HA | FIG. 12A; SEQ ID NO: 61 | FIG. 12B; SEQ ID NO: 62 | FIG. 12C; SEQ ID NO: 63 | FIG. 12D; SEQ ID NO: 64 |
| NA | FIG. 14A; SEQ ID NO: 69 | FIG. 14B; SEQ ID NO: 70 | FIG. 14C; SEQ ID NO: 71 | FIG. 14D; SEQ ID NO: 72 |
| M | FIG. 15A; SEQ ID NO: 73 | FIG. 15B; SEQ ID NO: 74 | FIG. 15C; SEQ ID NO: 75 | FIG. 15D; SEQ ID NO: 76 |
| NS | FIG. 16A; SEQ ID NO: 77 | FIG. 16B; SEQ ID NO: 78 | FIG. 16C; SEQ ID NO: 79 | FIG. 16D; SEQ ID NO: 80 |
| PA | FIG. 11A; SEQ ID NO: 57 | FIG. 11B; SEQ ID NO: 58 | FIG. 11C; SEQ ID NO: 59 | FIG. 11D; SEQ ID NO: 60 |
| PB1 | FIG. 10A; SEQ ID NO: 53 | FIG. 10B; SEQ ID NO: 54 | FIG. 10C; SEQ ID NO: 55 | FIG. 10D; SEQ ID NO: 56 |
| PB2 | FIG. 9A; SEQ ID NO: 49 | FIG. 9B; SEQ ID NO: 50 | FIG. 9C; SEQ ID NO: 51 | FIG. 9D; SEQ ID NO: 52 |
| NP | FIG. 13A; SEQ ID NO: 65 | FIG. 13B; SEQ ID NO: 66 | FIG. 13C; SEQ ID NO: 67 | FIG. 13D; SEQ ID NO: 68 |

In certain embodiments, a mORF may include a heterologous nucleotide sequence. The heterologous nucleotide sequence is generally in frame with the open reading frame of an influenza virus gene segment or a derivative or a fragment thereof. In a specific embodiment, the heterologous nucleotide sequence encodes an antigen of any infectious pathogen or associated with any disease that is capable of eliciting an immune response. In a specific embodiment, the antigen is a glycoprotein. In certain embodiments, the heterologous nucleotide sequence encodes a viral antigen. In other embodiments, the heterologous nucleotide sequence encodes a bacterial antigen (e.g., bacterial coat protein). In other embodiments, the heterologous nucleotide sequence encodes parasitic antigen (e.g., a protozoan antigen). In another embodiment, the heterologous nucleotide sequence encodes a fungal antigen.

In some embodiments, the heterologous nucleotide sequence encodes a tumor antigen or tumor associated antigen. In some embodiments, the heterologous nucleotide sequence encodes a cytokine or growth factor. In certain embodiments, the heterologous nucleotide sequence encodes a peptide tag, such as flag tag. In some embodiments, the heterologous nucleotide sequence encodes a detectable substance.

Non-limiting examples of viral antigens include antigens from adenoviridae (e.g., mastadenovirus and aviadenovirus), herpesviridae (e.g., herpes simplex virus 1, herpes simplex virus 2, herpes simplex virus 5, herpes simplex virus 6, Epstein-Barr virus, HHV6-HHV8 and cytomegalovirus), leviviridae (e.g., levivirus, enterobacteria phase MS2, allolevirus), poxyiridae (e.g., chordopoxyirinae, parapoxvirus, avipoxvirus, capripoxvirus, leporiipoxvirus, suipoxvirus, molluscipoxvirus, and entomopoxyirinae), papovaviridae (e.g., polyomavirus and papillomavirus), paramyxoviridae (e.g., paramyxovirus, parainfluenza virus 1, mobillivirus (e.g., measles virus), rubulavirus (e.g., mumps virus), pneumonovirinae (e.g., pneumovirus, human respiratory synctial virus), human respiratory syncytial virus and metapneumovirus (e.g., avian pneumovirus and human metapneumovirus)), picornaviridae (e.g., enterovirus, rhinovirus, hepatovirus (e.g., human hepatits A virus), cardiovirus, and apthovirus), reoviridae (e.g., orthoreovirus, orbivirus, rotavirus, cypovirus, fijivirus, phytoreovirus, and oryzavirus), retroviridae (e.g., mammalian type B retroviruses, mammalian type C retroviruses, avian type C retroviruses, type D retrovirus group, BLV-HTLV retroviruses, lentivirus (e.g. human immunodeficiency virus 1 and human immunodeficiency virus 2 (e.g., HIV gp160), spumavirus), flaviviridae (e.g., hepatitis C virus, dengue virus, West Nile virus), hepadnaviridae (e.g., hepatitis B virus), togaviridae (e.g., alphavirus (e.g., sindbis virus) and rubivirus (e.g., rubella virus)), rhabdoviridae (e.g., vesiculovirus, lyssavirus, ephemerovirus, cytorhabdovirus, and necleorhabdovirus), arenaviridae (e.g., arenavirus, lymphocytic choriomeningitis virus, Ippy virus, and lassa virus), and coronaviridae (e.g., coronavirus and torovirus). In a specific embodiment, the viral antigen is HIV gp120, HIV nef, RSV F glycoprotein, RSV G glycoprotein, HTLV tax, herpes simplex virus glycoprotein (e.g., gB, gC, gD, and gE) or hepatitis B surface antigen, hepatitis C virus E protein or coronavirus spike protein.

Non-limiting examples of bacterial antigens include antigens from bacteria of the Aquaspirillum family, Azospirillum family, Azotobacteraceae family, Bacteroidaceae family, *Bartonella* species, Bdellovibrio family, *Campylobacter* species, *Chlamydia* species (e.g., *Chlamydia pneumoniae*), *clostridium*, Enterobacteriaceae family (e.g., *Citrobacter* species, *Edwardsiella, Enterobacter aerogenes, Erwinia* species, *Escherichia coli, Hafnia* species, *Klebsiella* species, *Morganella* species, *Proteus vulgaris, Providencia, Salmonella* species, *Serratia marcescens*, and *Shigella flexneri*), Gardinella family, *Haemophilus influenzae*, Halobacteriaceae family, Helicobacter family, Legionallaceae family, *Listeria* species, Methylococcaceae family, mycobacteria (e.g., *Mycobacterium tuberculosis*), Neisseriaceae family, Oceanospirillum family, Pasteurellaceae family, *Pneumococcus* species, *Pseudomonas* species, Rhizobiaceae family, Spirillum family, Spirosomaceae family, *Staphylococcus* (e.g., methicillin resistant *Staphylococcus aureus* and *Staphylococcus pyrogenes*), *Streptococcus* (e.g., *Streptococcus enteritidis, Streptococcus fasciae*, and *Streptococcus pneumoniae*), Helicobacter family, Yersinia family, *Bacillus antracis* and Vampirovibrio family.

Non-limiting examples of parasite antigens include antigens from a parasite such as an amoeba, a malarial parasite, *Plasmodium, Trypanosoma cruzi*. Non-limiting examples of fungal antigens include antigens from fungus of *Absidia* species (e.g., *Absidia corymbifera* and *Absidia ramosa*), *Aspergillus* species, (e.g., *Aspergillus flavus, Aspergillus fumigatus, Aspergillus nidulans, Aspergillus niger,* and *Aspergillus terreus*), *Basidiobolus ranarum, Blastomyces dermatitidis, Candida* species (e.g., *Candida albicans, Candida glabrata, Candida kerr, Candida krusei, Candida parapsilosis, Candida pseudotropicalis, Candida quillermondii, Candida rugosa, Candida stellatoidea,* and *Candida tropicalis*), *Coccidioides immitis, Conidiobolus species, Cryptococcus neoforms, Cunninghamella* species, dermatophytes, *Histoplasma capsulatum, Microsporum gypseum, Mucor pusillus, Paracoccidioides brasiliensis, Pseudallescheria boydii, Rhinosporidium seeberi, Pneumocystis carinii, Rhizopus* species (e.g., *Rhizopus arrhizus, Rhizopus oryzae,* and *Rhizopus microsporus*), *Saccharomyces* species, *Sporothrix schenckii*, zygomycetes, and classes such as Zygomycetes, Ascomycetes, the Basidiomycetes, Deuteromycetes, and Oomycetes.

Non-limiting examples of tumor associated antigens include MAGE-1, MAGE-3, BAGE, GAGE-1, GAGE-2, N-acetylglucosaminyltransferase-V, p-15, MART-1/MelanA, TRP-1 (gp75), Tyrosinase, cyclin-dependent kinase 4, MUM-1, CDK4, HER-2/neu, human papillomavirus-E6, human papillomavirus E7, MUC-1, caspase-8, CD5, CD20, CEA, mucin-1, Lewisx, CA-125, epidermal growth factor receptor, p185HER2, IL-2R, tenascin, antigens associated with a metalloproteinase, and CAMPATH-1. Non-limiting examples of cytokines and growth factors include interleukin (IL)-2, IL-4, IL-5, IL-6, IL-7, IL-9, IL-10, IL-12, IL-15, IL-18, IL-22, IFN-alpha, IFN-beta, and IFN-beta. Non-limiting examples of detectable substances include various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; and bioluminescent materials, such as but not limited to, luciferase, luciferin, and aequorin.

In specific embodiments, the heterologous nucleotide sequence encodes a respiratory pathogen antigen. Non-limiting examples of respiratory virus antigens include the F, G, or M2 protein of RSV, the spike protein of a Coronavirus (e.g., SARS, HuCoV), the F protein of human metapneumovirus, the F or HN protein of parainfluenza virus, the G or F protein of Hendra virus, the G or F protein of Nipah virus, or the capsid protein of Adenovirus. In a specific embodiment, the respiratory virus antigen is an influenza virus antigen from a different type, subtype, or strain of influenza virus.

5.2 Influenza Virus Comprising Chimeric Influenza Virus Gene Segments

In one aspect, provided herein are recombinant influenza viruses comprising one, two, three, four, five, six, seven or eight chimeric influenza virus gene segments described herein. In a specific embodiment, provided herein are recombinant influenza viruses comprising two or more chimeric influenza virus gene segments described herein, wherein the two or more chimeric influenza virus gene segments cosegregate (otherwise referred to herein as a "cosegregating chimeric influenza virus gene segments"). A group of cosegregating chimeric influenza virus gene segments may include two, three, four, five, six, seven or eight chimeric influenza virus gene segments. In certain embodiments, two or more chimeric influenza virus gene segments cosegregate at least 10%, 15%, 20%, 25%, 30%, 35%, 40%, 45%, 50%, 55%, 60%, 65%, 70%, 75%, 80%, 85%, 90%, 95%, or 99% of the time as determined by a technique known to one of skill in the art. In some embodiments, two or more chimeric influenza virus gene segments cosegregate 10% to 50%, 10% to 75%, 10% to 95%, 10% to 99.5%, 25% to 50%, 25% to 75%, 25% to 99.5%, 50% to 75%, 50% to 99.5%, 75% to 99.5, 80% to 99.5%, 90% to 99.5%, or 95% to 99.5% of the time as determined by a technique known to one of skill in the art. One example of such a technique may comprise coinfecting the cells with a wild-type virus and a recombinant influenza virus described herein, picking single plaques, and determining the genomic composition of each plaque. Without being bound by theory, the chimeric influenza virus gene segments have a reduced the ability to reassort independently of each other with other influenza virus gene segments, and thus, the reassortment of the recombinant influenza virus with other influenza viruses (e.g., wild-type influenza viruses) is reduced or inhibited. In some embodiments, the reassortment of the recombinant influenza virus with other influenza viruses is less than 40%, 35%, 30%, 25%, 20%, 15%, 10% or 5% as determined by the percentage of viral plaques containing reassorted influenza viruses with one or more chimeric influenza virus gene segments that have reassorted independently from one or more other chimeric influenza virus gene segments. Recombinant influenza viruses that are unable to reassort will produce fewer viral plaques that contain viruses with one or more chimeric influenza virus gene segments that has reassorted independently of one or more other chimeric influenza virus gene segments.

In certain embodiments, a recombinant influenza virus provided herein comprises two chimeric influenza virus gene segments that cosegregate. The first and second chimeric influenza virus gene segments contain packaging signals obtained or derived from a first and a second type of influenza virus gene segment as provided, e.g., in Table 9, infra.

TABLE 9

|  | 3' NCR1 & 5' NCR1 | 3' CRS1 &/or 5' CRS1 | mORF |
| --- | --- | --- | --- |
| First Chimeric Influenza Virus Gene Segment | $1^{st}$ Type of Influenza Virus Gene Segment | $1^{st}$ Type of Influenza Virus Gene Segment | $2^{nd}$ Type of Influenza Virus Gene Segment |
| Second Chimeric Influenza Virus Gene Segment | $2^{nd}$ Type of Influenza Virus Gene Segment | $2^{nd}$ Type of Influenza Virus Gene Segment | $1^{st}$ Type of Influenza Virus Gene Segment |

The first and second types of influenza virus gene segments refer to two different influenza virus gene segments. For example, the first type of influenza virus gene segment may be an HA influenza virus gene segment and the second type of influenza virus gene segment may be an NS influenza virus gene segment.

In specific embodiments, a recombinant influenza virus may comprise a first and a second chimeric influenza virus gene segment, wherein:
(a) the first chimeric influenza virus gene segment comprises:
  (i) a 3' NCR of a first type of influenza virus gene segment or a fragment thereof, or a nucleotide sequence that is at least 50% (in some embodiments, at least 60%, at least 65%, at least 70%, at least 75%, at least 80%, at least 85%, at least 90%, at least 95%, or at least 98%) identical to a 3' NCR of a first type of influenza virus gene segment or a fragment thereof, or a nucleotide sequence that hybridizes under stringent conditions to a 3' NCR of a first type of influenza virus gene segment or a fragment thereof;
  (ii) a 3' proximal coding region sequence of the first type of influenza virus gene segment, or a nucleotide sequence that is at least 50% (in some embodiments, at least 60%, at least 65%, at least 70%, at least 75%, at least 80%, at least 85%, at least 90%, at least 95%, or at least 98%) identical to a 3' proximal coding region sequence of the first type of influenza virus gene segment, or a nucleotide sequence that hybridizes under stringent conditions to a 3' proximal coding region sequence of the first type of influenza virus gene segment, wherein any start codon present in the sequence in (ii) has been eliminated;
  (iii) an open reading frame of a second influenza virus gene segment, or an open reading frame comprising an open reading frame of a second type of influenza virus gene segment or a fragment thereof and a heterologous nucleotide sequence, wherein 3' and 5' proximal nucleotides of the open reading frame of the second type of influenza virus gene segment have been mutated;
  (iv) a 5' proximal coding region sequence of the first type of influenza virus gene segment, or a nucleotide sequence that is at least 50% (in some embodiments, at least 60%, at least 65%, at least 70%, at least 75%, at least 80%, at least 85%, at least 90%, at least 95%, or at least 98%) identical to a 5' proximal coding region sequence of the first type of influenza virus gene segment, or a nucleotide sequence that hybridizes under stringent conditions to a 5' proximal coding region sequence of the first type of influenza virus gene segment, wherein the sequence in (iv) is not translated; and
  (v) a 5' NCR of the first type of influenza virus gene segment or a fragment thereof, or a nucleotide sequence that is at least 50% (in some embodiments, at least 60%, at least 65%, at least 70%, at least 75%, at least 80%, at least 85%, at least 90%, at least 95%, or at least 98%) identical to a 5' NCR of the first type of influenza virus gene segment or a fragment thereof, or a nucleotide sequence that hybridizes under stringent conditions to a 5' NCR of the first type of influenza virus gene segment or a fragment thereof; and wherein
(b) the second chimeric influenza virus gene segment comprises:
  (i) a 3' NCR of the second type of influenza virus gene segment or a fragment thereof, or a nucleotide sequence that is at least 50% (in some embodiments, at least 60%, at least 65%, at least 70%, at least 75%, at least 80%, at least 85%, at least 90%, at least 95%, or at least 98%) identical to a 3' NCR of the second type of influenza virus gene segment or a fragment thereof, or a nucleotide sequence that hybridizes under stringent conditions to a 3' NCR of the second type of influenza virus gene segment or a fragment thereof;
  (ii) a 3' proximal coding region sequence of the second type of influenza virus gene segment, or a nucleotide sequence that is at least 50% (in some embodiments, at least 60%, at least 65%, at least 70%, at least 75%, at least 80%, at least 85%, at least 90%, at least 95%, or at least 98%) identical to a 3' proximal coding region sequence of the second type of influenza virus gene segment, or a nucleotide sequence that hybridizes under stringent conditions to a 3' proximal coding region sequence of the second type of influenza virus gene segment, wherein any start codon present in the sequence in (ii) has been eliminated;
  (iii) an open reading frame of the first type of influenza virus gene segment, or an open reading frame comprising an open reading frame of the first type of influenza virus gene segment and a heterologous nucleotide sequence, wherein 3' and 5' proximal nucleotides of the open reading frame of the first type of influenza virus gene segment have been mutated;
  (iv) a 5' proximal coding region sequence of the second type of influenza virus gene segment, or a nucleotide sequence that is at least 50% (in some embodiments, at least 60%, at least 65%, at least 70%, at least 75%, at least 80%, at least 85%, at least 90%, at least 95%, or at least 98%) identical to a 5' proximal coding region sequence of the second type of influenza virus gene segment, or a nucleotide sequence that hybridizes under stringent conditions to a 5' proximal coding region sequence of the second type of influenza virus gene segment, wherein the sequence in (iv) is not translated; and
  (v) a 5' NCR of the second type of influenza virus gene segment or a fragment thereof, or a nucleotide sequence that is at least 50% (in some embodiments, at least 60%, at least 65%, at least 70%, at least 75%, at least 80%, at least 85%, at least 90%, at least 95%, or at least 98%) identical to a 5' NCR of the second type of influenza virus gene segment or a fragment thereof, or a nucleotide sequence that hybridizes under stringent conditions to a 5' NCR of the second type of influenza virus gene segment or a fragment thereof.

In certain embodiments, the 3' proximal coding region sequence is derived from an influenza virus NS or M gene segment. In a specific embodiment, the 3' proximal coding region sequence is derived from an influenza virus NS gene segment and the 3' proximal coding region has been mutated so as to eliminate the mRNA 5' splice site. In another specific embodiment, the 3' proximal coding region sequence is derived from an influenza virus M gene segment and the 3' proximal coding region has been mutated so as to eliminate the distal 5' splice site In certain embodiments, a recombinant influenza virus provided herein comprises three chimeric influenza virus gene segments that cosegregate. The first, second and third chimeric influenza virus gene segments contain packaging signals obtained or derived from a first, a second and a third type of influenza virus gene segment as provided, e.g., in Table 10, infra.

TABLE 10

|  | 3' NCR1 & 5' NCR1 | 3' CRS1 &/or 5' CRS1 | mORF |
|---|---|---|---|
| First Chimeric Influenza Virus Gene Segment | 1$^{st}$ Type of Influenza Virus Gene Segment | 1$^{st}$ Type of Influenza Virus Gene Segment | 3$^{rd}$ Type of Influenza Virus Gene Segment |
| Second Chimeric Influenza Virus Gene Segment | 2$^{nd}$ Type of Influenza Virus Gene Segment | 2$^{nd}$ Type of Influenza Virus Gene Segment | 1st Type of Influenza Virus Gene Segment |
| Third Chimeric Influenza Virus Gene Segment | 3$^{rd}$ Type of Influenza Virus Gene Segment | 3$^{rd}$ Type of Influenza Virus Gene Segment | 2$^{nd}$ Type of Influenza Virus Gene Segment |

The first, second and third types of influenza virus gene segments refer to three different influenza virus gene segments. For example, the first type of influenza virus gene segment may be an HA influenza virus gene segment, the second type of influenza virus gene segment may be an NS influenza virus gene segment, and the third type of influenza virus gene segment may be an NP influenza virus gene segment.

In specific embodiments, a recombinant influenza virus may comprise a first, a second, and a third chimeric influenza virus gene segment, wherein:

(a) the first chimeric influenza virus gene segment comprises:
(i) a 3' NCR of a first type of influenza virus gene segment or a fragment thereof, or a nucleotide sequence that is at least 50% (in some embodiments, at least 60%, at least 65%, at least 70%, at least 75%, at least 80%, at least 85%, at least 90%, at least 95%, or at least 98%) identical to a 3' NCR of a first type of influenza virus gene segment or a fragment thereof, or a nucleotide sequence that hybridizes under stringent conditions to a 3' NCR of a first type of influenza virus gene segment or a fragment thereof;
(ii) a 3' proximal coding region sequence of the first type of influenza virus gene segment, or a nucleotide sequence that is at least 50% (in some embodiments, at least 60%, at least 65%, at least 70%, at least 75%, at least 80%, at least 85%, at least 90%, at least 95%, or at least 98%) identical to a 3' proximal coding region sequence of the first type of influenza virus gene segment, or a nucleotide sequence that hybridizes under stringent conditions to a 3' proximal coding region sequence of the first type of influenza virus gene segment, wherein any start codon present in the sequence in (ii) has been eliminated;
(iii) an open reading frame of a third type of influenza virus gene segment, or an open reading frame comprising an open reading frame of a third type of influenza virus gene segment or a fragment thereof and a heterologous nucleotide sequence, wherein 3' and 5' proximal nucleotides of the open reading frame of the third type of influenza virus gene segment have been mutated;
(iv) a 5' proximal coding region sequence of the first type of influenza virus gene segment, or a nucleotide sequence that is at least 50% (in some embodiments, at least 60%, at least 65%, at least 70%, at least 75%, at least 80%, at least 85%, at least 90%, at least 95%, or at least 98%) identical to a 5' proximal coding region sequence of the first type of influenza virus gene segment, or a nucleotide sequence that hybridizes under stringent conditions to a 5' proximal coding region sequence of the first type of influenza virus gene segment, wherein the sequence in (iv) is not translated; and
(v) a 5' NCR of the first type of influenza virus gene segment or a fragment thereof, or a nucleotide sequence that is at least 50% (in some embodiments, at least 60%, at least 65%, at least 70%, at least 75%, at least 80%, at least 85%, at least 90%, at least 95%, or at least 98%) identical to a 5' NCR of the first type of influenza virus gene segment or a fragment thereof, or a nucleotide sequence that hybridizes under stringent conditions to a 5' NCR of the first type of influenza virus gene segment or a fragment thereof; and wherein (b) the second chimeric influenza virus gene segment comprises:
(i) a 3' NCR of the second type of influenza virus gene segment or a fragment thereof, or a nucleotide sequence that is at least 50% (in some embodiments, at least 60%, at least 65%, at least 70%, at least 75%, at least 80%, at least 85%, at least 90%, at least 95%, or at least 98%) identical to a 3' NCR of the second type of influenza virus gene segment or a fragment thereof, or a nucleotide sequence that hybridizes under stringent conditions to a 3' NCR of the second type of influenza virus gene segment or a fragment thereof;
(ii) a 3' proximal coding region sequence of the second type of influenza virus gene segment, or a nucleotide sequence that is at least 50% (in some embodiments, at least 60%, at least 65%, at least 70%, at least 75%, at least 80%, at least 85%, at least 90%, at least 95%, or at least 98%) identical to a 3' proximal coding region sequence of the second type of influenza virus gene segment, or a nucleotide sequence that hybridizes under stringent conditions to a 3' proximal coding region sequence of the second type of influenza virus gene segment, wherein any start codon present in the sequence in (ii) has been eliminated;
(iii) an open reading frame of the first type of influenza virus gene segment, or an open reading frame comprising an open reading frame of the first type of influenza virus gene segment or a fragment thereof and a heterologous nucleotide sequence, wherein 3' and 5' proximal nucleotides of the open reading frame of the first type of influenza virus gene segment have been mutated;
(iv) a 5' proximal coding region sequence of the second type of influenza virus gene segment, or a nucleotide sequence that is at least 50% (in some embodiments, at least 60%, at least 65%, at least 70%, at least 75%, at least 80%, at least 85%, at least 90%, at least 95%, or at least 98%) identical to a 5' proximal coding region sequence of the second type of influenza virus gene segment, or a nucleotide sequence that hybridizes under stringent conditions to a 5' proximal coding region sequence of the second type of influenza virus gene segment, wherein the sequence in (iv) is not translated; and (v) a 5' NCR of the second type of influenza virus gene segment or a fragment thereof, or a nucleotide sequence that is at least 50% (in some embodiments, at least 60%, at least 65%, at least 70%, at least 75%, at least 80%, at least 85%, at least 90%, at least 95%, or at least 98%) identical to a 5' NCR of the second type of influenza virus gene segment or a fragment thereof, or a nucleotide sequence that hybridizes under stringent conditions to a 5' NCR of the second type of influenza virus gene segment or a fragment thereof; wherein (c) the third chimeric influenza virus gene segment comprises:
(i) a 3' NCR of the third type of influenza virus gene segment or a fragment thereof, or a nucleotide sequence that is at least 50% (in some embodiments, at least 60%, at least 65%, at least 70%, at least 75%, at least 80%, at least 85%, at least 90%, at least 95%, or at least 98%) identical to a 3' NCR of the third type of influenza virus gene segment or a fragment thereof, or a nucleotide sequence that hybridizes under stringent conditions to a 3' NCR of the third type of influenza virus gene segment or a fragment thereof;
(ii) a 3' proximal coding region sequence of the third type of influenza virus gene segment, or a nucleotide sequence that is at least 50% (in some embodiments, at least 60%, at least 65%, at least 70%, at least 75%, at least 80%, at least 85%, at least 90%, at least 95%, or at least 98%) identical to a 3' proximal coding region sequence of the third type of influenza virus gene segment, or a nucleotide sequence that hybridizes under stringent conditions to a 3' proximal coding region sequence of the third type of influenza virus gene segment, wherein any start codon present in the sequence in (ii) has been eliminated;
(iii) an open reading frame of the second type of influenza virus gene segment, or an open reading frame comprising an open reading frame of the second type of influenza virus gene segment or a fragment thereof and a heterologous nucleotide sequence, wherein 3' and 5' proximal nucleotides of the open reading frame of the second type of influenza virus gene segment have been mutated;
(iv) a 5' proximal coding region sequence of the third type of influenza virus gene segment, or a nucleotide sequence that is at least 50% (in some embodiments, at least 60%, at least 65%, at least 70%, at least 75%, at least 80%, at least 85%, at least 90%, at least 95%, or at least 98%) identical to a 5' proximal coding region sequence of the third type of influenza virus gene segment, or a nucleotide sequence that hybridizes under stringent conditions to a 5' proximal coding region sequence of the third type of influenza virus gene segment, wherein the sequence in (iv) is not translated; and
(v) a 5' NCR of the third type of influenza virus gene segment or a fragment thereof, or a nucleotide sequence that is at least 50% (in some embodiments, at least 60%, at least 65%, at least 70%, at least 75%, at least 80%, at least 85%, at least 90%, at least 95%, or at least 98%) identical to a 5' NCR of the third type of influenza virus gene segment or a fragment thereof, or a nucleotide sequence that hybridizes under stringent conditions to a 5' NCR of the third type of influenza virus gene segment or a fragment thereof.

In certain embodiments, the 3' proximal coding region sequence is derived from an influenza virus NS or M gene segment. In a specific embodiment, the 3' proximal coding region sequence is derived from an influenza virus NS gene segment and the 3' proximal coding region has been mutated so as to eliminate the mRNA 5' splice site. In another specific embodiment, the 3' proximal coding region sequence is derived from an influenza virus M gene segment and the 3' proximal coding region has been mutated so as to eliminate the distal 5' splice site.

In certain embodiments, a recombinant influenza virus provided herein comprises four chimeric influenza virus gene segments that cosegregate. The first, second, third and fourth chimeric influenza virus gene segments contain packaging signals obtained or derived from a first, a second, a third and a fourth type of influenza virus gene segment as provided, e.g., in Table 11, infra.

TABLE 11

|  | 3' NCR1 & 5' NCR1 | 3' CRS1 &/or 5' CRS1 | mORF |
| --- | --- | --- | --- |
| First Chimeric Influenza Virus Gene Segment | 1$^{st}$ Type of Influenza Virus Gene Segment | 1$^{st}$ Type of Influenza Virus Gene Segment | 4$^{rd}$ Type of Influenza Virus Gene Segment |
| Second Chimeric Influenza Virus Gene Segment | 2$^{nd}$ Type of Influenza Virus Gene Segment | 2$^{nd}$ Type of Influenza Virus Gene Segment | 3$^{rd}$ Type of Influenza Virus Gene Segment |
| Third Chimeric Influenza Virus Gene Segment | 3$^{rd}$ Type of Influenza Virus Gene Segment | 3$^{rd}$ Type of Influenza Virus Gene Segment | 2$^{nd}$ Type of Influenza Virus Gene Segment |
| Fourth Chimeric Influenza Virus Gene Segment | 4$^{th}$ Type of Influenza Virus Gene Segment | 4$^{th}$ Type of Influenza Virus Gene Segment | 1$^{st}$ Type of Influenza Virus Gene Segment |

The first, second, third and fourth types of influenza virus gene segments refer to four different influenza virus gene segments. For example, the first type of influenza virus gene segment may be an HA influenza virus gene segment, the second type of influenza virus gene segment may be an NS influenza virus gene segment, the third type of influenza virus gene segment may be an NP influenza virus gene segment, and the fourth type of influenza virus gene segment may be an PB1.

In certain embodiments, a recombinant influenza virus provided herein comprises five chimeric influenza virus gene segments that cosegregate. The first, second, third, fourth and fifth chimeric influenza virus gene segments contain packaging signals obtained or derived from a first, a second, a third, a fourth and a fifth type of influenza virus gene segment as provided, e.g., in Table 12, infra.

The first, second, third, fourth, fifth and sixth types of influenza virus gene segments refer to six different influenza virus

TABLE 12

|  | 3' NCR1 & 5' NCR1 | 3' CRS1 &/or 5' CRS1 | mORF |
| --- | --- | --- | --- |
| First Chimeric Influenza Virus Gene Segment | 1st Type of Influenza Virus Gene Segment | 1st Type of Influenza Virus Gene Segment | 3rd Type of Influenza Virus Gene Segment |
| Second Chimeric Influenza Virus Gene Segment | 2nd Type of Influenza Virus Gene Segment | 2nd Type of Influenza Virus Gene Segment | 1st Type of Influenza Virus Gene Segment |
| Third Chimeric Influenza Virus Gene Segment | 3rd Type of Influenza Virus Gene Segment | 3rd Type of Influenza Virus Gene Segment | 2nd Type of Influenza Virus Gene Segment |
| Fourth Chimeric Influenza Virus Gene Segment | 5th Type of Influenza Virus Gene Segment | 5th Type of Influenza Virus Gene Segment | 4th Type of Influenza Virus Gene Segment |
| Fifth Chimeric Influenza Virus Gene Segment | 4th Type of Influenza Virus Gene Segment | 4th Type of Influenza Virus Gene Segment | 5th Type of Influenza Virus Gene Segment |

The first, second, third, fourth and fifth types of influenza virus gene segments refer to five different influenza virus gene segments. For example, the first type of influenza virus gene segment may be an HA influenza virus gene segment, the second type of influenza virus gene segment may be an NS influenza virus gene segment, the third type of influenza virus gene segment may be an NP influenza virus gene segment, the fourth type of influenza virus gene segment may be a PB1 influenza virus gene segment, and the fifth type of influenza virus gene segment may be a PB2 influenza virus gene segment.

In certain embodiments, a recombinant influenza virus provided herein comprises six chimeric influenza virus gene segments that cosegregate. The first, second, third, fourth, fifth and sixth chimeric influenza virus gene segments contain packaging signals obtained or derived from a first, a second, a third, a fourth, a fifth and a sixth type of influenza virus gene segment as provided, e.g., in Table 13, infra.

gene segments. For example, the first type of influenza virus gene segment may be an HA influenza virus gene segment, the second type of influenza virus gene segment may be an NS influenza virus gene segment, the third type of influenza virus gene segment may be an NP influenza virus gene segment, the fourth type of influenza virus gene segment may be a PB1 influenza virus gene segment, the fifth type of influenza virus gene segment may be a PB2 influenza virus gene segment, and the sixth type of influenza virus gene segment from a PA influenza virus gene segment.

In certain embodiments, a recombinant influenza virus provided herein comprises seven chimeric influenza virus gene segments that cosegregate. The first, second, third, fourth, fifth, sixth and seventh chimeric influenza virus gene segments contain packaging signals obtained or derived from a first, a second, a third, a fourth, a fifth, a sixth and a seventh type of influenza virus gene segment as provided, e.g., in Table 14, infra.

TABLE 13

|  | 3' NCR1 & 5' NCR1 | 3' CRS1 &/or 5' CRS1 | mORF |
| --- | --- | --- | --- |
| First Chimeric Influenza Virus Gene Segment | 1st Type of Influenza Virus Gene Segment | 1st Type of Influenza Virus Gene Segment | 2nd Type of Influenza Virus Gene Segment |
| Second Chimeric Influenza Virus Gene Segment | 2nd Type of Influenza Virus Gene Segment | 2nd Type of Influenza Virus Gene Segment | 1st Type of Influenza Virus Gene Segment |
| Third Chimeric Influenza Virus Gene Segment | 3rd Type of Influenza Virus Gene Segment | 3rd Type of Influenza Virus Gene Segment | 4th Type of Influenza Virus Gene Segment |
| Fourth Chimeric Influenza Virus Gene Segment | 4th Type of Influenza Virus Gene Segment | 4th Type of Influenza Virus Gene Segment | 3rd Type of Influenza Virus Gene Segment |
| Fifth Chimeric Influenza Virus Gene Segment | 5th Type of Influenza Virus Gene Segment | 5th Type of Influenza Virus Gene Segment | 6th Type of Influenza Virus Gene Segment |
| Sixth Chimeric Influenza Virus Gene Segment | 6th Type of Influenza Virus Gene Segment | 6th Type of Influenza Virus Gene Segment | 5th Type of Influenza Virus Gene Segment |

TABLE 14

|  | 3' NCR1 & 5' NCR1 | 3' CRS1 &/or 5' CRS1 | mORF |
|---|---|---|---|
| First Chimeric Influenza Virus Gene Segment | $1^{st}$ Type of Influenza Virus Gene Segment | $1^{st}$ Type of Influenza Virus Gene Segment | $2^{nd}$ Type of Influenza Virus Gene Segment |
| Second Chimeric Influenza Virus Gene Segment | $2^{nd}$ Type of Influenza Virus Gene Segment | $2^{nd}$ Type of Influenza Virus Gene Segment | $1^{st}$ Type of Influenza Virus Gene Segment |
| Third Chimeric Influenza Virus Gene Segment | $3^{rd}$ Type of Influenza Virus Gene Segment | $3^{rd}$ Type of Influenza Virus Gene Segment | $4^{th}$ Type of Influenza Virus Gene Segment |
| Fourth Chimeric Influenza Virus Gene Segment | $4^{th}$ Type of Influenza Virus Gene Segment | $4^{th}$ Type of Influenza Virus Gene Segment | $3^{rd}$ Type of Influenza Virus Gene Segment |
| Fifth Chimeric Influenza Virus Gene Segment | $5^{th}$ Type of Influenza Virus Gene Segment | $5^{th}$ Type of Influenza Virus Gene Segment | $6^{th}$ Type of Influenza Virus Gene Segment |
| Sixth Chimeric Influenza Virus Gene Segment | $6^{th}$ Type of Influenza Virus Gene Segment | $6^{th}$ Type of Influenza Virus Gene Segment | $7^{th}$ Type of Influenza Virus Gene Segment |
| Seventh Chimeric Influenza Virus Gene Segment | $7^{th}$ Type of Influenza Virus Gene Segment | $7^{th}$ Type of Influenza Virus Gene Segment | $5^{th}$ Type of Influenza Virus Gene Segment |

The first, second, third, fourth, fifth, sixth and seventh types of influenza virus gene segments refer to seven different influenza virus gene segments. For example, the first type of influenza virus gene segment may be an HA influenza virus gene segment, the second type of influenza virus gene segment may be an NS influenza virus gene segment, the third type of influenza virus gene segment may be an NP influenza virus gene segment, the fourth type of influenza virus gene segment may be a PB1 influenza virus gene segment, the fifth type of influenza virus gene segment may be a PB2 influenza virus gene segment, the sixth type of influenza virus gene segment from a PA influenza virus gene segment, and a seventh type of influenza virus gene segment from an M influenza virus gene segment.

In certain embodiments, a recombinant influenza virus provided herein comprises eight chimeric influenza virus gene segments that cosegregate. The first, second, third, fourth, fifth, sixth, seventh and eight chimeric influenza virus gene segments contain packaging signals obtained or derived from a first, a second, a third, a fourth, a fifth, a sixth, a seventh and an eighth type of influenza virus gene segment as provided, e.g., in Table 15, infra.

TABLE 15

|  | 3' NCR1 & 5' NCR1 | 3' CRS1 &/or 5' CRS1 | mORF |
|---|---|---|---|
| First Chimeric Influenza Virus Gene Segment | $1^{st}$ Type of Influenza Virus Gene Segment | $1^{st}$ Type of Influenza Virus Gene Segment | $2^{nd}$ Type of Influenza Virus Gene Segment |
| Second Chimeric Influenza Virus Gene Segment | $2^{nd}$ Type of Influenza Virus Gene Segment | $2^{nd}$ Type of Influenza Virus Gene Segment | $1^{st}$ Type of Influenza Virus Gene Segment |
| Third Chimeric Influenza Virus Gene Segment | $3^{rd}$ Type of Influenza Virus Gene Segment | $3^{rd}$ Type of Influenza Virus Gene Segment | $4^{th}$ Type of Influenza Virus Gene Segment |
| Fourth Chimeric Influenza Virus Gene Segment | $4^{th}$ Type of Influenza Virus Gene Segment | $4^{th}$ Type of Influenza Virus Gene Segment | $3^{rd}$ Type of Influenza Virus Gene Segment |
| Fifth Chimeric Influenza Virus Gene Segment | $5^{th}$ Type of Influenza Virus Gene Segment | $5^{th}$ Type of Influenza Virus Gene Segment | $6^{th}$ Type of Influenza Virus Gene Segment |
| Sixth Chimeric Influenza Virus Gene Segment | $6^{th}$ Type of Influenza Virus Gene Segment | $6^{th}$ Type of Influenza Virus Gene Segment | $5^{th}$ Type of Influenza Virus Gene Segment |
| Seventh Chimeric Influenza Virus Gene Segment | $7^{th}$ Type of Influenza Virus Gene Segment | $7^{th}$ Type of Influenza Virus Gene Segment | $8^{th}$ Type of Influenza Virus Gene Segment |
| Eighth Chimeric Influenza Virus Gene Segment | $8^{th}$ Type of Influenza Virus Gene Segment | $8^{th}$ Type of Influenza Virus Gene Segment | $7^{th}$ Type of Influenza Virus Gene Segment |

The first, second, third, fourth, fifth, sixth, seventh and eighth types of influenza virus gene segments refer to eight different influenza virus gene segments. For example, the first type of influenza virus gene segment may be an HA influenza virus gene segment, the second type of influenza virus gene segment may be an NS influenza virus gene segment, the third type of influenza virus gene segment may be an NP influenza virus gene segment, the fourth type of influenza virus gene segment may be a PB1 influenza virus gene segment, the fifth type of influenza virus gene segment may be a PB2 influenza virus gene segment, the sixth type of influenza virus gene segment from a PA influenza virus gene segment, a seventh type of influenza virus gene segment from an M influenza virus gene segment, and an eighth type of influenza virus gene segment from a neuraminidase (NA) influenza virus gene segment.

In certain embodiments, a recombinant influenza virus comprises a chimeric influenza virus gene segment that includes a 3' NCR1, a 5' NCR1, a 3' CRS1 and a 5'CRS1 from the same type of influenza virus, the same subtype of influenza virus, or the same strain of influenza virus. In certain embodiments, a recombinant influenza virus comprises a chimeric influenza virus gene segment that includes a mORF, a 3' NCR1, a 5' NCR1, a 3' CRS1 and a 5'CRS1 from the same type of influenza virus, the same subtype of influenza virus, or the same strain of influenza virus.

In some embodiments, a recombinant influenza virus comprises a chimeric influenza virus gene segment that includes a 3' NCR1 and a 5' NCR1 from one type of influenza virus, one subtype of influenza virus, or one influenza virus strain and a 3' CRS1 and a 5'CRS1 from a different type of influenza virus, a different subtype of influenza virus, or a different strain of influenza virus. In some embodiments, a recombinant influenza virus comprises a chimeric influenza virus gene segment that includes a 3' NCR1, a 5' NCR1, a 3' CRS1 and a 5'CRS1 from one type of influenza virus, one subtype of influenza virus, or one influenza virus strain and a mORF from a different type of influenza virus, a different subtype of influenza virus, or a different strain of influenza virus.

In some embodiments, a recombinant influenza virus comprises a chimeric influenza virus gene segment that includes a 3' NCR1, a 5' NCR1, a 3' CRS1 and a 5'CRS1 from a pandemic influenza virus and a mORF from a seasonal influenza virus. In other embodiments, a recombinant influenza virus comprises a chimeric influenza gene segment that includes a 3' NCR1, a 5' NCR1, a 3' CRS1 and a 5'CRS1 from a seasonal influenza virus and a mORF from a pandemic influenza virus. In certain embodiments, a recombinant influenza virus comprises a chimeric influenza virus gene segment that includes a mORF from a seasonal or pandemic influenza virus.

In certain embodiments, a recombinant influenza virus comprises a chimeric influenza virus gene segment that includes a 3' NCR1, a 5' NCR1, a 3' CRS1 and a 5'CRS1 from an influenza A virus. In some embodiments, a recombinant influenza virus comprises a chimeric influenza virus gene segment that includes a 3' NCR1, a 5' NCR1, a 3' CRS1, a 5'CRS1 and a mORF from an influenza A virus. In specific embodiments, a recombinant influenza virus comprises a chimeric influenza virus gene segment that includes a 3' NCR1, a 5' NCR1, a 3' CRS1 and a 5'CRS1 from the same subtype or strain of influenza A virus. In certain embodiments, a recombinant influenza virus comprises a chimeric influenza virus gene segment that includes a mORF, a 3' NCR1, a 5' NCR1, a 3' CRS1 and a 5'CRS1 from the same subtype or strain of influenza A virus. In some embodiments, a recombinant influenza virus comprises a chimeric influenza virus gene segment that includes a 3' NCR1 and a 5' NCR1 from one subtype of influenza A virus or one influenza A virus strain and a 3' CRS1 and a 5'CRS1 from a different subtype of influenza A virus or a different strain of influenza A virus. In some embodiments, a recombinant influenza virus comprises a chimeric influenza virus gene segment that includes a 3' NCR1, a 5' NCR1, a 3' CRS1 and a 5'CRS1 from one subtype of influenza A virus or one influenza A virus strain and a mORF from a different subtype of influenza A virus or a different strain of influenza A virus.

Non-limiting examples of influenza A viruses include subtype H10N4, subtype H10N5, subtype H10N7, subtype H10N8, subtype H10N9, subtype H11N1, subtype H11N13, subtype H11N2, subtype H11N4, subtype H11N6, subtype H11N8, subtype H11N9, subtype H12N1, subtype H12N4, subtype H12N5, subtype H12N8, subtype H13N2, subtype H13N3, subtype H13N6, subtype H13N7, subtype H14N5, subtype H14N6, subtype H15N8, subtype H15N9, subtype H16N3, subtype H1N1, subtype H1N2, subtype H1N3, subtype H1N6, subtype H1N9, subtype H2N1, subtype H2N2, subtype H2N3, subtype H2N5, subtype H2N7, subtype H2N8, subtype H2N9, subtype H3N1, subtype H3N2, subtype H3N3, subtype H3N4, subtype H3N5, subtype H3N6, subtype H3N8, subtype H3N9, subtype H4N1, subtype H4N2, subtype H4N3, subtype H4N4, subtype H4N5, subtype H4N6, subtype H4N8, subtype H4N9, subtype H5N1, subtype H5N2, subtype H5N3, subtype H5N4, subtype H5N6, subtype H5N7, subtype H5N8, subtype H5N9, subtype H6N1, subtype H6N2, subtype H6N3, subtype H6N4, subtype H6N5, subtype H6N6, subtype H6N7, subtype H6N8, subtype H6N9, subtype H7N1, subtype H7N2, subtype H7N3, subtype H7N4, subtype H7N5, subtype H7N7, subtype H7N8, subtype H7N9, subtype H8N4, subtype H8N5, subtype H9N1, subtype H9N2, subtype H9N3, subtype H9N5, subtype H9N6, subtype H9N7, subtype H9N8, and subtype H9N9.

Specific examples of strains of influenza A virus include, but are not limited to: A/sw/Iowa/15/30 (H1N1); A/WSN/33 (H1N1); A/eq/Prague/1/56 (H7N7); A/PR/8/34; A/mallard/Potsdam/178-4/83 (H2N2); A/herring gull/DE/712/88 (H16N3); A/sw/Hong Kong/168/1993 (H1N1); A/mallard/Alberta/211/98 (H1N1); A/shorebird/Delaware/168/06 (H16N3); A/sw/Netherlands/25/80 (H1N1); A/sw/Germany/2/81 (H1N1); A/sw/Hannover/1/81 (H1N1); A/sw/Potsdam/1/81 (H1N1); A/sw/Potsdam/15/81 (H1N1); A/sw/Potsdam/268/81 (H1N1); A/sw/Finistere/2899/82 (H1N1); A/sw/Potsdam/35/82 (H3N2); A/sw/Cote d'Armor/3633/84 (H3N2); A/sw/Gent/1/84 (H3N2); A/sw/Netherlands/12/85 (H1N1); A/sw/Karrenzien/2/87 (H3N2); A/sw/Schwerin/103/89 (H1N1); A/turkey/Germany/3/91 (H1N1); A/sw/Germany/8533/91 (H1N1); A/sw/Belgium/220/92 (H3N2); A/sw/Gent/V230/92 (H1N1); A/sw/Leipzig/145/92 (H3N2); A/sw/Re220/92hp (H3N2); A/sw/Bakum/909/93 (H3N2); A/sw/Schleswig-Holstein/1/93 (H1N1); A/sw/Scotland/419440/94 (H1N2); A/sw/Bakum/5/95 (H1N1); A/sw/Best/5C/96 (H1N1); A/sw/England/17394/96 (H1N2); A/sw/Jena/5/96 (H3N2); A/sw/Oedenrode/7C/96 (H3N2); A/sw/Lohne/1/97 (H3N2); A/sw/Cote d'Armor/790/97 (H1N2); A/sw/Bakum/1362/98 (H3N2); A/sw/Italy/1521/98 (H1N2); A/sw/Italy/1553-2/98 (H3N2); A/sw/Italy/1566/98 (H1N1); A/sw/Italy/1589/98 (H1N1); A/sw/Bakum/8602/99 (H3N2); A/sw/Cotes d'Armor/604/99 (H1N2); A/sw/Cote d'Armor/1482/99 (H1N1); A/sw/Gent/7625/99 (H1N2); A/Hong Kong/1774/99 (H3N2); A/sw/Hong Kong/5190/99 (H3N2); A/sw/Hong Kong/5200/99 (H3N2); A/sw/Hong Kong/5212/99 (H3N2); A/sw/Ille et Villaine/1455/99 (H1N1); A/sw/Italy/1654-1/99 (H1N2); A/sw/Italy/2034/99 (H1N1); A/sw/Italy/2064/99 (H1N2); A/sw/Berlin/1578/00 (H3N2); A/sw/Bakum/1832/00 (H1N2); A/sw/Bakum/1833/00 (H1N2); A/sw/Cote d'Armor/800/00 (H1N2); A/sw/Hong Kong/7982/00 (H3N2); A/sw/Italy/1081/00 (H1N2); A/sw/Belzig/2/01 (H1N1); A/sw/Belzig/54/01 (H3N2); A/sw/Hong Kong/9296/01 (H3N2); A/sw/Hong Kong/9745/01 (H3N2); A/sw/Spain/33601/01 (H3N2); A/sw/Hong Kong/1144/02 (H3N2); A/sw/Hong Kong/1197/02 (H3N2); A/sw/Spain/39139/02 (H3N2); A/sw/Spain/42386/02 (H3N2); A/Switzerland/8808/2002 (H1N1); A/sw/Bakum/1769/03 (H3N2); A/sw/Bissendorf/IDT1864/03 (H3N2); A/sw/Ehren/IDT2570/03 (H1N2); A/sw/Gescher/IDT2702/03 (H1N2);

A/sw/Haselünne/2617/03hp (H1N1); A/sw/Löningen/IDT2530/03 (H1N2); A/sw/IVD/IDT2674/03 (H1N2); A/sw/Nordkirchen/IDT1993/03 (H3N2); A/sw/Nordwalde/IDT2197/03 (H1N2); A/sw/Norden/IDT2308/03 (H1N2); A/sw/Spain/50047/03 (H1N1); A/sw/Spain/51915/03 (H1N1); A/sw/Vechta/2623/03 (H1N1); A/sw/Visbek/IDT2869/03 (H1N2); A/sw/Waltersdorf/IDT2527/03 (H1N2); A/sw/Damme/IDT2890/04 (H3N2); A/sw/Geldern/IDT2888/04 (H1N1); A/sw/Granstedt/IDT3475/04 (H1N2); A/sw/Greven/IDT2889/04 (H1N1); A/sw/Gudensberg/IDT2930/04 (H1N2); A/sw/Gudensberg/IDT2931/04 (H1N2); A/sw/Lohne/IDT3357/04 (H3N2); A/sw/Nortrup/IDT3685/04 (H1N2); A/sw/Seesen/IDT3055/04 (H3N2); A/sw/Spain/53207/04 (H1N1); A/sw/Spain/54008/04 (H3N2); A/sw/Stolzenau/IDT3296/04 (H1N2); A/sw/Wedel/IDT2965/04 (H1N1); A/sw/Bad Griesbach/IDT4191/05 (H3N2); A/sw/Cloppenburg/IDT4777/05 (H1N2); A/sw/Dötlingen/IDT3780/05 (H1N2); A/sw/Dötlingen/IDT4735/05 (H1N2); A/sw/Egglham/IDT5250/05 (H3N2); A/sw/Harkenblek/IDT4097/05 (H3N2); A/sw/Hertzen/IDT4317/05 (H3N2); A/sw/Krogel/IDT4192/05 (H1N1); A/sw/Laer/IDT3893/05 (H1N1); A/sw/Laer/IDT4126/05 (H3N2); A/sw/Merzen/IDT4114/05 (H3N2); A/sw/Muesleringen-S./IDT4263/05 (H3N2); A/sw/Osterhofen/IDT4004/05 (H3N2); A/sw/Sprenge/IDT3805/05 (H1N2); A/sw/Stadtlohn/IDT3853/05 (H1N2); A/sw/Voglarn/IDT4096/05 (H1N1); A/sw/Wohlerst/IDT4093/05 (H1N1); A/sw/Bad Griesbach/IDT5604/06 (H1N1); A/sw/Herzlake/IDT5335/06 (H3N2); A/sw/Herzlake/IDT5336/06 (H3N2); A/sw/Herzlake/IDT5337/06 (H3N2); and A/wild boar/Germany/R169/2006 (H3N2).

Other specific examples of strains of influenza A virus include, but are not limited to: A/Toronto/3141/2009 (H1N1); A/Regensburg/D6/2009 (H1N1); A/Bayern/62/2009 (H1N1); A/Bayern/62/2009 (H1N1); A/Bradenburg/19/2009 (H1N1); A/Bradenburg/20/2009 (H1N1); A/Distrito Federal/2611/2009 (H1N1); A/Mato Grosso/2329/2009 (H1N1); A/Sao Paulo/1454/2009 (H1N1); A/Sao Paulo/2233/2009 (H1N1); A/Stockholm/37/2009 (H1N1); A/Stockholm/41/2009 (H1N1); A/Stockholm/45/2009 (H1N1); A/swine/Alberta/OTH-33-1/2009 (H1N1); A/swine/Alberta/OTH-33-14/2009 (H1N1); A/swine/Alberta/OTH-33-2/2009 (H1N1); A/swine/Alberta/OTH-33-21/2009 (H1N1); A/swine/Alberta/OTH-33-22/2009 (H1N1); A/swine/Alberta/OTH-33-23/2009 (H1N1); A/swine/Alberta/OTH-33-24/2009 (H1N1); A/swine/Alberta/OTH-33-25/2009 (H1N1); A/swine/Alberta/OTH-33-3/2009 (H1N1); A/swine/Alberta/OTH-33-7/2009 (H1N1); A/Beijing/502/2009 (H1N1); A/Firenze/10/2009 (H1N1); A/Hong Kong/2369/2009 (H1N1); A/Italy/85/2009 (H1N1); A/Santo Domingo/572N/2009 (H1N1); A/Catalonia/385/2009 (H1N1); A/Catalonia/386/2009 (H1N1); A/Catalonia/387/2009 (H1N1); A/Catalonia/390/2009 (H1N1); A/Catalonia/394/2009 (H1N1); A/Catalonia/397/2009 (H1N1); A/Catalonia/398/2009 (H1N1); A/Catalonia/399/2009 (H1N1); A/Sao Paulo/2303/2009 (H1N1); A/Akita/1/2009 (H1N1); A/Castro/JXP/2009 (H1N1); A/Fukushima/1/2009 (H1N1); A/Israel/276/2009 (H1N1); A/Israel/277/2009 (H1N1); A/Israel/70/2009 (H1N1); A/Iwate/1/2009 (H1N1); A/Iwate/2/2009 (H1N1); A/Kagoshima/1/2009 (H1N1); A/Osaka/180/2009 (H1N1); A/Puerto Montt/Bio87/2009 (H1N1); A/Sao Paulo/2303/2009 (H1N1); A/Sapporo/1/2009 (H1N1); A/Stockholm/30/2009 (H1N1); A/Stockholm/31/2009 (H1N1); A/Stockholm/32/2009 (H1N1); A/Stockholm/33/2009 (H1N1); A/Stockholm/34/2009 (H1N1); A/Stockholm/35/2009 (H1N1); A/Stockholm/36/2009 (H1N1); A/Stockholm/38/2009 (H1N1); A/Stockholm/39/2009 (H1N1); A/Stockholm/40/2009 (H1N1) A/Stockholm/42/2009 (H1N1); A/Stockholm/43/2009 (H1N1); A/Stockholm/44/2009 (H1N1); A/Utsunomiya/2/2009 (H1N1); A/WRAIR/0573N/2009 (H1N1); and A/Zhejiang/DTID-ZJU01/2009 (H1N1).

In certain embodiments, a recombinant influenza virus comprises a chimeric influenza virus gene segment that includes a 3' NCR1, a 5' NCR1, a 3' CRS1 and a 5'CRS1 from an influenza B virus. In some embodiments, a recombinant influenza virus comprises a chimeric influenza virus gene segment that includes a 3' NCR1, a 5' NCR1, a 3' CRS1, a 5'CRS1 and a mORF from an influenza B virus. In specific embodiments, a recombinant influenza virus comprises a chimeric influenza virus gene segment that includes a 3' NCR1, a 5' NCR1, a 3' CRS1 and a 5'CRS1 from the same strain of influenza B virus. In certain embodiments, a recombinant influenza virus comprises a chimeric influenza virus gene segment that includes a mORF, a 3' NCR1, a 5' NCR1, a 3' CRS1 and a 5'CRS1 from the same strain of influenza B virus. In some embodiments, a recombinant influenza virus comprises a chimeric influenza virus gene segment that includes a 3' NCR1 and a 5' NCR1 from one influenza B virus strain and a 3' CRS1 and a 5'CRS1 from a different strain of influenza B virus. In some embodiments, a recombinant influenza virus comprises a chimeric influenza virus gene segment that includes a 3' NCR1, a 5' NCR1, a 3' CRS1 and a 5'CRS1 from one influenza B virus strain and a mORF from a strain of influenza B virus.

Non-limiting examples of influenza B viruses include strain Aichi/5/88, strain Akita/27/2001, strain Akita/5/2001, strain Alaska/16/2000, strain Alaska/1777/2005, strain Argentina/69/2001, strain Arizona/146/2005, strain Arizona/148/2005, strain Bangkok/163/90, strain Bangkok/34/99, strain Bangkok/460/03, strain Bangkok/54/99, strain Barcelona/215/03, strain Beijing/15/84, strain Beijing/184/93, strain Beijing/243/97, strain Beijing/43/75, strain Beijing/5/76, strain Beijing/76/98, strain Belgium/WV106/2002, strain Belgium/WV107/2002, strain Belgium/WV109/2002, strain Belgium/WV114/2002, strain Belgium/WV122/2002, strain Bonn/43, strain Brazil/952/2001, strain Bucharest/795/03, strain Buenos Aires/161/00), strain Buenos Aires/9/95, strain Buenos Aires/SW16/97, strain Buenos Aires/VL518/99, strain Canada/464/2001, strain Canada/464/2002, strain Chaco/366/00, strain Chaco/R113/00, strain Cheju/303/03, strain Chiba/447/98, strain Chongqing/3/2000, strain clinical isolate SA1 Thailand/2002, strain clinical isolate SA10 Thailand/2002, strain clinical isolate SA100 Philippines/2002, strain clinical isolate SA101 Philippines/2002, strain clinical isolate SA110 Philippines/2002), strain clinical isolate SA112 Philippines/2002, strain clinical isolate SA113 Philippines/2002, strain clinical isolate SA114 Philippines/2002, strain clinical isolate SA2 Thailand/2002, strain clinical isolate SA20 Thailand/2002, strain clinical isolate SA38 Philippines/2002, strain clinical isolate SA39 Thailand/2002, strain clinical isolate SA99 Philippines/2002, strain CNIC/27/2001, strain Colorado/2597/2004, strain Cordoba/VA418/99, strain Czechoslovakia/16/89, strain Czechoslovakia/69/90, strain Daeku/10/97, strain Daeku/45/97, strain Daeku/47/97, strain Daeku/9/97, strain B/Du/4/78, strain B/Durban/39/98, strain Durban/43/98, strain Durban/44/98, strain B/Durban/52/98, strain Durban/55/98, strain Durban/56/98, strain England/1716/2005, strain England/2054/2005), strain England/23/04, strain Finland/154/2002, strain Finland/159/2002, strain Finland/160/2002, strain Finland/161/2002, strain Finland/162/03, strain Finland/162/2002, strain Finland/162/91, strain Finland/164/2003, strain Finland/172/91, strain Finland/173/2003, strain Finland/176/2003, strain Finland/184/91, strain Finland/188/2003, strain Finland/190/

2003, strain Finland/220/2003, strain Finland/WV5/2002, strain Fujian/36/82, strain Geneva/5079/03, strain Genoa/11/02, strain Genoa/2/02, strain Genoa/21/02, strain Genoa/54/02, strain Genova/55/02, strain Guangdong/05/94, strain Guangdong/08/93, strain Guangdong/5/94, strain Guangdong/55/89, strain Guangdong/8/93, strain Guangzhou/7/97, strain Guangzhou/86/92, strain Guangzhou/87/92, strain Gyeonggi/592/2005, strain Hannover/2/90, strain Harbin/07/94, strain Hawaii/10/2001, strain Hawaii/1990/2004, strain Hawaii/38/2001, strain Hawaii/9/2001, strain Hebei/19/94, strain Hebei/3/94), strain Henan/22/97, strain Hiroshima/23/2001, strain Hong Kong/110/99, strain Hong Kong/1115/2002, strain Hong Kong/112/2001, strain Hong Kong/123/2001, strain Hong Kong/1351/2002, strain Hong Kong/1434/2002, strain Hong Kong/147/99, strain Hong Kong/156/99, strain Hong Kong/157/99, strain Hong Kong/22/2001, strain Hong Kong/22/89, strain Hong Kong/336/2001, strain Hong Kong/666/2001, strain Hong Kong/9/89, strain Houston/1/91, strain Houston/1/96, strain Houston/2/96, strain Hunan/4/72, strain Ibaraki/2/85, strain ncheon/297/2005, strain India/3/89, strain India/77276/2001, strain Israel/95/03, strain Israel/WV187/2002, strain Japan/1224/2005, strain Jiangsu/10/03, strain Johannesburg/1/99, strain Johannesburg/96/01, strain Kadoma/1076/99, strain Kadoma/122/99, strain Kagoshima/15/94, strain Kansas/22992/99, strain Khazkov/224/91, strain Kobe/1/2002, strain, strain Kouchi/193/99, strain Lazio/1/02, strain Lee/40, strain Leningrad/129/91, strain Lissabon/2/90), strain Los Angeles/1/02, strain Lusaka/270/99, strain Lyon/1271/96, strain Malaysia/83077/2001, strain Maputo/1/99, strain Mar del Plata/595/99, strain Maryland/1/01, strain Memphis/1/01, strain Memphis/12/97-MA, strain Michigan/22572/99, strain Mie/1/93, strain Milano/1/01, strain Minsk/318/90, strain Moscow/3/03, strain Nagoya/20/99, strain Nanchang/1/00, strain Nashville/107/93, strain Nashville/45/91, strain Nebraska/2/01, strain Netherland/801/90, strain Netherlands/429/98, strain New York/1/2002, strain NIB/48/90, strain Ningxia/45/83, strain Norway/1/84, strain Oman/16299/2001, strain Osaka/1059/97, strain Osaka/983/97-V2, strain Oslo/1329/2002, strain Oslo/1846/2002, strain Panama/45/90, strain Paris/329/90, strain Parma/23/02, strain Perth/211/2001, strain Peru/1364/2004, strain Philippines/5072/2001, strain Pusan/270/99, strain Quebec/173/98, strain Quebec/465/98, strain Quebec/7/01, strain Roma/1/03, strain Saga/S172/99, strain Seoul/13/95, strain Seoul/37/91, strain Shangdong/7/97, strain Shanghai/361/2002), strain Shiga/T30/98, strain Sichuan/379/99, strain Singapore/222/79, strain Spain/WV27/2002, strain Stockholm/10/90, strain Switzerland/5441/90, strain Taiwan/0409/00, strain Taiwan/0722/02, strain Taiwan/97271/2001, strain Tehran/80/02, strain Tokyo/6/98, strain Trieste/28/02, strain Ulan Ude/4/02, strain United Kingdom/34304/99, strain USSR/100/83, strain Victoria/103/89, strain Vienna/1/99, strain Wuhan/356/2000, strain WV194/2002, strain Xuanwu/23/82, strain Yamagata/1311/2003, strain Yamagata/K500/2001, strain Alaska/12/96, strain GA/86, strain NAGASAKI/1/87, strain Tokyo/942/96, and strain Rochester/02/2001.

In certain embodiments, a recombinant influenza virus comprises a chimeric influenza virus gene segment that includes a 3' NCR1, a 5' NCR1, a 3' CRS1 and a 5'CRS1 from an influenza C virus. In some embodiments, a recombinant influenza virus comprises a chimeric influenza virus gene segment that includes a 3' NCR1, a 5' NCR1, a 3' CRS1, a 5'CRS1 and a mORF from an influenza C virus. In specific embodiments, a recombinant influenza virus comprises a chimeric influenza virus gene segment that includes a 3' NCR1, a 5' NCR1, a 3' CRS1 and a 5'CRS1 from the same strain of influenza C virus. In certain embodiments, a recombinant influenza virus comprises a chimeric influenza virus gene segment that includes a mORF, a 3' NCR1, a 5' NCR1, a 3' CRS1 and a 5'CRS1 from the same strain of influenza C virus. In some embodiments, a recombinant influenza virus comprises a chimeric influenza virus gene segment that includes a 3' NCR1 and a 5' NCR1 from one influenza C virus strain and a 3' CRS1 and a 5'CRS1 from a different strain of influenza C virus. In some embodiments, a recombinant influenza virus comprises a chimeric influenza virus gene segment that includes a 3' NCR1, a 5' NCR1, a 3' CRS1 and a 5'CRS1 from one influenza C virus strain and a mORF from a strain of influenza C virus.

Non-limiting examples of influenza C viruses include strain Aichi/1/81, strain Ann Arbor/1/50, strain Aomori/74, strain California/78, strain England/83, strain Greece/79, strain Hiroshima/246/2000, strain Hiroshima/252/2000, strain Hyogo/1/83, strain Johannesburg/66, strain Kanagawa/1/76, strain Kyoto/1/79, strain Mississippi/80, strain Miyagi/1/97, strain Miyagi/5/2000, strain Miyagi/9/96, strain Nara/2/85, strain NewJersey/76, strain pig/Beijing/115/81, strain Saitama/3/2000), strain Shizuoka/79, strain Yamagata/2/98, strain Yamagata/6/2000, strain Yamagata/9/96, strain BERLIN/1/85, strain ENGLAND/892/8, strain GREAT LAKES/1167/54, strain JJ/50, strain PIG/BEIJING/10/81, strain PIG/BEIJING/439/82), strain TAYLOR/1233/47, and strain C/YAMAGATA/10/81.

In certain embodiments, when a recombinant influenza virus described herein comprises a group of cosegregating chimeric influenza virus gene segments that includes less than the full set of gene segments found in a genome of an influenza virus (i.e., less than the eight types of gene segments for an influenza A virus, less than eight types of gene segments for an influenza B virus, or less than the seven types of gene segments for an influenza C virus), the virus further comprises gene segments to complete the full set of gene segments found in a genome of an influenza virus. For example, if a recombinant influenza virus comprises a chimeric influenza virus gene segment that encodes an HA protein and a chimeric influenza virus gene segment that encodes a PA protein, the recombinant influenza may further comprise NS, PB1, PB2, M, NP, and NA (for influenza A and B viruses) influenza virus gene segments or derivatives thereof. The influenza virus gene segments or derivatives thereof that complete the full set of gene segments found in a genome of an influenza virus are referred to herein as "complementing influenza virus gene segments." By way of example and not by limitation, a recombinant influenza virus may comprise the following gene segments:

TABLE 16

| Chimeric Influenza Virus Gene Segment Derived From: | Complementing Influenza Virus Gene Segments |
|---|---|
| HA, NS | PB2, PB1, PA, NP, NA, M |
| HA, NA | PB2, PB1, PA, NP, NS, M |
| NA, NS | PB2, PB1, PA, HA, NP, M |
| HA, NA, NS | PB2, PB1, PA, NP, M |
| HA, PB1, PB2 | PA, NP, NS, M, NA |
| HA, PB1, PB2, NS | PA, NP, M, NA |
| HA, PB1, PB2, PA | NS, NP, M, NA |
| HA, PA, NS | PB1, PB2, NP, M, NA |
| HA, M, NS | PB1, PB2, PA, M, NA |
| HA, PA, PB1, PB2, PA | M, NA, NS |
| NS, PB1, PB2, PA | HA, M, NA, NP |
| HA, NA, PA, NS | NP, PB1, PB2, |

TABLE 16-continued

| Chimeric Influenza Virus Gene Segment Derived From: | Complementing Influenza Virus Gene Segments |
|---|---|
| HA, NA, NS | NP, PA, PB1, PB2 |
| HA, NP, PB1, PB2 | M, NA, NS, PA |

In certain embodiments, the complementing influenza virus gene segments may all be derived from the same type or subtype of an influenza virus. In other embodiments, the complementing influenza virus gene segments may be derived from one, two or more different types or subtypes of an influenza virus. In some embodiments, the complementing influenza virus gene segments may all be derived from the same strain of an influenza virus. In other embodiments, the complementing influenza virus gene segments may be derived from one, two or more different strains of an influenza virus. In certain embodiments, the complementing influenza virus gene segments can be derived from an attenuated influenza virus strain.

In certain embodiments, one, two or more chimeric influenza virus gene segments and one, two or more of the complementing influenza virus gene segments may be derived from the same type or subtype of an influenza virus. In other embodiments, one, two or more chimeric influenza virus gene segments and one, two or more of the complementing influenza virus gene segments may be derived from one, two or more different types or subtypes of an influenza virus. In some embodiments, one, two or more chimeric influenza virus gene segments and one, two or more of the complementing influenza virus gene segments may be derived from the same strain of an influenza virus. In other embodiments, one, two or more chimeric influenza virus gene segments and one, two or more of the complementing influenza virus gene segments may be derived from one, two or more different strains of an influenza virus.

In certain embodiments, a recombinant influenza virus described herein comprises at least one gene segment that encodes a fusion protein. The fusion protein can be encoded by a chimeric influenza virus gene segment or a complementing influenza virus gene segment. A fusion protein can be a fusion of an influenza virus protein or a fragment thereof with a heterologous protein (such as a viral antigen, a bacterial antigen, a parasitic antigen, a fungal antigen, a tumor antigen, a tumor associated antigen, a cytokine, a growth factor, a peptide tag, or a detectable substance (see Section 5.1.3 for examples of such antigens, cytokines, growth factors, peptide tags, and detectable substances))

In certain embodiments, a recombinant influenza virus comprises nine gene segments, wherein (a) at least one gene segment comprises: (i) the packaging signals found in the 3' non-coding region of a first type of influenza virus gene segment or a derivative thereof; (ii) the packaging signals found in the 3' proximal coding region of the first type of influenza virus gene segment or a derivative thereof, wherein any start codon in the 3' proximal coding region of the first type of influenza virus gene segment is mutated; (iii) an open reading frame of a second type of influenza virus gene segment or a fragment or a derivative thereof, wherein the 3' and 5' proximal nucleotides in the open reading frame are mutated; (iv) the packaging signals found in the 5' proximal coding region of the first type of influenza virus gene segment or a derivative thereof; and (v) the packaging signals found in the 5' non-coding region of the first type of influenza virus gene segment or a derivative thereof; and (b) at least one gene segment comprises: (i) the packaging signals found in the 3' non-coding region of the second type of influenza virus gene segment or a derivative thereof; (ii) the packaging signals found in the 3' proximal coding region of the second type of influenza virus gene segment or a derivative thereof, wherein any start codon in the 3' proximal coding region of the first type of influenza virus gene segment is mutated; (iii) an open reading frame heterologous to 1, 2, 3, 4, 5, 6, 7 or 8 of the influenza virus gene segments; (iv) the packaging signals found in the 5' proximal coding region of the second type of influenza virus gene segment or a derivative thereof; and (v) the packaging signals found in the 5' non-coding region of the second type of influenza virus gene segment or a derivative thereof. In other embodiments, the 3' and/or the 5' proximal coding region sequences flank the open reading frame and are not translated. In some embodiments, the 3' proximal coding region sequence has been mutated so as to preclude the translation of the 3' proximal coding region sequence. In some embodiments, the 5' proximal coding region sequence has one or more mutations so as to ensure that the 5' proximal coding region sequence is not translated. In a specific embodiment, the mutations introduced into the open reading frame of the influenza virus gene segment or a fragment are silent mutations. See, e.g., Examples 2 and 3 and FIGS. 29 and 30 for examples of nine-segmented recombinant influenza viruses. In certain embodiments, the nine-segmented recombinant influenza virus is attenuated.

In another embodiment, a recombinant influenza virus comprises nine gene segments, wherein: (a) at least one of the gene segments comprises: (i) the 3' non-coding region of a first type of influenza virus gene segment; (ii) a 3' proximal coding region of the first type of influenza virus gene segment, wherein any start codon in the 3' proximal coding region of the first type of influenza virus gene segment is mutated; (iii) an open reading frame of a second type of influenza virus gene segment, wherein a certain number of the 3' proximal nucleotides and a certain number of the 5' proximal nucleotides have been mutated; and (v) a 5' proximal coding region of the first type of influenza virus gene segment; and (vi) the 5' non-coding region of the first type of influenza virus gene segment; and (b) at least one gene segment comprises: (i) the 3' non-coding region of the second type of influenza virus gene segment; (ii) a 3' proximal coding region of the second type of influenza virus gene segment, wherein any start codon in the 3' proximal coding region of the second type of influenza virus gene segment is mutated; (iii) an open reading frame heterologous to 1, 2, 3, 4, 5, 6, 7 or 8 of the influenza virus gene segments; and (v) a 5' proximal coding region of the second type of influenza virus gene segment; and (vi) the 5' non-coding region of the second type of influenza virus gene segment. In certain embodiments, 5 to 25 or 5 to 50 of the 3' proximal nucleotides and 5 to 25 or 5 to 50 of the 5' proximal nucleotides of the open reading frame of the second influenza virus gene segment carry one or more mutations. In a specific embodiment, such mutations are silent mutations. In some embodiments, the 5' proximal coding regions of the first and second influenza virus gene segment are mutated so that the 5' proximal coding regions are not translated.

In some embodiments, the nine-segmented recombinant influenza virus encodes and/or expresses influenza virus antigens from two different types, subtypes or strains of influenza virus. In a specific embodiment, the recombinant influenza virus encodes and/or expresses HA antigens from two different types, subtypes or strains of influenza virus. For example, the nine-segmented recombinant influenza virus encodes and/or expresses an H1 HA and an H3 HA antigen. In some embodiments, the one HA antigens is from a seasonal influenza virus and the other HA antigen is from a pandemic influenza virus. In specific embodiments, each of the two HA antigens may comprise an attenuating mutation. In certain embodiments, the nine-segmented recombinant influenza virus encodes and/or expresses influenza virus antigens and at least one, two, three or four, or 1 to 3, 1 to 4, or 2 to 4 non-influenza virus antigens (e.g., antigens from bacterial pathogens, or viral pathogens other an influenza virus). In accordance with these embodiments, in some embodiments, the heterologous open reading frame of the one gene segment can encode an influenza virus antigen from a different type, subtype or strain of influenza virus than the influenza virus antigens encoded by the other gene segments. In other embodiments, the heterologous open reading frame of the one gene segment can encode a non-influenza virus antigen (e.g., a bacterial antigen, tumor antigen, or viral antigen other than an influenza virus antigen). In yet other embodiments, the heterologous open reading frame encodes a detectable protein, such as, e.g., GFP or luciferase.

In certain embodiments, a recombinant influenza virus described herein comprises at least one gene segment that encodes a bicistronic mRNA. The bicistronic mRNA can be encoded by a chimeric influenza virus gene segment or a complementing influenza virus gene segment. Techniques for creating an influenza virus gene segment that encodes a bicistronic mRNA are known in the art. Bicistronic techniques allow the engineering of coding sequences of multiple proteins into a single mRNA through the use of internal ribosome entry site (IRES) sequences. Briefly, a coding region of one protein is inserted into the open reading frame of a second protein. The insertion is flanked by an IRES and any untranslated signal sequences necessary for proper expression and/or function. The insertion must not disrupt the open reading frame, polyadenylation or transcriptional promoters of the second protein (see, e.g., García-Sastre et al., 1994, J. Virol. 68:6254-6261 and García-Sastre et al., 1994 Dev. Biol. Stand. 82:237-246, each of which is hereby incorporated by reference in its entirety). See also, e.g., U.S. Pat. No. 6,887,699, U.S. Pat. No. 6,001,634, U.S. Pat. No. 5,854,037 and U.S. Pat. No. 5,820,871, each of which is incorporated herein by reference in its entirety. Any IRES known in the art or described herein may be used in accordance with the invention (e.g., the IRES of BiP gene, nucleotides 372 to 592 of GenBank database entry HUMGRP78; or the IRES of encephalomyocarditis virus (EMCV), nucleotides 1430-2115 of GenBank database entry CQ867238). One of the open reading frames of the bicistronic mRNA may encode an influenza virus protein or a fragment thereof and the other open reading frame of the bicistronic mRNA may encode a heterologous protein (such as a viral antigen, a bacterial antigen, a parasitic antigen, a fungal antigen, a tumor antigen, a tumor associated antigen, a cytokine, a growth factor, a peptide tag, or a detectable substance (see Section 5.1.3 for examples of such antigens, cytokines, growth factors, peptide tags, and detectable substances)).

In specific embodiments, a recombinant influenza virus described herein is attenuated. In a particular embodiment, the recombinant influenza virus is attenuated such that the virus remains, at least partially, infectious and can replicate in vivo, but only generate low titers resulting in subclinical levels of infection that are non-pathogenic. Such attenuated viruses are especially suited for embodiments described herein wherein the virus or an immunogenic composition thereof is administered to a subject to induce an immune response.

In some embodiments, a recombinant influenza virus described herein comprises one or more attenuating mutations in a chimeric influenza virus gene segment. In certain embodiments, a recombinant influenza virus described herein comprises one or more attenuating mutations in two, three or more chimeric influenza virus gene segments. In some embodiments, a recombinant influenza virus described herein comprises one or more attenuating mutations in a complementing influenza virus gene segment. In certain embodiments, a recombinant influenza virus described herein comprises one or more attenuating mutations in two, three or more complementing influenza virus gene segments. In some embodiments, a recombinant influenza virus described herein comprises one or more attenuating mutations in a chimeric influenza virus gene segment and one or more attenuating mutations in a complementing influenza virus gene segment. In certain embodiments, a recombinant influenza virus described herein comprises one or more attenuating mutations in one, two, three or more chimeric influenza virus gene segments and one or more attenuating mutations in one, two, three or more complementing influenza virus gene segments.

In certain embodiments, the one or more attenuating mutations may be in the open reading frame of a gene segment encoding one or more of the following: NS1, NP, HA, NA, PB1, PB2 and/or PA. In a specific embodiment, the one or more attenuating mutations may be in the open reading frame of an HA gene segment. In another specific embodiment, the one or more attenuating mutations may be in the open reading of an NP gene segment. In another embodiment, the one or more attenuating mutations may be in the open reading frame of an PB1 gene segment In another embodiment, the one or more attenuating mutations may be in the open reading frame of an PB2 gene segment. In certain embodiments, the one or more attenuating mutations in a gene segment of an influenza virus can be accomplished according to any method known in the art, such as, e.g., selecting viral mutants generated by chemical mutagenesis, mutation of the genome by genetic engineering, selecting reassortant viruses that contain segments with attenuated function, or selecting for conditional virus mutants (e.g., cold-adapted viruses such as A/Leningrad/134/47/57 (H2N2), A/Ann Arbor/6/60 (H2N2), B/Ann Arbor/1/66, and B/Lee/40). In a specific embodiment, one or more temperature sensitive mutations that are attenuating may be introduced in an open reading frame of a gene segment. In some embodiments, the one or more temperature sensitive mutations include one or more of the following: PB1 (K391E, E581G, A661T), PB2 (N265S), and NP (D34G).

In some embodiments, an attenuated recombinant influenza virus expresses the following NP, PB1 and PB2 proteins encoded by cold adapted vaccine master strain A/Ann Arbor/6/60 (see, e.g., Jin et al., 2003, Virology 306: 18-24 for a description of the virus).

In some embodiments, an attenuated recombinant influenza virus expresses a mutated NS1 protein that impairs the ability of the virus to antagonize the cellular interferon (IFN) response. Examples of the types of mutations that can be introduced into the open reading frame of influenza virus NS1 include deletions, substitutions, insertions and combinations thereof. One or more mutations can be introduced anywhere throughout the open reading frame of NS1 (e.g., the N-terminus, the C-terminus or somewhere in between) and/or the regulatory elements of the NS1 gene. In one embodiment, an attenuated recombinant influenza virus comprises a genome having a mutation in an influenza virus NS1 open reading frame resulting in a deletion consisting of 5, preferably 10, 15, 20, 25, 30, 35, 40, 45, 50, 55, 60, 65, 75, 80, 85, 90, 95, 99, 100, 105, 110, 115, 120, 125, 126, 130, 135, 140, 145, 150, 155, 160, 165, 170 or 175 amino acid residues from the C-terminus of NS1, or a deletion of between 5-170, 25-170, 50-170, 100-170, 100-160, or 105-160 amino acid residues from the C-terminus. In another embodiment, a recombinant attenuated influenza virus comprises a genome having a mutation in an influenza virus NS1 open reading frame such that it encodes an NS1 protein of amino acid residues 1-130, amino acid residues 1-126, amino acid residues 1-125, amino acid residues 1-124, amino acid residues 1-120, amino acid residues 1-115, amino acid residues 1-110, amino acid residues 1-100, amino acid residues 1-99, amino acid residues 1-95, amino acid residues 1-85, amino acid residues 1-83, amino acid residues 1-80, amino acid residues 1-75, amino acid residues 1-73, amino acid residues 1-70, amino acid residues 1-65, or amino acid residues 1-60, wherein the N-terminus amino acid is number 1. For examples of NS1 mutations and influenza viruses comprising a mutated NS1, see, e.g., U.S. Pat. Nos. 6,468,544 and 6,669,943; and Li et al., 1999, J. Infect. Dis. 179:1132-1138, each of which is incorporated by reference herein in its entirety.

In some embodiments, an attenuated recombinant influenza virus expresses a mutated M2 protein such as described by Watanabe et al., 2008, J. Virol. 82(5): 2486-2492.

In a specific embodiment, an attenuated recombinant influenza virus comprises a first chimeric influenza virus gene segment encoding an HA from a pandemic or seasonal influenza virus and a second chimeric influenza virus gene segment encoding a viral polymerase subunit (i.e., e.g., PA, PB1 or PB2) with one or more attenuating mutations.

5.3 Construction of Influenza Virus

Techniques known to one skilled in the art may be used to produce a recombinant influenza virus containing one, two or more chimeric influenza virus gene segments described herein. For example, reverse genetics techniques may be used to generate such an influenza virus. Briefly, reverse genetics techniques generally involve the preparation of synthetic recombinant viral RNAs that contain the non-coding regions of the negative-strand, viral RNA which are essential for the recognition by viral polymerases and for packaging signals necessary to generate a mature virion. The recombinant RNAs are synthesized from a recombinant DNA template and reconstituted in vitro with purified viral polymerase complex to form recombinant ribonucleoproteins (RNPs) which can be used to transfect cells. A more efficient transfection is achieved if the viral polymerase proteins are present during transcription of the synthetic RNAs either in vitro or in vivo. The synthetic recombinant RNPs can be rescued into infectious virus particles. The foregoing techniques are described in U.S. Pat. No. 5,166,057 issued Nov. 24, 1992; in U.S. Pat. No. 5,854,037 issued Dec. 29, 1998; in European Patent Publication EP 0702085A1, published Feb. 20, 1996; in U.S. patent application Ser. No. 09/152,845; in International Patent Publications PCT WO 97/12032 published Apr. 3, 1997; WO 96/34625 published Nov. 7, 1996; in European Patent Publication EP A780475; WO 99/02657 published Jan. 21, 1999; WO 98/53078 published Nov. 26, 1998; WO 98/02530 published Jan. 22, 1998; WO 99/15672 published Apr. 1, 1999; WO 98/13501 published Apr. 2, 1998; WO 97/06270 published Feb. 20, 1997; and EPO 780 475A1 published Jun. 25, 1997, each of which is incorporated by reference herein in its entirety.

Alternatively, helper-free plasmid technology may be used to produce a recombinant influenza virus containing one or more chimeric influenza virus gene segments. Briefly, full length cDNAs of viral segments are amplified using PCR with primers that include unique restriction sites, which allow the insertion of the PCR product into the plasmid vector (Flandorfer et al., 2003, J. Virol. 77:9116-9123; Nakaya et al., 2001, J. Virol. 75:11868-11873; both of which are incorporated herein by reference in their entireties). The plasmid vector is designed so that an exact negative (vRNA sense) transcript is expressed. For example, the plasmid vector may be designed to position the PCR product between a truncated human RNA polymerase I promoter and a hepatitis delta virus ribozyme sequence such that an exact negative (vRNA sense) transcript is produced from the polymerase I promoter. Separate plasmid vectors comprising each viral segment as well as expression vectors comprising necessary viral proteins may be transfected into cells leading to production of recombinant viral particles. In another example, plasmid vectors from which both the viral genomic RNA and mRNA encoding the necessary viral proteins are expressed may be used. For a detailed description of helper-free plasmid technology see, e.g., International Publication No. WO 01/04333; U.S. Pat. Nos. 6,951,754, 7,384,774, 6,649,372, and 7,312,064; Fodor et al., 1999, J. Virol. 73:9679-9682; Quinlivan et al., 2005, J. Virol. 79:8431-8439; Hoffmann et al., 2000, Proc. Natl. Acad. Sci. USA 97:6108-6113; and Neumann et al., 1999, Proc. Natl. Acad. Sci. USA 96:9345-9350, which are incorporated herein by reference in their entireties.

In specific embodiments, one, two or more nucleic acid sequences encoding one, two or more chimeric influenza virus gene segments or the complements thereof are transfected into a host cell that provides the remainder of the gene segments found in an influenza virus genome and expresses the proteins necessary for production of viral particles. Techniques known in the art can be used to isolate/purify the recombinant influenza virus that results (see, e.g., Section 5.4, infra for techniques for isolation/purification of influenza virus).

5.4 Propagation of Influenza Virus

The recombinant influenza viruses described herein can be propagated in any substrate that allows the virus to grow to titers that permit the uses of the viruses described herein. In one embodiment, the substrate allows the recombinant influenza viruses described herein to grow to titers comparable to those determined for the corresponding wild-type viruses.

The recombinant influenza virus described herein may be grown in host cells (e.g., avian cells, chicken cells, etc.) that are susceptible to infection by the viruses, embryonated eggs or animals (e.g., birds). Specific examples of host cells include Vero cells, MDCK cells, MBCK cells, COS cells, 293 cells, 293T cells, A549 cells, MDBK cells, etc. Such methods are well-known to those skilled in the art. In a specific embodiment, the recombinant influenza viruses described herein may be propagated in cell lines. In another embodiment, the recombinant influenza viruses described herein described herein are propagated in chicken cells or embryonated eggs. Representative chicken cells include, but are not limited to, chicken embryo fibroblasts and chicken embryo kidney cells.

The recombinant influenza viruses described herein may be propagated in embryonated eggs, e.g., from 6 to 14 days old, 6 to 9 days old, 10 to 12 days old, or 10 to 14 days old. Young or immature embryonated eggs can be used to propagate the recombinant influenza viruses described herein. Immature embryonated eggs encompass eggs which are less than ten day old eggs, e.g., eggs 6 to 9 days that are interferon (IFN)-deficient. Immature embryonated eggs also encompass eggs which artificially mimic immature eggs up to, but less than ten day old, as a result of alterations to the growth conditions, e.g., changes in incubation temperatures; treating with drugs; or any other alteration which results in an egg with a retarded development, such that the IFN system is not fully developed as compared with ten to twelve day old eggs. In one embodiment, the recombinant influenza viruses may be propagated in 10 day old embryonated eggs. The recombinant influenza viruses described herein can be propagated in different locations of the embryonated egg, e.g., the allantoic cavity. In a specific embodiment, the embryonated egg is an embryonated chicken egg. For a detailed discussion on the growth and propagation viruses, see, e.g., U.S. Pat. No. 6,852, 522 and U.S. Pat. No. 6,852,522, both of which are hereby incorporated by reference in their entireties.

For virus isolation, the recombinant influenza viruses described herein can be removed from cell culture and separated from cellular components, typically by well known clarification procedures, e.g., such as gradient centrifugation and column chromatography, and may be further purified as desired using procedures well known to those skilled in the art, e.g., plaque assays.

5.5 Compositions & Routes of Administration

The recombinant influenza viruses described herein may be incorporated into compositions. In a specific embodiment, the compositions are pharmaceutical compositions, such as immunogenic compositions (e.g., vaccine formulations). The pharmaceutical compositions provided herein can be in any form that allows for the composition to be administered to a subject. In a specific embodiment, the pharmaceutical compositions are suitable for veterinary and/or human administration. The compositions may be used in methods of preventing and/or treating an influenza virus infection. The compositions may also be used in methods or preventing and/or treating influenza virus disease.

In one embodiment, a pharmaceutical composition comprises a recombinant influenza virus in an admixture with a pharmaceutically acceptable carrier. In some embodiments, a pharmaceutical composition may comprise one or more other therapies in addition to a recombinant influenza virus. In specific embodiments, a recombinant influenza virus described herein that is incorporated into a pharmaceutical composition (e.g., an immunogenic composition such as a vaccine) is a live virus. An immunogenic composition comprising a live recombinant influenza virus for administration to a subject may be preferred because multiplication of the virus in the subject may lead to a prolonged stimulus of similar kind and magnitude to that occurring in natural infections, and therefore, confer substantial, long lasting immunity.

In some embodiments, a recombinant influenza virus described herein that is incorporated into a pharmaceutical composition (e.g., an immunogenic composition such as a vaccine) is inactivated. Techniques known to one of skill in the art may be used to inactivate recombinant influenza viruses described herein. Common methods use formalin, heat, or detergent for inactivation. See, e.g., U.S. Pat. No. 6,635,246, which is herein incorporated by reference in its entirety. Other methods include those described in U.S. Pat. Nos. 5,891,705; 5,106,619 and 4,693,981, which are incorporated herein by reference in their entireties.

In specific embodiments, immunogenic compositions described herein are monovalent formulations. In other embodiments, immunogenic compositions described herein are multivalent formulations. In one example, a multivalent formulation comprises one or more recombinant influenza viruses that expresses antigens from an influenza A virus and one or more recombinant influenza viruses that expresses antigens from an influenza B virus.

In a specific embodiment, an immunogenic composition comprises a recombinant influenza virus described herein which contains nine gene segments. In certain embodiments, such a nine-segmented influenza virus expresses influenza virus antigens from two different types, subtypes, or strains of influenza virus. In a specific embodiment, the nine-segmented recombinant influenza virus expresses HA antigens from two different types, subtypes, or strains of influenza virus. In some embodiments, the nine-segmented influenza virus expresses influenza virus antigens and at least one, two, three, or four or 1 to 3, 1 to 4, or 2 to 4 non-influenza virus antigens.

As used herein, the term "pharmaceutically acceptable" means approved by a regulatory agency of the Federal or a state government or listed in the U.S. Pharmacopeia or other generally recognized pharmacopeiae for use in animals, and more particularly in humans. The term "carrier" refers to a diluent, adjuvant, excipient, or vehicle with which the pharmaceutical composition is administered. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Examples of suitable pharmaceutical carriers are described in "Remington's Pharmaceutical Sciences" by E. W. Martin.

In certain embodiments, biodegradable polymers, such as ethylene vinyl acetate, polyanhydrides, polyethylene glycol (PEGylation), polymethyl methacrylate polymers, polylactides, poly(lactide-co-glycolides), polyglycolic acid, collagen, polyorthoesters, and polylactic acid, may be used as carriers. Liposomes or micelles can also be used as pharmaceutically acceptable carriers. These can be prepared according to methods known to those skilled in the art, for example, as described in U.S. Pat. No. 4,522,811.

In a specific embodiment, pharmaceutical compositions are formulated to be suitable for the intended route of administration to a subject. For example, the pharmaceutical composition may be formulated to be suitable for parenteral, oral, intradermal, intransal, transdermal, pulmonary, colorectal, intraperitoneal, and rectal administration. In a specific embodiment, the pharmaceutical composition may be formulated for intravenous, oral, intraperitoneal, intranasal, intratracheal, subcutaneous, intramuscular, topical, intradermal, transdermal or pulmonary administration.

In certain embodiments, the compositions described herein comprise, or are administered in combination with, an adjuvant. The adjuvant for administration in combination with a composition described herein may be administered before, concomitantly with, or after administration of the composition. In specific embodiments, an inactivated virus immunogenic composition described herein comprises one or more adjuvants. In some embodiments, the term "adjuvant" refers to a compound that when administered in conjunction with or as part of a composition described herein augments, enhances and/or boosts the immune response to a recombinant influenza virus, but when the compound is administered alone does not generate an immune response to the virus. In some embodiments, the adjuvant generates an immune response to a recombinant influenza virus and does not produce an allergy or other adverse reaction. Adjuvants can enhance an immune response by several mechanisms including, e.g., lymphocyte recruitment, stimulation of B and/or T cells, and stimulation of macrophages.

Specific examples of adjuvants include, but are not limited to, aluminum salts (alum) (such as aluminum hydroxide, aluminum phosphate, and aluminum sulfate), 3 De-O-acylated monophosphoryl lipid A (MPL) (see GB 2220211), MF59 (Novartis), AS03 (GlaxoSmithKline), AS04 (GlaxoSmithKline), polysorbate 80 (Tween 80; ICL Americas, Inc.), imidazopyridine compounds (see International Application No. PCT/US2007/064857, published as International Publication No. WO2007/109812), imidazoquinoxaline compounds (see International Application No. PCT/US2007/064858, published as International Publication No. WO2007/109813) and saponins, such as QS21 (see Kensil et al., in Vaccine Design: The Subunit and Adjuvant Approach (eds. Powell & Newman, Plenum Press, NY, 1995); U.S. Pat. No. 5,057,540). In some embodiments, the adjuvant is Freund's adjuvant (complete or incomplete). Other adjuvants are oil in water emulsions (such as squalene or peanut oil), optionally in combination with immune stimulants, such as monophosphoryl lipid A (see Stoute et al., N. Engl. J. Med. 336, 86-91 (1997)). Another adjuvant is CpG (Bioworld Today, Nov. 15, 1998). Such adjuvants can be used with or without other specific immunostimulating agents such as MPL or 3-DMP, QS21, polymeric or monomeric amino acids such as polyglutamic acid or polylysine.

The pharmaceutical compositions described herein can be included in a container, pack, or dispenser together with instructions for administration.

5.5.1. Live Virus Vaccines

In one embodiment, provided herein are immunogenic compositions (e.g., vaccines) comprising one or more live recombinant influenza viruses described herein. In some embodiments, the live virus is attenuated. In some embodiments, an immunogenic composition comprises two, three, four or more live viruses.

In certain embodiments, provided herein are immunogenic compositions (e.g., vaccines) comprising about $10^5$ to about $10^{10}$ fluorescent focus units (FFU) of live attenuated recombinant influenza virus described herein, about 0.1 to about 0.5 mg monosodium glutamate, about 1.0 to about 5.0 mg hydrolyzed procine gelatin, about 1.0 to about 5.0 mg arginine, about 10 to about 15 mg sucrose, about 1.0 to about 5.0 mg dibasic potassium phosphate, about 0.5 to about 2.0 mg monobasic potassium phosphate, and about 0.001 to about 0.05 μg/ml gentamicin sulfate per dose. In some embodiments, the immunogenic compositions (e.g., vaccines) are packaged as pre-filled sprayers containing single 0.2 ml doses.

In a specific embodiment, provided herein are immunogenic compositions (e.g., vaccines) comprising $10^{6.5}$ to $10^{7.5}$ FFU of live attenuated recombinant influenza virus described herein, 0.188 mg monosodium glutamate, 2.0 mg hydrolyzed procine gelatin, 2.42 mg arginine, 13.68 mg sucrose, 2.26 mg dibasic potassium phosphate, 0.96 mg monobasic potassium phosphate, and $<0.015$ μg/ml gentamicin sulfate per dose. In some embodiments, the immunogenic compositions (e.g., vaccines) are packaged as pre-filled sprayers containing single 0.2 ml doses.

In a specific embodiment, the live virus is propagated in embryonated chicken eggs before its use in an immunogenic composition described herein. In another specific embodiment, the live virus is not propagated in embryonated chicken eggs before its use in an immunogenic composition described herein. In another specific embodiment, the live virus is propagated in mammalian cells, e.g., immortalized human cells (see, e.g., International Application No. PCT/EP2006/067566 published as International Publication No. WO 07/045,674 which is herein incorporated by reference in its entirety) or canine kidney cells such as MDCK cells (see, e.g., International Application No. PCT/IB2007/003536 published as International Publication No. WO 08/032,219 which is herein incorporated by reference in its entirety) before its use in an immunogenic composition described herein.

An immunogenic composition comprising a live virus for administration to a subject may be preferred because multiplication of the virus in the subject may lead to a prolonged stimulus of similar kind and magnitude to that occurring in natural infections, and therefore, confer substantial, long lasting immunity.

5.6 Generation of Antibodies that Specifically Bind to Influenza Virus

The recombinant influenza viruses described herein may be used to elicit neutralizing antibodies against influenza, for example, against influenza virus hemagglutinin. In a specific embodiment, a recombinant influenza virus described herein or a composition thereof may be administered to a non-human subject (e.g., a mouse, rabbit, rat, guinea pig, etc.) to induce an immune response that includes the production of antibodies which may be isolated using techniques known to one of skill in the art (e.g., immunoaffinity chromatography, centrifugation, precipitation, etc.).

In certain embodiments, the non-human subjects administered a recombinant influenza virus described herein or an immunogenic composition thereof in accordance with the methods described herein are transgenic animals (e.g., transgenic mice) that are capable of producing human antibodies. Human antibodies can be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65-93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entirety. Companies such as Abgenix, Inc. (Freemont, Calif.), Genpharm (San Jose, Calif.), and Medarex, Inc. (Princeton, N.J.) can be engaged to provide human antibodies directed against a selected antigen.

Alternatively, a recombinant influenza virus described herein may be used to screen for antibodies from antibody libraries. For example, a recombinant influenza virus may be immobilized to a solid support (e.g., a silica gel, a resin, a derivatized plastic film, a glass bead, cotton, a plastic bead, a polystyrene bead, an alumina gel, or a polysaccharide, a magnetic bead), and screened for binding to antibodies. As an alternative, the antibodies may be immobilized to a solid support and screened for binding to a recombinant influenza virus described herein. Any screening assay, such as a panning assay, ELISA, surface plasmon resonance, or other antibody screening assay known in the art may be used to screen for antibodies that bind to a recombinant influenza virus. The antibody library screened may be a commercially available antibody library, an in vitro generated library, or a library obtained by identifying and cloning or isolating antibodies from an individual infected with influenza. In particular embodiments, the antibody library is generated from a survivor of an influenza virus outbreak. Antibody libraries may be generated in accordance with methods known in the art. In a particular embodiment, the antibody library is generated by cloning the antibodies and using them in phage display libraries or a phagemid display library.

Antibodies elicited or identified in accordance with the methods described herein may be tested for specificity for influenza virus antigens and the ability to neutralize influenza virus using the biological assays known in the art or described herein. In one embodiment, an antibody identified or isolated from a non-human animal antibody specifically binds to an influenza virus antigen. In another embodiment, an antibody identified or isolated from a non-human animal specifically binds to an influenza virus antigen expressed by two or more types, subtypes or strains of influenza virus. In one embodiment, an antibody identified or isolated from a non-human animal neutralizes one, two or more influenza virus types, subtypes or strains. In some embodiments, an antibody elicited or identified using a recombinant influenza virus described herein neutralizes 1, 2, 3, 4, 5, 6, 7, 8, 9, 10, 11, 12, 13, 14, 15, or 16 or more subtypes or strains of influenza virus. In one embodiment, the neutralizing antibody neutralizes one or more strains or subtypes of influenza A viruses. In another embodiment, the neutralizing antibody neutralizes one or more strains of influenza B viruses. In another embodiment, the neutralizing antibody neutralizes one or more strains of influenza A virus and one or more strains of influenza B viruses.

Antibodies elicited or identified using a recombinant influenza virus described herein include immunoglobulin molecules and immunologically active portions of immunoglobulin molecules, i.e., molecules that contain an antigen binding site that specifically binds to a hemagglutinin polypeptide. The immunoglobulin molecules may be of any type (e.g., IgG, IgE, IgM, IgD, IgA and IgY), class (e.g., IgG1, IgG2, IgG3, IgG4, IgA1 and IgA2) or subclass of immunoglobulin molecule. Antibodies include, but are not limited to, monoclonal antibodies, multispecific antibodies, human antibodies, humanized antibodies, chimeric antibodies, single-chain Fvs (scFv), single chain antibodies, Fab fragments, F(ab') fragments, disulfide-linked Fvs (sdFv), and anti-idiotypic (anti-Id) antibodies (including, e.g., anti-Id antibodies to antibodies elicited or identified using a method described herein), and epitope-binding fragments of any of the above.

Antibodies elicited or identified using a recombinant influenza virus described herein may be used in diagnostic immunoassays, passive immunotherapy, and generation of antiidiotypic antibodies. The antibodies before being used in passive immunotherapy may be modified, e.g., the antibodies may be chimerized or humanized. See, e.g., U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741, each of which is incorporated herein by reference in its entirety, for reviews on the generation of chimeric and humanized antibodies. In addition, the ability of the antibodies to neutralize influenza virus and the specificity of the antibodies for influenza virus antigens may be tested prior to using the antibodies in passive immunotherapy. See Section 5.7, infra for a discussion regarding use of neutralizing antibodies for the prevention and/or treatment of an influenza virus infection and the disease caused by an influenza virus infection.

The antibodies elicited or identified using a recombinant influenza virus described herein may be incorporated into compositions. In a specific embodiment, the compositions are pharmaceutical compositions. In some embodiments, a pharmaceutical composition may comprise one or more other therapies in addition to an antibody. The pharmaceutical compositions provided herein can be in any form that allows for the composition to be administered to a subject. In a specific embodiment, the pharmaceutical compositions are suitable for veterinary and/or human administration. In another specific embodiment, the antibody compositions are formulated for the intended route of administration (e.g., parenteral, intransal, or pulmonary administration). The antibody compositions may be used in methods of preventing and/or treating an influenza virus infection. The antibody compositions may also be used in methods or preventing and/or treating influenza virus disease.

Antibodies elicited or identified using a recombinant influenza virus described herein may be used to monitor the efficacy of a therapy and/or disease progression. Any immunoassay system known in the art may be used for this purpose including, but not limited to, competitive and noncompetitive assay systems using techniques such as radioimmunoassays, ELISA (enzyme linked immunosorbent assays), "sandwich" immunoassays, precipitin reactions, gel diffusion precipitin reactions, immunodiffusion assays, agglutination assays, complement fixation assays, immunoradiometric assays, fluorescent immunoassays, protein A immunoassays and immunoelectrophoresis assays, to name but a few.

Antibodies elicited or identified using a recombinant influenza virus described herein may be used in the production of antiidiotypic antibody. The antiidiotypic antibody can then in turn be used for immunization, in order to produce a subpopulation of antibodies that bind a particular antigen of influenza, e.g., a neutralizing epitope of a hemagglutinin polypeptide (Jerne, 1974, Ann. Immunol. (Paris) 125c:373; Jerne et al., 1982, EMBO J. 1:234, incorporated herein by reference in its entirety).

5.7 Prophylactic and Therapeutic Uses

In one aspect, provided herein are methods for inducing an immune response in a subject utilizing a recombinant influenza virus described herein or an immunogenic composition thereof. In a specific embodiment, a method for inducing an immune response to an influenza virus in a subject comprises administering to a subject in need thereof an effective amount of a recombinant influenza virus or an immunogenic composition thereof. In certain embodiments, the recombinant influenza virus or immunogenic composition thereof expresses influenza virus proteins from two or more types, subtypes, or strains of influenza virus, and thus, may be used to induce an immune response to two or more types, subtypes, or strains of influenza virus. In a specific embodiment, a method for inducing an immune response to an influenza virus in a subject comprises administering to a subject in need thereof a recombinant influenza virus described herein as a live virus vaccine. In particular embodiments, the live virus vaccine comprises an attenuated virus. In another embodiment, a method for inducing an immune response to an influenza virus in a subject comprises administering to a subject in need thereof a recombinant influenza virus described herein as an inactivated virus vaccine.

In a specific embodiment, a method for inducing an immune response in a subject comprises administering to the subject a recombinant influenza virus described herein which contains nine gene segments, or an immunogenic composition thereof. In certain embodiments, the nine segmented recombinant influenza virus encodes and/or expresses influenza virus antigens from two different types, subtypes, or strains of influenza virus. In a specific embodiment, the nine segmented recombinant influenza virus encodes and/or expresses HA antigens from two different types, subtypes, or strains of influenza virus. In some embodiments, the nine segmented recombinant influenza virus encodes and/or expresses influenza virus antigens and at least one, two, three, or four or 1 to 3, 1 to 4, or 2 to 4 non-influenza virus antigens.

In another aspect, provided herein are methods for preventing and/or treating an influenza virus infection in a subject utilizing a recombinant influenza virus described herein or a pharmaceutical composition thereof. In one embodiment, a method for preventing or treating an influenza virus infection in a subject comprises administering to a subject in need thereof an effective amount of a recombinant influenza virus or a composition thereof. In another embodiment, a method for preventing or treating an influenza virus infection in a subject comprises administering to a subject in need thereof an effective amount of a recombinant influenza virus or a pharmaceutical composition thereof and one or more other therapies. In another embodiment, a method for preventing or treating an influenza virus infection in a subject comprises administering to a subject in need thereof a recombinant influenza virus described herein as a live virus vaccine. In particular embodiments, the live virus vaccine comprises an attenuated virus. In another embodiment, a method for preventing or treating an influenza virus infection in a subject comprises administering to a subject in need thereof a recombinant influenza virus described herein as an inactivated virus vaccine.

In a specific embodiment, a method for preventing or treating an influenza virus infection in a subject comprises administering to a subject in need thereof a recombinant influenza virus described herein which contains nine gene segments, or a pharmaceutical composition thereof. In certain embodiments, the nine segmented recombinant influenza virus encodes and/or expresses influenza virus antigens from two different types, subtypes, or strains of influenza virus. In a specific embodiment, the nine segmented recombinant influenza virus encodes and/or expresses HA antigens from two different types, subtypes, or strains of influenza virus. In some embodiments, the nine segmented recombinant influenza virus encodes and/or expresses influenza virus antigens and at least one, two, three, or four or 1 to 3, 1 to 4, or 2 to 4 non-influenza virus antigens.

In another aspect, provided herein are methods for preventing and/or treating an influenza virus disease in a subject utilizing a recombinant influenza virus described herein or a pharmaceutical composition thereof. In a specific embodiment, a method for preventing or treating an influenza virus disease in a subject comprises administering to a subject in need thereof an effective amount of a recombinant influenza virus or a pharmaceutical composition thereof. In another embodiment, a method for preventing or treating an influenza virus disease in a subject comprises administering to a subject in need thereof an effective amount of a recombinant influenza virus or a pharmaceutical composition thereof and one or more other therapies. In another embodiment, a method for preventing or treating an influenza virus disease in a subject comprises administering to a subject in need thereof a recombinant influenza virus described herein as a live virus vaccine. In particular embodiments, the live virus vaccine comprises an attenuated virus. In another embodiment, a method for preventing or treating an influenza virus disease in a subject comprises administering to a subject in need thereof a recombinant influenza virus described herein as an inactivated virus vaccine.

In a specific embodiment, a method for preventing or treating an influenza virus disease in a subject comprises administering to a subject in need thereof a recombinant influenza virus described herein which contains nine gene segments, or a pharmaceutical composition thereof. In certain embodiments, the nine segmented recombinant influenza virus encodes and/or expresses influenza virus antigens from two different types, subtypes, or strains of influenza virus. In a specific embodiment, the nine segmented recombinant influenza virus encodes and/or expresses HA antigens from two different types, subtypes, or strains of influenza virus. In some embodiments, the nine segmented recombinant influenza virus encodes and/or expresses influenza virus antigens and at least one, two, three, or four or 1 to 3, 1 to 4, or 2 to 4 non-influenza virus antigens.

In another aspect, a recombinant influenza virus described herein may be used as a delivery vector. In a specific embodiment, a recombinant influenza virus described herein that expresses a protein heterologous to influenza virus may be used as a vector to deliver the protein to a subject. For example, a recombinant influenza virus described herein may express a cytokine or growth factor which is beneficial to a subject. In another specific embodiment, a recombinant influenza virus described herein that expresses an antigen heterologous to influenza virus may be used as a vector to deliver the antigen to a subject to induce an immune response to the antigen. In some embodiments, the antigen is derived from an infectious pathogen, such as a non-influenza virus antigen, a bacterial antigen, a fungal antigen, or a parasitic antigen. In certain embodiments, the antigen is a tumor antigen or a tumor-associated antigen. In some embodiments, the antigen is derived or obtained from a respiratory pathogen (e.g., RSV). Recombinant influenza viruses described herein that express influenza virus antigens and one or more antigens heterologous to influenza virus may induce an immune response to influenza virus and the heterologous antigen(s).

In a specific embodiment, a recombinant influenza virus described herein which contains nine gene segments is used as a delivery vector. In certain embodiments, the nine segmented recombinant influenza virus encodes and/or expresses influenza virus antigens from two different types, subtypes, or strains of influenza virus. In a specific embodiment, the nine segmented recombinant influenza virus encodes and/or expresses HA antigens from two different types, subtypes, or strains of influenza virus. In some embodiments, the nine segmented recombinant influenza virus encodes and/or expresses influenza virus antigens and at least one, two, three, or four or 1 to 3, 1 to 4, or 2 to 4 non-influenza virus antigens.

In another aspect, provided herein are methods of preventing and/or treating an influenza virus infection in a subject by administering neutralizing antibodies described herein. In a specific embodiment, a method for preventing or treating an influenza virus infection in a subject comprises administering to a subject in need thereof an effective amount of a neutralizing antibody described herein, or a pharmaceutical composition thereof. In another embodiment, a method for preventing or treating an influenza virus infection in a subject comprises administering to a subject in need thereof an effective amount of a neutralizing antibody described herein, or a pharmaceutical composition thereof and one or more other therapies. In particular embodiments, the neutralizing antibody is a monoclonal antibody.

In another aspect, provided herein are methods of preventing and/or treating an influenza virus disease in a subject by administering neutralizing antibodies described herein. In a specific embodiment, a method for preventing or treating an influenza virus disease in a subject comprises administering to a subject in need thereof an effective amount of a neutralizing antibody described herein, or a pharmaceutical composition thereof. In another embodiment, a method for preventing or treating an influenza virus disease in a subject comprises administering to a subject in need thereof an effective amount of a neutralizing antibody described herein, or a pharmaceutical composition thereof and one or more other therapies. In particular embodiments, the neutralizing antibody is a monoclonal antibody.

A recombinant influenza virus described herein or a neutralizing antibody described herein may be administered alone or in combination with another/other type of therapy known in the art to reduce influenza virus infection, to reduce titers of influenza virus in a subject, to reduce the spread of influenza virus between subjects, to inhibit influenza virus replication, to inhibit influenza virus-induced fusion, to reduce the number and/or frequency of symptoms, and/or to inhibit binding of influenza virus to its host cell receptor.

In a specific embodiment, administration of a recombinant influenza virus described herein or a neutralizing antibody described herein inhibits or reduces influenza virus replication by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to replication of Influenza virus in the absence of said antibody(ies) or in the presence of a negative control (e.g., an influenza virus that is not a recombinant influenza virus described herein (e.g., a wild-type influenza virus) or a control antibody (e.g., an antibody that does not bind influenza virus)) in an assay known to one of skill in the art or described herein. Inhibition of influenza virus replication can be determined by detecting the Influenza virus titer in a biological specimens from a subject using methods known in the art (e.g., Northern blot analysis, RT-PCR, Western Blot analysis, etc.).

In a specific embodiment, administration of a recombinant influenza virus described herein or a neutralizing antibody described herein described herein results in reduction of about 1-fold, about 1.5-fold, about 2-fold, about 3-fold, about 4-fold, about 5-fold, about 8-fold, about 10-fold, about 15-fold, about 20-fold, about 25-fold, about 30-fold, about 35-fold, about 40-fold, about 45-fold, about 50-fold, about 55-fold, about 60-fold, about 65-fold, about 70-fold, about 75-fold, about 80-fold, about 85-fold, about 90-fold, about 95-fold, about 100-fold, about 105 fold, about 110-fold, about 115-fold, about 120 fold, about 125-fold or higher in Influenza virus titer in the subject. The fold-reduction in Influenza virus titer may be as compared to a negative control (e.g., an influenza virus that is not a recombinant influenza virus described herein (e.g., a wild-type influenza virus) or a control antibody (e.g., an antibody that does not bind influenza virus)), as compared to another treatment in a patient or patient population, or as compared to the titer in the patient prior to antibody administration.

In a specific embodiment, administration of a recombinant influenza virus described herein or a neutralizing antibody described herein results in a reduction of approximately 1 log or more, approximately 2 logs or more, approximately 3 logs or more, approximately 4 logs or more, approximately 5 logs or more, approximately 6 logs or more, approximately 7 logs or more, approximately 8 logs or more, approximately 9 logs or more, approximately 10 logs or more, 1 to 5 logs, 2 to 10 logs, 2 to 5 logs, or 2 to 10 logs in Influenza virus titer in the subject. The log-reduction in Influenza virus titer may be as compared to a negative control (e.g., an influenza virus that is not a recombinant influenza virus described herein (e.g., a wild-type influenza virus) or a control antibody (e.g., an antibody that does not bind influenza virus)), as compared to another treatment, or as compared to the titer in the patient prior to administration of the antibody or recombinant influenza virus.

In a specific embodiment, administration of a recombinant influenza virus described herein or a neutralizing antibody described herein inhibits or reduces Influenza virus infection of a subject by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to Influenza virus infection of a subject in the absence of said antibody or recombinant influenza virus or in the presence of a negative control (e.g., an influenza virus that is not a recombinant influenza virus described herein (e.g., a wild-type influenza virus) or a control antibody (e.g., an antibody that does not bind influenza virus)) in an assay known to one of skill in the art or described herein.

In a specific embodiment, administration of a recombinant influenza virus described herein or a neutralizing antibody described herein inhibits or reduces the spread of Influenza virus in a subject by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the spread of Influenza virus in a subject in the absence of said antibody or recombinant influenza virus or in the presence of a negative control (e.g., an influenza virus that is not a recombinant influenza virus described herein (e.g., a wild-type influenza virus) or a control antibody (e.g., an antibody that does not bind influenza virus)) in an assay known to one of skill in the art or described herein.

In a specific embodiment, administration of a recombinant influenza virus described herein or a neutralizing antibody described herein inhibits or reduces the spread of Influenza virus between a subject and at least one other subject by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the spread of Influenza virus between a subject and at least one other subject in the absence of said antibody or recombinant influenza virus or in the presence of a negative control (e.g., an influenza virus that is not a recombinant influenza virus described herein (e.g., a wild-type influenza virus) or a control antibody (e.g., an antibody that does not bind influenza virus)) in an assay known to one of skill in the art or described herein.

In a specific embodiment, administration of a recombinant influenza virus described herein or a neutralizing antibody described herein reduces the number of and/or the frequency of symptoms of Influenza virus disease or infection in a subject (exemplary symptoms of influenza virus disease include, but are not limited to, body aches (especially joints and throat), fever, nausea, headaches, irritated eyes, fatigue, sore throat, reddened eyes or skin, and abdominal pain).

In a specific embodiment, administration of a recombinant influenza virus or antibody described herein reduces the incidence of hospitalization by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the incidence of hospitalization in the absence of administration of said recombinant influenza virus or antibody.

In a specific embodiment, administration of a recombinant influenza virus or antibody described herein reduces mortality by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the mortality in the absence of administration of said recombinant influenza virus or antibody.

In a specific embodiment, administration of a neutralizing antibody described herein prevents or inhibits influenza virus from binding to its host cell receptor by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to Influenza virus binding to its host cell receptor in the absence of said antibody(ies) or in the presence of a negative control (e.g., a control antibody (e.g., an antibody that does not bind influenza virus)) in an assay known to one of skill in the art or described herein.

In a specific embodiment, administration of a neutralizing antibody described herein prevents or inhibits influenza virus-induced fusion by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to Influenza virus-induced fusion in the absence of said antibody(ies) or in the presence of a negative control (e.g., a control antibody (e.g., an antibody that does not bind influenza virus)) in an assay known to one of skill in the art or described herein.

In a specific embodiment, administration of a neutralizing antibody described herein prevents or inhibits influenza virus-induced fusion after viral attachment to cells by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to Influenza virus-induced fusion after viral attachment to cells in the absence of said antibody(ies) or in the presence of a negative control (e.g., a control antibody (e.g., an antibody that does not bind influenza virus)) in an assay known to one of skill in the art or described herein.

In accordance with the methods encompassed herein, a recombinant influenza virus or antibody described herein or generated in accordance with the methods provided herein may be used as any line of therapy, including, but not limited to, a first, second, third, fourth and/or fifth line of therapy. Further, in accordance with the methods encompassed herein, a recombinant influenza virus or antibody described herein or generated in accordance with the methods provided herein can be used before or after any adverse effects or intolerance of the therapies other than a recombinant influenza virus or antibody described herein or generated in accordance with the methods provided herein occurs. Encompassed herein are methods for administering one or more recombinant influenza viruses and/or antibodies described herein or generated in accordance with the methods provided herein to prevent the onset of an Influenza virus disease and/or to treat or lessen the recurrence of an Influenza virus disease.

5.7.1. Patient Population

In one embodiment, a patient treated or prevented in accordance with the methods provided herein is a naïve subject, i.e., a subject that does not have a disease caused by influenza virus infection or has not been and is not currently infected with an influenza virus infection. In another embodiment, a patient treated or prevented in accordance with the methods provided herein is a naïve subject that is at risk of acquiring an influenza virus infection. In another embodiment, a patient treated or prevented in accordance with the methods provided herein is a patient suffering from or expected to suffer from an influenza virus disease. In another embodiment, a patient treated or prevented in accordance with the methods provided herein is a patient diagnosed with an influenza virus infection or a disease associated therewith. In some embodiments, a patient treated or prevented in accordance with the methods provided herein is a patient infected with an influenza virus that does not manifest any symptoms of influenza virus disease.

In another embodiment, a patient treated or prevented in accordance with the methods provided herein is a patient experiencing one or more symptoms of influenza virus disease. Symptoms of influenza virus disease include, but are not limited to, body aches (especially joints and throat), fever, nausea, headaches, irritated eyes, fatigue, sore throat, reddened eyes or skin, and abdominal pain. In another embodiment, a patient treated or prevented in accordance with the methods provided herein is a patient with influenza virus disease who does not manifest symptoms of the disease that are severe enough to require hospitalization.

In another embodiment, a patient treated or prevented in accordance with the methods provided herein is a patient infected with an influenza A virus, an influenza B virus or influenza C virus. In another embodiment, a patient treated or prevented in accordance with the methods provided herein is a patient infected with a particular subtype of influenza A virus. In another embodiment, a patient treated or prevented in accordance with the methods provided herein is a patient infected with an H1 or H3 subtype influenza A virus. In accordance with such embodiments, the patients that are infected with the virus may manifest symptoms of influenza virus disease.

In some embodiments, a subject to be administered an active compound or composition described herein is an animal. In certain embodiments, the animal is a bird. In certain embodiments, the animal is a canine. In certain embodiments, the animal is a feline. In certain embodiments, the animal is a horse. In certain embodiments, the animal is a cow. In certain embodiments, the animal is a mammal, e.g., a horse, swine, mouse, or primate, preferably a human.

In a specific embodiment, a patient treated or prevented in accordance with the methods provided herein is a human. In certain embodiments, a patient treated or prevented in accordance with the methods provided herein is a human infant. In some embodiments, a patient treated or prevented in accordance with the methods provided herein is a human toddler. In certain embodiments, a patient treated or prevented in accordance with the methods provided herein is a human child. In other embodiments, a patient treated or prevented in accordance with the methods provided herein is a human adult. In some embodiments, a patient treated or prevented in accordance with the methods provided herein is an elderly human.

In specific embodiments, a patient treated or prevented in accordance with the methods provided herein is any infant or child more than 6 months of age and any adult over 50 years of age. In other embodiments, the subject is an individual who is pregnant. In another embodiment, the subject is an individual who may or will be pregnant during the influenza season (e.g., November to April in the Northern hemisphere). In specific embodiments, a patient treated or prevented in accordance with the methods provided herein is a woman who has given birth 1, 2, 3, 4, 5, 6, 7, or 8 weeks earlier.

In some embodiments, a patient treated or prevented in accordance with the methods provided herein is any subject at increased risk of influenza virus infection or disease resulting from influenza virus infection (e.g., an immunocompromised or immunodeficient individual). In some embodiments, a patient treated or prevented in accordance with the methods provided herein is any subject in close contact with an individual with increased risk of influenza virus infection or disease resulting from influenza virus infection (e.g., immunocompromised or immunosuppressed individuals).

In some embodiments, a patient treated or prevented in accordance with the methods provided herein is a subject affected by any condition that increases susceptibility to influenza virus infection or complications or disease resulting from influenza virus infection. In other embodiments, a patient treated or prevented in accordance with the methods provided herein is a subject in which an influenza virus infection has the potential to increase complications of another condition that the individual is affected by, or for which they are at risk. In particular embodiments, such conditions that increase susceptibility to influenza virus complications or for which influenza virus increases complications associated with the condition are, e.g., conditions that affect the lung, such as cystic fibrosis, emphysema, asthma, or bacterial infections (e.g., infections caused by *Haemophilus influenzae, Streptococcus pneumoniae, Legionella pneumophila*, and *Chlamydia trachomatus*); cardiovascular disease (e.g., congenital heart disease, congestive heart failure, and coronary artery disease); endocrine disorders (e.g., diabetes); and neurological and neuron-developmental conditions (e.g., disorders of the brain, the spinal cord, the peripheral nerve, and muscle (such as cerebral palsy, epilepsy (seizure disorders), stroke, intellectual disability (e,g, mental retardation), muscular dystrophy, and spinal cord injury)). Other conditions that may increase influenza virus complications include kidney disorders; blood disorders (including anemia or sickle cell disease); or weakened immune systems (including immunosuppression caused by medications, malignancies such as cancer, organ transplant, or HIV infection).

In some embodiments, a patient treated or prevented in accordance with the methods provided herein is a subject that resides in a group home, such as a nursing home or orphanage. In some embodiments, a patient treated or prevented in accordance with the methods provided herein is subject that works in, or spends a significant amount of time in, a group home, e.g., a nursing home or orphanage. In some embodiments, a patient treated or prevented in accordance with the methods provided herein is a health care worker (e.g., a doctor or nurse). In some embodiments, a patient treated or prevented in accordance with the methods provided herein resides in a dormitory (e.g., a college dormitory). In some embodiments, a patient treated or prevented in accordance with the methods provided herein is a member of the military. In some embodiments, a patient treated or prevented in accordance with the methods provided herein is a child that attends school.

In some embodiments, a patient treated or prevented in accordance with the methods provided herein is a subject at increased risk of developing complications from influenza virus infection including: any individual who can transmit influenza viruses to those at high risk for complications, such as, e.g., members of households with high-risk individuals, including households that will include infants younger than 6 months, individuals coming into contact with infants less than 6 months of age, or individuals who will come into contact with individuals who live in nursing homes or other long-term care facilities; individuals with long-term disorders of the lungs, heart, or circulation; individuals with metabolic diseases (e.g., diabetes); individuals with kidney disorders; individuals with blood disorders (including anemia or sickle cell disease); individuals with weakened immune systems (including immunosuppression caused by medications, malignancies such as cancer, organ transplant, or HIV infection); and children who receive long-term aspirin therapy (and therefore have a higher chance of developing Reye syndrome if infected with influenza).

In other embodiments, a patient treated or prevented in accordance with the methods provided herein includes healthy individuals six months of age or older, who: plan to travel to foreign countries and areas where flu outbreaks may be occurring, such, e.g., as the tropics and the Southern Hemisphere from April through September; travel as a part of large organized tourist groups that may include persons from areas of the world where influenza viruses are circulating; attend school or college and reside in dormitories, or reside in institutional settings; or wish to reduce their risk of becoming ill with influenza virus disease.

In specific embodiments, a patient treated or prevented in accordance with the methods provided herein is an individual who is susceptible to adverse reactions to conventional therapies. In other embodiments, the patient may be a person who has proven refractory to therapies other than a recombinant influenza virus or antibody described herein but are no longer on these therapies. In certain embodiments, a patient with an influenza virus disease is refractory to a therapy when the infection has not significantly been eradicated and/or the symptoms have not been significantly alleviated. The determination of whether a patient is refractory can be made either in vivo or in vitro by any method known in the art for assaying the effectiveness of a therapy for infections, using art-accepted meanings of "refractory" in such a context. In various embodiments, a patient with an influenza virus disease is refractory when viral replication has not decreased or has increased following therapy.

In certain embodiments, patients treated or prevented in accordance with the methods provided herein are patients already being treated with antibiotics, anti-virals, anti-fungals, or other biological therapy/immunotherapy. Among these patients are refractory patients, patients who are too young for conventional therapies, and patients with reoccurring influenza virus disease or a symptom relating thereto despite treatment with existing therapies.

In certain embodiments, patients receiving a recombinant influenza virus described herein that expresses a protein heterologous to influenza virus are patients that may benefit from the expression of such a protein. For example, if the heterologous protein is a cytokine or growth factor and the patient has a condition or disease, the expression of the cytokine or growth factor may beneficial for the treatment of the condition or disease.

In certain embodiments, patients receiving a recombinant influenza virus described herein that expresses an antigen heterologous to influenza virus are patients that are infected or susceptible to infection with the pathogen from which the heterologous antigen is derived. In some embodiments, patients receiving a recombinant influenza virus described herein that expresses an antigen heterologous to influenza virus are patients that are diagnosed with an infection with the pathogen from which the heterologous antigen is derived. In some embodiments, patients receiving a recombinant influenza virus described herein that expresses an antigen heterologous to influenza virus are patients manifest one or more symptoms of a disease associated with an infection with the pathogen from which the heterologous antigen is derived. In some embodiments, patients receiving a recombinant influenza virus described herein that expresses an antigen heterologous to influenza virus are patients that are diagnosed with a disease associated with an infection with the pathogen from which the heterologous antigen is derived. In some embodiments, the antigen is from a respiratory pathogen, e.g., the antigen is or is derived from the F, G, or M2 protein of RSV, the spike protein of a Coronavirus (e.g., SARS, HuCoV), the F protein of human metapneumovirus, the F or HN protein of parainfluenza virus, the G or F protein of Hendra virus, the G or F protein of Nipah virus, or the capsid protein of Adenovirus.

In certain embodiments, patients receiving a recombinant influenza virus described herein that expresses a tumor antigen or tumor associated antigen are patients with cancer, susceptible to cancer or at risk of getting cancer. In some embodiments, patients receiving a recombinant influenza virus described herein that expresses a tumor antigen or tumor associated antigen are patients with a genetic predisposition for cancer. In certain embodiments, patients receiving a recombinant influenza virus described herein that expresses a tumor antigen or tumor associated antigen are patients with diagnosed with cancer. In specific embodiments, the tumor antigen or tumor associated antigen expressed by a recombinant influenza virus makes sense with respect to the cancer being treated. For example, if a subject has lung cancer, a recombinant influenza virus that expresses an antigen associated with the lung cancer is administered the subject. In a specific embodiment, the cancer is a solid tumor cancer, such as, e.g., a sarcoma, melanoma, lymphoma and carcinoma. In another embodiment, the cancer is a non-solid cancer, such as leukemia. Non-limiting examples of cancers include brain cancer, lung cancer, colon cancer, pancreatic cancer, liver cancer, skin cancer, breast cancer, prostate cancer, bone cancer, and uterine cancer.

In some embodiments, it may be advisable not to administer a live virus vaccine to one or more of the following patient populations: elderly humans; infants younger than 6 months old; pregnant individuals; infants under the age of 1 years old; children under the age of 2 years old; children under the age of 3 years old; children under the age of 4 years old; children under the age of 5 years old; adults under the age of 20 years old; adults under the age of 25 years old; adults under the age of 30 years old; adults under the age of 35 years old; adults under the age of 40 years old; adults under the age of 45 years old; adults under the age of 50 years old; elderly humans over the age of 70 years old; elderly humans over the age of 75 years old; elderly humans over the age of 80 years old; elderly humans over the age of 85 years old; elderly humans over the age of 90 years old; elderly humans over the age of 95 years old; children and adolescents (2-17 years of age) receiving aspirin or aspirin-containing medications, because of the complications associated with aspirin and wild-type influenza virus infections in this age group; individuals with a history of asthma or other reactive airway diseases; individuals with chronic underlying medical conditions that may predispose them to severe influenza infections; individuals with a history of Guillain-Barre syndrome; individuals with acute serious illness with fever; or individuals who are moderately or severely ill. For such individuals, administration of inactivated virus vaccines, split virus vaccines, subunit vaccines, virosomes, viral-like particles or the non-viral vectors described herein may be preferred. In certain embodiments, subjects preferably administered a live virus vaccine may include healthy children and adolescents, ages 2-17 years, and healthy adults, ages 18-49.

In certain embodiments, an immunogenic formulation comprising a live virus is not given concurrently with other live-virus vaccines.

5.7.2. Dosage & Frequency of Administration

A recombinant influenza virus, an antibody or a composition described herein may be delivered to a subject by a variety of routes. These include, but are not limited to, intranasal, intratracheal, oral, intradermal, intramuscular, topical intraperitoneal, transdermal, intravenous, pulmonary, conjunctival and subcutaneous routes. In some embodiments, a composition is formulated for topical administration, for example, for application to the skin. In specific embodiments, the composition is formulated for nasal administration, e.g., as part of a nasal spray. In certain embodiments, a composition is formulated for intramuscular administration. In some embodiments, a composition is formulated for subcutaneous administration. In specific embodiments for live virus vaccines, the vaccine is formulated for administration by a route other than injection.

When a recombinant influenza virus is to be administered to a subject, it may be preferable to introduce an immunogenic composition via the natural route of infection of influenza virus. The ability of a recombinant influenza virus to induce a vigorous secretory and cellular immune response can be used advantageously. For example, infection of the respiratory tract by a recombinant influenza virus may induce a strong secretory immune response, for example in the urogenital system, with concomitant protection against an influenza virus. In addition, in a preferred embodiment it may be desirable to introduce the pharmaceutical compositions into the lungs by any suitable route. Pulmonary administration can also be employed, e.g., by use of an inhaler or nebulizer, and formulation with an aerosolizing agent for use as a spray.

In some embodiments, when a recombinant influenza virus or a composition thereof is administered to a non-human subject (e.g., a non-human subject), the virus or composition is administered orally to the subject in the subject's food. In other embodiments, when a recombinant influenza virus or a composition thereof is administered to a subject (e.g., a non-human subject), the virus or composition is administered orally to the subject in the subject's water. In other embodiments, when a recombinant influenza virus or a composition thereof is administered to a non-human subject, the virus or composition is administered by spraying the subject with the virus or composition.

The amount of a recombinant influenza virus, an antibody or composition described herein which will be effective in the treatment and/or prevention of an influenza virus infection or an influenza virus disease will depend on the nature of the disease, and can be determined by standard clinical techniques. The precise dose to be employed in the formulation will also depend on the route of administration, and the seriousness of the infection or disease caused by it, and should be decided according to the judgment of the practitioner and each subject's circumstances. For example, effective doses may also vary depending upon means of administration, target site, physiological state of the patient (including age, body weight, health), whether the patient is human or an animal, whether other medications are administered, and whether treatment is prophylactic or therapeutic. Similarly, the amount of a recombinant influenza virus or a composition thereof that will be effective as a delivery vector will vary and can be determined by standard clinical techniques. Treatment dosages are optimally titrated to optimize safety and efficacy.

In certain embodiments, an in vitro assay is employed to help identify optimal dosage ranges. Effective doses may be extrapolated from dose response curves derived from in vitro or animal model test systems.

Exemplary doses for live recombinant influenza virus may vary from 10-100, or more, virions per dose. In some embodiments, suitable dosages of a live recombinant influenza virus are $10^2$, $5\times10^2$, $10^3$, $5\times10^3$, $10^4$, $5\times10^4$, $10^5$, $5\times10^5$, $10^6$, $5\times10^6$, $10^7$, $5\times10^7$, $10^8$, $5\times10^8$, $1\times10^9$, $5\times10^9$, $1\times10^{19}$, $5\times10^{19}$, $1\times10^{11}$, $5\times10^{11}$ or $10^{12}$ pfu, and can be administered to a subject once, twice, three or more times with intervals as often as needed. In another embodiment, a live recombinant influenza virus is formulated such that a 0.2-mL dose contains $10^{6.5-7.5}$ fluorescent focal units of live recombinant influenza viruses. In another embodiment, an inactivated vaccine is formulated such that it contains about 15 μg to about 100 μg, about 15 μg to about 75 μg, about 15 μg to about 50 μg, or about 15 μg to about 30 μg of an influenza hemagglutinin.

In certain embodiments, a recombinant influenza virus described herein or a composition thereof is administered to a subject as a single dose followed by a second dose 3 to 6 weeks later. In accordance with these embodiments, booster inoculations may be administered to the subject at 6 to 12 month intervals following the second inoculation. In certain embodiments, the booster inoculations may utilize a different recombinant influenza virus or a composition thereof. In some embodiments, the administration of the same recombinant influenza virus or a composition thereof may be repeated and the administrations may be separated by at least 1 day, 2 days, 3 days, 5 days, 10 days, 15 days, 30 days, 45 days, 2 months, 75 days, 3 months, or at least 6 months.

In specific embodiments for administration to children, two doses of a recombinant influenza virus described herein or a composition thereof, given at least one month apart, are administered to a child. In specific embodiments for administration to adults, a single dose of a recombinant influenza virus described herein or a composition thereof is given. In another embodiment, two doses of a recombinant influenza virus described herein or a composition thereof, given at least one month apart, are administered to an adult. In another embodiment, a young child (six months to nine years old) may be administered a recombinant influenza virus described herein or a composition thereof for the first time in two doses given one month apart. In a particular embodiment, a child who received only one dose in their first year of vaccination should receive two doses in the following year. In some embodiments, two doses administered 4 weeks apart are preferred for children 2-8 years of age who are administered an immunogenic composition described herein, for the first time. In certain embodiments, for children 6-35 months of age, a half dose (0.25 ml) may be preferred, in contrast to 0.5 ml which may be preferred for subjects over three years of age.

In particular embodiments, a recombinant influenza virus or a composition thereof is administered to a subject in the fall or winter, i.e., prior to or during the influenza season in each hemisphere. In one embodiment, children are administered their first dose early in the season, e.g., late September or early October for the Northern hemisphere, so that the second dose can be given prior to the peak of the influenza season.

For passive immunization with an antibody, the dosage ranges from about 0.0001 to 100 mg/kg, and more usually 0.01 to 50 mg/kg or 0.1 to 15 mg/kg, of the patient body weight. For example, dosages can be 1 mg/kg body weight or 10 mg/kg body weight or within the range of 1-10 mg/kg or in other words, 70 mg or 700 mg or within the range of 70-700 mg, respectively, for a 70 kg patient. An exemplary treatment regime entails administration once per every two weeks or once a month or once every 3 to 6 months for a period of one year or over several years, or over several year-intervals. In some methods, two or more monoclonal antibodies with different binding specificities are administered simultaneously, in which case the dosage of each antibody administered falls within the ranges indicated. Antibody is usually administered on multiple occasions. Intervals between single dosages can be weekly, monthly or yearly. Intervals can also be irregular as indicated by measuring blood levels of antibody to the recombinant influenza virus in the patient.

5.7.3. Additional Therapies

In various embodiments, a recombinant influenza virus or an antibody described herein may be administered to a subject in combination with one or more other therapies (e.g., antiviral or immunomodulatory therapies). In some embodiments, a pharmaceutical composition described herein may be administered to a subject in combination with one or more therapies. The one or more other therapies may be beneficial in the treatment or prevention of an influenza virus disease or may ameliorate a condition associated with an influenza virus disease.

In some embodiments, the one or more other therapies that are supportive measures, such as pain relievers, anti-fever medications, or therapies that alleviate or assist with breathing. Specific examples of supportive measures include humidification of the air by an ultrasonic nebulizer, aerolized racemic epinephrine, oral dexamethasone, intravenous fluids, intubation, fever reducers (e.g., ibuprofen, acetometaphin), and antibiotic and/or anti-fungal therapy (i.e., to prevent or treat secondary bacterial and/or fungal infections).

In certain embodiments, the therapies are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In specific embodiments, two or more therapies are administered within the same patent visit.

Any anti-viral agents well-known to one of skill in the art may be used in combination with a recombinant influenza virus or an antibody described herein or pharmaceutical composition thereof. Non-limiting examples of anti-viral agents include proteins, polypeptides, peptides, fusion proteins antibodies, nucleic acid molecules, organic molecules, inorganic molecules, and small molecules that inhibit and/or reduce the attachment of a virus to its receptor, the internalization of a virus into a cell, the replication of a virus, or release of virus from a cell. In particular, anti-viral agents include, but are not limited to, nucleoside analogs (e.g., zidovudine, acyclovir, gangcyclovir, vidarabine, idoxuridine, trifluridine, and ribavirin), foscarnet, amantadine, rimantadine, saquinavir, indinavir, ritonavir, alpha-interferons and other interferons, AZT, zanamivir (Relenza®), and oseltamavir (Tamiflu®). In certain embodiments, a recombinant influenza virus described herein, an antibody generated in accordance with the methods described herein or a pharmaceutical composition described herein is administered in combination with an influenza virus vaccine, e.g., Fluarix® (GlaxoSmithKline), FluMist® (Med-Immune Vaccines), Fluvirin® (Chiron Corporation), Fluzone® (Aventis Pasteur). In specific embodiments, the antiviral agent is an immunomodulatory agent that is specific for a viral antigen. In particular embodiments, the viral antigen is an influenza virus antigen.

In a specific embodiment, one or more therapies that prevent or treat secondary responses to a primary influenza virus infection are administered in combination with a recombinant influenza virus described herein, an antibody generated in accordance with the methods provided herein, or a pharmaceutical composition described herein. Examples of secondary responses to a primary influenza virus infection include, but are not limited to, asthma-like responsiveness to mucosal stimuli, elevated total respiratory resistance, increased susceptibility to secondary viral, bacterial, and fungal infections, and development of conditions such as, but not limited to, bronchiolitis, pneumonia, croup, and febrile bronchitis.

In some embodiments, a recombinant influenza virus described herein or a pharmaceutical composition thereof is administered in combination with an antibody that specifically binds to an influenza virus antigen.

5.8 Biological Assays

Reassortment Assays

A reverse genetics approach can be used to assess whether each of the chimeric gene segments of the recombinant influenza viruses shown in, e.g., FIGS. 35 to 37, can reassort. Cells expressing the necessary influenza virus proteins can be cotransfected with influenza virus chimeric segments that have had their packaging signals swapped and influenza virus gene segments from a wild-type or lab strain of influenza virus, wherein the wild-type or lab strain influenza virus gene segments include a gene segment that encodes an influenza virus protein encoded by one of the chimeric influenza virus gene segments and the other gene segments necessary to produce a replication-competent influenza virus. For example, cells, such as 293T cells, MDCK cells or Vero cells, expressing the necessary viral proteins (e.g., PA, PB1, PB2, and NP) can be transfected with plasmids encoding four of the chimeric gene segments shown in FIG. 35 (NA-PB2mut-NA, PB2-PB1mut-PB2, PB1-PAmut-PB1, and PA-NAmut-PA) and plasmids encoding five gene segments (pDZ-NP, NA, M, NS, and HA) of a wild-type influenza virus or a lab strain, such as A/PR/8/34, using techniques previously described (see, e.g., Gao et al., 2008, J. Virol. 82: 6419-6426; Quinlivan et al., 2005, J. Virol. 79: 8431-8439; Fodor et al., 1999, J. Virol. 73: 9679-9682). The recombinant viruses rescued can then be grown in tissue culture or embryonated eggs and plaque purified using known techniques. The gene segments present in the plaque purified viruses can then be determined by, e.g., amplifying single plaques, isolating the vRNA from the virus, subjecting the vRNA to RT-PCR using primers designed to hybridize to specific gene segments and running the RT-PCR products on an agarose gel. Alternatively, the vRNA segments from the plaque performed viruses can be sequenced using techniques known in the art, such as deep sequencing. The inability to detect influenza viruses containing less than the combination of the chimeric gene segments that have had their packaging signals swapped indicates that those chimeric gene segments are unable to reassort freely. For example, with respect to the chimeric gene segments of the recombinant virus shown in FIG. 35, the inability to detect influenza viruses containing the three chimeric NA-PB2mut-NA, PB2-PB1mut-PB2, and PB1-PAmut-PB1 gene segments and the wild-type or lab strain influenza virus NA, NP, M, NS and HA gene segments indicates that the four chimeric gene segments (NA-PB2mut-NA, PB2-PB1mut-PB2, PB1-PAmut-PB1, and PA-NAmut-PA) are unable to reassort freely.

As another approach to determine whether the chimeric gene segments of the recombinant influenza viruses shown in, e.g., FIGS. 35 to 37 can freely reassort in tissue culture, cells (e.g., 293T cells, MDCK cells or Vero cells) can be co-infected with the recombinant virus shown in, e.g., FIG. 35, 36 or 37, and a wild-type or lab strain of influenza virus at certain multiplicity of infection ("moi") for each virus (e.g., an moi of 10). The resulting viruses can then be plaque purified. The gene segments present in the plaque purified viruses can then be determined by, e.g., amplifying single plaques, isolating the vRNA from the virus, subjecting the vRNA to RT-PCR using primers designed to hybridize to specific gene segments and running the RT-PCR products on an agarose gel. Alternatively, the vRNA segments from the plaque performed viruses can be sequenced using techniques known in the art, such as deep sequencing. The inability to detect viruses containing less than the combination of the chimeric segments that have had their packaging signals swapped are unable to reassort freely. For example, with respect to the chimeric gene segments of the recombinant virus shown in FIG. 35, the inability to detect influenza viruses containing the three chimeric NA-PB2mut-NA, PB2-PB1mut-PB2, and PB1-PAmut-PB1 gene segments and the wild-type or lab strain influenza virus NA, NP, M, NS and HA gene segments indicates that the four chimeric gene segments (NA-PB2mut-NA, PB2-PB1mut-PB2, PB1-PAmut-PB1, and PA-NAmut-PA) are unable to reassort freely.

Assays to Detect the Presence of a Chimeric Influenza Virus Gene Segment

Any technique known in the art may be used to detect a chimeric influenza virus gene segment or the complement thereof, or a nucleic acid encoding a chimeric influenza virus gene segment. For example, primers may be designed that are specific for a particular chimeric influenza virus gene segment and RT-PCR or PCR using those primers may be performed to amplify a fragment of the segment. The amplified fragment may be detected by, e.g., running the fragment on an agarose gel. Alternatively, primers may be designed that are specific for a particular chimeric influenza virus gene segment and real-time RT-PCR using those primers may be performed. In one embodiment, a pair primers are designed that are specific for a particular chimeric influenza virus gene segment, wherein the one of the primers is a sense primer that anneals to the 3' NCR1 or 3' CRS1 derived from a first type influenza virus gene segment, and the other primer is an antisense primer that anneals to the mORF derived from a second type of influenza virus gene segment. In another embodiment, a pair primers are designed that are specific for a particular chimeric influenza virus gene segment, wherein the one of the primers is an antisense primer that anneals to the 5' NCR1 or 5' CRS1 derived from a first type influenza virus gene segment, and the other primer is a sense primer that anneals to the mORF derived from a second type of influenza virus gene segment. Techniques known to one of skill in the art may be used to design primers that are specific for a particular chimeric influenza virus gene segment.

Packaging Assays

Incorporation of a chimeric influenza virus gene segment into a virus particle, i.e., packaging, can be assessed by any method known in the art or described herein (e.g., in cell culture, animal model or viral culture in embryonated eggs).

In one example, viral particles may be purified and RNA isolated and run on a 2.8% denaturing polyacrylamide gel which is then stained with a silver staining kit (Invitrogen) to determine the presence of a chimeric influenza virus gene segment (see, e.g., Gao et al., 2008, J. Virol. 82: 6419-6426 for a description of such an assay).

In another example, viral particles from cell culture of the allantoic fluid of embryonated eggs can be purified by centrifugation through a sucrose cushion and subsequently analyzed for the presence of a chimeric influenza virus gene segment by RT-PCR.

Packaging assays can be used to determine the regions of an influenza virus gene segment that are necessary and/or sufficient for packaging. In these cases, a reporter gene can be used to facilitate the assay. Packaging assays can also be used to determine whether, and if so, to what degree, the chimeric influenza virus gene segments are packaged into a virus particle, wherein the chimeric influenza virus gene segment does not encode a reporter gene.

Illustrative packaging assays include the packaging assay disclosed in Liang et al., 2005, J Virol 79:10348-10355 and the packaging assay disclosed in Muramoto et al., 2006, J Virol 80:2318-2325. The description of the packaging assays described in Liang et al. and Muramoto et al. are incorporated herein by reference. Several parameters of the protocols of Liang and Muramoto can be modified; for example various host cells can be used and various reporter genes can be used.

In certain embodiments, the packaging assay of Muramoto et al. is used ("Muramoto protocol"). Briefly, a reporter influenza virus gene segment may be constructed, wherein the reporter gene is flanked by the 3' NCR and the 3' proximal coding region of one type of influenza virus gene segment or a derivative or a fragment thereof, wherein any start codon in the 3' proximal coding region is mutated, on one side and the 5' NCR and the 5' proximal coding region of this type of influenza virus gene segment or derivatives or fragments thereof on the other side. The reporter gene can be GFP. The reporter influenza virus gene segment is transfected with seven plasmids that encode the other seven types of influenza virus gene segments into a host cell, such as 293T cells. In addition, expression plasmids encoding all 10 influenza virus proteins are transfected into the host cell. After virus like particles ("VLPs") are released from the host cell, e.g., after 48 hours, supernatant is collected. The supernatant is then used to infect fresh host cells, e.g., MDCK cells, concurrently with a helper influenza virus. At least one protein of the helper influenza virus is antigenically distinguishable from the same type of protein in the VLP such that cells that are infected with VLP can be identified. The number of cells expressing the reporter gene is determined using, e.g., FACS, and the number of cells expressing VLP protein is determined using immunocytochemistry coupled with FACS. The ratio of reporter gene expressing cells to VLP protein expressing cells is a measure for the efficiency of packaging of the reporter influenza virus gene segment into a virion.

In certain embodiments, the packaging assay of Liang et al. is used. Briefly, the eight-plasmid rescue system (Hoffmann et al., 2000, PNAS 97:6208-6113) is combined with a reporter influenza virus gene segment. The reporter influenza virus gene segment is constructed as discussed above for the Muramoto protocol. The eight-plasmid rescue system provides all eight influenza gene segments as plasmids with promoters such that the gene segments can be transcribed in both directions thereby generating all eight wild-type vRNAs and all viral proteins needed for virion production. The eight plasmids and the reporter gene segment are transfected into a host cell, such as 293T cells. After virions are released from the host cell, e.g., after 48 hours, supernatant is collected. Fresh host cells, such as MDBK cells, are infected with the supernatant until the reporter gene is expressed, e.g., for 15 hours. Subsequently, the level of reporter gene expression is tested. An assay suitable for the reporter gene can be selected by the skilled artisan. For example, if the reporter gene is a fluorescent protein, such as GFP, FACS analysis can be used to determine the number of cells that express the reporter gene. The number of cells expressing the reporter gene is representative of the efficiency of packaging, such that a relative low number of cells expressing the reporter gene indicates a low efficiency of packaging of the reporter gene segment and a relative high number of cells expressing the reporter gene indicates a high efficiency of packaging of the reporter gene segment. In certain embodiments, the number of cells expressing the reporter gene is normalized over the cells that produce virus. The number of virus-producing cells can be determined, e.g., by a plaque assay or immunocytochemistry using an antibody against a viral protein, such as NP, paired with FACS analysis.

The principle of the packaging assays described above with a reporter gene also applies to packaging assays without reporter genes. The skilled artisan could use any known technique to adapt the packaging assays described above to assays without a reporter gene. Instead of relying on detection of the reporter gene product as a read-out of packaging efficiency as described above, the skilled artisan could detect instead either the influenza virus gene segment of interest or the gene product of the influenza virus gene segment of interest. RT-PCR can be used with primers that are specific to the influenza virus gene segment to detect and quantify the influenza virus gene segment of interest. Western blot, ELISA, radioimmunoassay, immunoprecipitation, immunocytochemistry, or immunocytochemistry in conjunction with FACS can be used to quantify the gene product of the influenza virus gene segment of interest as a read-out of packaging efficiency. In is also possible to fuse the gene in the influenza virus gene segment of interest to a sequence that encodes a peptide tag such that the gene product of the gene of the influenza virus gene segment of interest encodes a fusion protein with a peptide tag, wherein the peptide tag can be detected.

Viral Assays

Viral assays include those that measure viral replication (as determined, e.g., by plaque formation) or the production of viral proteins (as determined, e.g., by western blot analysis) or viral RNAs (as determined, e.g., by RT-PCR or northern blot analysis) in cultured cells in vitro using methods which are well known in the art.

Growth of a recombinant influenza virus described herein can be assessed by any method known in the art or described herein (e.g., in cell culture (e.g., cultures of chicken embryonic kidney cells or cultures of chicken embryonic fibroblasts (CEF)). Viral titer may be determined by inoculating serial dilutions of a recombinant influenza virus described herein into cell cultures (e.g., CEF, MDCK, EFK-2 cells, Vero cells, primary human umbilical vein endothelial cells (HUVEC), H292 human epithelial cell line or HeLa cells), chick embryos, or live animals (e.g., avians). After incubation of the virus for a specified time, the virus is isolated using standard methods. An hemagglutinin (HA) assay may be carried out in V-bottom 96-well plates. Serial twofold dilutions of each sample in PBS are incubated for 1 h on ice with an equal volume of a 0.5% suspension of chicken erythrocytes in PBS. Positive wells contain an adherent, homogeneous layer of erythrocytes; negative wells contain a nonadherent pellet. Physical quantitation of the virus titer can be performed using PCR applied to viral supernatants (Quinn & Trevor, 1997; Morgan et al., 1990), hemagglutination assays, tissue culture infectious doses (TCID50) or egg infectious doses (E1D50).

Antibody Assays

Antibodies generated or identified in accordance with the methods described herein may be characterized in a variety of ways well-known to one of skill in the art (e.g., ELISA, Surface Plasmon resonance display (BIAcore), Western blot, immunofluorescence, immunostaining and/or microneutralization assays). In particular, antibodies generated or identified in accordance may be assayed for the ability to specifically bind to an antigen of the recombinant influenza virus. Such an assay may be performed in solution (e.g., Houghten, 1992, Bio/Techniques 13:412 421), on beads (Lam, 1991, Nature 354:82 84), on chips (Fodor, 1993, Nature 364:555 556), on bacteria (U.S. Pat. No. 5,223,409), on spores (U.S. Pat. Nos. 5,571,698; 5,403,484; and 5,223,409), on plasmids (Cull et al., 1992, Proc. Natl. Acad. Sci. USA 89:1865 1869) or on phage (Scott and Smith, 1990, Science 249:386 390; Cwirla et al., 1990, Proc. Natl. Acad. Sci. USA 87:6378 6382; and Felici, 1991, J. Mol. Biol. 222:301 310) (each of these references is incorporated herein in its entirety by reference). Antibodies that specifically bind to an antigen of a recombinant influenza virus can then be assayed for their specificity to said antigen.

Antibodies generated or identified in accordance with the methods described herein may be assayed for specific binding to an antigen of a recombinant virus described herein and cross-reactivity with other antigens by any method known in the art. Immunoassays which can be used to analyze specific binding and cross-reactivity include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds., 1994, Current Protocols in Molecular Biology, Vol. 1, John Wiley & Sons, Inc., New York, which is incorporated by reference herein in its entirety).

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^{3}H$ or $^{125}I$) with the antibody of interest in the presence of increasing amounts of unlabeled antigen, and the detection of the antibody bound to the labeled antigen. The affinity of the antibody can be determined from the data by scatchard plot analysis. Competition with a second antibody can also be determined using radioimmunoassays. In this case, a recombinant virus of described herein or an antigen thereof is incubated with an antibody against the antigen conjugated to a labeled compound (e.g., $^{3}H$ or $^{125}I$) in the presence of increasing amounts of an unlabeled second antibody.

BIAcore kinetic analysis can be used to determine the binding on and off rates of an antibody to an antigen of a recombinant influenza virus described herein. BIAcore kinetic analysis comprises analyzing the binding and dissociation of polypeptide comprising the antigen of interest from chips with immobilized antibodies generated or identified in accordance with methods described herein on their surface. A typical BIAcore kinetic study involves the injection of 250 μL of an antibody reagent (mAb, Fab) at varying concentration in HBS buffer containing 0.005% Tween-20 over a sensor chip surface, onto which has been immobilized the antigen. The flow rate is maintained constant at 75 μL/min Dissociation data is collected for 15 min or longer as necessary. Following each injection/dissociation cycle, the bound mAb is removed from the antigen surface using brief, 1 min. pulses of dilute acid, typically 10-100 mM HCl, though other regenerants are employed as the circumstances warrant. More specifically, for measurement of the rates of association, kon, and dissociation, koff, the polypeptide comprising the antigen is directly immobilized onto the sensor chip surface through the use of standard amine coupling chemistries, namely the EDC/NHS method (EDC=N-diethylaminopropyl)-carbodiimide). Briefly, a 5-100 nM solution of the polypeptide comprising the antigen in 10 mM NaOAc, pH4 or pH5 is prepared and passed over the EDC/NHS-activated surface until approximately 30-50 RU's worth of antigen are immobilized. Following this, the unreacted active esters are "capped" off with an injection of 1M Et-NH2. A blank surface, containing no antigen, is prepared under identical immobilization conditions for reference purposes. Once an appropriate surface has been prepared, a suitable dilution series of each one of the antibody reagents is prepared in HBS/Tween-20, and passed over both the antigen and reference cell surfaces, which are connected in series. The range of antibody concentrations that are prepared varies, depending on what the equilibrium binding constant, KD, is estimated to be. As described above, the bound antibody is removed after each injection/dissociation cycle using an appropriate regenerant.

Antibodies generated or identified in accordance with the methods described herein can also be assayed for their ability to inhibit the binding of an antigen of a recombinant influenza virus to a host cell using techniques known to those of skill in the art. For example, cells expressing receptors known to bind to influenza virus can be contacted with influenza virus in the presence or absence of an antibody generated or identified in accordance with the methods described herein and the ability of the antibody to inhibit the binding can measured by, for example, flow cytometry or a scintillation assay. The antigen or the antibody can be labeled with a detectable compound such as a radioactive label (e.g., $^{32}P$, $^{35}S$, and $^{125}I$) or a fluorescent label (e.g., fluorescein isothiocyanate, rhodamine, phycoerythrin, phycocyanin, allophycocyanin, o-phthaldehyde and fluorescamine) to enable detection of an interaction between the influenza virus and a cell.

Antiviral Activity Assays

Antibodies described herein or compositions thereof can be assessed in vitro for antiviral activity. In one embodiment, the antibodies or compositions thereof are tested in vitro for their effect on growth of an influenza virus. Growth of influenza virus can be assessed by any method known in the art or described herein (e.g., in cell culture). In a specific embodiment, cells are infected at a MOI of 0.0005 and 0.001, 0.001 and 0.01, 0.01 and 0.1, 0.1 and 1, or 1 and 10, or a MOI of 0.0005, 0.001, 0.005, 0.01, 0.05, 0.1, 0.5, 1, 5 or 10 and incubated with serum free media supplemented. Viral titers are determined in the supernatant by hemagglutinin plaques or any other viral assay described herein. Cells in which viral titers can be assessed include, but are not limited to, EFK-2 cells, Vero cells, primary human umbilical vein endothelial cells (HUVEC), H292 human epithelial cell line and HeLa cells. In vitro assays include those that measure altered viral replication (as determined, e.g., by plaque formation) or the production of viral proteins (as determined, e.g., by Western blot analysis) or viral RNAs (as determined, e.g., by RT-PCR or northern blot analysis) in cultured cells in vitro using methods which are well known in the art or described herein.

In one non-limiting example, a monolayer of the target mammalian cell line is infected with different amounts (e.g., multiplicity of 3 plaque forming units (pfu) or 5 pfu) of influenza and subsequently cultured in the presence or absence of various dilutions of antibodies (e.g., 0.1 µg/ml, 1 µg/ml, 5 µg/ml, or 10 µg/ml). Infected cultures are harvested 48 hours or 72 hours post infection and titered by standard plaque assays known in the art on the appropriate target cell line (e.g., Vero cells).

In a non-limiting example of a hemagglutination assay, cells are contacted with an antibody and are concurrently or subsequently infected with the virus (e.g., at an MOI of 1) and the virus is incubated under conditions to permit virus replication (e.g., 20-24 hours). The antibodies are preferably present throughout the course of infection. Viral replication and release of viral particles is then determined by hemagglutination assays using 0.5% chicken red blood cells. See, e.g., Kashyap et al., PNAS USA 105: 5986-5991. In some embodiments, an antibody compound is considered an inhibitor of viral replication if it reduces viral replication by at least 2 wells of HA, which equals approximately a 75% reduction in viral titer. In specific embodiments, an inhibitor reduces viral titer in this assay by 50% or more, by 55% or more, by 60% or more, by 65% or more, by 70% or more, by 75% or more, by 80% or more, by 85% or more, by 90% or more, or by 95% or more.

Cytotoxicity Assays

Many assays well-known in the art can be used to assess viability of cells (infected or uninfected) or cell lines following exposure to a recombinant influenza virus, an antibody described herein or a composition thereof, and, thus, determine the cytotoxicity thereof. For example, cell proliferation can be assayed by measuring Bromodeoxyuridine (BrdU) incorporation (see, e.g., Hoshino et al., 1986, Int. J. Cancer 38, 369; Campana et al., 1988, J. Immunol. Meth. 107:79), ($^{3}$H) thymidine incorporation (see, e.g., Chen, J., 1996, Oncogene 13:1395-403; Jeoung, J., 1995, J. Biol. Chem. 270: 18367 73), by direct cell count, or by detecting changes in transcription, translation or activity of known genes such as proto-oncogenes (e.g., fos, myc) or cell cycle markers (Rb, cdc2, cyclin A, D1, D2, D3, E, etc). The levels of such protein and mRNA and activity can be determined by any method well known in the art. For example, protein can be quantitated by known immunodiagnostic methods such as ELISA, Western blotting or immunoprecipitation using antibodies, including commercially available antibodies. mRNA can be quantitated using methods that are well known and routine in the art, for example, using northern analysis, RNase protection, or polymerase chain reaction in connection with reverse transcription. Cell viability can be assessed by using trypan-blue staining or other cell death or viability markers known in the art. In a specific embodiment, the level of cellular ATP is measured to determined cell viability.

In specific embodiments, cell viability is measured in three-day and seven-day periods using an assay standard in the art, such as the CellTiter-Glo Assay Kit (Promega) which measures levels of intracellular ATP. A reduction in cellular ATP is indicative of a cytotoxic effect. In another specific embodiment, cell viability can be measured in the neutral red uptake assay. In other embodiments, visual observation for morphological changes may include enlargement, granularity, cells with ragged edges, a filmy appearance, rounding, detachment from the surface of the well, or other changes. These changes are given a designation of T (100% toxic), PVH (partially toxic—very heavy—80%), PH (partially toxic—heavy—60%), P (partially toxic—40%), Ps (partially toxic—slight—20%), or 0 (no toxicity—0%), conforming to the degree of cytotoxicity seen. A 50% cell inhibitory (cytotoxic) concentration (IC50) is determined by regression analysis of these data.

In a specific embodiment, the cells used in the cytotoxicity assay are animal cells, including primary cells and cell lines. In some embodiments, the cells are human cells. In certain embodiments, cytotoxicity is assessed in one or more of the following cell lines: U937, a human monocyte cell line; primary peripheral blood mononuclear cells (PBMC); Huh7, a human hepatoblastoma cell line; 293T, a human embryonic kidney cell line; and THP-1, monocytic cells. In certain embodiments, cytotoxicity is assessed in one or more of the following cell lines: MDCK, MEF, Huh 7.5, Detroit, or human tracheobronchial epithelial (HTBE) cells.

A recombinant influenza virus, an antibody or a composition thereof can be tested for in vivo toxicity in animal models. For example, animal models known in the art can also be used to determine the in vivo toxicity of to test the activities of a recombinant influenza virus, an antibody or a composition thereof. For example, animals are administered a range of concentrations of to test the activities of a recombinant influenza virus, an antibody or a composition thereof. Subsequently, the animals are monitored over time for lethality, weight loss or failure to gain weight, and/or levels of serum markers that may be indicative of tissue damage (e.g., creatine phosphokinase level as an indicator of general tissue damage, level of glutamic oxalic acid transaminase or pyruvic acid transaminase as indicators for possible liver damage). These in vivo assays may also be adapted to test the toxicity of various administration mode and/or regimen in addition to dosages.

The toxicity and/or efficacy of a recombinant influenza virus, an antibody or a composition thereof can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. A recombinant influenza virus, an antibody or a composition thereof that exhibits large therapeutic indices is preferred. While a recombinant influenza virus, an antibody or a composition thereof that exhibits toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of a recombinant influenza virus, an antibody or a composition thereof for use in humans. The dosage of such agents lies preferably within a range of circulating concentrations that include the ED50 with little or no toxicity. The dosage may vary within this range depending upon the dosage form employed and the route of administration utilized. For any active compound used in a method described herein, the effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high-performance liquid chromatography. Additional information concerning dosage determination is provided herein.

Further, any assays known to those skilled in the art can be used to evaluate the prophylactic and/or therapeutic utility of a recombinant influenza virus, an antibody or a composition thereof, for example, by measuring viral infection or a condition or symptoms associated therewith.

Animal Model Assays

The virulence of a recombinant influenza virus described herein can be assessed in a subject, in particular an animal model. In one example, the ability to induce lung lesions and cause infection in an animal model of virus infection is compared to wild-type virus and mock virus. Lung lesions can be assessed as a percentage of lung lobes that are healthy by visual inspection. Animals are euthanized 5 days p.i. by intravenous administration of pentobarbital, and their lungs are removed in toto. The percentage of the surface of each pulmonary lobe that is affected by macroscopic lesions is estimated visually. The percentages are averaged to obtain a mean value for the 7 pulmonary lobes of each animal. In other assays, nasal swabs can be tested to determine virus burden or titer. Nasal swabs can be taken during necropsy to determine viral burden post-infection.

A recombinant influenza virus, an antibody or a composition thereof is preferably assayed in vivo for the desired therapeutic or prophylactic activity prior to use in humans. For example, to assess the use of a recombinant influenza virus, an antibody or a composition thereof to prevent an influenza virus disease, the virus, antibody or composition can be administered before the animal is infected with a wild-type influenza virus. Alternatively, or in addition, a recombinant influenza virus, an antibody or a composition thereof can be administered to the animal at the same time that the animal is infected with a wild-type influenza virus. To assess the use of a recombinant influenza virus, an antibody or a composition thereof to treat an influenza virus infection or disease associated therewith, the virus, antibody or composition may be administered after infecting the animal with wild-type influenza virus. In a specific embodiment, a recombinant influenza virus, an antibody or a composition thereof is administered to the animal more than one time.

A recombinant influenza virus, an antibody or a composition thereof can be tested for antiviral activity in animal model systems including, but are not limited to, rats, mice, chicken, cows, monkeys, pigs, goats, sheep, dogs, rabbits, guinea pigs, etc. In a specific embodiment, active compounds and compositions thereof are tested in a mouse model system. Such model systems are widely used and well-known to the skilled artisan. In a specific embodiment, a recombinant influenza virus, an antibody or a composition thereof is tested in a mouse model system. Non-limiting examples of animal models for influenza virus are provided in this section.

In general, animals are infected with wild-type influenza virus and concurrently or subsequently treated with a recombinant influenza virus, an antibody or a composition thereof, or placebo. Alternatively, animals are treated with a recombinant influenza virus, an antibody or a composition thereof, or placebo and subsequently infected with wild-type influenza virus. Samples obtained from these animals (e.g., serum, urine, sputum, semen, saliva, plasma, or tissue sample) can be tested for viral replication via well known methods in the art, e.g., those that measure altered viral titers (as determined, e.g., by plaque formation), the production of viral proteins (as determined, e.g., by Western blot, ELISA, or flow cytometry analysis) or the production of viral nucleic acids (as determined, e.g., by RT-PCR or northern blot analysis). For quantitation of virus in tissue samples, tissue samples are homogenized in phosphate-buffered saline (PBS), and dilutions of clarified homogenates are adsorbed for 1 hour at 37° C. onto monolayers of cells (e.g., Vero, CEF or MDCK cells). In other assays, histopathologic evaluations are performed after infection, preferably evaluations of the organ(s) the virus is known to target for infection. Virus immunohistochemistry can be performed using a viral-specific monoclonal antibody.

The effect of a recombinant influenza virus, an antibody or a composition thereof on the virulence of a virus can also be determined using in vivo assays in which the titer of the virus in an infected subject administered a recombinant influenza virus, an antibody or a composition thereof, the length of survival of an infected subject administered a recombinant influenza virus, an antibody or a composition thereof, the immune response in an infected subject administered a recombinant influenza virus, an antibody or a composition thereof, the number, duration and/or severity of the symptoms in an infected subject administered a recombinant influenza virus, an antibody or a composition thereof, and/or the time period before onset of one or more symptoms in an infected subject administered a recombinant influenza virus, an antibody or a composition thereof, is assessed. Techniques known to one of skill in the art can be used to measure such effects.

Influenza virus animal models, such as ferret, mouse, guinea pig, and chicken, developed for use to test antiviral agents against influenza virus have been described. See, e.g., Sidwell et al., Antiviral Res., 2000, 48:1-16; Lowen A. C. et al. PNAS., 2006, 103: 9988-92; and McCauley et al., Antiviral Res., 1995, 27:179-186. For mouse models of influenza, non-limiting examples of parameters that can be used to assay antiviral activity of active compounds administered to the influenza-infected mice include pneumonia-associated death, serum $\alpha$1-acid glycoprotein increase, animal weight, lung virus assayed by hemagglutinin, lung virus assayed by plaque assays, and histopathological change in the lung. Statistical analysis is carried out to calculate significance (e.g., a P value of 0.05 or less).

In one example, the ability to induce lung lesions and cause infection in an animal model of virus infection is compared using wild-type virus and mock virus. Lung lesions can be assessed as a percentage of lung lobes that are healthy by visual inspection. Animals are euthanized 5 days p.i. by intravenous administration of pentobarbital, and their lungs are removed in toto. The percentage of the surface of each pulmonary lobe that is affected by macroscopic lesions is estimated visually. The percentages are averaged to obtain a mean value for the 7 pulmonary lobes of each animal. In other assays, nasal swabs can be tested to determine virus burden or titer. Nasal swabs can be taken during necropsy to determine viral burden post-infection.

In one embodiment, virus is quantified in tissue samples. For example, tissue samples are homogenized in phosphate-buffered saline (PBS), and dilutions of clarified homogenates adsorbed for 1 h at 37° C. onto monolayers of cells (e.g., MDCK cells). Infected monolayers are then overlaid with a solution of minimal essential medium containing 0.1% bovine serum albumin (BSA), 0.01% DEAE-dextran, 0.1% NaHCO3, and 1% agar. Plates are incubated 2 to 3 days until plaques could be visualized. Tissue culture infectious dose (TCID) assays to titrate virus from PR8-infected samples are carried out as follows. Confluent monolayers of cells (e.g., MDCK cells) in 96-well plates are incubated with log dilutions of clarified tissue homogenates in media. Two to three days after inoculation, 0.05-ml aliquots from each well are assessed for viral growth by hemagglutination assay (HA assay).

Assays in Humans

In one embodiment, a recombinant influenza virus, an antibody or a composition thereof is assessed in infected human subjects. In accordance with this embodiment, a recombinant influenza virus, an antibody or a composition thereof is administered to the human subject, and the effect of the virus, antibody or composition on viral replication is determined by, e.g., analyzing the level of the virus or viral nucleic acids in a biological sample (e.g., serum or plasma). A recombinant influenza virus, an antibody or a composition thereof that alters virus replication can be identified by comparing the level of virus replication in a subject or group of subjects treated with a control to that in a subject or group of subjects treated with a recombinant influenza virus, an antibody or a composition thereof. Alternatively, alterations in viral replication can be identified by comparing the level of the virus replication in a subject or group of subjects before and after the administration of a recombinant influenza virus, an antibody or a composition thereof. Techniques known to those of skill in the art can be used to obtain the biological sample and analyze the mRNA or protein expression.

In another embodiment, the effect of a recombinant influenza virus, an antibody or a composition thereof on the severity of one or more symptoms associated with an influenza virus infection/disease are assessed in an infected subject. In accordance with this embodiment, a recombinant influenza virus, an antibody or a composition thereof, or a control is administered to a human subject suffering from influenza virus infection and the effect of the virus, antibody or composition on one or more symptoms of the virus infection is determined. A recombinant influenza virus, an antibody or a composition thereof that reduces one or more symptoms can be identified by comparing the subjects treated with a control to the subjects treated with the virus, antibody or composition. Techniques known to physicians familiar with infectious diseases can be used to determine whether an ative compound or composition thereof reduces one or more symptoms associated with the influenza virus disease.

For quantitation of virus in tissue samples, tissue samples are homogenized in phosphate-buffered saline (PBS), and dilutions of clarified homogenates adsorbed for 1 h at 37° C. onto monolayers of cells (e.g., CEF or MDCK cells). Infected monolayers are then overlaid with a solution of minimal essential medium containing 0.1% bovine serum albumin (BSA), 0.01% DEAE-dextran, 0.1% NaHCO3, and 1% agar. Plates are incubated 2 to 3 days until plaques could be visualized. Tissue culture infectious dose (TCID) assays to titrate virus from PR8-infected samples are carried out as follows. Confluent monolayers of cells (e.g., CEF or MDCK cells) in 96-well plates are incubated with log dilutions of clarified tissue homogenates in media. Two to three days after inoculation, 0.05-ml aliquots from each well are assessed for viral growth by hemagglutination assay (HA assay).

In yet other assays, histopathologic evaluations are performed after infection. Nasal turbinates and trachea may be examined for epithelial changes and subepithelial inflammation. The lungs may be examined for bronchiolar epithelial changes and peribronchiolar inflammation in large, medium, and small or terminal bronchioles. The alveoli are also evaluated for inflammatory changes. The medium bronchioles are graded on a scale of 0 to 3+ as follows: 0 (normal: lined by medium to tall columnar epithelial cells with ciliated apical borders and basal pseudostratified nuclei; minimal inflammation); 1+ (epithelial layer columnar and even in outline with only slightly increased proliferation; cilia still visible on many cells); 2+ (prominent changes in the epithelial layer ranging from attenuation to marked proliferation; cells disorganized and layer outline irregular at the luminal border); 3+ (epithelial layer markedly disrupted and disorganized with necrotic cells visible in the lumen; some bronchioles attenuated and others in marked reactive proliferation).

The trachea is graded on a scale of 0 to 2.5+ as follows: 0 (normal: Lined by medium to tall columnar epithelial cells with ciliated apical border, nuclei basal and pseudostratified. Cytoplasm evident between apical border and nucleus. Occasional small focus with squamous cells); 1+ (focal squamous metaplasia of the epithelial layer); 2+ (diffuse squamous metaplasia of much of the epithelial layer, cilia may be evident focally); 2.5+ (diffuse squamous metaplasia with very few cilia evident).

Virus immunohistochemistry is performed using a viral-specific monoclonal antibody (e.g. NP-, N- or HN-specific monoclonal antibodies). Staining is graded 0 to 3+ as follows: 0 (no infected cells); 0.5+ (few infected cells); 1+ (few infected cells, as widely separated individual cells); 1.5+ (few infected cells, as widely separated singles and in small clusters); 2+ (moderate numbers of infected cells, usually affecting clusters of adjacent cells in portions of the epithelial layer lining bronchioles, or in small sublobular foci in alveoli); 3+ (numerous infected cells, affecting most of the epithelial layer in bronchioles, or widespread in large sublobular foci in alveoli).

5.9 Screening Assays

In one aspect, a recombinant influenza virus described herein may be used to study the life cycle of an influenza virus. For example, a recombinant influenza virus described herein that expresses a detectable heterologous sequence (e.g., a detectable substance such as GFP or luciferase, or another detectable substance described herein or known in the art) is introduced into a host cell and the life cycle of the virus is monitored by the assessing the expression of the detectable heterologous sequence. A recombinant influenza virus described herein that expresses a detectable heterologous sequence may also be administered to a non-human animal and the infection monitored by assessing the expression of the detectable heterologous sequence. In certain embodiments, the recombinant influenza virus is a nine segmented influenza virus described herein.

In another aspect, provided herein are high throughput screening assays for the identification or validation of compounds that modulate the replication of influenza viruses. In a specific embodiment, the high throughput screening assay to identify a compound that modulates the replication of an influenza virus comprises: (a) contacting a compound or a member of a library of compounds with a host cell infected with a recombinant influenza virus described herein that expresses a detectable heterologous nucleotide sequence; and (b) measuring the expression or activity of a product encoded by the detectable heterologous nucleotide sequence. In another embodiment, the high throughput screening assay to identify a compound that modulates the replication of an influenza virus comprises: (a) infecting a host cell with a recombinant influenza virus described herein that expresses a detectable heterologous nucleotide sequence in the presence of a compound or a member of a library of compounds; and (b) measuring the expression or activity a product encoded by the detectable heterologous nucleotide sequence. In another embodiment, the high throughput screening assay to identify a compound that modulates the replication of an influenza virus comprises: (a) contacting a host cell with a compound or a member of a library of compounds; (b) infecting the host cell with a recombinant influenza virus described herein that expresses a detectable heterologous nucleotide sequence; and (c) measuring the expression or activity a product encoded by the detectable heterologous nucleotide sequence. In a specific embodiment, the recombinant influenza virus is a nine-segmented influenza virus described herein.

In some embodiments, the high throughput screening assays involve: (a) contacting a compound or a member of a library of compounds with a cell before (e.g., 15 minutes, 30 minutes, 1 hour, 2 hours, 4 hours, 6 hours, 12 hours, 24 hours or more before), concurrently and/or subsequent to (e.g., 15 minutes, 30 minutes, 1 hour, 2 hours, 4 hours, 6 hours, 12 hours, 24 hours or more after) infection with a recombinant influenza virus described herein that expresses a detectable heterologous nucleotide sequence; and (b) measuring the expression or activity a product encoded by the detectable heterologous nucleotide sequence. The cells can be infected with different MOIs (e.g., 0.001, 0.005, 0.01, 0.05, 0.1, 0.5, 1, 2.5, or 5) and the effect of compounds can be assessed in the screening assays. The effect of different concentrations of the compounds can also be assessed using in the screening assays. The expression or activity of a product encoded by the detectable heterologous nucleotide sequence can be measured at different times post-infection. For example, the expression or activity of the detectable heterologous nucleotide sequence may be measured 6 hours, 12 hours, 24 hours, 48 hours or 72 hours post-infection. A compound that increases the replication of an influenza virus is identified if the level of expression or activity a product encoded by the detectable heterologous nucleotide sequence is increased in the host cell contacted with the compound relative to the level of expression or activity a product encoded by the detectable heterologous nucleotide sequence in a host cell contacted with a negative control (e.g., an influenza virus that is not a recombinant influenza virus described herein (e.g., a wild-type influenza virus)). In contrast, a compound that decreases the replication of an influenza virus is identified if the level of expression or activity a product encoded by the detectable heterologous nucleotide sequence is decreased in the host cell contacted with the compound relative to the level of expression or activity of a product encoded by the detectable heterologous nucleotide sequence in a host cell contacted with a negative control (e.g., an influenza virus that is not a recombinant influenza virus described herein (e.g., a wild-type influenza virus)). In some embodiments, an embryonated egg or any other substrate that permits the replication of an influenza virus may be used in place of the cells used in the high throughput screening assays described herein.

In a specific embodiment, the host cell used in the high throughput assay for screening for compounds that modulate replication of an influenza virus is a host cell that permits infection with the influenza virus. In some embodiments, the high throughput assay for screening for compounds that modulate replication of an influenza virus uses any substrate that allows the virus to grow to titers that permits the use of such viruses in the screening assays. By way of non-limiting example, substrates useful in the high throughput screening assays described herein include cells (e.g. avian cells, chicken cells (e.g., primary chick embryo cells or chick kidney cells), Vero cells, MDCK cells, human respiratory epithelial cells (e.g., A549 cells), calf kidney cells, mink lung cells, etc.) that are susceptible to infection by the viruses or embryonated eggs (e.g., embryonated chick eggs 6 to 9 days old, 6 to 10 days old, 10 to 12 days, or 10 to 14 days old) or animals (e.g., birds). In one embodiment, the cells used in the high throughput screening assay are biologically relevant to the type of infection.

In a specific embodiment, a product encoded by the detectable heterologous nucleotide sequence measured in the high throughput screening assays described above is an RNA product. In another embodiment, a product encoded by the detectable heterologous nucleotide sequence measured in the high throughput screening assays described above is a protein product. In another embodiment, the activity of a product encoded by the detectable heterologous nucleotide sequence is measured in the high throughput screening assays described above and the product is protein.

Any method known to one of skill in the art can be used measure the expression or activity of a product encoded by the detectable heterologous nucleotide sequence. In one embodiment, the product encoded by the detectable heterologous nucleotide sequence is RNA and a technique known to one of skill in the art, such as RT-PCR or Northern blot analysis, is used to measure the expression of the RNA product. In another embodiment, the product encoded by the detectable heterologous nucleotide sequence is protein and a technique known to one of skill in the art, such as western blot analysis or an ELISA, is used to measure the expression of the protein product. In another embodiment, the product encoded by the detectable heterologous nucleotide sequence is protein and the activity of the protein is measured using a technique known to one of skill in the art.

Any screening assay described herein can be performed individually, e.g., just with the test compound, or with appropriate controls. For example, a parallel assay without the test compound, or other parallel assays without other reaction components (e.g., virus) can be performed. In one embodiment, a parallel screening assay as described above is performed except that a negative control and/or a positive control are used in place of a test compound. In another embodiment, to eliminate cytotoxic compounds that appear as false positives, a counter screen is performed in which uninfected cells are transfected with a nucleic acid construct (e.g., a plasmid) comprising a detectable heterologous nucleotide sequence and the expression or activity of a product encoded by the detectable heterologous nucleotide sequence is measured. Alternatively, it is possible to compare assay results to a reference, e.g., a reference value, e.g., obtained from the literature, a prior assay, and so forth. Appropriate correlations and art known statistical methods can be used to evaluate an assay result.

In some embodiments, the average expression or activity of the product encoded by the detectable heterologous nucleotide sequence when a negative control (e.g., PBS) is contacted with cell is determined and the percent expression or activity of the product for each compound is determined in relation to this internal control. In one embodiment, the average percent expression or activity the product encoded by the detectable heterologous nucleotide sequence is calculated and the compounds are classified as strong or medium inhibitors of virus replication based on a 90% to 100% or 70% to 89% reduction in the expression or activity of the product, respectively. In another embodiment, the compounds are classified as enhancers of viral replication if at least a 2 fold increase in the expression or activity of a product encoded by the detectable heterologous nucleotide sequence above relative to the negative control is obtained.

In another aspect, the antiviral effect of a compound on influenza virus can be assessed in a non-human animal using a recombinant influenza virus described herein. In one embodiment, the antiviral effect of a compound on influenza virus can be assessed by a method comprising: (a) administering (for example, parenterally, subcutaneously, intranasally, or intraperitoneally) to a non-human subject, concurrently, subsequently or prior to administration of a compound, an effective amount of a recombinant influenza virus described herein; b) waiting for a time interval following the administration of the recombinant influenza virus; and d) detecting the recombinant influenza virus in the subject or in a biological specimen from the subject. In a specific embodiment, the recombinant influenza virus is a nine-segmented influenza virus described herein.

5.10 Kits

In one aspect, provided herein is a kit comprising, in one or more containers, one or more nucleic acid sequences described herein. In a specific embodiment, a kit comprises, in one, two or more containers, one, two or more chimeric influenza virus gene segments or the complements thereof. In another embodiment, a kit comprises, in one, two or more containers, one or more nucleic acid sequences encoding one, two or more chimeric influenza virus gene segments or the complements thereof. The kit may further comprise one or more of the following: host cells suitable for rescue of the virus, reagents suitable for transfecting plasmid DNA into a host cell, helper virus, plasmids encoding one or more types of influenza virus gene segments, one or more expression plasmids encoding viral proteins, and/or one or more primers specific for one, two or more chimeric influenza virus gene segments or the complements thereof, or nucleic acid sequences encoding the same.

In certain embodiments, a kit comprises, in one, two or more containers, nucleic acid sequences comprising or encoding a combination of: (i) the following or the complement thereof from one type of influenza virus gene segment: 5' and 3' non-coding regions and either a 3' proximal coding region sequence with any start codon eliminated so that it is not translated, a 5' proximal coding region sequence that is not translated, or both a 3' proximal coding region sequence with any start codon eliminated so that it is not translated and a 5' proximal coding region sequence that is not translated; and (ii) either at least the 3' proximal 20 nucleotides of an open reading frame from a different type of influenza virus gene segment or the complement thereof with one, two three or more mutations, at least the 5' proximal 30 nucleotides of an open reading frame from a different type of influenza virus gene segment or the complement thereof with one, two, three or more mutations, or both the at least 3' proximal 20 nucleotides of an open reading frame and at least the 5' proximal 30 nucleotides of an open reading frame from a different type of influenza virus gene segment or the complement thereof with one, two, three or more mutations. In some embodiments, such nucleic acid sequences may be used as a template to engineer in a nucleotide sequence (e.g., a heterologous nucleotide sequence) which is in frame with the 3' proximal 20 nucleotides and/or the 5' proximal 30 nucleotides of the open reading frame from the different type of influenza virus gene segment. The chimeric influenza virus gene segment or complement thereof, or a nucleic acid encoding the gene segment or complement thereof may contain one, two or more restriction enzyme sites that would enable the incorporation of a nucleotide sequence (e.g., a heterologous nucleotide sequence) in frame with the 3' and/or 5' proximal nucleotides of the open reading frame of the different type of influenza virus gene segment. In certain embodiments, such kits further comprise one or more restriction enzymes that cleave the nucleic acid sequence.

In another aspect, provided herein is a kit comprising one or more containers filled with one or more of the one or more recombinant influenza virus described herein or a composition thereof. In a specific embodiment, provided herein is a pharmaceutical pack or kit comprising, in one or more containers, a composition comprising one or more recombinant influenza viruses described herein. In another aspect, provided herein is a kit comprising, in one or more containers, primers specific for a particular chimeric influenza virus gene segment.

In another aspect, provided herein is a kit comprising one or more containers filled with one or more antibodies generated or identified using a recombinant influenza virus described herein. In one embodiment, a kit comprises an antibody described herein, preferably an isolated antibody, in one or more containers. In a specific embodiment, a kit encompassed herein contains an isolated influenza virus antigen that the antibodies encompassed herein react with as a control. In a specific, a kit provided herein further comprise a control antibody which does not react with an influenza virus antigen that an antibody encompassed herein reacts with. In another specific embodiment, a kit provided herein contains a means for detecting the binding of an antibody to an influenza virus antigen that an antibody encompassed herein reacts with (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate). In specific embodiments, a kit may include a recombinantly produced or chemically synthesized influenza virus antigen. The influenza virus antigen provided in the kit may also be attached to a solid support. In a more specific embodiment the detecting means of the above described kit includes a solid support to which an influenza virus antigen is attached. Such a kit may also include a non-attached reporter-labeled anti-human antibody. In this embodiment, binding of the antibody to the Influenza virus antigen can be detected by binding of the said reporter-labeled antibody.

Optionally associated with such a kit can be a notice in the form prescribed by a governmental agency regulating the manufacture, use or sale of pharmaceuticals or biological products, which notice reflects approval by the agency of manufacture, use or sale for human administration.

6. EXAMPLE 1

This example describes the production of chimeric influenza virus gene segments and the use of those gene segments to produce an influenza virus that is not able to reassort with other influenza viruses to produce replicating reassortant virus.

6.1 Materials & Methods

Cells and Viruses.

293T cells were maintained in Dulbecco's modified Eagle's medium with 10% fetal calf serum. MDCK cells were grown in Eagle's minimal essential medium with 10% fetal calf serum. Viruses were grown in 10-day-old specific-pathogen-free chicken embryos (Charles River Laboratories, SPAFAS, Preston, Conn.).

Plasmid Construction.

Figures 25A, 25B:
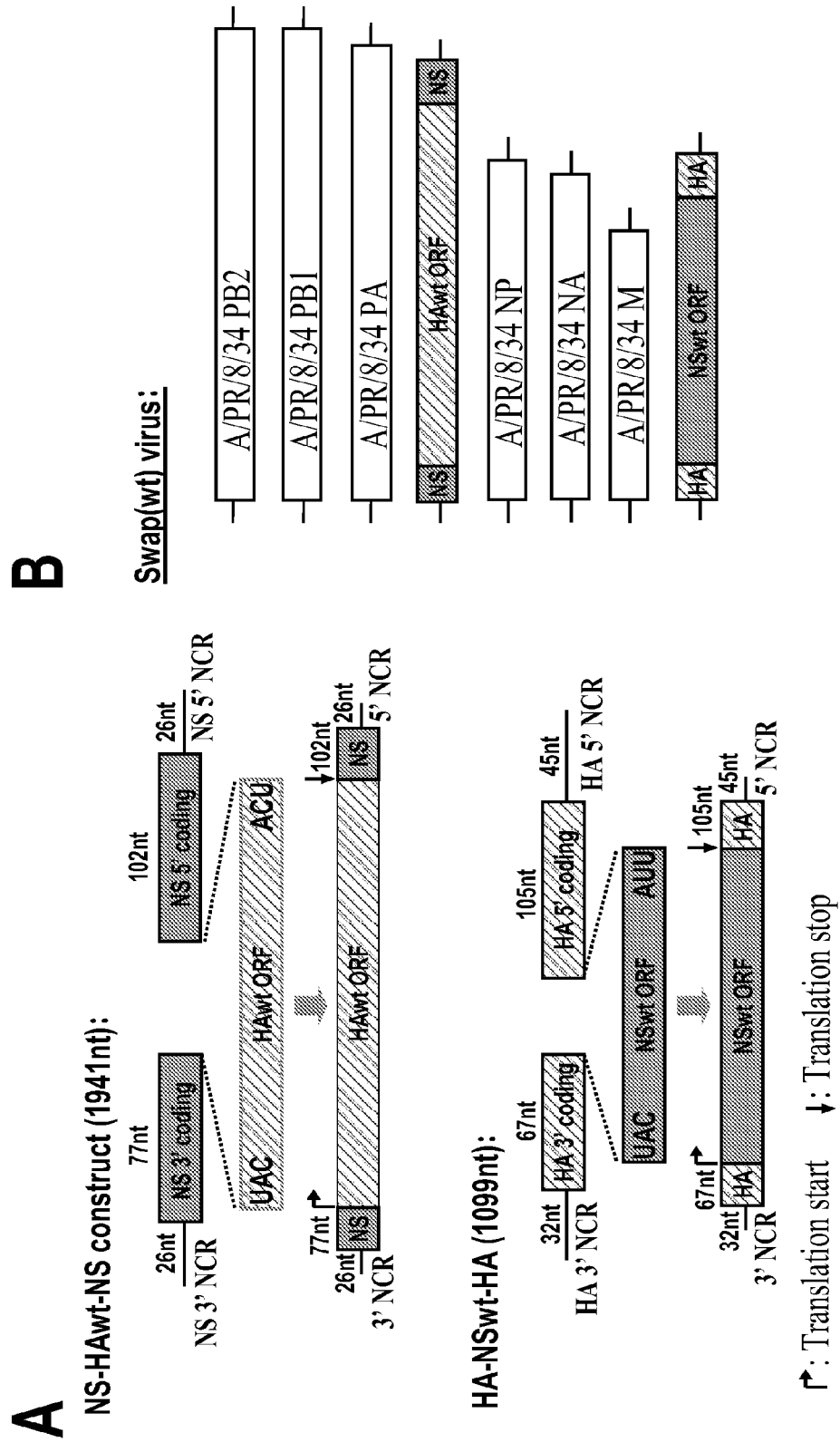

(i) Generation of NS-HAwt-NS construct (FIG. 25A). The 1.2 kb Kpn I fragment from the previously constructed pDZ-NS plasmid (Quinlivan M, et al. (2005) Attenuation of equine influenza viruses through truncations of the NS1 protein. *J Virol* 79:8431-8439) was transferred to the Kpn I site of pUC18 vector and subjected to site-directed mutagenesis to mutate two ATGs (A27T, A76T), one splice site (G57C), and to generate one Nhe I site (A104G, G109C) and one Xho I site (G759C, A760G). The 1.2 kb NS Kpn I fragment was then transferred back to the pDZ vector (Quinlivan M, et al. (2005) Attenuation of equine influenza viruses through truncations of the NS1 protein. *J Virol* 79:8431-8439) (in which the Nhe I and Xho I sites have been removed), resulting in a plasmid pDZ-NS-ps. The ORF of the A/PR/8/34 HA protein, which is 1,698 bp long, was amplified from an ambisense pDZ-HA plasmid (Quinlivan M, et al. (2005) Attenuation of equine influenza viruses through truncations of the NS1 protein. *J Virol* 79:8431-8439) and subjected to mutagenesis to mutate an internal Xho I site (C143G). Two restriction sites, Nhe I and Xho I, were introduced to flank the HA ORF, which was then used to replace the Nhe I and Xho I fragment of the NS ORF of pDZ-NS-ps plasmid to form the NS-HAwt-NS construct (FIG. 25A). (ii) Generation of HA-NSwt-HA construct (FIG. 25A). Using the same strategy, three ATGs were mutated on the 3' HA packaging signal (A33T, A79T and A92T). The ORF of the A/PR/8/34 NS proteins (NS1, NS2), which is 838 bp long, was amplified and ligated to the HA packaging sequences in a pDZ vector to form the HA-NSwt-HA construct (FIG. 25A). (iii) Generation of NS-HAmut-NS construct (FIG. 26A). The method was the same as described for NS-HAwt-NS (FIG. 25A) except that the primers used to amplify the HA ORF carried synonymous mutations. The forward primer is: 5'-ca gctagc atg aaA gcG aaT TtG TtA gtT TtA CtG TCC gcG TtG gcG gcC gcG gaC gca gac aca ata tgt ata ggc tac c-3' (SEQ ID NO:114); and the two reverse primers are 5'-cca Aaa GGA Aat Cgc Tcc TaA ACT Aac TaG CaA Tac TaA GCT GGA Agc gac agt tga gta gat cgc c-3'(SEQ ID NO:115) and 5'-gt ctcgag tca Aat Aca Aat CcG Aca Ttg TaG GCT Ccc Gtt GCT Gca cat cca Aaa GGA Aat Cgc Tcc TaA AC-3' (SEQ ID NO:116). (iv) Generation of the HA-NSmut-HA construct (FIG. 26A). The method was also the same as described for HA-NSwt-HA (FIG. 25A) except that synonymous mutations were introduced into the NS ORF. The forward primer is: 5'-ca gctagc atg gaC ccG aaT acC gtA AGT TCT ttt cag gta gaC tgc ttt ctt tgg cat gtc c-3' (SEQ ID NO:117); the reverse primer is: 5'-gt ctcgag tta Gat CaA Ttg Gaa GCT Aaa Ggt CcG Gat Ttc Ctg ctc cac ttc aag c-3' (SEQ ID NO:118). (The capitalized letters in these primer sequences designate mutated nucleotides.)

Reverse Genetics for Recombinant Viruses.

The method for generating recombinant influenza viruses was slightly modified from previous protocols (Gao Q, Brydon E W, Palese P (2008) A seven-segmented influenza A virus expressing the influenza C virus glycoprotein HEF. *J Virol* 82:6419-6426, Quinlivan M, et al. (2005) Attenuation of equine influenza viruses through truncations of the NS1 protein. J Virol 79:8431-8439; Fodor E, et al. (1999) Rescue of influenza A virus from recombinant DNA. *J Virol* 73:9679-9682). For the generation of the Swap(wt) and Swap(mut) viruses (FIGS. 25B & 26B), 293T cells were transfected with six A/PR/8/34 plasmids (pDZ-PB2, PB1, PA, NP, NA, M), and the two chimeric HA and NS constructs [NS-HAwt-NS and HA-NSwt-HA, or NS-HAmut-NS and HA-NSmut-HA] (FIGS. 25A & 26A). For the generation of the Reassortant (NS) virus (FIG. 25C), 293T cells were transfected with seven A/PR/8/34 plasmids (pDZ-PB2, PB1, PA, HA, NP, NA, M), and the HA-NSwt-HA construct. Seven A/PR/8/34 plasmids (pDZ-PB2, PB1, PA, NP, NA, M, NS), and the NS-HAwt-NS construct were used to rescue the Reassortant(HA) virus (FIG. 25D).

Acrylamide Gel Electrophoresis of Purified vRNA.

The viruses were grown in 10-day-old eggs at 37° C. and were subsequently processed by using a previously reported method (Gao Q, Brydon E W, Palese P (2008) A seven-segmented influenza A virus expressing the influenza C virus glycoprotein HEF. *J Virol* 82:6419-6426). Briefly, virus was purified and RNA was isolated and run on a 2.8% denaturing polyacrylamide gel which was then stained with a silver staining kit (Invitrogen).

Immunostaining of Plaques.

Previous methods were followed (Gao Q, Brydon E W, Palese P (2008) A seven-segmented influenza A virus expressing the influenza C virus glycoprotein HEF. *J Virol* 82:6419-6426; Matrosovich M, Matrosovich T, Garten W, Klenk H D (2006) New low-viscosity overlay medium for viral plaque assays. *Virol J* 3:63). A rabbit anti-A/PR/8/34 polyclonal antibody (1:2,000 dilution) was used for plaque visualization.

Viral Growth Kinetics.

10-day-old embryonated chicken eggs were inoculated with influenza viruses (100 PFU/egg) and incubated at 37° C. At 24, 48 and 72 hr post inoculation, the allantoic fluids were harvested and the titers of the viruses were determined by plaque assay or immunostaining of the plaques in MDCK cells. At each time point, three eggs were analyzed for each virus.

6.2 Results

A chimeric influenza A virus segment containing the ORF of the HA gene and the packaging signals from the NS gene, and a chimeric influenza A virus segment containing the ORF of the NS gene and the packaging sequences of the HA gene were generated and used to construct a recombinant influenza virus. To do this, the wild type HA ORF was amplified by polymerase chain reaction (PCR), and ligated to the flanking NS packaging sequences which include: the 3' and 5' NCRs, the 3' seventy seven nt, and the 5' one hundred and two nt of the NS ORF. This generated the chimeric NS-HAwt-NS construct of 1941 nt in length (FIG. 25A). The two translation initiation codons and one splice site in the 77 nt of the NS 3' ORF packaging signal were mutated in order to allow the HA to translate from its own start codon (FIG. 25A). Following the same strategy, a 1099 nt long HA-NSwt-HA construct was also made (FIG. 25A). In this construct, the NS ORF—which encodes both NS1 and NS2 proteins—was flanked by the 3' and 5' NCRs of the HA, the 3' sixty seven nt, and the 5' one hundred and five nt of the HA ORF. The three start codons located in the 67 nt of the 3' ORF packaging region of the HA were also mutated. Since the A/PR/8/34 virus was used as a backbone and since the currently known HA and NS packaging signals were all identified in the A/WSN/33 virus (Fujii K, et al. (2005) Importance of both the coding and the segment-specific noncoding regions of the influenza A virus NS segment for its efficient incorporation into virions. J Virol 79:3766-3774; Watanabe T, Watanabe S, Noda T, Fujii Y, Kawaoka Y (2003) Exploitation of nucleic acid packaging signals to generate a novel influenza virus-based vector stably expressing two foreign genes. *J Virol* 77:10575-10583), the flanking packaging sequences used in these experiments were made slightly longer than those identified in A/WSN/33 in order to assure proper packaging.

Using previously established methods, the Swap(wt) virus was successfully rescued and was shown to be stable for multiple passages in embryonated chicken eggs (FIG. 25B). This virus contains six A/PR/8/34 wild type segments (PB2, PB1, PA, NP, NA, and M) and the two chimeric segments: NS-HAwt-NS and HA-NSwt-HA (FIG. 25B). The Swap(wt) virus grew well in eggs, and titers could reach more than $10^8$ plaque forming units per ml (PFU/ml) one day post inoculation (FIG. 25F). Nevertheless, it was still slightly attenuated in growth compared to the recombinant A/PR/8/34 virus. In Madin-Darby canine kidney (MDCK) cells, the plaques formed by the Swap(wt) virus were slightly smaller than those of A/PR/8/34 virus (FIG. 25E), while in eggs, the titers of the Swap(wt) virus were about 10-fold lower than those of A/PR/8/34 virus (FIG. 25F).

In order to determine whether the HA-NSwt-HA and NS-HAwt-NS segments could each freely reassort with wild type virus genes, viruses were constructed which carried just one of these chimeric genes. Surprisingly, two recombinant viruses were rescued: Reassortant(NS) and Reassortant(HA)

Figure 25C:
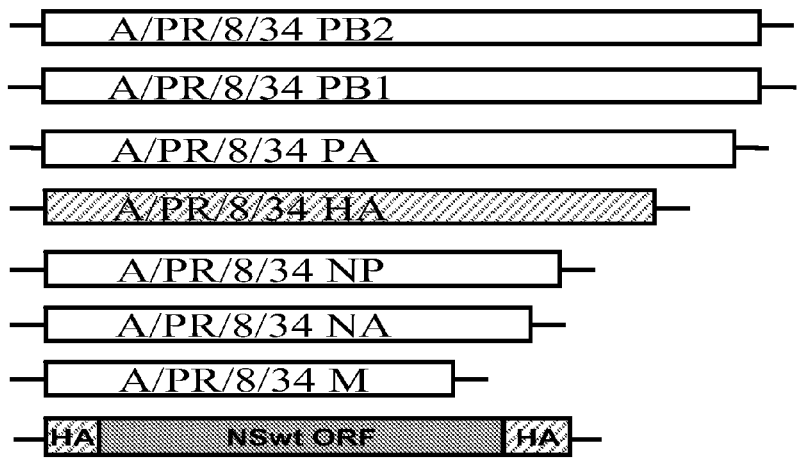
Figure 25D:
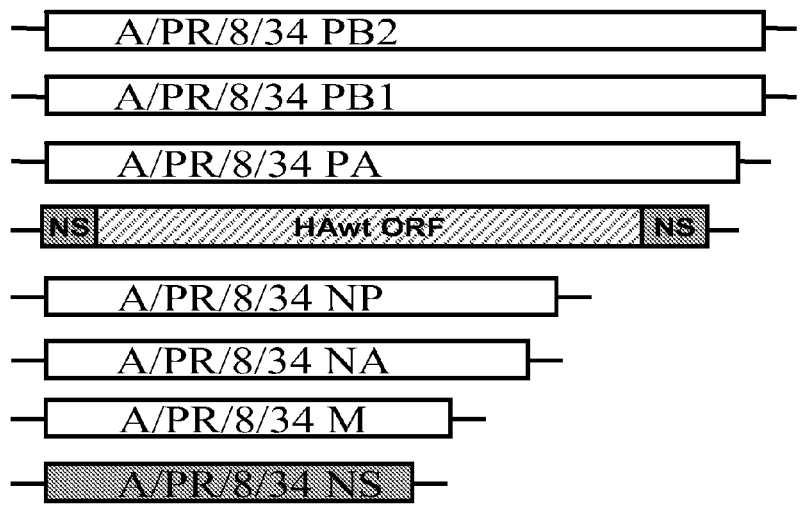
Figure 25E:
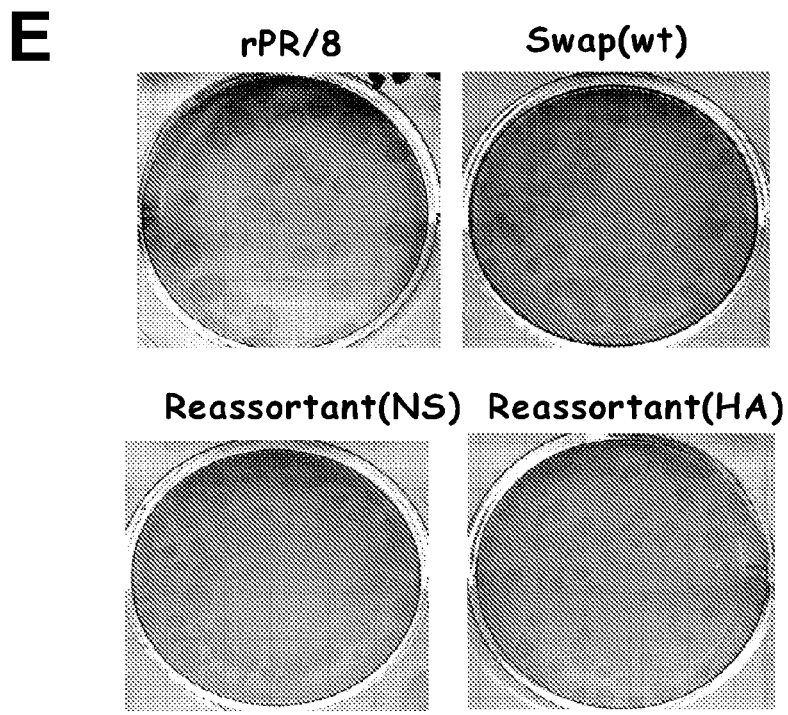
Figure 25F:
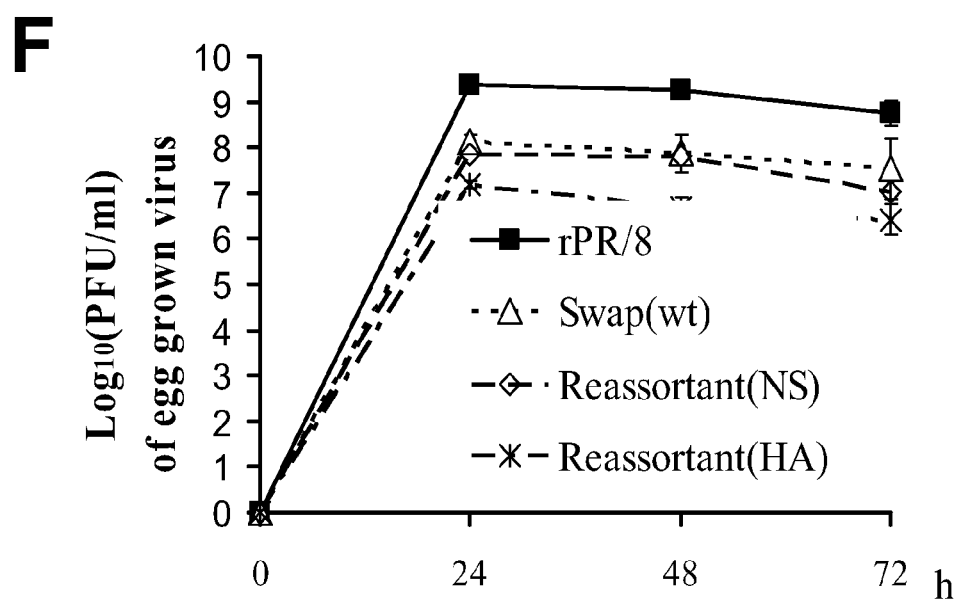

(FIGS. 25C & 25D). The Reassortant(NS) virus contains seven A/PR/8/34 segments (PB2, PB1, PA, HA, NP, NA, and M) and one chimeric HA-NSwt-HA segment (FIG. 25C); the Reassortant(HA) virus has seven A/PR/8/34 vRNAs (PB2, PB1, PA, NP, NA, M and NS) and one chimeric NS-HAwt-NS segment (FIG. 25D). Interestingly, the Reassortant(NS) virus exhibited efficient growth (FIG. 25F). The plaque sizes in MDCK cells and the titers in eggs were both similar to those of the Swap(wt) virus (FIGS. 25E & 25F). The Reassortant (HA) virus was more attenuated, with smaller plaques in MDCK cells and lower titers in eggs (FIGS. 25E & 25F). The rescue of both viruses indicated that each of the chimeric segments of the Swap(wt) virus could independently reassort to form a reassortant virus.

The ability of the NS-HAwt-NS or HA-NSwt-HA segment to independently form a reassortant virus could be due to the fact that two sets of segment-specific packaging signals co-exist on the same vRNA (FIG. 25). The NS-HAwt-NS segment still maintains its original HA-specific packaging sequences in its HA ORF region in addition to the flanking NS packaging signals (FIG. 25A). The same is true for the HA-NSwt-HA segment. The original packaging signals may still be functional (FIG. 25A). Considering this possibility, serial synonymous mutations were introduced into the 3' and 5' ends of the ORFs in these chimeric constructs in order to force utilization of the flanking packaging signals only (FIG. 26A). Previous studies have showed that the serial synonymous mutations in the coding region packaging sequences of the HA and NS segments indeed diminished the vRNA packaging efficiency (Fujii K, et al. (2005) Importance of both the coding and the segment-specific noncoding regions of the influenza A virus NS segment for its efficient incorporation into virions. *J Virol* 79:3766-3774; Marsh G A, Hatami R, Palese P (2007) Specific residues of the influenza A virus hemagglutinin viral RNA are important for efficient packaging into budding virions. *J Virol* 81:9727-9736). In this study, 22 and 45 nt mutations were introduced to the 3' and 5' ends of the HA ORF, respectively, forming a new construct NS-HAmut-NS (FIG. 26A, and materials and methods); a similar method was applied to the HA-NSwt-HA and 12 and 15 nt mutations were introduced to construct the HA-NSmut-HA (FIG. 26A, and materials and methods).

Figure 26C:
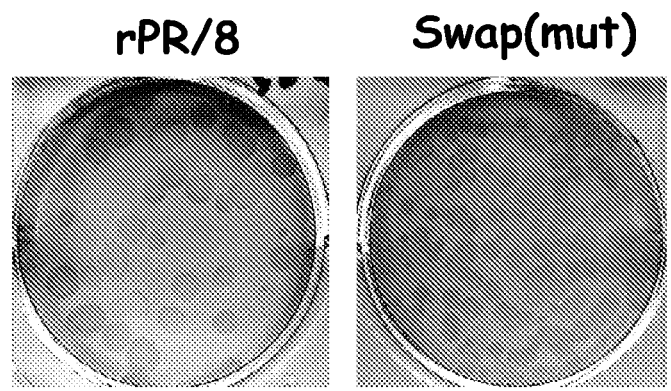
Figure 26D:
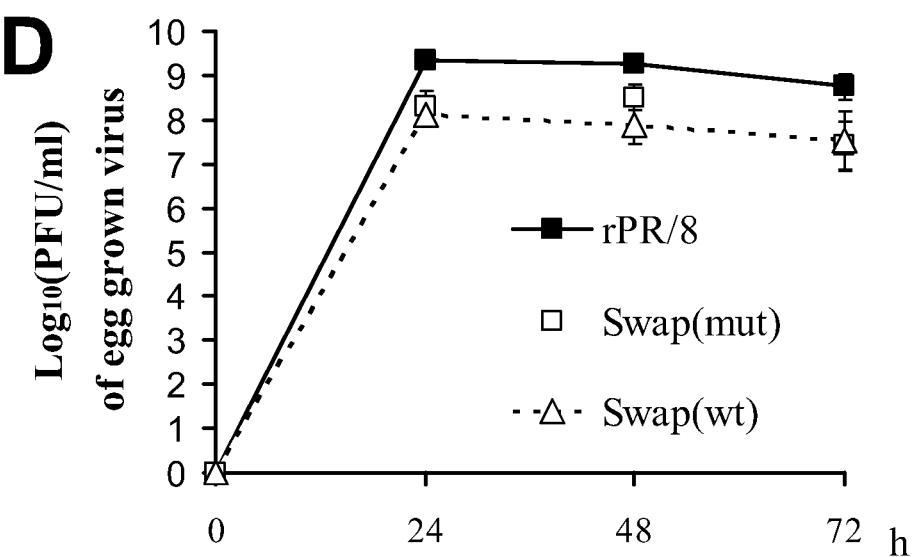

By using the same procedure as that in FIG. 25B, the Swap(mut) virus (FIG. 26B), which contains six A/PR/8/34 segments (PB2, PB1, PA, NP, NA, and M) and the two chimeric segments NS-HAmut-NS and HA-NSmut-HA (FIG. 26B), was successfully rescued. Right after the rescue, the titer of the Swap(mut) virus was low. After one passage in eggs, the virus grew to higher titers and maintained the same yield over multiple passages. The plaque sizes of the Swap (mut) virus were similar to those of the Swap(wt) virus (FIGS. 25E & 26C). However, in eggs, the Swap(mut) virus grew slightly better than Swap(wt), although it was still slightly attenuated compared to the A/PR/8/34 virus (FIG. 26D). It should be noted that eight and two nucleotide conversions were identified on the 3' ends of the NS-HAmut-NS and HA-NSmut-HA vRNAs of the passaged virus, respectively (see FIG. 26B legend).

Figure 26E:
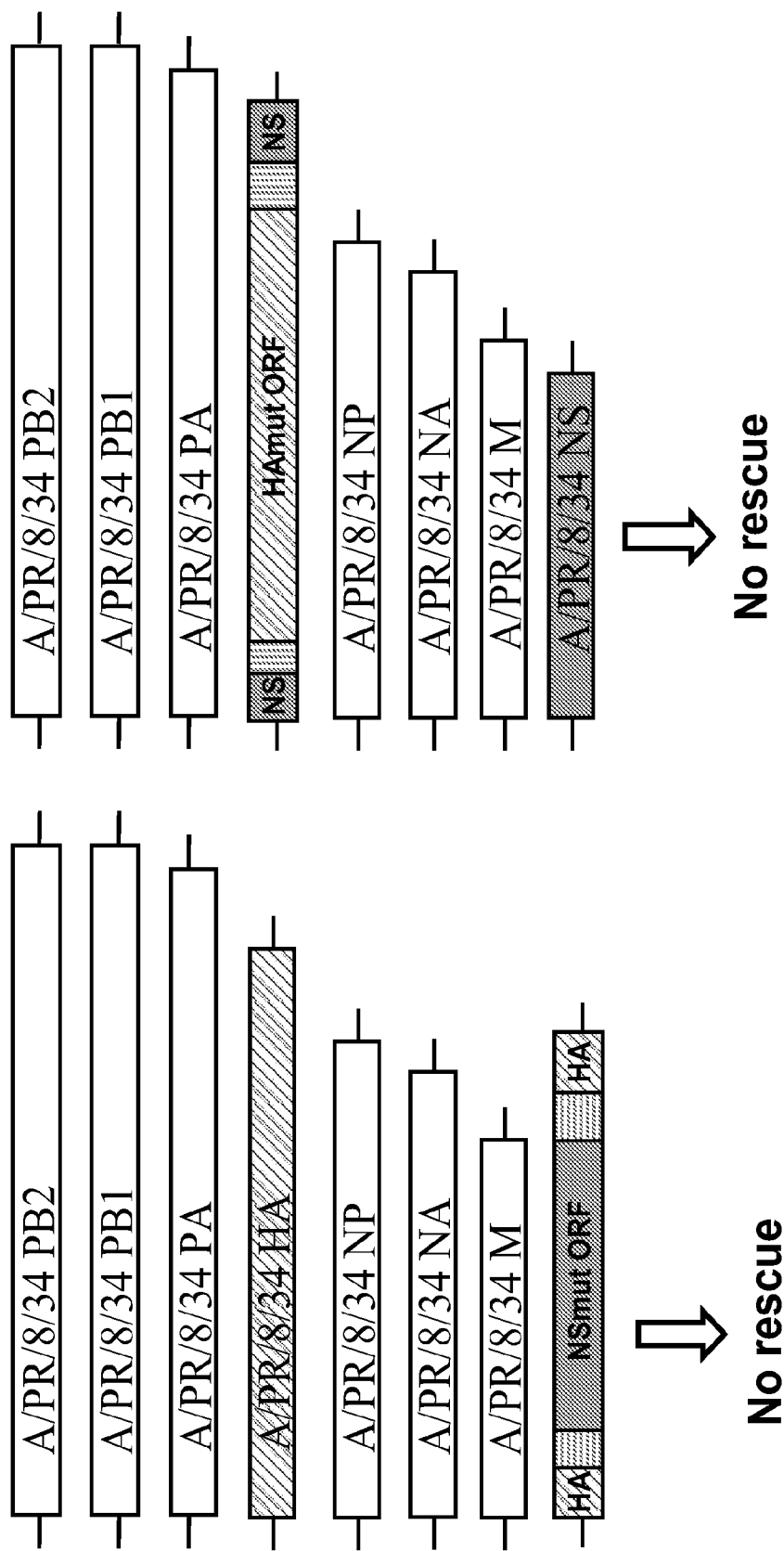

In order to determine whether the chimeric genes in FIG. 26A are able to independently reassort with wild type ones, the rescue of two viruses was attempted (shown in FIG. 26E). The genetic compositions of these two viruses are similar to those of the Reassortant(NS) (FIG. 25C) and the Reassortant (HA) (FIG. 25D) viruses, except that now the HA-NSmut-HA and NS-HAmut-NS constructs (FIG. 26A) have been substituted for their counterparts (see FIG. 26E). If each chimeric segment still maintains its ability to reassort freely, then the two viruses in FIG. 26E should have been rescued. However, while the Reassortant(NS) (FIG. 25C) and Reassortant(HA) viruses (FIG. 1D) were easily rescued, neither of the viruses shown in FIG. 26E could be obtained. The failure of the rescue suggests that, unlike HA-NSwt-HA and NS-HAwt-NS, the HA-NSmut-HA and NS-HAmut-NS segments cannot freely reassort with wild type genes.

Figure 27:
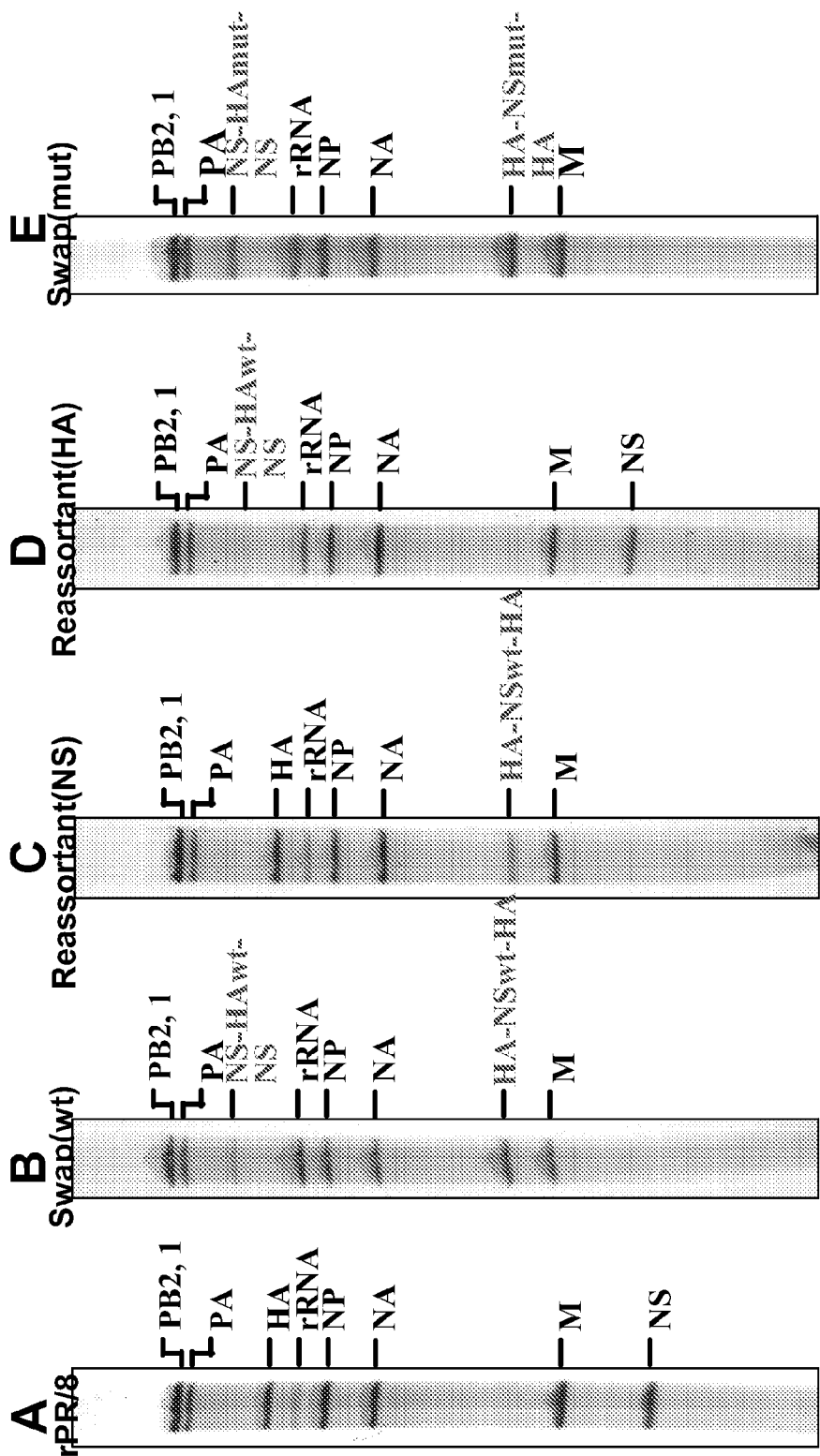

Five recombinant viruses [rA/PR/8/34 (FIG. 27A), Swap (wt) (FIG. 27B), Reassortant(NS) (FIG. 27C), Reassortant (HA) (FIG. 27D) and Swap(mut) (FIG. 27E)] were grown in eggs and concentrated through a 30% sucrose cushion. RNA was isolated from purified virus and resolved on a 2.8% acrylamide gel to visualize the virus genome composition by silver staining. The NS-HAwt-NS segment of the Swap(wt) virus was inefficiently packaged while the other chimeric segment HA-NSwt-HA has better packaging efficiency (FIG. 27B). For the two reasssortant viruses [Reassortant(NS) and Reassortant(HA)], neither chimeric segment [HA-NSwt-HA in FIG. 27C and NS-HAwt-NS in FIG. 27D] was efficiently incorporated. The packaging efficiency of the NS-HAwt-NS segment of the Reassortant(HA) virus was very low (FIG. 27D), which might explain the attenuation observed in both MDCK cells and eggs (FIGS. 25E & 25F). The two chimeric segments of the Swap(mut) virus were efficiently incorporated compared to the other segments (FIG. 27E). The NS-HAmut-NS segment of the Swap(mut) virus (FIG. 27E) was incorporated more efficiently than the NS-HAwt-NS segment of the Swap(wt) virus (FIG. 27B), suggesting that disruption of the original packaging signals of the HA ORF of the chimeric HA segment is critical to achieve efficient packaging. There was no significant difference in the levels of incorporation between HA-NSwt-HA and HA-NSmut-HA segments and both were packaged efficiently (FIGS. 27B & 27E).

Figure 28A:
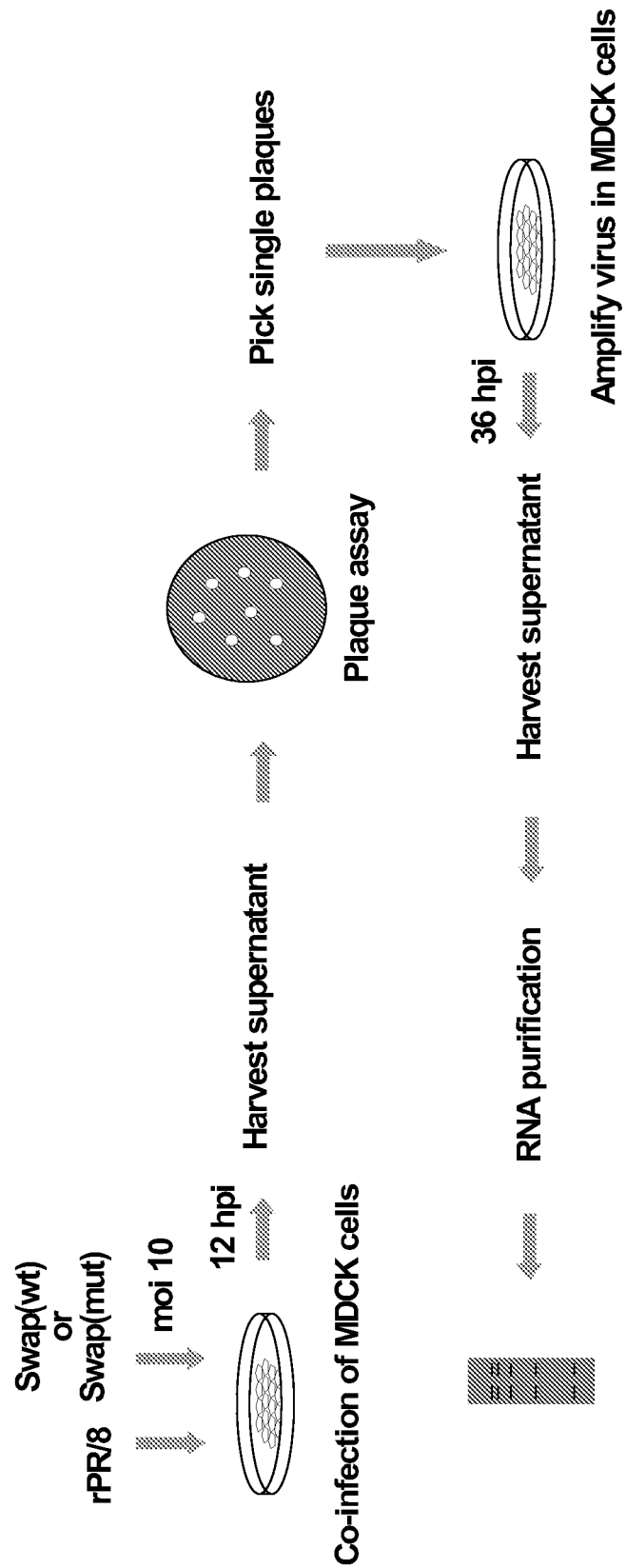
Figure 28D:
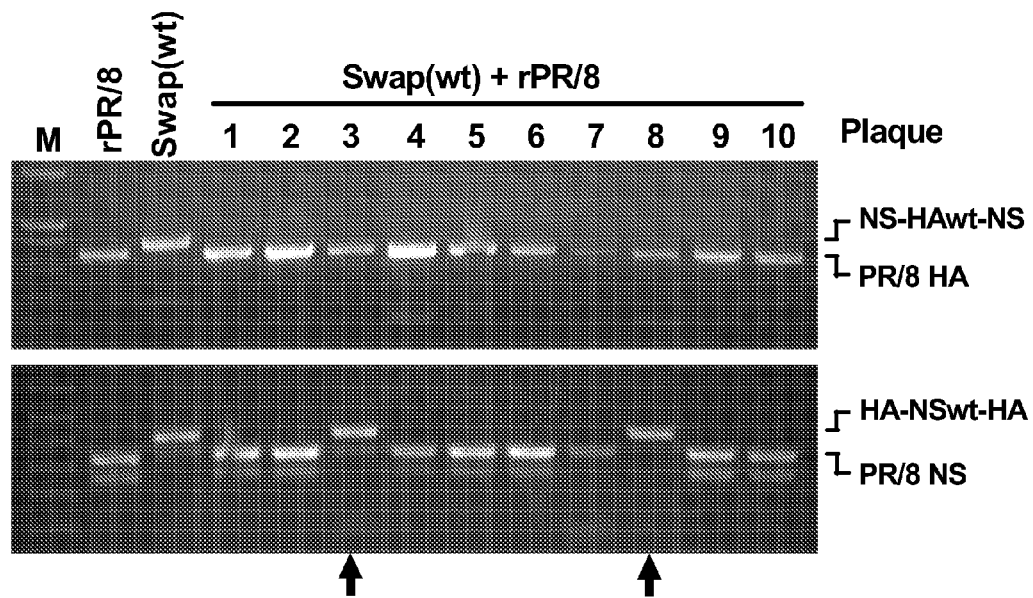
Figure 28E:
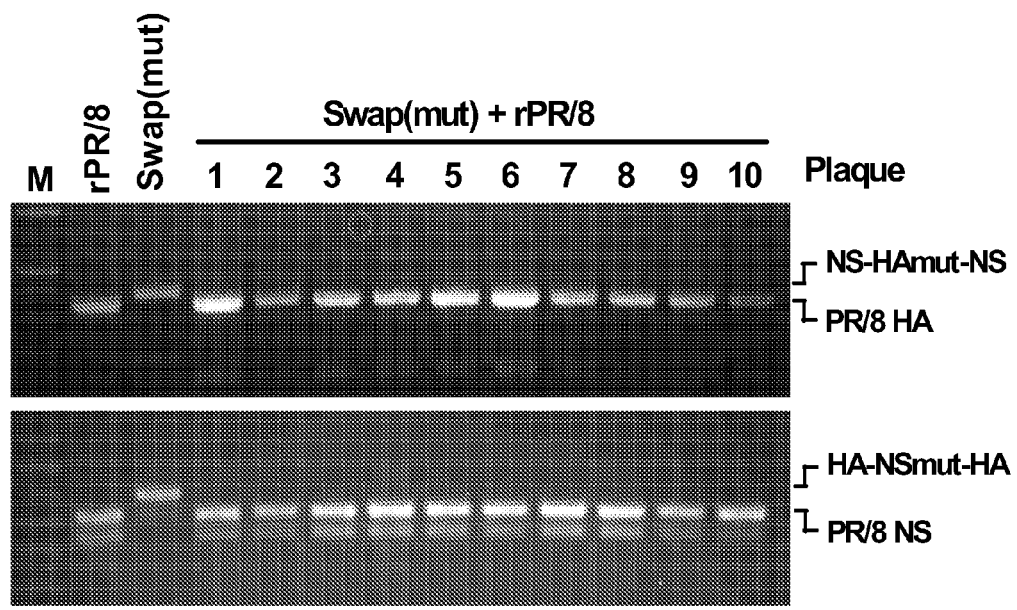

Although the rescue of the two viruses in FIGS. 25C and 25D, but not the two hypothetical viruses in FIG. 26E, did indicate which chimeric segment can freely form reassortant virus with wild type segments, these experiments per se did not directly assay reassortment. In order to determine whether the chimeric segments can freely reassort in tissue culture, MDCK cells were co-infected with the Swap(wt) [or Swap (mut)] virus and rA/PR/8/34 virus at an moi of 10 for each one (FIG. 10A). Single plaques were isolated and subsequently amplified in MDCK cells. RNA was purified from amplified virus and RT-PCR was done to detect the HA and NS segments (FIG. 28A). An 824 base pair (bp) product was observed for both the NS-HAwt-NS and NS-HAmut-NS segments, while for the rA/PR/8/34 HA, a 747 bp band was obtained (FIGS. 28B, 28D & 28E). The PCR products for chimeric and wild type NS segments, on the other hand, were 405 and 326 bp long, respectively (FIGS. 28C, 28D & 28E). For the Swap(wt) and rA/PR/8/34 co-infection experiment, 24 plaques were characterized, and two of them (plaques 3 and 8, indicated by arrows) showed reassortment of the HA-NSwt-HA segment with wild type virus (FIG. 28D). The genetic makeup of these two plaques is the same as the Reassortant(NS) virus (FIG. 25C). Reassortment of the NS-HAwt-NS segment was not observed, possibly due to its lower packaging efficiency (FIG. 27D). For the Swap(mut) and rA/PR/8/34 co-infection experiment, 48 plaques were picked and they all contained wild type HA and NS genes, indicating the inability of NS-HAmut-NS or HA-NSmut-HA to reassort freely.

6.3 Discussion

Interestingly, for the two chimeric constructs [NS-HAwt-NS and HA-NSwt-HA (FIG. 25A)], each contained two sets of segment specific packaging sequences: the NS-HAwt-NS contained the NS-specific NCRs and ORF packaging regions in addition to the ORF packaging regions of the HA gene; the HA-NSwt-HA contained the HA-specific NCRs and ORF packaging regions in addition to the ORF packaging regions of the NS gene (FIG. 25A). The efficient growth of the Swap (wt) virus in both MDCK cells and eggs indicates that two sets of signals can co-exist on one vRNA (FIGS. 25E & 25F). It is unclear, however, which set plays the major role during the genome recruitment process.

The levels of the NS-HAwt-NS RNA in the Swap(wt) (FIG. 27B) and Reassortant(HA) (FIG. 27D) viruses were significantly lower than those of the other segments. This suggests that two sets of signals may interfere with each other during the influenza RNA packaging process if they co-exist on one segment. This also suggests the incompatibility of two sets of packaging signals on one segment. The successful rescue of the two reassortant viruses [Reassortant (NS) (FIG. 25C) & Reassortant (HA) (FIG. 25D)] demonstrates that one virus can incorporate the same packaging signals twice. For example, the Reassortant(NS) virus contains two copies of HA packaging sequences derived from both the wild type HA segment and the HA-NSwt-HA chimeric segment (FIG. 25C); the Reassortant(HA) virus carries two copies of NS packaging signals derived from both the wild type NS segment and the NS-HAwt-NS chimeric segment (FIG. 25D). This phenomenon agrees with a previous finding that a nine-segmented influenza virus can incorporate two NS segments (Enami M, Sharma G, Benham C, Palese P (1991) An influenza virus containing nine different RNA segments, *Virology* 185:291-298).

The data presented herein show that, by simply flanking the ORF with packaging sequences from another segment, inhibition of reassortment cannot be achieved. It was possible to rescue viruses containing a single chimeric gene [the HA-NSwt-HA in the Reassortant(NS) virus (FIG. 25C), and the NS-HAwt-NS in the Reassortant(HA) virus (FIG. 25D)], and to identify in a reassortment experiment, viruses with a chimeric HA-NSwt-HA segment (FIG. 28D). In the reassortment experiment, viruses with the NS-HAwt-NS segment or the Swap(wt) genotype were not isolated. This can be explained by the relatively low number of plaques analyzed. Considering the possibility that the ORF terminal packaging signals in the chimeric segments might still be functional, serial silent mutations were introduced into these signals and subsequently, each segment [NS-HAmut-NS or HA-NSmut-HA] lost its ability to freely reassort (FIGS. 26 & 28). Without being bound by any theory, the remaining flanking regions of these two chimeric segments become the main signals for packaging and as a result, the HA is recognized as an NS gene and the NS is recognized as an HA gene. Single reassortants with the NS-HAmut-NS or HA-NSmut-HA segment could not be rescued because such viruses would lack an HA or NS packaging signal. Also, in the tissue culture reassortment experiment, no single reassortant was isolated. However, a limitation of the experimental setup holds true for the reassortment between the Swap(mut) and rA/PR/8/34 viruses. Only 48 plaques were isolated and thus one cannot exclude the possibility that a virus with a single rewired segment could be formed. Nevertheless, the data suggest that rewiring of the packaging signals results in a deficiency for reassortment. Only viruses which contain a full complement of all eight packaging signals will grow to high yields. In the case of rewiring one segment by eliminating the original packaging signal, a virus will lose viability which can be regained only by rewiring a second segment to provide the missing packaging sequences. Thus, a virus with an HA gene with the NS packaging identity must also have an NS gene with the HA packaging identity.

Thus, this study offers a method for rewiring the influenza virus RNAs to prevent reassortment, which can be used for future live influenza vaccine constructions.

7. EXAMPLE 2

This example describes the production of recombinant influenza viruses using reverse genetics.

Three recombinant A/PR/8/34 viruses with 6 or 7 rewired RNA segments were successfully generated (FIGS. 34-36). Each of the chimeric segments that carried packaging signals from a different segment either lost or significantly decreased its ability to form reassortant virus with wild type RNAs.

To generate the chimeric constructs used to rescue the recombinant viruses shown in FIGS. 34-36, two sets of plasmids were used: one set of 8 plasmids carried the segment-specific packaging sequences derived from the 8 RNA segments of the influenza A/PR/8/34 virus (see FIGS. 1-8). Importantly, the ATGs located on each 3' end-proximal ORF region packaging signal and the 5' splice site on the M and NS segment-derived packaging sequences were all mutated to allow for correct initiation of downstream ORFs (see FIGS. 1-8); the second set of 8 plasmids carried all 8 ORFs of the influenza A/PR/8/34 virus segments. For each ORF, serial silent mutations were introduced to both the 3' and 5' ends of the ORFs to inactivate the ORF region packaging signals (see FIGS. 9-16). All the 8 ORFs that carried silent mutations at the two ends were flanked by one Nhe I and one Xho I for ligation to the constructs carrying segment-specific packaging sequences. In addition, the pre-existing Nhe I or Xho I sites located on some ORF regions were all mutated by site-directed mutagenesis.

The method for generating recombinant influenza viruses was modified from that described in Example 1 and in Gao and Palese, 2009, PNAS106:15891. For the generation of the recombinant virus in FIG. 35, 293T cells were transfected with 6 chimeric plasmids (NA-PB2mut-NA, PB2-PB1mut-PB2, PB1-PAmut-PB1, M-NPmut-M, PA-NAmut-PA, NP-Mmut-NP), and 2 plasmids carrying the wild type A/PR/8/34 HA and NS segments. 24 hours post transfection, the cells were harvested and inoculated into 10-day-old specific-pathogen-free chicken embryos (Charles River Laboratories, SPAFAS, Preston, Conn.). Three days later, the allantoic fluids were harvested and an HA assay was used to determine the existence of rescued virus. The other two chimeric viruses shown in FIGS. 36 and 37 were generated by using the same method. The virus in FIG. 36 contained 6 chimeric segments (NA-PB2mut-NA, PB2-PB1mut-PB2, PB1-PAmut-PB1, NS-HAmut-NS, PA-NAmut-PA, HA-NSmut-HA), and 2 wild type A/PR/8/34 NP and M segments. The virus in FIG. 37 contained 7 chimeric segments (NA-PB2mut-NA, PB2-PB1mut-PB2, PB1-PAmut-PB1, NP-HAmut-NP, NS-NPmut-NS, PA-NAmut-PA, HA-NSmut-HA), and 1 wild type A/PR/8/34 M segments. All these three chimeric viruses grew well, with titers of >$10^8$ pfu/ml in embryonated chicken eggs.

8. EXAMPLE 3

This example describes the production of nine-segmented influenza viruses based on the manipulation of the segment-specific packaging signals.

8.1 Materials & Methods

Cells and Viruses.

293T cells were maintained in Dulbecco's modified Eagle's medium with 10% fetal calf serum (FCS). MDCK cells were grown in Eagle's minimal essential medium with 10% FCS. Viruses were grown in 10-day-old specific-pathogen-free chicken embryos at 37° C. (Charles River Laboratories, SPAFAS).

Plasmid Construction.

Figure 29A:
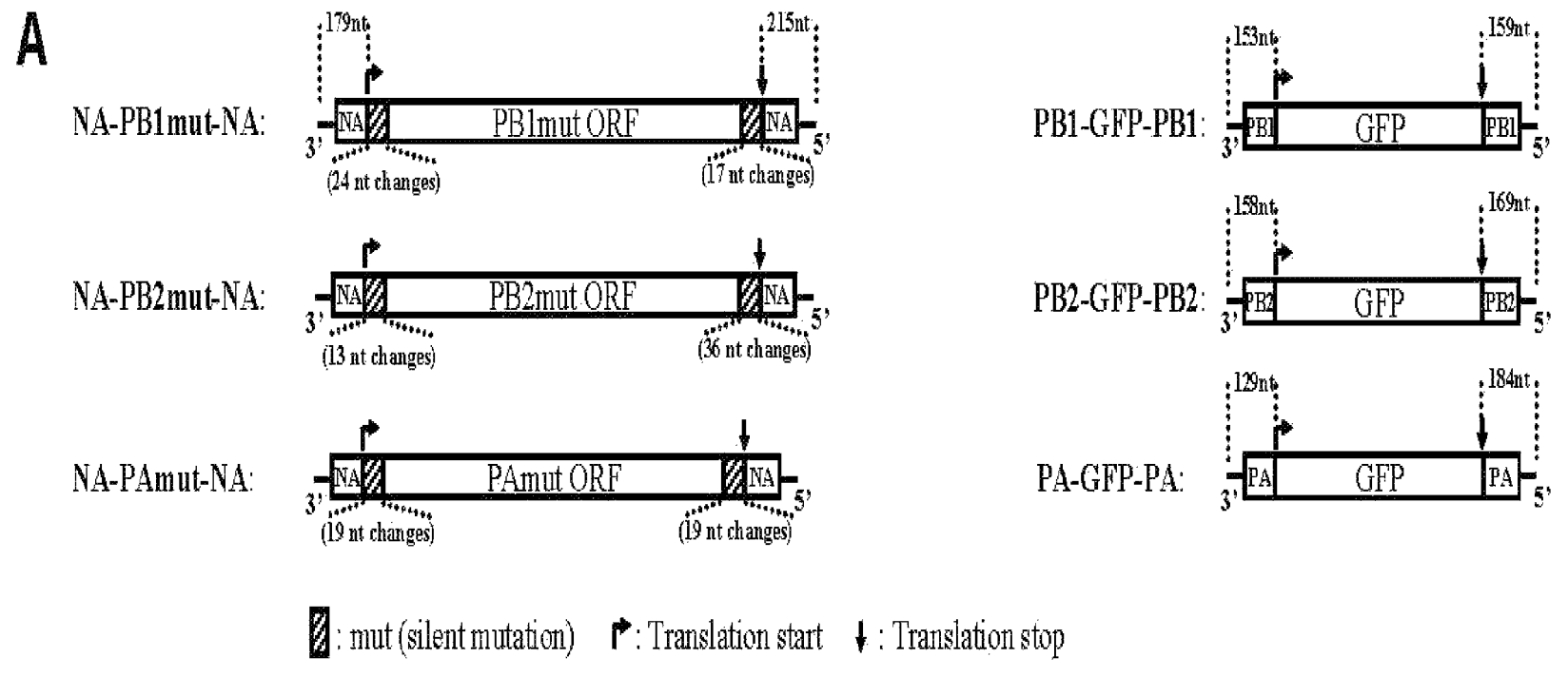
Figures 30A, 30B, 30C, 30D:
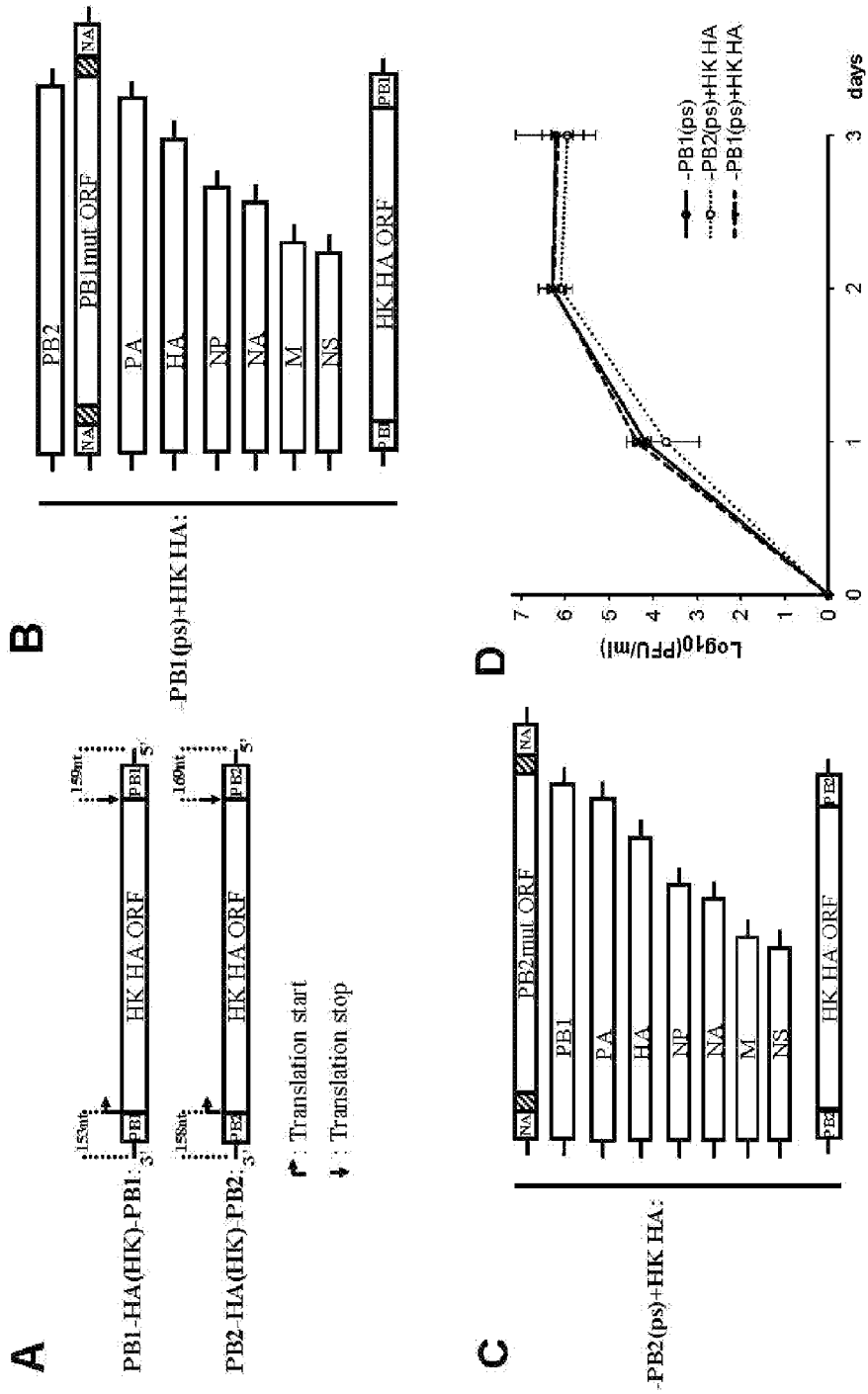
Figures 30E, 30F:
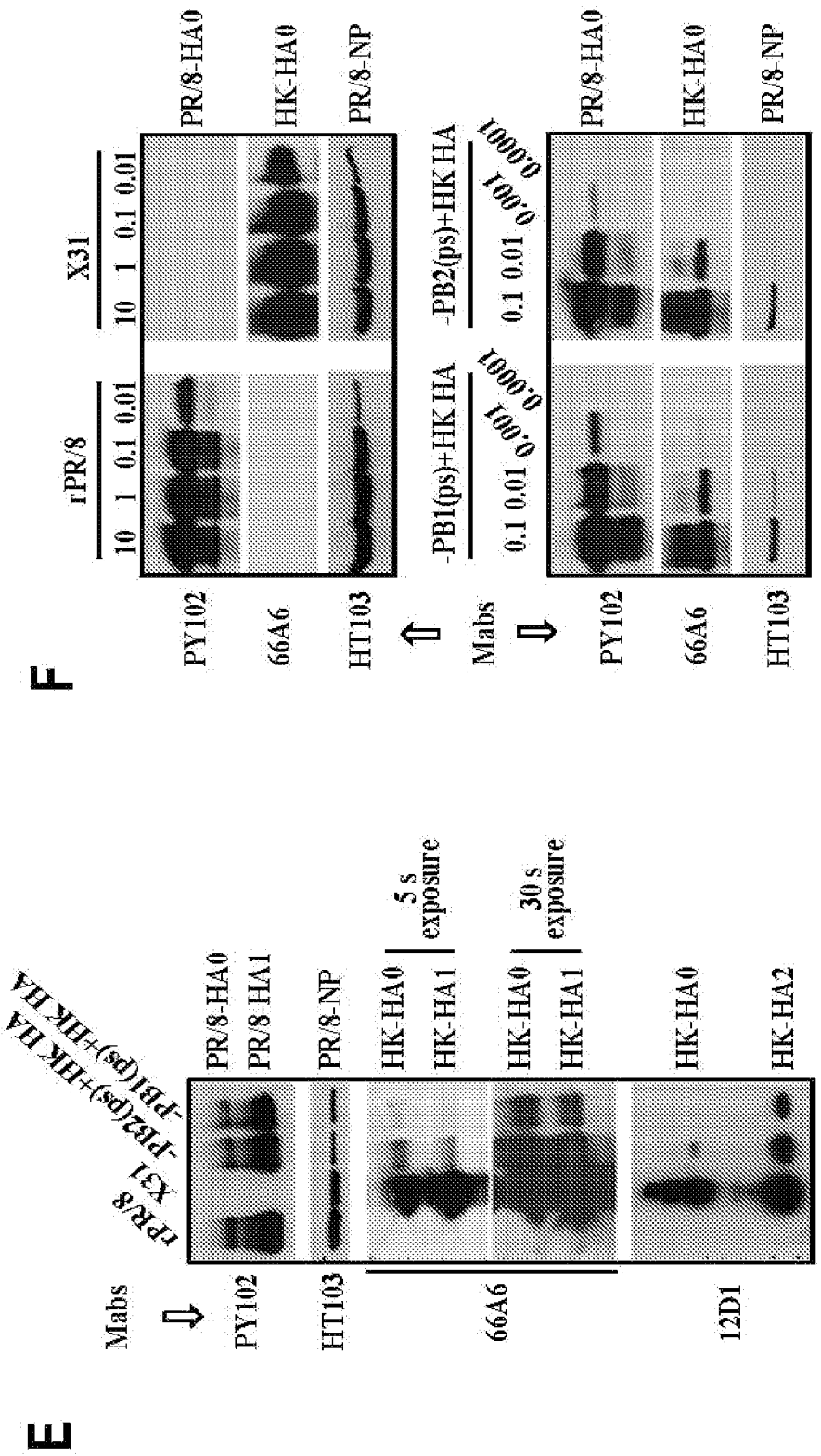
Figure 30G:
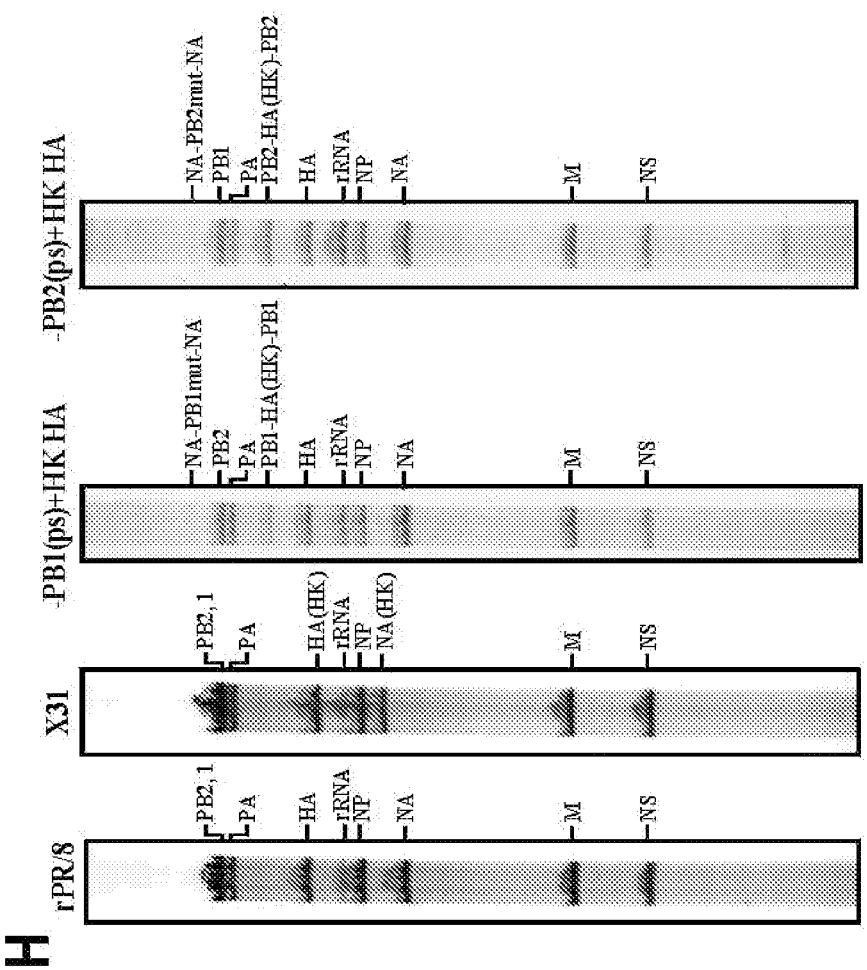
Figure 30H:
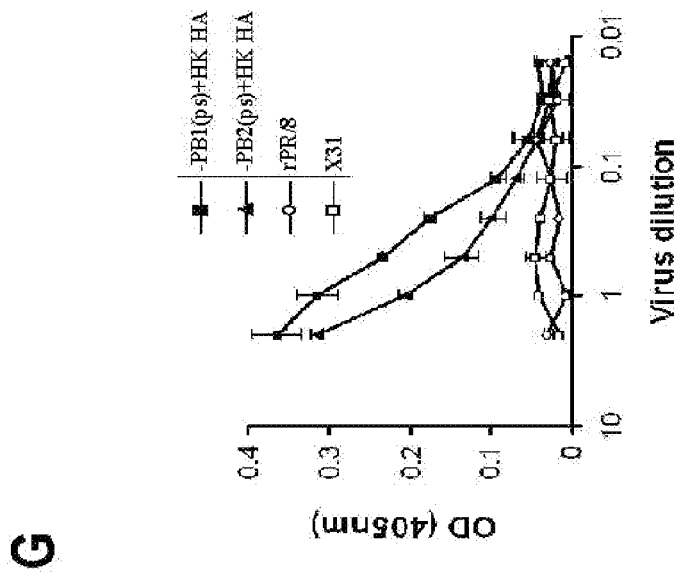
Figure 31A:
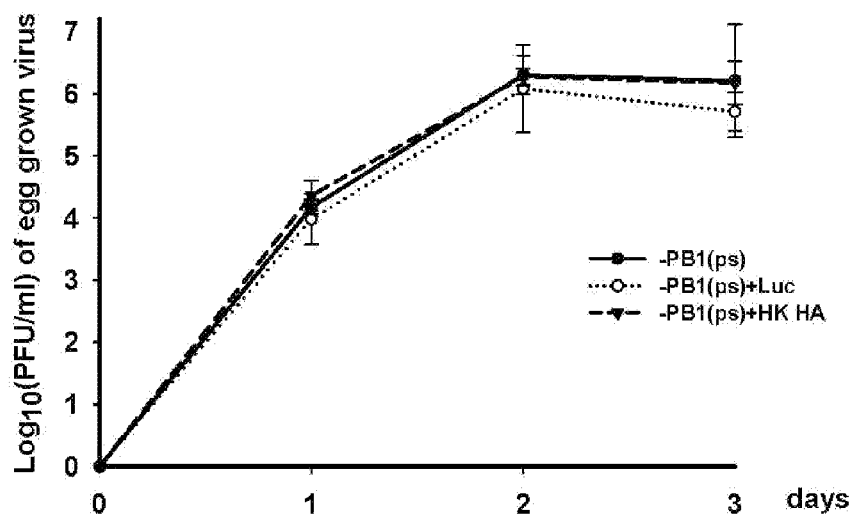

(i) Generation of NA-PB1mut-NA, NA-PB2mut-NA, and NA-PAmut-NA constructs (FIG. 29A left). To introduce silent mutations at the two ends of each ORF, the ORFs of the PB1, PB2, and PA genes were amplified by PCR from previously constructed pDZ-PB1, PB2, and PA constructs (Quinlivan et al., 2005, J Virol 79:8431-9) and cloned into a pGEM-T vector (Promega). Primers (forward: 5'-ca gctagc atg gaC gtT aaC ccA acT CtG TtA ttT CtG aaG gtA ccG gcG caG aaC gcC atC agT acG acC ttT cct tat act gga gac-3' (SEQ ID NO:128); reverse: 5'-gt ctcgag cta Ctt Ctg TcT CcG Aag Ttc Ctc Gat Tgt ACT Gca Aat Ttt cat gat ctc agt gaa c-3' (SEQ ID NO:129)) were used to amplify PB1mut ORF; Primers (forward: 5'-ca gctagc atg gaG CgG atC aaG gaG TtG CgG aaC TtG atg tcg cag tct cg cac-3' (SEQ ID NO:130); two reverse primers: 5'-tg TGA Atc Cgt CaA Gat AGA GCT Atc TcT Ctt TcT Ctt cat Cac TaG Tac cac gtc tcc ttg ccc-3' (SEQ ID NO:131) and 5'-ga ctcgag cta Gtt Aat Agc cat Acg Gat Cct Ctt Agt Tgc Cgt Ttg TGA Atc Cgt CaA G-3' (SEQ ID NO:132)) were used to amplify PB2mut ORF; Primers (forward: 5'-ca gctagc atg gaG gaC ttC gtA AgG caG tgT ttT aaC ccA atg atC gtT gaA ctC gcA gaG aaG acG atg aaG gag tat ggg gag g-3' (SEQ ID NO:133); reverse: 5'-gt ctcgag cta TGA TaG Cgc Gtg Cgt CaA Aaa Aga Att Aaa cca GCT Ggc Gtt aag caa aac cca g-3' (SEQ ID NO:134)) were used to amplify PAmut ORF. The capitalized letters in these primer sequences designate mutated nucleotides. Site-directed mutagenesis was used to remove one Nhe I site in PB1mut ORF (A1143G), and one Nhe I site in PAmut ORF (A1233G). The PB1mut, PB2mut and PAmut ORFs were subsequently used to replace the GFP ORF of previously constructed plasmid pDZ-GFP-2 using the Nhe I and Xho I sites (Gao et al., 2008, J Virol 82:6419-26), generating the NA-PB1mut-NA, NA-PB2mut-NA, and NA-PAmut-NA constructs (FIG. 29A). (ii) Generation of PB1-GFP-PB1, PB2-GFP-PB2, and PA-GFP-PA constructs (FIG. 29A right). The 2.7 kb Kpn I fragment from previously constructed pDZ-PB1 plasmid (Quinlivan et al., 2005, J Virol 79:8431-9) was transferred to the Kpn I site of the pUC18 vector and subjected to site-directed mutagenesis to mutate six ATGs (A25T, A29T, A71T, A119T, A142T, A146T), and to generate one Nhe I site (A148G, G151A, T152G) and one Xho I site (C2184T, A2185C). The 2.7 kb PB1 Kpn I fragment was then transferred back to the pDZ vector (Quinlivan et al., 2005, J Virol 79:8431-9) (in which the Nhe I and Xho I sites had been removed), resulting in a plasmid pDZ-PB1-ps. Following the same strategy, three ATGs (A28T, A58T, A109T) were mutated in the PB2 gene, and four mutations (C153G, C155T, T2175C, C2177A) were introduced to generate one Nhe I site and one Xho I site, resulting a plasmid pDZ-PB2-ps; six ATGs (A25T, A45T, A58T, A85T, A95T, A138T) were mutated in the PA gene, and five mutations (A142T, C143A, T144G, T2052C, A2055G) were introduced to generate one Nhe I site and one Xho I site, resulting a plasmid pDZ-PA-ps. The ORF of the GFP protein was digested from the pDZ-GFP-2 plasmid (Gao et al., 2008, J Virol 82:6419-26), and ligated to the Nhe I and Xho I sites of pDZ-PB1-ps, pDZ-PB2-ps and pDZ-PA-ps plasmids, respectively, generating the PB1-GFP-PB1, PB2-GFP-PB2, and PA-GFP-PA constructs (FIG. 29A). (iii) Generation of PB1-HA(HK)-PB1, PB2-HA(HK)-PB2 constructs (FIG. 30A). The A/HK/1/68 HA ORF was amplified by PCR from the pCAGGS-HK HA plasmid (Wang et al., 2009, PLoS Pathog 6:e1000796) using primers (forward: 5'-ca gctagc atg aag acc atc att get ttg age tgc att ttc-3' (SEQ ID NO:135); reverse: 5'-gt ctcgag tca aat gca aat gtt gca cct aat gtt gcc tct c-3' (SEQ ID NO:136)). One internal Xho I site was deleted using site directed mutagenesis. The full length A/HK/1/68 HA ORF was then used to replace the GFP gene of the PB1-GFP-PB1 and PB2-GFP-PB2 constructs (FIG. 29A), generating the PB1-HA(HK)-PB1, PB2-HA(HK)-PB2 constructs (FIG. 30A). The GFP gene of the PB1-GFP-PB1 construct (FIG. 29A) was also replaced by a *Renilla* luciferase ORF amplified from the plasmid pRLtk (Promega), generating the PB1-Luc-PB1 construct which was used to rescue the control virus -PB1(ps)+Luc (FIG. 31A). The nucleic acid sequences of the chimeric segments (in positive sense) generated are listed in FIG. 32.

Reverse Genetics for Recombinant Viruses.

The method for generating recombinant influenza viruses was as described previously (Fodor et al., 1999, J Virol 73:9679-82, Gao et al., 2008, J Virol 82:6419-26; and Quinlivan et al., 2005, J Virol 79:8431-9).

Acrylamide Gel Electrophoresis of Purified vRNA.

The viruses were grown in 10-day-old eggs at 37° C. and were subsequently processed by using a previously reported method (Gao et al., 2008, J Virol 82:6419-26). Briefly, virus was purified and RNA was isolated and run on a 2.8% denaturing polyacrylamide gel which was then stained with a silver staining kit (Invitrogen).

Western Blot.

To detect the viral protein within virions, viruses [rA/PR/8/34, X31, -PB1(ps)+HK HA and -PB2(ps)+HK HA] were grown in embryonated chicken eggs at 37° C. and concentrated through a 30% sucrose cushion. The pelleted virions were suspended in PBS and dissolved in 2× protein loading buffer (100 mM Tris-HCl [pH 6.8], 4% sodium dodecyl sulfate, 20% glycerol, 5% β-mercaptoethanol, and 0.2% bromophenol blue). To detect the expression of viral proteins in infected cells, 80% confluent MDCK cell monolayers in six-well dishes were infected with viruses [rA/PR/8/34, X31, -PB1(ps)+HK HA and -PB2(ps)+HK HA] at an moi of 10 to 0.0001. One day after infection, the cells were washed with PBS and harvested and lysed in 2× protein loading buffer. The protein lysates were separated on a 10% sodium dodecyl sulfate-polyacrylamide gel and transferred onto a nitrocellulose membrane (Whatman, Inc.). The membrane was then probed with mouse monoclonal antibodies against A/PR/8/34 HA (PY102, 1:2,000 dilution) (Reale et al., 1986, J Immunol 137:1352-8), A/PR/8/34 NP(HT103, 1:1,000 dilution) (O'Neill et al., 1998, Embo J 17:288-96), A/HK/1/68 HA1 (66A6, 1:2,000 dilution) (Wang et al., 2009, PLoS Pathog 6:e1000796), and A/HK/1/68 HA2 (12D1, 1:2,000 dilution) (Wang et al., 2009, PLoS Pathog 6:e1000796).

Immunostaining of Plaques.

Previous methods were followed (Gao et al., 2008, J Virol 82:6419-26; Matrosovich et al., 2006, Virol J 3:63). A rabbit anti-A/PR/8/34 polyclonal antibody (1:2,000 dilution) was used for plaque visualization.

Viral Growth Kinetics.

10-day-old embryonated chicken eggs were inoculated with influenza viruses (100 PFU/egg) and incubated at 37° C. At 24, 48 and 72 hr post inoculation, the allantoic fluids were harvested and the titers of the viruses were determined by plaque assay or immunostaining of the plaques in MDCK cells. At each time point, three eggs were analyzed for each virus.

Mouse Immunization and Challenge.

Eight-week-old female C57BL/6 mice (CRL) were anesthetized intraperitoneally with a mixture of ketamine and xylazine, and immunized intranasally with 50 µl of PBS or influenza viruses [-PB1(ps)+HK HA or -PB1(ps)+Luc, in a dose of $10^3$ or $10^4$ PFU/mouse]. The mice were monitored daily for weight loss over a 2-week period. Three weeks after immunization, mice were challenged by intranasal infection with either 100 mouse lethal dose 50 ($MLD_{50}$) of A/PR/8/34 or 33.3 $MLD_{50}$ of X31 virus. Again mice were monitored daily for weight loss or other signs of disease over a 2-week period.

Hemagglutination Inhibition (HI) Assay.

Blood samples were collected from mice prior to vaccination (at day 0) and prior to challenge (at day 21). Receptor destroying enzyme (Sigma) treatment was used to eliminate nonspecific inhibitors of hemagglutination. The protocols on "WHO manual on animal influenza diagnosis and surveillance" were followed.

H1/H3 Sandwich ELISA.

96-well Immulon 2HB plates (NUNC) were coated with mouse anti-H3 HA monoclonal antibody 66A6 (IgG1) (Wang et al., 2009, PLoS Pathog 6:e1000796) (5 µg/ml in PBS) by overnight incubation at 4° C. Plates were then blocked with 1% BSA in PBS at room temperature for 30 minutes. Two-fold dilutions of intact egg grown virus were added and plates were incubated for 3 hours at 37° C. The H1 subtype HA protein on captured virus particles was then probed with 1 µg/ml anti-H1 HA antibody C179 (mouse IgG2a) (Okuno et al., 1993, J Virol 67:2552-8) for 3 hours at 37° C. and detected by goat anti-mouse IgG2a-AP (Southern Biotech) (1:2000 dilution).

8.2 Results 8.2.1. Generation of Recombinant A/PR/8/34 Viruses Carrying a Ninth GFP Segment At restrictive temperature, a temperature sensitive influenza A virus has been shown capable of containing two sets of nonstructural protein (NS) segment-specific packaging signals located in two different segments: one set was derived from an NS segment that has a temperature sensitive defect in the NS1 gene and a second set was from the segment that encodes a wild type NS1 gene (Enami et al., 1991, Virology 185:291-8). To determine whether influenza A virus was able to incorporate two copies of NA segment-specific packaging sequences, the packaging signals of the PB1 segment were switched to those from the NA segment (FIG. 29A, left) while the original NA segment was unchanged. To accomplish this, the A/PR/8/34 PB1ORF that carried serial synonymous mutations at the two ends, named PB1mut (FIG. 29A, left), was flanked by the NA segment-specific packaging sequences (including the 3' and 5' NCRs, as well as the terminal coding sequence of the NA ORF), thus generating the NA-PB1mut-NA segment (FIG. 29A, left). Based on findings described herein and in Gao and Palese, 2009, Proc Natl Acad Sci USA 106:15891-6 that the partial packaging signals in the HA or NS ORF region can affect viral RNA incorporation, the two ends of the PB1ORF were silently mutated. The synonymous mutations in the PB1mut ORF region include 24 nucleotides (nt) and 17 nt changes in the 3' and 5'-proximal regions, respectively. The ATGs in the 3' proximal NA region of the chimeric NA-PB1mut-NA segment were all mutated by site-directed mutagenesis so that translation would be initiated at the PB1mut gene start codon. Based on findings described herein and in Gao and Palese, 2009, Proc Natl Acad Sci USA 106:15891-6 for the HA and NS segments and data from other studies (Fujii et al., 2005, J Virol 79:3766-74; Gog et al., 2007, Nucleic Acids Res 35:1897-907; Hutchinson et al., 2008, J Virol 82:11869-79; Liang et al., 2008, J Virol 82:229-36; Marsh et al., 2007, J Virol 81:9727-36; and Marsh et al., 2008, J Virol 82:2295-304), it was surmised that this chimeric NA-PB1mut-NA construct in FIG. 29A would most likely utilize the flanking NA packaging signals due to the absence of proper PB1-specific packaging sequences.

Figures 29B, 29C, 29D, 29E:
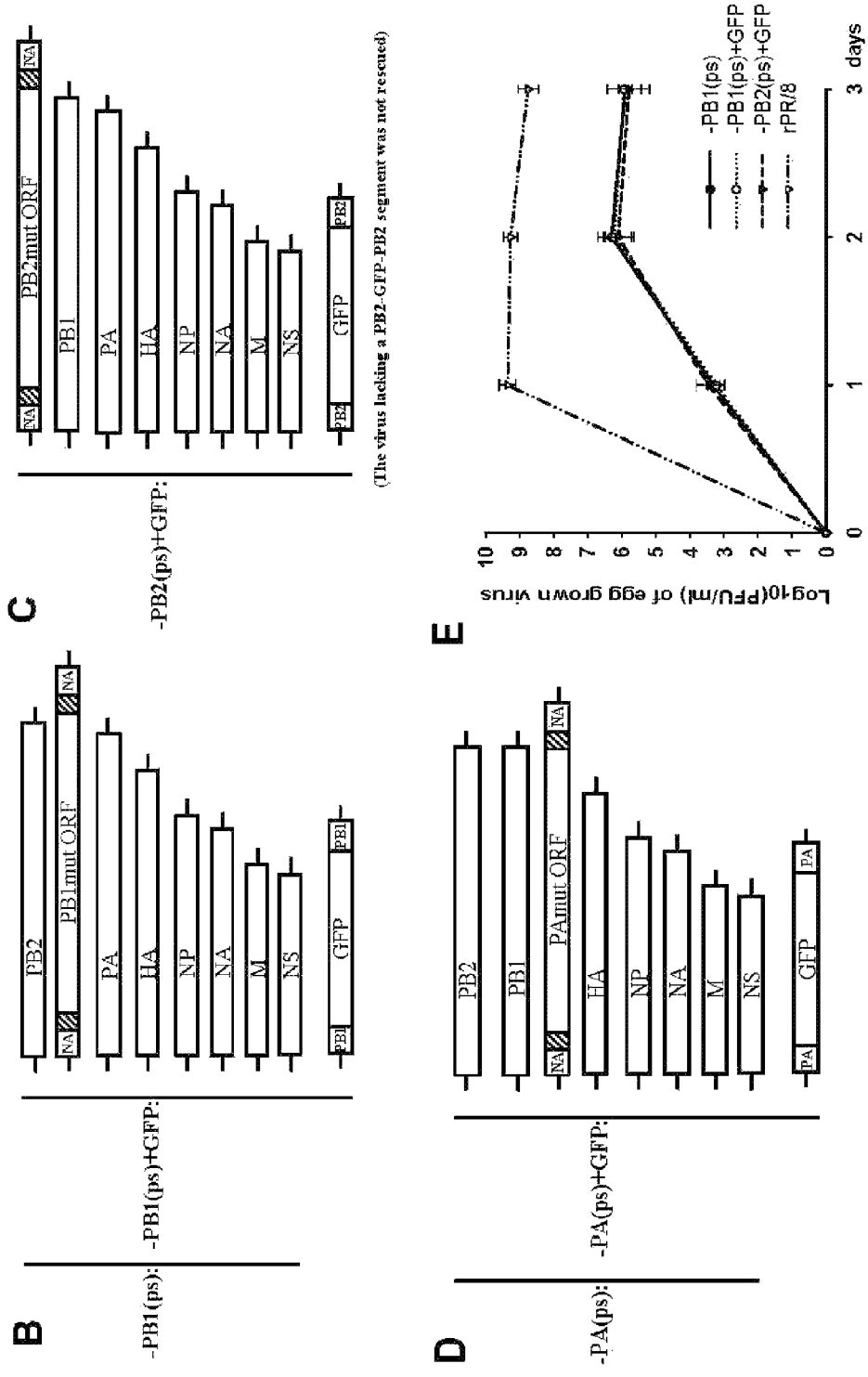

Using reverse genetics, a -PB1(ps) virus that carries seven wild type A/PR/8/34 RNA segments (PB2, PA, HA, NP, NA, M, NS) and one chimeric NA-PB1mut-NA segment was successfully rescued (FIG. 29B). The -PB1(ps) virus was attenuated compared with wild type A/PR/8/34 virus, with lower titers in eggs and smaller plaques in MDCK cells (FIGS. 29E & F). To determine whether the -PB1(ps) virus was able to incorporate a ninth segment that had PB1 segment-specific packaging signals, a PB1-GFP-PB1 construct was generated that carried 153 nt of PB1 packaging sequences in the 3' end and 159 nt in the 5' end (FIG. 29A, right). These 153 nt and 159 nt sequences consisted of both NCRs and terminal coding region packaging sequences and the six ATGs located in the 3' 153 nt PB1 packaging sequences were all mutated by site-directed mutagenesis. The -PB1(ps)+GFP virus that had all eight segments of the -PB1(ps) virus and a ninth GFP segment with PB1 segment-specific packaging signals (FIG. 29B) then was generated. -PB1(ps)+GFP virus exhibited similar growth characteristics to the -PB1(ps) virus, with similar titers in eggs and similar plaque phenotypes in MDCK cells (FIGS. 29E & F). The -PB1(ps)+GFP virus was stable, and GFP expression in infected cells (FIG. 29G) was maintained over 5 passages in eggs by the limiting dilution technique. The percentage of GFP expressing plaques formed by the -PB1(ps)+GFP virus also did not change over 5 passages in eggs (FIG. 33).

Figures 29F, 29G, 29H:
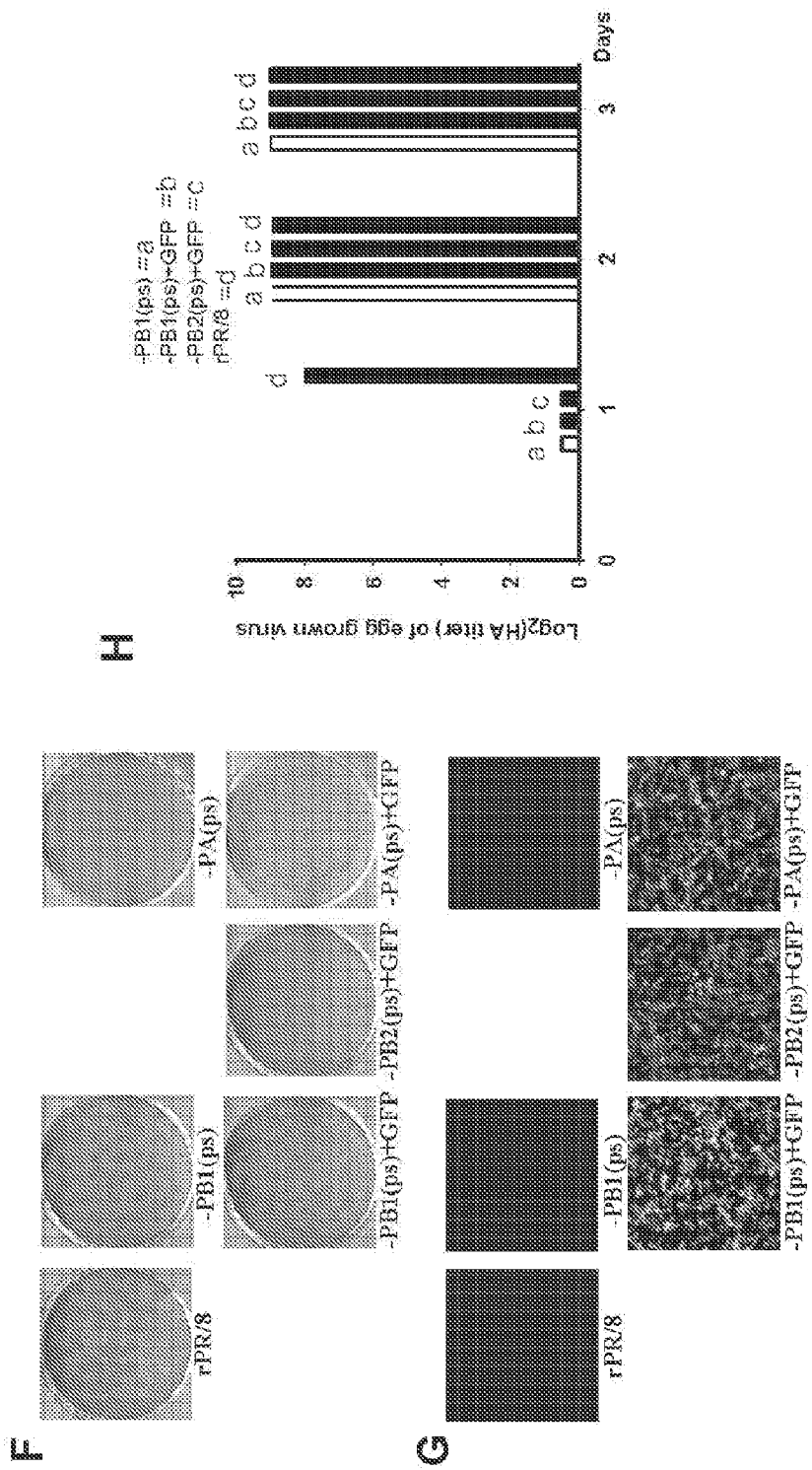

Following the same strategy, the packaging signals of the PB2 and PA segments were also each replaced with those of NA. Chimeric constructs NA-PB2mut-NA and NA-PAmut-NA were generated (FIG. 29A, left). PB2mut ORF had 13 nt synonymous changes in the 3' end and 36 nt in the 5' end to inactivate the PB2 ORF region packaging signals; and PAmut ORF region carried 19 nt synonymous changes in the 3' end and the same number of changes in the 5' end to inactivate the PA ORF region packaging signals (FIG. 29A, left). The two chimeric GFP constructs PB2-GFP-PB2 and PA-GFP-PA that respectively carried PB2 and PA segment-specific packaging sequences were made using the same method utilized to produce the PB1-GFP-PB1 construct (FIG. 29A, right). The 3 ATGs in the 3' end 158 nt PB2 packaging sequences of the PB2-GFP-PB2, and 3 ATGs in the 3' end 129 nt PA packaging sequences of the PA-GFP-PA construct, were all mutated to TTGs in order for the GFP gene to utilize its own initiation codon (FIG. 29A, right). For the PB2 segment, a virus that has seven wild type A/PR/8/34 RNA segments (PB1, PA, HA, NP, NA, M, NS) and one chimeric segment NA-PB2mut-NA was not rescued. However, when a ninth PB2-GFP-PB2 construct was added, the -PB2(ps)+GFP virus was successfully rescued (FIG. 29C). The -PB2(ps)+GFP virus grew in eggs to a titer similar to that of the -PB1(ps)+GFP virus (FIG. 29E), but it produced slightly smaller plaques in MDCK cells (FIG. 29F). The expression of GFP in infected cells (FIG. 29G) and the percentage of GFP expressing plaques (FIG. 33) were also stably maintained over at least five passages in embryonated chicken eggs by the limiting dilution technique. For the PA segment, a -PA(ps) virus that has seven wild type A/PR/8/34 segments (PB2, PB1, HA, NP, NA, M, NS) and one chimeric segment NA-PAmut-NA (FIG. 29D) was successfully rescued. The -PA(ps)+GFP virus carrying the ninth PA-GFP-PA segment was also successfully rescued (FIG. 29D). The -PA (ps) and -PA(ps)+GFP viruses were more attenuated compared with the -PB1(ps), -PB1(ps)+GFP and the -PB2(ps)+GFP viruses, growing to lower titers in eggs and generating smaller plaques in MDCK cells (FIG. 29F). Due to small plaque size, the infectious titers of the -PA(ps) and -PA(ps)+GFP viruses could not be accurately measured and their growth rates in eggs was not further characterized. The GFP expression by the -PA(ps)+GFP virus in infected cells (FIG. 29G) was, however, stably maintained over at least five passages in embryonated chicken eggs. Finally, although the infectious titers of the -PB1(ps), -PB1(ps)+GFP and the -PB2 (ps)+GFP viruses from eggs were much lower than that of recombinant (r)A/PR/8/34 virus (FIG. 29E), their hemagglutination assay titers were comparable to that of the rA/PR/8/34 virus two and three days post inoculation (FIG. 29H), suggesting that these viruses produced more defective virions than does the wild type virus. The number of synonymous mutations introduced to disrupt the packaging signals in the ORF region and the length of the flanking packaging sequences used in the chimeric constructs (FIG. 29A) were decided upon previous characterization of the A/WSN/33 viral RNA packaging signals (Fujii et al., 2003, Proc Natl Acad Sci USA 100:2002-7; Liang et al., 2005, J Virol 79:10348-55; Liang et al., 2008, J Virol 82:229-36; Marsh et al., 2008, J Virol 82:2295-304; and Muramoto et al., 2006, J Virol 80:2318-25).

Figure 31B:
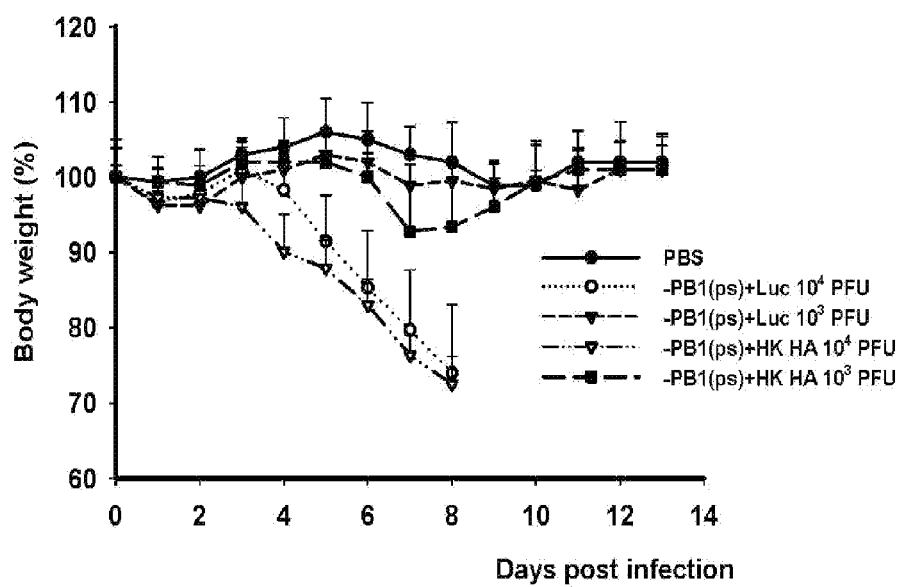

In conclusion, a novel approach to construct several nine-segmented influenza viruses simply by manipulating the RNA packaging sequences was generated. The resulting viruses were genetically stable and carried an extra GFP segment. Linearity between dilutions and plaque numbers was also observed for these nine-segmented viruses, suggesting indeed more than eight RNAs can be incorporated into one particle.

8.2.2. Generation of Recombinant Influenza Viruses Carrying Both A/PR/8/34(H1N1) and A/HK/1/68(H3N2) Hemagglutinins Whether the method for generating the nine-segmented GFP virus could be used to generate influenza viruses coding for two subtypes of HA (the A/PR/8/34(H1N1) HA and the HA from A/HK/1/68(H3N2)) was determined. To do this, the GFP ORF regions of the PB1-GFP-PB1 and PB2-GFP-PB2 constructs (FIG. 29A, right) were each replaced by the A/HK/1/68 HA ORF, generating the PB1-HA(HK)-PB1 and PB2-HA(HK)-PB2 constructs (FIG. 30A). Using reverse genetics, two nine-segmented viruses named -PB1(ps)+HK HA (FIG. 2B) and -PB2(ps)+HK HA (FIG. 30C) were rescued. The -PB1(ps)+HK HA virus and the -PB2(ps)+HK HA virus had similar growth characteristics as the -PB1(ps)+GFP and the -PB2(ps)+GFP viruses (FIGS. 29E & 30D), respectively. In order to show that both the A/PR/8/34 and the A/HK/1/68 HAs were incorporated into particles of the -PB1(ps)+HK HA and -PB2(ps)+HK HA viruses, four viruses [rA/PR/8/34, X31 that has six A/PR/8/34 internal genes and the A/HK/1/68 HA and NA genes, -PB2(ps)+HK HA and -PB1(ps)+HK HA viruses] were grown in eggs and concentrated by passing through a sucrose cushion. Western blotting was then performed to detect the A/PR/8/34 and A/HK/1/68 HAs in purified virions (FIG. 30E). The results showed that when the same amounts of virus proteins were loaded, the -PB1(ps)+HK HA and -PB2(ps)+HK HA viruses had similar levels of A/PR/8/34 HA protein when compared with the wild type rA/PR/8/34 virus; this includes uncleaved HA0 and cleaved HA1 detected by the monoclonal mouse antibody (Mab) PY102 (FIG. 30E). Also, when comparable amounts of virus proteins were loaded, rA/PR/8/34 and X31 had the same amount of NP protein detected by Mab HT103 (FIG. 30E). However, for the -PB1(ps)+HK HA and -PB2(ps)+HK HA chimeric viruses, the NP levels were about five times lower than those of rA/PR/8/34 and X31 viruses (FIG. 30E), indicating a less efficient RNP incorporation by the nine-segmented viruses. Both HA0 and HA1 from A/HK/1/68 were detected in the -PB1(ps)+HK HA and the -PB2(ps)+HK HA virus particles using Mab 66A6; notably, when normalized for total protein, H3 HA incorporation by the chimeric viruses was much lower than incorporation by the X31 virus, with lowest levels seen in the PB1(ps)+HK HA virus (FIG. 30E). The Western blot using Mab 12D1 to detect A/HK/1/68 HA0 and cleaved HA2 showed similar results (FIG. 30E). Western blotting then was used to detect the expression of both A/PR/8/34 and A/HK/1/68 HAs by the -PB1(ps)+HK HA and -PB2(ps)+HK HA viruses in infected cells (FIG. 30F). Both A/PR/8/34 and A/HK/1/68 HAs were detected in MDCK cells infected by these viruses (FIG. 30F, lower panel). In contrast, as with FIG. 30E, cells infected with rA/PR/8/34 virus only expressed A/PR/8/34 HA and the X31 virus-infected cells only expressed H3 HA (FIG. 30F, upper panel).

Finally, a sandwich ELISA was performed to confirm that both H1 and H3 subtype HA proteins were incorporated into the nine-segmented virus particles (FIG. 30G). 96-well plates were coated with Mab 66A6 (Wang et al., 2009, PLoS Pathog 6:e1000796) to capture intact virus particles in an H3-dependent manner. Virus particles were then probed for H1 content with Mab C179, an antibody with activity against H1 and H2 subtype HA, but that does not react with H3 HA (Okuno et al., 1993, J Virol 67:2552-8). Signals were detected for the two nine-segmented viruses, indicating that indeed two types of HA proteins were incorporated into the virus particles. In contrast, both rA/PR/8/34 and X31 viruses gave negative results (FIG. 30G).

In conclusion, two recombinant viruses, each of which carried two subtypes of HA, one A/PR/8/34(H1N1) HA and one A/HK/1/68(H3N2) HA were successfully rescued. Both HAs were incorporated into virus particles and were expressed in virus infected MDCK cells.

To determine the RNA packaging efficiencies of the recombinant -PB1(ps)+HK HA and -PB2(ps)+HK HA viruses, RNA was isolated from the purified viruses and resolved on a 2.8% acrylamide gel followed by silver staining (FIG. 30H). The X31 virus has six A/PR/8/34 internal genes along with the A/HK/1/68 HA and NA segments which migrated to distinct positions from those of the A/PR/8/34 HA and NA (FIG. 30H). By comparing density of bands, it was observed that the -PB1(ps)+HK HA virus inefficiently incorporated the NA-PB1mut-NA segment. The PB1-HA(HK)-PB1 segment was also packaged somewhat inefficiently when compared with the A/PR/8/34 HA segment (FIG. 30H). For the -PB2(ps)+HK HA virus, the NA-PB2mut-NA segment was inefficiently packaged. In contrast, the PB2-HA(HK)-PB2 segment was packaged efficiently, with a level similar to that of A/PR/8/34 HA (FIG. 30H).

8.2.3. Immunization of Mice with a Recombinant Nine-Segmented Virus Confers Protection from Lethal Challenges of RA/PR/8/34 and X31 Viruses To test whether the nine-segmented influenza viruses carrying two subtypes of HA could be used as live vaccines, mouse challenge experiments were conducted. The -PB1(ps)+HK HA virus was arbitrarily chosen for the study. As a negative control immunogen the -PB1(ps)+Luc virus was used, which carries a ninth PB1-Luc-PB1 instead of a PB1-HA(HK)-PB1 segment (FIG. 30B and FIG. 34). Both -PB1(ps)+Luc and -PB1(ps)+HK HA viruses grew to similar titers as the -PB1(ps) virus in eggs (FIG. 31A). To test whether the nine-segmented viruses were pathogenic in mice, groups of eight-week-old female C57BL/6 mice were given PBS, -PB1(ps)+HK HA virus, or the -PB1(ps)+Luc virus, at either $10^3$ or $10^4$ PFU by intranasal administration (FIG. 31B). The mice infected with $10^4$ PFU of either -PB1(ps)+Luc or -PB1(ps)+HK HA virus died or lost more than 25% of their initial body weight by day eight post infection (FIG. 31B). The group of mice given $10^3$ PFU of -PB1(ps)+Luc exhibited little or no weight loss and exhibited no signs of disease, similar to the PBS group (FIG. 31B). The group of mice given $10^3$ PFU of -PB1(ps)+HK HA virus lost approximately 5% of their body weight by day seven post infection followed by full recovery within three days; no other signs of disease were observed (FIG. 31B). Since administration of $10^3$ PFU of either chimeric virus caused very little or no changes associated with illness, exposure to this dose was considered to be analogous with vaccination.

Figure 31C:
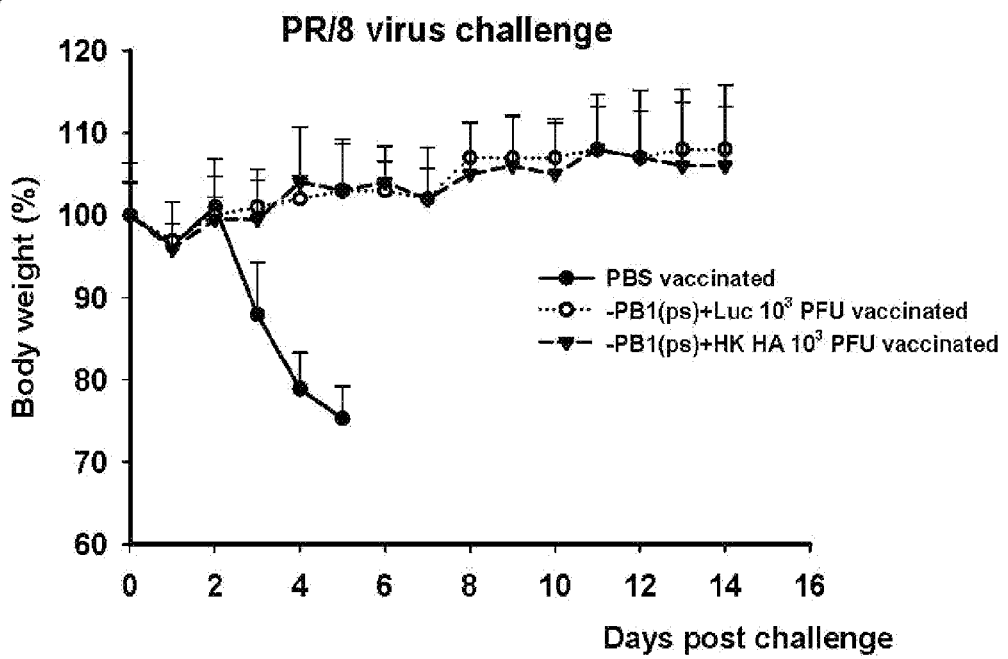
Figure 31D:
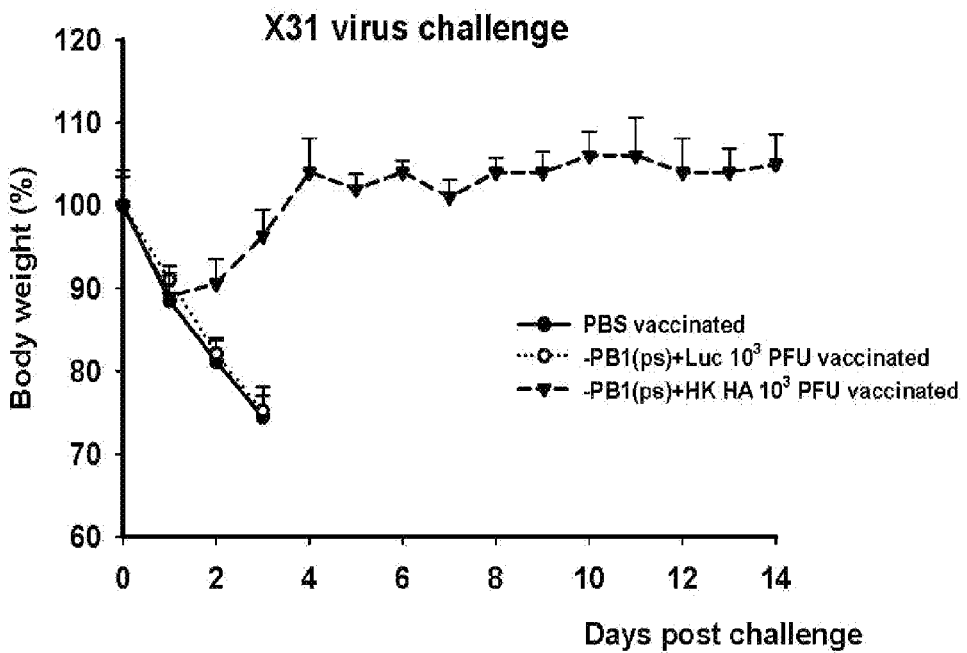

Three weeks post infection, lethal virus challenge experiments were performed on the groups of mice infected with $10^3$ PFU of -PB1(ps)+Luc virus, $10^3$ PFU of -PB1(ps)+HK HA virus, or mice that were mock vaccinated with PBS. Mice were given 3,000 PFU (100 $MLD_{50}$) of rA/PR/8/34 virus by intranasal administration (FIG. 31C). In contrast to the PBS group, the groups vaccinated with either the PB1(ps)+Luc or the -PB1(ps)+HK HA viruses were completely protected from lethal challenge: no loss of body weight or signs of disease were observed (FIG. 31C). Following the same methods, $10^7$ PFU (33 $MLD_{50}$) of X31 virus was administered intranasally to a second set of mice that were mock vaccinated (PBS group), vaccinated with $10^3$ PFU -PB1(ps)+Luc, or vaccinated with $10^3$ PFU -PB1(ps)+HK HA virus (FIG. 31D). The groups of mice that were mock or -PB1(ps)+Luc vaccinated quickly lost 25% of their body weight in three days and were sacrificed. Although previous findings showed that cellular responses to the internal NP and M proteins conferred some protection against heterologous challenges (Yewdell et al., 1985, Proc Natl Acad Sci USA 82:1785-9), no protection was observed in the -PB1(ps)+Luc vaccinated group possibly due to the high dosage of challenge virus used. In contrast, vaccination with $10^3$ PFU of -PB1(ps)+HK HA virus protected the mice from the lethal challenge with X31 virus. Average body weight was reduced by 10% on the day following challenge and all mice quickly recovered (FIG. 31D).

Analysis of serum samples from this experiment indicated that by day 21 postvaccination all animals vaccinated with $10^3$ PFU of -PB1(ps)+HK HA virus produced hemagglutination-inhibiting antibodies against rA/PR/8/34 virus, with titers ranging from 320 to 640. Four out of five animals produced low but detectable level of hemagglutination-inhibiting antibodies against X31 virus, with titers ranging from 20 to 40 (Table 17). As expected, animals vaccinated with $10^3$ PFU of -PB1(ps)+Luc virus had only hemagglutination-inhibiting antibodies against rA/PR/8/34 virus, with titers ranging from 160 to 320 (Table 17). No hemagglutination-inhibiting antibodies against either rA/PR/8/34 or X31 virus were detected in serum from animals mock-vaccinated with PBS.

TABLE 17

Hemagglutination-inhibitory activity against rA/PR/8/34 and X31 viruses of sera from mice immunized with nine-segmented viruses.

| Vaccine | Mouse | Titer against rA/PR/8/34 | | Titer against X31 | |
|---|---|---|---|---|---|
| | | Pre-immune | Post-vaccination | Pre-immune | Post-vaccination |
| PBS | 1 | <10 | <10 | <10 | <10 |
| | 2 | <10 | <10 | <10 | <10 |
| | 3 | <10 | <10 | <10 | <10 |
| | 4 | <10 | <10 | <10 | <10 |
| | 5 | <10 | <10 | <10 | <10 |

TABLE 17-continued

Hemagglutination-inhibitory activity against rA/PR/8/34 and X31 viruses of sera from mice immunized with nine-segmented viruses.

| Vaccine | Mouse | Titer against rA/PR/8/34 | | Titer against X31 | |
|---|---|---|---|---|---|
| | | Pre-immune | Post-vaccination | Pre-immune | Post-vaccination |
| -PB1(ps) + Luc | 1 | <10 | 160 | <10 | <10 |
| | 2 | <10 | 320 | <10 | <10 |
| | 3 | <10 | 160 | <10 | <10 |
| | 4 | <10 | 320 | <10 | <10 |
| | 5 | <10 | 320 | <10 | <10 |
| -PB1(ps) + HK HA | 1 | <10 | 320 | <10 | 20 |
| | 2 | <10 | 640 | <10 | <10 |
| | 3 | <10 | 320 | <10 | 40 |
| | 4 | <10 | 320 | <10 | 20 |
| | 5 | <10 | 320 | <10 | 40 |

In conclusion, vaccination with $10^3$ PFU of -PB1(ps) + HK HA virus was protective in mice against lethal challenge with influenza viruses from two separate subtypes: one H1N1 subtype (rA/PR/8/34) and one H3N2 subtype (X31).

8.3 Discussion

Two recombinant viruses were generated, named -PB1(ps) (FIG. 29B) and -PA(ps) (FIG. 29D) which lacked either PB1 or PA packaging sequences, respectively, and carried NA packaging sequences in their place. These viruses were viable, however, both the PB1 and the PA packaging signals were important for virus growth since the replacement of the PB1 segment by NA-PB1mut-NA, or the PA segment by NA-PAmut-NA did have a significant effect on the packaging of both chimeric segments (FIG. 30H) as well as on virus growth rates (FIG. 29E, F). The ability to rescue both viruses might indicate that influenza genomic RNA packaging does not absolutely require PB1 or PA packaging signals. Based on findings of packaging of the HA and NS segments described herein and in Gao and Palese, 2009, Proc Natl Acad Sci USA 106:15891-6, it was hypothesized that the two chimeric segments, NA-PB1mut-NA and NA-PAmut-NA (FIG. 29A, left), would likely utilize the flanking NA packaging signals instead of the PB1 and PA packaging signals, respectively. However, it is possible that the PB1 or PA ORF region carrying the serial synonymous mutations (FIG. 29A) partially retained the PB1 or PA packaging signals. Although 24 and 17 nt changes were introduced to the PB1 ORF and two sets of 19 nt changes were made in the PA ORF (FIG. 29A, left), some residual PB1 or PA packaging signals could still exist, enabling PB1 or PA segment-specific recognition (FIG. 29A, left). Interestingly, both viruses were able to incorporate a ninth segment coding for GFP. When supplied with a ninth PB1-GFP-PB1 segment (FIG. 29A, right) flanked by the PB1 packaging sequence, the -PB1(ps) virus was able to stably incorporate it into the virus genome, generating the -PB1(ps)+GFP virus (FIG. 29B); likewise, the -PA(ps)+GFP virus was able to maintain an extra PA-GFP-PA segment flanked by the PA packaging signals (FIG. 29D). The generation of both viruses with an extra GFP segment reflected the tendency of influenza virus to have a complete set of packaging signals on its genomic RNAs.

For the PB2 segment, when the wild type PB2 was replaced by the NA-PB2mut-NA chimeric segment (FIG. 29A, left), the virus could not be rescued. This was also seen in previous studies using A/WSN/33 virus in which mutating or deleting the PB2 packaging sequences resulted in a more severe packaging defect than did manipulation of other segments (Liang et al., 2008, J Virol 82:229-36; Muramoto et al., 2006, J Virol 80:2318-25). However, when a ninth PB2-GFP-PB2 segment that carried PB2 packaging signals was included (FIG. 29A, right), the -PB2(ps)+GFP virus was successfully rescued (FIG. 29C). This result also reflected the preference of influenza virus to carry sets of eight unique packaging signals.

Using the strategy that was designed for generation of the -PB1(ps)+GFP (FIG. 29B) and -PB2(ps)+GFP (FIG. 29C) viruses, two recombinant viruses were rescued that encoded two different full length HAs: both -PB1(ps)+HK HA virus (FIG. 2B) and -PB2(ps)+HK HA virus (FIG. 2C) encoded an A/PR/8/34 HA and an A/HK/1/68 HA. Thus, a novel approach to engineer viruses encoding two different HAs was generated. These viruses are significantly attenuated compared to the wild type virus, with lower growth rates in eggs and smaller plaques in MDCK cells (FIGS. 29 & 30). The $MLD_{50}$ of -PB1(ps)+HK HA was between $10^3$ and $10^4$ PFU (FIG. 31B), significantly higher than that of wild type A/PR/8/34 virus, which has an $MLD_{50}$ of about 30 PFU Immunization of mice with 1000 PFU of -PB1(ps)+HK HA virus completely protected them from the lethal challenge with rA/PR/8/34 virus or X31 virus, suggesting that this nine-segmented virus strategy might be utilized for the development of bivalent live attenuated influenza vaccines. Although the -PB1(ps)+HK HA virus is potentially lethal to mice, a similar approach can be applied to other less virulent viruses for a live vaccine purpose. Current seasonal influenza vaccines must include three distinct influenza viruses: one A (H3N2) virus, one regular seasonal A (H1N1) virus, and one B virus. The bivalent, nine-segmented influenza viruses described herein offer a means of combining two major antigens (e.g. H1 and H3 HAs) into one vaccine strain. This may be particular useful if the number of co-circulating influenza virus lineages increases to more than three: for example, in 2009, a novel swine origin influenza A virus of the H1N1 subtype, which is different from seasonal H1N1 virus, emerged from North America and caused an influenza pandemic. Furthermore, by carrying specific antigens on its ninth chimeric segment, this nine-segmented influenza virus platform could also be applied to generate vaccines against other bacterial or viral pathogens.

9. EXAMPLE 4

This example demonstrates how reassortment of viruses can be measured.

A reverse genetics approach can be used to assess whether each of the chimeric gene segments of the recombinant influenza viruses shown in, e.g., FIGS. 35 to 37, can reassort. Cells expressing the necessary influenza virus proteins can be co-transfected with influenza virus chimeric segments that have had their packaging signals swapped and influenza virus gene segments from a wild-type or lab strain of influenza virus, wherein the wild-type or lab strain influenza virus gene segments include a gene segment that encodes an influenza virus protein encoded by one of the chimeric influenza virus gene segments and the other gene segments necessary to produce a replication-competent influenza virus. For example, cells, such as 293T cells, MDCK cells or Vero cells, expressing the necessary viral proteins (e.g., PA, PB1, PB2, and NP) can be transfected with plasmids encoding four of the chimeric gene segments shown in FIG. 35 (NA-PB2mut-NA, PB2-PB1mut-PB2, PB1-PAmut-PB1, and PA-NAmut-PA) and plasmids encoding five gene segments (pDZ-NP, NA, M, NS, and HA) of a wild-type influenza virus or a lab strain, such as A/PR/8/34, using techniques previously described (see, e.g., Gao et al., 2008, J. Virol. 82: 6419-6426; Quinlivan et al., 2005, J. Virol. 79: 8431-8439; Fodor et al., 1999, J. Virol. 73: 9679-9682). The recombinant viruses rescued can then be grown in tissue culture or embryonated eggs and plaque purified using known techniques. The gene segments present in the plaque purified viruses can then be determined by, e.g., amplifying single plaques, isolating the vRNA from the virus, subjecting the vRNA to RT-PCR using primers designed to hybridize to specific gene segments and running the RT-PCR products on an agarose gel. Alternatively, the vRNA segments from the plaque performed viruses can be sequenced using techniques known in the art, such as deep sequencing. The inability to detect influenza viruses containing less than the combination of the chimeric gene segments that have had their packaging signals swapped indicates that those chimeric gene segments are unable to reassort freely. For example, with respect to the chimeric gene segments of the recombinant virus shown in FIG. 35, the inability to detect influenza viruses containing the three chimeric NA-PB2mut-NA, PB2-PB1mut-PB2, and PB1-PAmut-PB1 gene segments and the wild-type or lab strain influenza virus NA, NP, M, NS and HA gene segments indicates that the four chimeric gene segments (NA-PB2mut-NA, PB2-PB1mut-PB2, PB1-PAmut-PB1, and PA-NAmut-PA) are unable to reassort freely.

As another approach to determine whether the chimeric gene segments of the recombinant influenza viruses shown in, e.g., FIGS. 35 to 37 can freely reassort in tissue culture, cells (e.g., 293T cells, MDCK cells or Vero cells) can be co-infected with the recombinant virus shown in, e.g., FIG. 35, 36 or 37, and a wild-type or lab strain of influenza virus at certain multiplicity of infection ("moi") for each virus (e.g., an moi of 10). The resulting viruses can then be plaque purified. The gene segments present in the plaque purified viruses can then be determined by, e.g., amplifying single plaques, isolating the vRNA from the virus, subjecting the vRNA to RT-PCR using primers designed to hybridize to specific gene segments and running the RT-PCR products on an agarose gel. Alternatively, the vRNA segments from the plaque performed viruses can be sequenced using techniques known in the art, such as deep sequencing. The inability to detect viruses containing less than the combination of the chimeric segments that have had their packaging signals swapped are unable to reassort freely. For example, with respect to the chimeric gene segments of the recombinant virus shown in FIG. 35, the inability to detect influenza viruses containing the three chimeric NA-PB2mut-NA, PB2-PB1mut-PB2, and PB1-PAmut-PB1 gene segments and the wild-type or lab strain influenza virus NA, NP, M, NS and HA gene segments indicates that the four chimeric gene segments (NA-PB2mut-NA, PB2-PB1mut-PB2, PB1-PAmut-PB1, and PA-NAmut-PA) are unable to reassort freely.

10. EXAMPLE 5

This example describes the production of a nine segment recombinant influenza virus.

A chimeric construct designated PA-NAmut-PA was generated as follows: the A/PR/8/34 NA ORF that carries silent mutations at the two ends, named NAmut, was ligated to the A/PR/8/34 PA packaging sequences, generating the PA-NAmut-PA construct. A chimeric construct designated NA-GFP-NA was generated as follows: a GFP ORF was ligated to the A/PR/8/34 NA packaging sequence, generating the NA-GFP-NA construct. A chimeric construct designated NA-HA(HK)-NA was generated as follows: the HA ORF from the A/Hong Kong/1/68 (A/HK/1/68) HA gene was ligated to the A/PR/8/34 NA packaging sequences, generating the NA-HA(HK)-NA construct. (See FIG. 38.)

Recombinant influenza viruses (see FIG. 38) were generated using a method modified Example 1 and from Gao and Palese, 2009, PNAS106:15891. 293T cells were transfected with 2 chimeric plasmids [PA-NAmut-PA and NA-GFP-NA or NA-HA(HK)—NA], and 7 plasmids carrying the wild type A/PR/8/34 PB2, PB1, PA, HA, NP, M, NS segments. 24 hours post transfection, the cells were harvested and inoculated into 10-day-old specific-pathogen-free chicken embryos (Charles River Laboratories, SPAFAS, Preston, Conn.). Three days later, the allantoic fluids were harvested and HA assay was used to determine the existence of rescued virus. The virus titers were determined by plaque assay in MDCK cells. This 9-segment chimeric virus grew well, with titers of >$10^8$ pfu/ml in embryonated chicken eggs.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references cited herein are incorporated herein by reference in their entirety and for all purposes to the same extent as if each individual publication or patent or patent application was specifically and individually indicated to be incorporated by reference in its entirety for all purposes.

What is claimed:

1. A recombinant influenza virus comprising
   a) a first chimeric influenza virus gene segment comprising, in 3' to 5' order:
      (i) a 3' non-coding region of a first type of influenza virus gene segment;
      (ii) a 3' proximal coding region of the first type of influenza virus gene segment, wherein any start codon in the 3' proximal coding region of the first influenza virus gene segment is mutated;
      (iii) an open reading frame of a second type of influenza virus gene segment, wherein at least one packaging signal in the 3' or 5' proximal nucleotides in the open reading frame is mutated;
      (iv) a 5' proximal coding region of the first type of influenza virus gene segment; and
      (v) a 5' non-coding region of the first type of influenza virus gene segment; and
   b) a second chimeric influenza virus gene segment comprising, in 3' to 5' order:
      (i) a 3' non-coding region of the second type of influenza virus gene segment;
      (ii) a 3' proximal coding region of the second type of influenza virus gene segment, wherein any start codon in the 3' proximal coding region of the second influenza virus gene segment is mutated;
      (iii) an open reading frame of the first type of influenza virus gene segment, wherein at least one packaging signal in the 3' or 5' proximal nucleotides in the open reading frame is mutated;
      (iv) a 5' proximal coding region of the second type of influenza virus gene segment; and
      (v) a 5' non-coding region of the second type of influenza virus influenza gene segment.

2. The recombinant influenza virus of claim 1, wherein only progeny of the virus comprising the chimeric influenza virus gene segments is capable of forming plaques in a plaque assay.

3. A recombinant influenza virus comprising
   a) a first chimeric influenza virus gene segment comprising, in 3' to 5' order:
      (i) a 3' non-coding region of a third type of influenza virus gene segment;
      (ii) a 3' proximal coding region of the third type of influenza virus gene segment, wherein any start codon in the 3' proximal coding region of the third influenza virus gene segment is mutated;
      (iii) an open reading frame of a first type of influenza virus gene segment, wherein at least one packaging signal in the 3' or 5' proximal nucleotides in the open reading frame is mutated;
      (iv) a 5' proximal coding region of the third type of influenza virus gene segment; and
      (v) a 5' non-coding region of the third type of influenza virus gene segment; and
   b) a second chimeric influenza virus gene segment comprising, in 3' to 5' order:
      (i) a 3' non-coding region of the first type of influenza virus gene segment;
      (ii) a 3' proximal coding region of the first type of influenza virus gene segment, wherein any start codon in the 3' proximal coding region of the first influenza virus gene segment is mutated;
      (iii) an open reading frame of a second type of influenza virus gene segment, wherein at least one packaging signal in the 3' or 5' proximal nucleotides in the open reading frame is mutated;
      (iv) a 5' proximal coding region of the first type of influenza virus gene segment; and
      (v) a 5' non-coding region of the first type of influenza virus gene segment; and
   c) a third chimeric influenza virus gene segment comprising, in 3' to 5' order:
      (i) a 3' non-coding region of the second type of influenza virus gene segment;
      (ii) a 3' proximal coding region of the second type of influenza virus gene segment, wherein any start codon in the 3' proximal coding region of the second influenza virus gene segment is mutated;
      (iii) an open reading frame of the third type of influenza virus gene segment, wherein at least one packaging signal in the 3' or 5' proximal nucleotides in the open reading frame is mutated;
      (iv) a 5' proximal coding region of the second type of influenza virus gene segment; and
      (v) a 5' non-coding region of the second type of influenza virus gene segment.

4. The recombinant influenza virus of claim 3, wherein only progeny comprising the first, second and third chimeric influenza virus gene segments is capable of forming plaques in a plaque assay.

5. The virus of claim 3, wherein the first, second, and third influenza virus gene segments encode the HA, NA, and NS proteins, respectively.

6. The recombinant influenza virus of claim 1, which comprises nine gene segments.

7. The recombinant influenza virus of claim 1, wherein: (a) the first influenza virus gene segment is NS, and wherein a mRNA 5' splice site of the 3' proximal coding region is mutated; or (b) the first influenza virus gene segment is M, and wherein a distal mRNA 5' splice site of the 3' proximal coding region is mutated.

8. The recombinant influenza virus of claim 1, wherein the virus comprises an attenuating mutation.

9. A substrate comprising the recombinant influenza virus of claim 1.

10. A pharmaceutical composition or immunogenic composition comprising the recombinant influenza virus of claim 1.

11. A method for eliciting an immune response against an influenza virus in a subject, wherein the method comprises administering the recombinant influenza virus of claim 1 to the subject.

12. A method of preventing or treating an influenza virus disease, or treating an influenza virus infection, in a subject, wherein the method comprises administering the recombinant influenza virus of claim 1 to the subject.

13. A method for propagating a recombinant influenza virus, wherein the method comprises infecting a substrate with the recombinant influenza virus of claim 1; and purifying the virus subsequently from the substrate.

14. The recombinant influenza virus of claim 1, wherein said mutation of at least one packaging signal in the 3' or 5' proximal nucleotides is a silent mutation.

15. The recombinant influenza virus of claim 1, wherein at least one packaging signal in the 3' and the 5' proximal nucleotides in each open reading frame is mutated.

* * * * *

```
                        SEQUENCE LISTING

<160> NUMBER OF SEQ ID NOS: 136

<210> SEQ ID NO 1
<211> LENGTH: 27
<212> TYPE: DNA
<213> ORGANISM: Influenza PR8 virus
<220> FEATURE:
<223> OTHER INFORMATION: 3 prime non-coding region (NCR) of PB2
      Packaging Sequences of PR8

<400> SEQUENCE: 1
agcgaaagca ggtcaattat attcaat                                        27

<210> SEQ ID NO 2
<211> LENGTH: 125
<212> TYPE: DNA
<213> ORGANISM: Influenza PR8 virus
<220> FEATURE:
<223> OTHER INFORMATION: 3 prime proximal coding region (NCR) of PB2
      Packaging Sequences of PR8

<400> SEQUENCE: 2
ttggaaagaa taaaagaact aagaaatcta ttgtcgcagt ctcgcacccg cgagatactc    60
acaaaaacca ccgtggacca tttggccata atcaagaagt acacatcagg aagacaggag   120
aagaa                                                              125

<210> SEQ ID NO 3
<211> LENGTH: 158
<212> TYPE: DNA
<213> ORGANISM: Artificial Sequence
<220> FEATURE:
<223> OTHER INFORMATION: PB2 Packaging Sequences of PR8 with NheI
      restriction enzyme recognition site

<400> SEQUENCE: 3
agcgaaagca ggtcaattat attcaatttg gaaagaataa aagaactaag aaatctattg    60
tcgcagtctc gcaccgcga gatactcaca aaaccaccg tggaccattt ggccataatc    120
aagaagtaca catcaggaag acaggagaag aagctagc                          158

<210> SEQ ID NO 4
<211> LENGTH: 34
<212> TYPE: DNA
<213> ORGANISM: Influenza PR8 virus
<220> FEATURE:
<223> OTHER INFORMATION: 5 prime non-coding region (NCR) of PB2
      Packaging Sequences of PR8

<400> SEQUENCE: 4
tgtcgaatag tttaaaaacg accttgtttc tact                                34

<210> SEQ ID NO 5
```

```
<211> LENGTH: 130
<212> TYPE: DNA
<213> ORGANISM: Influenza PR8 virus
<220> FEATURE:
<223> OTHER INFORMATION: 5 prime proximal coding region (NCR) of PB2
      Packaging Sequences of PR8

<400> SEQUENCE: 5
gaaaggagag aaggctaatg tgctaattgg gcaaggagac gtggtgttgg taatgaaacg    60
gaaacgggac tctagcatac ttactgacag ccagacagcg accaaaagaa ttcggatggc   120
catcaattag                                                          130

<210> SEQ ID NO 6
<211> LENGTH: 169
<212> TYPE: DNA
<213> ORGANISM: Artificial Sequence
<220> FEATURE:
<223> OTHER INFORMATION: PB2 Packaging Sequences of PR8 with XhoI
      restriction enzyme recognition site

<400> SEQUENCE: 6
ctcgagaaag gagagaaggc taatgtgcta attgggcaag gagacgtggt gttggtaatg    60
aaacggaaac gggactctag catacttact gacagccaga cagcgaccaa aagaattcgg   120
atggccatca attagtgtcg aatagtttaa aaacgacctt gtttctact                169

<210> SEQ ID NO 7
<211> LENGTH: 24
<212> TYPE: DNA
<213> ORGANISM: Influenza PR8 virus
<220> FEATURE:
<223> OTHER INFORMATION: 3 prime non-coding region (NCR) of PB1
      Packaging Sequences of PR8

<400> SEQUENCE: 7
agcgaaagca ggcaaaccat ttga                                           24

<210> SEQ ID NO 8
<211> LENGTH: 123
<212> TYPE: DNA
<213> ORGANISM: Influenza PR8 virus
<220> FEATURE:
<223> OTHER INFORMATION: 3 prime proximal coding region (NCR) of PB1
      Packaging Sequences of PR8

<400> SEQUENCE: 8
ttggttgtca atccgacctt actttcttta aaagtgccag cacaaattgc tataagcaca    60
actttccctt atactggaga ccctccttac agccttggga caggaacagg atacaccttg   120
gtt                                                                 123

<210> SEQ ID NO 9
<211> LENGTH: 153
<212> TYPE: DNA
<213> ORGANISM: Artificial Sequence
<220> FEATURE:
<223> OTHER INFORMATION: PB1 Packaging Sequences of PR8 with NheI
      restriction enzyme recognition site

<400> SEQUENCE: 9
agcgaaagca ggcaaaccat ttgattggtt gtcaatccga ccttactttt cttaaaagtg    60
ccagcacaaa ttgctataag cacaactttc ccttatactg agaccctcc ttacagcctt   120 gggacaggaa caggatacac cttggttgct agc                                153
```

<210> SEQ ID NO 10
<211> LENGTH: 42
<212> TYPE: DNA
<213> ORGANISM: Influenza PR8 virus
<220> FEATURE:
<223> OTHER INFORMATION: 5 prime non-coding region (NCR) of PB1
      Packaging Sequences of PR8

<400> SEQUENCE: 10
tgaatttagc ttgtccttca tgaaaaaatg ccttgtttct ac                         42

<210> SEQ ID NO 11
<211> LENGTH: 110
<212> TYPE: DNA
<213> ORGANISM: Influenza PR8 virus
<220> FEATURE:
<223> OTHER INFORMATION: 5 prime proximal coding region (NCR) of PB1
      Packaging Sequences of PR8

<400> SEQUENCE: 11
cccgaattga tgcacggatt gatttcgaat ctggaaggat aaagaaagaa gagttcactg     60
agatcatgaa gatctgttcc accattgaag agctcagacg gcaaaaatag                110

<210> SEQ ID NO 12
<211> LENGTH: 159
<212> TYPE: DNA
<213> ORGANISM: Artificial Sequence
<220> FEATURE:
<223> OTHER INFORMATION: PB1 Packaging Sequences of PR8 with XhoI
      restriction enzyme recognition site

<400> SEQUENCE: 12
ctcgagcccg aattgatgca cggattgatt tcgaatctgg aaggataaag aaagaagagt     60
tcactgagat catgaagatc tgttccacca ttgaagagct cagacggcaa aatagtgaa     120 tttagcttgt ccttcatgaa aaatgcctt gtttctact                            159

<210> SEQ ID NO 13
<211> LENGTH: 24
<212> TYPE: DNA
<213> ORGANISM: Influenza PR8 virus
<220> FEATURE:
<223> OTHER INFORMATION: 3 prime non-coding region (NCR) of PA Packaging
      Sequences of PR8

<400> SEQUENCE: 13
agcgaaagca ggtactgatc caaa                                            24

<210> SEQ ID NO 14
<211> LENGTH: 115
<212> TYPE: DNA
<213> ORGANISM: Influenza PR8 virus
<220> FEATURE:
<223> OTHER INFORMATION: 3 prime proximal coding region (NCR) of PA
      Packaging Sequences of PR8

<400> SEQUENCE: 14
ttggaagatt tgtgcgaca ttgcttcaat ccgttgattg tcgagcttgc ggaaaaaaca      60
ttgaaagagt tggggagga cctgaaaatc gaaacaaaca aatttgcagc aattt          115

<210> SEQ ID NO 15
<211> LENGTH: 145
<212> TYPE: DNA
<213> ORGANISM: Artificial Sequence
<220> FEATURE:

<223> OTHER INFORMATION: PA Packaging Sequences of PR8 with NheI
        restriction enzyme recognition site

<400> SEQUENCE: 15
agcgaaagca ggtactgatc caaattggaa gattttgtgc gacattgctt caatccgttg      60
attgtcgagc ttgcggaaaa aacattgaaa gagtttgggg aggacctgaa aatcgaaaca     120
aacaaatttg cagcaatttg ctagc                                           145

<210> SEQ ID NO 16
<211> LENGTH: 58
<212> TYPE: DNA
<213> ORGANISM: Influenza PR8 virus
<220> FEATURE:
<223> OTHER INFORMATION: 5 prime non-coding region (NCR) of PA Packaging
        Sequences of PR8

<400> SEQUENCE: 16
ttgtggcagt gctactattt gctatccata ctgtccaaaa aagtaccttg tttctact        58

<210> SEQ ID NO 17
<211> LENGTH: 120
<212> TYPE: DNA
<213> ORGANISM: Influenza PR8 virus
<220> FEATURE:
<223> OTHER INFORMATION: 5 prime proximal coding region (NCR) of PA
        Packaging Sequences of PR8

<400> SEQUENCE: 17
cctgggacct ttgatcttgg ggggctatat gaagcaattg aggagtgcct gattaatgat      60
ccctgggttt tgcttaatgc ttcttggttc aactccttcc ttacacatgc attgagttag    120

<210> SEQ ID NO 18
<211> LENGTH: 184
<212> TYPE: DNA
<213> ORGANISM: Artificial Sequence
<220> FEATURE:
<223> OTHER INFORMATION: PA Packaging Sequences of PR8 with XhoI
        restriction enzyme recognition site

<400> SEQUENCE: 18
ctcgagcctg ggacctttga tcttgggggg ctatatgaag caattgagga gtgcctgatt      60
aatgatccct gggttttgct taatgcttct tggttcaact ccttccttac acatgcattg    120
agttagttgt ggcagtgcta ctatttgcta tccatactgt ccaaaaaagt accttgtttc    180
tact                                                                 184

<210> SEQ ID NO 19
<211> LENGTH: 32
<212> TYPE: DNA
<213> ORGANISM: Influenza PR8 virus
<220> FEATURE:
<223> OTHER INFORMATION: 3 prime non-coding region (NCR) of HA Packaging
        Sequences of PR8

<400> SEQUENCE: 19
agcaaaagca ggggaaaata aaacaaccaa aa                                    32

<210> SEQ ID NO 20
<211> LENGTH: 67
<212> TYPE: DNA
<213> ORGANISM: Influenza PR8 virus
<220> FEATURE:
<223> OTHER INFORMATION: 3 prime proximal coding region (NCR) of HA
        Packaging Sequences of PR8

```
<400> SEQUENCE: 20
ttgaaggcaa acctactggt cctgttaagt gcacttgcag ctgcagttgc agacacaatt    60
tgtatag                                                              67

<210> SEQ ID NO 21
<211> LENGTH: 105
<212> TYPE: DNA
<213> ORGANISM: Artificial Sequence
<220> FEATURE:
<223> OTHER INFORMATION: HA Packaging Sequences of PR8 with NheI
      restriction enzyme recognition site

<400> SEQUENCE: 21
agcaaaagca ggggaaaata aaacaacca aattgaaggc aaacctactg gtcctgttaa    60
gtgcacttgc agctgcagtt gcagacacaa tttgtatagg ctagc                  105

<210> SEQ ID NO 22
<211> LENGTH: 45
<212> TYPE: DNA
<213> ORGANISM: Influenza PR8 virus
<220> FEATURE:
<223> OTHER INFORMATION: 5 prime non-coding region (NCR) of HA Packaging
      Sequences of PR8

<400> SEQUENCE: 22
gattagaatt tcagaaatat gaggaaaaac acccttgttt ctact                   45

<210> SEQ ID NO 23
<211> LENGTH: 105
<212> TYPE: DNA
<213> ORGANISM: Influenza PR8 virus
<220> FEATURE:
<223> OTHER INFORMATION: 5 prime proximal coding region (NCR) of HA
      Packaging Sequences of PR8

<400> SEQUENCE: 23
atctactcaa ctgtcgccag ttcactggtg cttttggtct ccctgggggc aatcagtttc    60
tggatgtgtt ctaatggatc tttgcagtgc agaatatgca tctga                  105

<210> SEQ ID NO 24
<211> LENGTH: 156
<212> TYPE: DNA
<213> ORGANISM: Artificial Sequence
<220> FEATURE:
<223> OTHER INFORMATION: HA Packaging Sequences of PR8 with XhoI
      restriction enzyme recognition site

<400> SEQUENCE: 24
ctcgagatct actcaactgt cgccagttca ctggtgcttt tggtctccct gggggcaatc    60
agtttctgga tgtgttctaa tggatctttg cagtgcagaa tatgcatctg agattagaat  120
ttcagaaata tgaggaaaaa cacccttgtt tctact                            156

<210> SEQ ID NO 25
<211> LENGTH: 45
<212> TYPE: DNA
<213> ORGANISM: Influenza PR8 virus
<220> FEATURE:
<223> OTHER INFORMATION: 3 prime non-coding region (NCR) of NP Packaging
      Sequences of PR8

<400> SEQUENCE: 25
agcaaaagca gggtagataa tcactcactg agtgacatca aaatc                   45
```

<210> SEQ ID NO 26
<211> LENGTH: 126
<212> TYPE: DNA
<213> ORGANISM: Influenza PR8 virus
<220> FEATURE:
<223> OTHER INFORMATION: 3 prime proximal coding region (NCR) of NP
      Packaging Sequences of PR8

<400> SEQUENCE: 26
ttggcgtccc aaggcaccaa acggtcttac gaacagttgg agactgttgg agaacgccag    60
attgccactg aaatcagagc atccgtcgga aaattgattg gtggaattgg acgattctac   120
atccaa                                                              126

<210> SEQ ID NO 27
<211> LENGTH: 177
<212> TYPE: DNA
<213> ORGANISM: Artificial Sequence
<220> FEATURE:
<223> OTHER INFORMATION: NP Packaging Sequences of PR8 with NheI
      restriction enzyme recognition site

<400> SEQUENCE: 27
agcaaaagca gggtagataa tcactcactg agtgacatca aaatcttggc gtcccaaggc    60
accaaacggt cttacgaaca gttggagact gttggagaac gccagattgc cactgaaatc   120
agagcatccg tcggaaaatt gattggtgga attggacgat tctacatcca agctagc     177

<210> SEQ ID NO 28
<211> LENGTH: 23
<212> TYPE: DNA
<213> ORGANISM: Influenza PR8 virus
<220> FEATURE:
<223> OTHER INFORMATION: 5 prime non-coding region (NCR) of NP Packaging
      Sequences of PR8

<400> SEQUENCE: 28
agaaaaatac ccttgtttct act                                            23

<210> SEQ ID NO 29
<211> LENGTH: 120
<212> TYPE: DNA
<213> ORGANISM: Influenza PR8 virus
<220> FEATURE:
<223> OTHER INFORMATION: 5 prime proximal coding region (NCR) of NP
      Packaging Sequences of PR8

<400> SEQUENCE: 29
gggcggggag tcttcgagct ctcggacgaa aaggcagcga gcccgatcgt gccttccttt    60
gacatgagta atgaaggatc ttatttcttc ggagacaatg cagaggagta cgacaattaa   120

<210> SEQ ID NO 30
<211> LENGTH: 149
<212> TYPE: DNA
<213> ORGANISM: Artificial Sequence
<220> FEATURE:
<223> OTHER INFORMATION: NP Packaging Sequences of PR8 with XhoI
      restriction enzyme recognition site

<400> SEQUENCE: 30
ctcgaggggc ggggagtctt cgagctctcg gacgaaaagg cagcgagccc gatcgtgcct    60
tcctttgaca tgagtaatga aggatcttat ttcttcggag acaatgcaga ggagtacgac   120
aattaaagaa aaatacccct tgtttctact                                    149

<210> SEQ ID NO 31
<211> LENGTH: 20
<212> TYPE: DNA
<213> ORGANISM: Influenza PR8 virus
<220> FEATURE:
<223> OTHER INFORMATION: 3 prime non-coding region (NCR) of NA Packaging
      Sequences of PR8

<400> SEQUENCE: 31
agcgaaagca ggggtttaaa                                                    20

<210> SEQ ID NO 32
<211> LENGTH: 111
<212> TYPE: DNA
<213> ORGANISM: Influenza PR8 virus
<220> FEATURE:
<223> OTHER INFORMATION: 3 prime proximal coding region (NCR) of NA
      Packaging Sequences of PR8

<400> SEQUENCE: 32
ttgaatccaa atcagaaaat aacaaccatt ggatcaatct gtctggtagt cggactaatt        60
agcctaatat tgcaaatagg gaatataatc tcaatttgga ttagccattc a                111

<210> SEQ ID NO 33
<211> LENGTH: 137
<212> TYPE: DNA
<213> ORGANISM: Artificial Sequence
<220> FEATURE:
<223> OTHER INFORMATION: NA Packaging Sequences of PR8 with NheI
      restriction enzyme recognition site

<400> SEQUENCE: 33
agcgaaagca ggggtttaaa ttgaatccaa atcagaaaat aacaaccatt ggatcaatct        60
gtctggtagt cggactaatt agcctaatat tgcaaatagg gaatataatc tcaatttgga       120
ttagccattc agctagc                                                      137

<210> SEQ ID NO 34
<211> LENGTH: 28
<212> TYPE: DNA
<213> ORGANISM: Influenza PR8 virus
<220> FEATURE:
<223> OTHER INFORMATION: 5 prime non-coding region (NCR) of NA Packaging
      Sequences of PR8

<400> SEQUENCE: 34
tctgttcaaa aaactccttg tttctact                                           28

<210> SEQ ID NO 35
<211> LENGTH: 157
<212> TYPE: DNA
<213> ORGANISM: Influenza PR8 virus
<220> FEATURE:
<223> OTHER INFORMATION: 5 prime proximal coding region (NCR) of NA
      Packaging Sequences of PR8

<400> SEQUENCE: 35
gaggccgtgc ttctgggttg aattaatcag gggacgacct aaagaaaaaa caatctggac        60
tagtgcgagc agcatttctt tttgtggcgt gaatagtgat actgtagatt ggtcttggcc       120
agacggtgct gagttgccat tcagcattga caagtag                                157

<210> SEQ ID NO 36
<211> LENGTH: 191

```
<212> TYPE: DNA
<213> ORGANISM: Artificial Sequence
<220> FEATURE:
<223> OTHER INFORMATION: NA Packaging Sequences of PR8 with XhoI
      restriction enzyme recognition site

<400> SEQUENCE: 36
ctcgaggagg ccgtgcttct gggttgaatt aatcagggga cgacctaaag aaaaaacaat     60
ctggactagt gcgagcagca tttctttttg tggcgtgaat agtgatactg tagattggtc    120
ttggccagac ggtgctgagt tgccattcag cattgacaag tagtctgttc aaaaaactcc    180
ttgtttctac t                                                         191

<210> SEQ ID NO 37
<211> LENGTH: 25
<212> TYPE: DNA
<213> ORGANISM: Influenza PR8 virus
<220> FEATURE:
<223> OTHER INFORMATION: 3 prime non-coding region (NCR) of M Packaging
      Sequences of PR8

<400> SEQUENCE: 37
agcgaaagca ggtagatatt gaaag                                           25

<210> SEQ ID NO 38
<211> LENGTH: 255
<212> TYPE: DNA
<213> ORGANISM: Influenza PR8 virus
<220> FEATURE:
<223> OTHER INFORMATION: 3 prime proximal coding region (NCR) of M
      Packaging Sequences of PR8

<400> SEQUENCE: 38
ttgagtcttc taaccgaggt cgaaacctac gtactctcta tcatcccgtc aggccccctc     60
aaagccgaga tcgcacagag acttgaagtt gtctttgcag ggaagaacac tgatcttgag    120
gttctcttgg attggctaaa gacaagacca atcctgtcac ctctgactaa ggggatttta    180
ggatttgtgt tcacgctcac cgtgcccagt gagcgaggac tgcagcgtag acgctttgtc    240
caaattgccc ttatt                                                     255

<210> SEQ ID NO 39
<211> LENGTH: 286
<212> TYPE: DNA
<213> ORGANISM: Artificial Sequence
<220> FEATURE:
<223> OTHER INFORMATION: M Packaging Sequences of PR8 with NheI
      restriction enzyme recognition site

<400> SEQUENCE: 39
agcgaaagca ggtagatatt gaaagttgag tcttctaacc gaggtcgaaa cctacgtact     60
ctctatcatc ccgtcaggcc ccctcaaagc cgagatcgca cagagacttg aagttgtctt    120
tgcagggaag aacactgatc ttgaggttct cttggattgg ctaaagacaa gaccaatcct    180
gtcacctctg actaagggga ttttaggatt tgtgttcacg ctcaccgtgc ccagtgagcg    240
aggactgcag cgtagacgct ttgtccaaat tgcccttatt gctagc                   286

<210> SEQ ID NO 40
<211> LENGTH: 20
<212> TYPE: DNA
<213> ORGANISM: Influenza PR8 virus
<220> FEATURE:
<223> OTHER INFORMATION: 5 prime non-coding region (NCR) of M Packaging
      Sequences of PR8
```

```
<400> SEQUENCE: 40
aaaactacct tgtttctact                                                    20

<210> SEQ ID NO 41
<211> LENGTH: 215
<212> TYPE: DNA
<213> ORGANISM: Influenza PR8 virus
<220> FEATURE:
<223> OTHER INFORMATION: 5 prime proximal coding region (NCR) of M
      Packaging Sequences of PR8

<400> SEQUENCE: 41
ctattgccgc aaatatcatt gggatcttgc acttgacatt gtggattctt gatcgtcttt        60
ttttcaaatg catttaccgt cgctttaaat acggactgaa aggagggcct tctacggaag       120
gagtgccaaa gtctatgagg gaagaatatc gaaaggaaca gcagagtgct gtggatgctg       180
acgatggtca ttttgtcagc atagagctgg agtaa                                  215

<210> SEQ ID NO 42
<211> LENGTH: 241
<212> TYPE: DNA
<213> ORGANISM: Artificial Sequence
<220> FEATURE:
<223> OTHER INFORMATION: M Packaging Sequences of PR8 with XhoI
      restriction enzyme recognition site

<400> SEQUENCE: 42
ctcgagctat tgccgcaaat atcattggga tcttgcactt gacattgtgg attcttgatc        60
gtcttttttt caaatgcatt taccgtcgct ttaaatacgg actgaaagga gggccttcta       120
cggaaggagt gccaaagtct atgagggaag aatatcgaaa ggaacagcag agtgctgtgg       180
atgctgacga tggtcatttt gtcagcatag agctggagta aaaaactacc ttgtttctac       240
t                                                                       241

<210> SEQ ID NO 43
<211> LENGTH: 26
<212> TYPE: DNA
<213> ORGANISM: Influenza PR8 virus
<220> FEATURE:
<223> OTHER INFORMATION: 3 prime non-coding region (NCR) of NS Packaging
      Sequences of PR8

<400> SEQUENCE: 43
agcaaaagca gggtgacaaa gacata                                             26

<210> SEQ ID NO 44
<211> LENGTH: 77
<212> TYPE: DNA
<213> ORGANISM: Influenza PR8 virus
<220> FEATURE:
<223> OTHER INFORMATION: 3 prime proximal coding region (NCR) of NS
      Packaging Sequences of PR8

<400> SEQUENCE: 44
ttggatccaa acactgtgtc aagctttcag ctagattgct ttctttggct tgtccgcaaa        60
cgagttgcag accaaga                                                       77

<210> SEQ ID NO 45
<211> LENGTH: 109
<212> TYPE: DNA
<213> ORGANISM: Artificial Sequence
<220> FEATURE:
```

-continued

<223> OTHER INFORMATION: NS Packaging Sequences of PR8 with NheI restriction enzyme recognition site

<400> SEQUENCE: 45
agcaaaagca gggtgacaaa gacatattgg atccaaacac tgtgtcaagc tttcagctag 60
attgctttct ttggcttgtc cgcaaacgag ttgcagacca agagctagc 109

<210> SEQ ID NO 46
<211> LENGTH: 26
<212> TYPE: DNA
<213> ORGANISM: Influenza PR8 virus
<220> FEATURE:
<223> OTHER INFORMATION: 5 prime non-coding region (NCR) of NS Packaging Sequences of PR8

<400> SEQUENCE: 46
taataaaaaa cacccttgtt tctact 26

<210> SEQ ID NO 47
<211> LENGTH: 102
<212> TYPE: DNA
<213> ORGANISM: Influenza PR8 virus
<220> FEATURE:
<223> OTHER INFORMATION: 5 prime proximal coding region (NCR) of NS Packaging Sequences of PR8

<400> SEQUENCE: 47
ataacagaga atagttttga gcaaataaca tttatgcaag ccttacatct attgcttgaa 60
gtggagcaag agataagaac tttctcgttt cagcttattt aa 102

<210> SEQ ID NO 48
<211> LENGTH: 134
<212> TYPE: DNA
<213> ORGANISM: Artificial Sequence
<220> FEATURE:
<223> OTHER INFORMATION: NS Packaging Sequences of PR8 with XhoI restriction enzyme recognition site

<400> SEQUENCE: 48
ctcgagataa cagagaatag ttttgagcaa ataacattta tgcaagcctt acatctattg 60
cttgaagtgg agcaagagat aagaactttc tcgtttcagc ttatttaata ataaaaaaca 120
cccttgtttc tact 134

<210> SEQ ID NO 49
<211> LENGTH: 33
<212> TYPE: DNA
<213> ORGANISM: Influenza PR8 virus
<220> FEATURE:
<223> OTHER INFORMATION: Wild-type ORF 3 prime termini sequence

<400> SEQUENCE: 49
atggaaagaa taaaagaact aagaaatcta atg 33

<210> SEQ ID NO 50
<211> LENGTH: 33
<212> TYPE: DNA
<213> ORGANISM: Artificial Sequence
<220> FEATURE:
<223> OTHER INFORMATION: mutated ORF 3 prime termini sequence for PB2

<400> SEQUENCE: 50
atggagcgga tcaaggagtt gcggaacttg atg 33

```
<210> SEQ ID NO 51
<211> LENGTH: 87
<212> TYPE: DNA
<213> ORGANISM: Influenza PR8 virus
<220> FEATURE:
<223> OTHER INFORMATION: Wild-type ORF 5 prime termini sequence for PB2

<400> SEQUENCE: 51
gtgttggtaa tgaaacggaa acgggactct agcatactta ctgacagcca gacagcgacc      60
aaaagaattc ggatggccat caattag                                         87

<210> SEQ ID NO 52
<211> LENGTH: 87
<212> TYPE: DNA
<213> ORGANISM: Artificial Sequence
<220> FEATURE:
<223> OTHER INFORMATION: mutated ORF 5 prime termini sequence for PB2

<400> SEQUENCE: 52
gtactagtga tgaagagaaa gagagatagc tctatcttga cggattcaca aacggcaact      60
aagaggatcc gtatggctat taactag                                         87

<210> SEQ ID NO 53
<211> LENGTH: 66
<212> TYPE: DNA
<213> ORGANISM: Influenza PR8 virus
<220> FEATURE:
<223> OTHER INFORMATION: Wild-type ORF 3 prime termini sequence for PB1

<400> SEQUENCE: 53
atggatgtca atccgacctt actttcttaa aaagtgccag cacaaaatgc tataagcaca      60
actttc                                                                66

<210> SEQ ID NO 54
<211> LENGTH: 66
<212> TYPE: DNA
<213> ORGANISM: Artificial Sequence
<220> FEATURE:
<223> OTHER INFORMATION: mutated ORF 3 prime termini sequence for PB1

<400> SEQUENCE: 54
atggacgtta acccaactct gttatttctg aaggtaccgg cgcagaacgc catcagtacg      60
acctttt                                                               66

<210> SEQ ID NO 55
<211> LENGTH: 42
<212> TYPE: DNA
<213> ORGANISM: Influenza PR8 virus
<220> FEATURE:
<223> OTHER INFORMATION: Wild-type ORF 5 prime termini sequence for PB1

<400> SEQUENCE: 55
aagatctgtt ccaccattga agagctcaga cggcaaaaat ag                        42

<210> SEQ ID NO 56
<211> LENGTH: 42
<212> TYPE: DNA
<213> ORGANISM: Artificial Sequence
<220> FEATURE:
<223> OTHER INFORMATION: mutated ORF 5 prime termini sequence for PB1

<400> SEQUENCE: 56
aaaatttgca gtacaatcga ggaacttcgg agacagaagt ag                        42
```

<210> SEQ ID NO 57
<211> LENGTH: 66
<212> TYPE: DNA
<213> ORGANISM: Influenza PR8 virus
<220> FEATURE:
<223> OTHER INFORMATION: Wild-type ORF 3 prime termini sequence for PA

<400> SEQUENCE: 57
atggaagatt tgtgcgaca atgcttcaat ccgatgattg tcgagcttgc ggaaaaaaca    60
atgaaa                                                              66

<210> SEQ ID NO 58
<211> LENGTH: 66
<212> TYPE: DNA
<213> ORGANISM: Artificial Sequence
<220> FEATURE:
<223> OTHER INFORMATION: mutated ORF 3 prime termini sequence for PA

<400> SEQUENCE: 58
atggaggact tcgtaaggca gtgttttaac ccaatgatcg ttgaactcgc agagaagacg 60
atgaag 66

<210> SEQ ID NO 59
<211> LENGTH: 45
<212> TYPE: DNA
<213> ORGANISM: Influenza PR8 virus
<220> FEATURE:
<223> OTHER INFORMATION: Wild-type ORF 5 prime termini sequence for PA

<400> SEQUENCE: 59
aatgcttctt ggttcaactc cttccttaca catgcattga gttag 45

<210> SEQ ID NO 60
<211> LENGTH: 45
<212> TYPE: DNA
<213> ORGANISM: Artificial Sequence
<220> FEATURE:
<223> OTHER INFORMATION: mutated ORF 5 prime termini sequence for PA

<400> SEQUENCE: 60
aacgccagct ggtttaattc ttttttgacg cacgcgctat catag 45

<210> SEQ ID NO 61
<211> LENGTH: 48
<212> TYPE: DNA
<213> ORGANISM: Influenza PR8 virus
<220> FEATURE:
<223> OTHER INFORMATION: Wild-type ORF 3 prime termini sequence for HA

<400> SEQUENCE: 61
atgaaggcaa acctactggt cctgttaagt gcacttgcag ctgcagat 48

<210> SEQ ID NO 62
<211> LENGTH: 48
<212> TYPE: DNA
<213> ORGANISM: Artificial Sequence
<220> FEATURE:
<223> OTHER INFORMATION: mutated ORF 3 prime termini sequence for HA

<400> SEQUENCE: 62
atgaaagcga atttgttagt tttactgtcc gcgttggcgg ccgcggac 48

<210> SEQ ID NO 63
<211> LENGTH: 90

```
<212> TYPE: DNA
<213> ORGANISM: Influenza PR8 virus
<220> FEATURE:
<223> OTHER INFORMATION: Wild-type ORF 5 prime termini sequence for HA

<400> SEQUENCE: 63
gccagttcac tggtgctttt ggtctccctg ggggcaatca gtttctggat gtgttctaat      60
ggatctttgc agtgcagaat atgcatctga                                       90

<210> SEQ ID NO 64
<211> LENGTH: 90
<212> TYPE: DNA
<213> ORGANISM: Artificial Sequence
<220> FEATURE:
<223> OTHER INFORMATION: mutated ORF 5 prime termini sequence for HA

<400> SEQUENCE: 64
gcttccagct tagtattgct agttagttta ggagcgattt ccttttggat gtgcagcaac      60
gggagcctac aatgtcggat ttgtatttga                                       90

<210> SEQ ID NO 65
<211> LENGTH: 60
<212> TYPE: DNA
<213> ORGANISM: Influenza PR8 virus
<220> FEATURE:
<223> OTHER INFORMATION: Wild-type ORF 3 prime termini sequence for NP

<400> SEQUENCE: 65
atggcgtccc aaggcaccaa acggtcttac gaacagatgg agactgatgg agaacgccag      60

<210> SEQ ID NO 66
<211> LENGTH: 60
<212> TYPE: DNA
<213> ORGANISM: Artificial Sequence
<220> FEATURE:
<223> OTHER INFORMATION: mutated ORF 3 prime termini sequence for NP

<400> SEQUENCE: 66
atggcaagtc agggtactaa gagaagctat gagcaaatgg aaaccgacgg ggagagacaa      60

<210> SEQ ID NO 67
<211> LENGTH: 63
<212> TYPE: DNA
<213> ORGANISM: Influenza PR8 virus
<220> FEATURE:
<223> OTHER INFORMATION: Wild-type ORF 5 prime termini sequence for NP

<400> SEQUENCE: 67
tttgacatga gtaatgaagg atcttatttc ttcggagaca atgcagagga gtacgacaat      60
taa                                                                    63

<210> SEQ ID NO 68
<211> LENGTH: 63
<212> TYPE: DNA
<213> ORGANISM: Artificial Sequence
<220> FEATURE:
<223> OTHER INFORMATION: mutated ORF 5 prime termini sequence for NP

<400> SEQUENCE: 68
ttcgatatgt ccaacgaggg gagctacttt tttggggata acgcggaaga atatgataac      60
taa                                                                    63

<210> SEQ ID NO 69
```

```
<211> LENGTH: 60
<212> TYPE: DNA
<213> ORGANISM: Influenza PR8 virus
<220> FEATURE:
<223> OTHER INFORMATION: Wild-type ORF 3 prime termini sequence for NA

<400> SEQUENCE: 69
atgaatccaa atcagaaaat aacaaccatt ggatcaatct gtctggtagt cggactaatt    60

<210> SEQ ID NO 70
<211> LENGTH: 60
<212> TYPE: DNA
<213> ORGANISM: Artificial Sequence
<220> FEATURE:
<223> OTHER INFORMATION: mutated ORF 3 prime termini sequence for NA

<400> SEQUENCE: 70
atgaacccga accaaaagat cacgactatc gggagcattt gcttagtggt tgggttgatc    60

<210> SEQ ID NO 71
<211> LENGTH: 60
<212> TYPE: DNA
<213> ORGANISM: Influenza PR8 virus
<220> FEATURE:
<223> OTHER INFORMATION: Wild-type ORF 5 prime termini sequence for NA

<400> SEQUENCE: 71
gatactgtag attggtcttg gccagacggt gctgagttgc cattcagcat tgacaagtag    60

<210> SEQ ID NO 72
<211> LENGTH: 60
<212> TYPE: DNA
<213> ORGANISM: Artificial Sequence
<220> FEATURE:
<223> OTHER INFORMATION: mutated ORF 5 prime termini sequence for NA

<400> SEQUENCE: 72
gacaccgtag actggagctg gccggatggc gccgaactac cgttttctat cgataaatag    60

<210> SEQ ID NO 73
<211> LENGTH: 63
<212> TYPE: DNA
<213> ORGANISM: Influenza PR8 virus
<220> FEATURE:
<223> OTHER INFORMATION: Wild-type ORF 3 prime termini sequence for M

<400> SEQUENCE: 73
atgagtcttc taaccgaggt cgaaacgtac gtactctcta tcatcccgtc aggccccctc    60
aaa                                                                  63

<210> SEQ ID NO 74
<211> LENGTH: 63
<212> TYPE: DNA
<213> ORGANISM: Artificial Sequence
<220> FEATURE:
<223> OTHER INFORMATION: mutated ORF 3 prime termini sequence for M

<400> SEQUENCE: 74
atgagcttgt tgactgaagt cgaaacgtac gtattgagca ttattccaag tggtcccttta   60 aag                                                                  63

<210> SEQ ID NO 75
<211> LENGTH: 60
<212> TYPE: DNA
<213> ORGANISM: Influenza PR8 virus
```

```
<220> FEATURE:
<223> OTHER INFORMATION: Wild-type ORF 5 prime termini sequence for M

<400> S

<210> SEQ ID NO 82
<211> LENGTH: 1698
<212> TYPE: DNA
<213> ORGANISM: Influenza virus A/WSN/33
<220> FEATURE:
<223> OTHER INFORMATION: ORF of Influenza virus A/WSN/33 NA gene segment

<400> SEQUENCE: 82

| | |
|---|---|
| atgaaggcaa aactactggt cctgttatat gcatttgtag ctacagatgc agacacaata | 60 |
| tgtataggct accatgcgaa caactcaacc gacactgttg acacaatatt cgagaagaat | 120 |
| gtggcagtga cacattctgt taacctgctc gaagacagac acaacgggaa actatgtaaa | 180 |
| ttaaaaggaa tagccccact acaattgggg aaatgtaaca tcaccggatg gctcttggga | 240 |
| aatccagaat gcgactcact gcttccagcg agatcatggt cctacattgt agaaacacca | 300 |
| aactctgaga atggagcatg ttatccagga gatttcatcg actatgagga actgagggag | 360 |
| caattgagct cagtatcatc attagaaaga ttcgaaatat ttcccaagga agttcatgg | 420 |
| cccaaccaca cattcaacgg agtaacagta tcatgctccc ataggggaaa aagcagtttt | 480 |
| tacagaaatt tgctatggct gacgaagaag ggggattcat acccaaagct gaccaattcc | 540 |
| tatgtgaaca ataaagggaa agaagtcctt gtactatggg tgttcatca cccgtccagc | 600 |
| agtgatgagc aacagagtct ctatagtaat ggaaatgctt atgtctctgt agcgtcttca | 660 |
| aattataaca ggagattcac cccggaaata gctgcaaggc ccaaagtaaa agatcaacat | 720 |
| gggaggatga actattactg gaccttgcta gaacccggag acacaataat atttgaggca | 780 |
| actggtaatc taatagcacc atggtatgct ttcgcactga gtagagggtt tgagtccggc | 840 |
| atcatcacct caaacgcgtc aatgcatgag tgtaacacga agtgtcaaac accccaggga | 900 |
| tctataaaca gcaatctccc tttccagaat atacacccag tcacaatagg agagtgccca | 960 |
| aaatatgtca ggagtaccaa attgaggatg gttacaggac taagaaacat cccatccatt | 1020 |
| caatacagag gtctatttgg agccattgct ggttttattg agggggatg gactggaatg | 1080 |
| atagatggat ggtatggtta tcatcatcag aatgaacagg gatcaggcta tgcagcggat | 1140 |
| caaaaaagca cacagaatgc cattaacggg attacaaaca aggtgaactc tgttatcgag | 1200 |
| aaaatgaaca ctcaattcac agctgtgggt aaagaattca acaacttaga aaaaggatg | 1260 |
| gaaaatttaa ataaaaaagt tgatgatggg tttctggaca tttggacata taatgcagaa | 1320 |
| ttgttagttc tactggaaaa tgaaagaact ttggatttcc atgacttaaa tgtgaagaat | 1380 |
| ctgtacgaga aagtaaaaag ccaattaaag aataatgcca agaaatcgg aaatgggtgt | 1440 |
| tttgagttct accacaagtg tgacaatgaa tgcatggaaa gtgtaagaaa tgggacttat | 1500 |
| gattatccaa atattcaga agaatcaaag ttgaacaggg aaaagataga tggagtgaaa | 1560 |
| ttggaatcaa tggggtgta tcagattctg gcgatctact caactgtcgc cagttcactg | 1620 |
| gtgcttttgg tctccctggg ggcaatcagt tctggatgt gttctaatgg gtctttgcag | 1680 |
| tgcagaatat gcatctga | 1698 |

<210> SEQ ID NO 83
<211> LENGTH: 45
<212> TYPE: DNA
<213> ORGANISM: Influenza virus A/WSN/33
<220> FEATURE:
<223> OTHER INFORMATION: 5 prime NCR of Influenza virus A/WSN/33 HA gene segment

<400> SEQUENCE: 83

```
gattaggatt tcagaaatat aaggaaaaac acccttgttt ctact              45
```

<210> SEQ ID NO 84
<211> LENGTH: 1775
<212> TYPE: DNA
<213> ORGANISM: Influenza virus A/WSN/33
<220> FEATURE:
<223> OTHER INFORMATION: Influenza virus A/WSN/33 HA gene segment

<400> SEQUENCE: 84

```
agcaaaagca ggggaaaata aaaacaacca aaatgaaggc aaaactactg gtcctgttat    60
atgcatttgt agctacagat gcagacacaa tatgtatagg ctaccatgcg aacaactcaa   120
ccgacactgt tgacacaata ttcgagaaga atgtggcagt gacacattct gttaacctgc   180
tcgaagacag acacaacggg aaactatgta aattaaaagg aatagcccca ctacaattgg   240
ggaaatgtaa catcaccgga tggctcttgg gaaatccaga atgcgactca ctgcttccag   300
cgagatcatg gtcctacatt gtagaaacac caaactctga gatggagca tgttatccag   360
gagatttcat cgactatgag gaactgaggg agcaattgag ctcagtatca tcattagaaa   420
gattcgaaat atttcccaag gaaagttcat ggcccaacca cattcaac ggagtaacag   480
tatcatgctc ccataggga aaaagcagtt tttacagaaa tttgctatgg ctgacgaaga   540
aggggggattc atacccaag ctgaccaatt cctatgtgaa caataaaggg aaagaagtcc   600
ttgtactatg gggtgttcat cacccgtcca gcagtgatga gcaacagagt ctctatagta   660
atggaaatgc ttatgtctct gtagcgtctt caaattataa caggagattc accccggaaa   720
tagctgcaag gcccaaagta aagatcaac atgggaggat gaactattac tggaccttgc   780
tagaacccgg agacacaata atatttgagg caactggtaa tctaatagca ccatggtatg   840
ctttcgcact gagtagaggg tttgagtccg gcatcatcac ctcaaacgcg tcaatgcatg   900
agtgtaacac gaagtgtcaa acacccccagg gatctataaa cagcaatctc cctttccaga   960
atatacaccc agtcacaata ggagagtgcc caaaatatgt caggagtacc aaattgagga  1020
tggttacagg actaagaaac atcccatcca ttcaatacag aggtctattt ggagccattg  1080
ctggttttat tgagggggga tggactggaa tgatagatgg atggtatggt tatcatcatc  1140
agaatgaaca gggatcaggc tatgcagcgg atcaaaaaag cacacagaat gccattaacg  1200
ggattacaaa caaggtgaac tctgttatcg agaaaatgaa cactcaattc acagctgtgg  1260
gtaaagaatt caacaactta gaaaaaagga tggaaatttt aataaaaaa gttgatgatg  1320
ggtttctgga catttggaca tataatgcag aattgttagt tctactggaa aatgaaagaa  1380
ctttggattt ccatgactta atgtgaaga atctgtacga aaagtaaaa gccaattaa  1440
agaataatgc caaagaaatc ggaaatgggt gttttgagtt ctaccacaag tgtgacaatg  1500
aatgcatgga aagtgtaaga aatgggactt atgattatcc aaaatattca gaagaatcaa  1560
agttgaacag ggaaaagata gatggagtga aattggaatc aatgggggtg tatcagattc  1620
tggcgatcta ctcaactgtc gccagttcac tggtgctttt ggtctccctg ggggcaatca  1680
gtttctggat gtgttctaat gggtctttgc agtgcagaat atgcatctga gattaggatt  1740
tcagaaatat aaggaaaaac acccttgttt ctact                             1775
```

<210> SEQ ID NO 85
<211> LENGTH: 19
<212> TYPE: DNA
<213> ORGANISM: Influenza virus A/WSN/33
<220> FEATURE:

-continued

<223> OTHER INFORMATION: 3 prime NCR of Influenza virus A/WSN/33 NA gene
      segment

<400> SEQUENCE: 85
agcgaaagca ggagtttaa                                                  19

<210> SEQ ID NO 86
<211> LENGTH: 1362
<212> TYPE: DNA
<213> ORGANISM: Influenza virus A/WSN/33
<220> FEATURE:
<223> OTHER INFORMATION: ORF of Influenza virus A/WSN/33 NA gene segment

<400> SEQUENCE: 86
atgaatccaa accagaaaat aataaccatt gggtcaatct gtatggtagt cggaataatt      60
agcctaatat tgcaaatagg aaatataatc tcaatatgga ttagccattc aattcaaacc     120
ggaaatcaaa accatactgg aatatgcaac caaggcagca ttacctataa agttgttgct     180
gggcaggact caacttcagt gatattaacc ggcaattcat ctctttgtcc catccgtggg     240
tgggctatac acagcaaaga caatggcata agaattggtt ccaaaggaga cgttttttgtc    300 ataagagagc cttttatttc atgttctcac ttggaatgca ggaccttttt tctgactcaa     360
ggcgccttac tgaatgacaa gcattcaagg gggacccttta aggacagaag cccttatagg    420
gccttaatga gctgccctgt cggtgaagct ccgtccccgt acaattcaag gtttgaatcg     480
gttgcttggt cagcaagtgc atgtcatgat ggagtgggct ggctaacaat cggaatttct    540
ggtccagatg atggagcagt ggctgtatta aaatacaacc gcataataac tgaaaccata     600
aaaagttgga ggaagaatat attgagaaca caagagtctg aatgtacctg tgtaaatggt    660 tcatgttttta ccataatgac cgatggccca agtgatgggc tggcctcgta caaaattttc    720
aagatcgaga aggggaaggt tactaaatca atagagttga atgcacctaa ttctcactac    780
gaggaatgtt cctgttaccc tgataccggc aaagtgatgt gtgtgtgcag agacaattgg    840
cacggttcga accgaccatg ggtgtccttc gaccaaaacc tagattataa aataggatac    900
atctgcagtg gggttttcgg tgacaacccg cgtcccaaag atggaacagg cagctgtggc    960
ccagtgtctg ctgatggagc aaacggagta aagggatttt catataagta tggcaatggt   1020
gtttggatag aaggactaa aagtgacagt tccagacatg gtttgagat gatttgggat     1080 cctaatggat ggacagagac tgatagtagg ttctctatga caagatgt tgtggcaata     1140 actaatcggt cagggtacag cggaagttc gttcaacatc ctgagctaac agggctagac   1200
tgtatgaggc cttgcttctg ggttgaatta atcagggggc tacctgagga ggacgcaatc   1260
tggactagtg ggagcatcat ttcttttttgt ggtgtgaata gtgatactgt agattggtct   1320
tggccagacg gtgctgagtt gccgttcacc attgacaagt ag                      1362

<210> SEQ ID NO 87
<211> LENGTH: 28
<212> TYPE: DNA
<213> ORGANISM: Influenza virus A/WSN/33
<220> FEATURE:
<223> OTHER INFORMATION: 5 prime NCR of Influenza virus A/WSN/33 NA gene
      segment

<400> SEQUENCE: 87
tttgttcaaa aaactccttg tttctact                                       28

<210> SEQ ID NO 88
<211> LENGTH: 1409

<212> TYPE: DNA
<213> ORGANISM: Influenza virus A/WSN/33
<220> FEATURE:
<223> OTHER INFORMATION: Influenza virus A/WSN/33 NA gene segment

<400> SEQUENCE: 88

```
agcgaaagca ggagtttaaa tgaatccaaa ccagaaaata ataaccattg ggtcaatctg    60
tatggtagtc ggaataatta gcctaatatt gcaaatagga aatataatct caatatggat   120
tagccattca attcaaaccg gaaatcaaaa ccatactgga atatgcaacc aaggcagcat   180
tacctataaa gttgttgctg gcaggactca acttcagtg atattaaccg gcaattcatc   240
tctttgtccc atccgtgggt gggctataca cagcaaagac aatggcataa gaattggttc   300
caaaggagac gttttgtca taagagagcc ttttatttca tgttctcact ggaatgcag    360
gaccttttt ctgactcaag cgccttact gaatgacaag cattcaaggg ggacctttaa    420
ggacagaagc ccttataggg ccttaatgag ctgccctgtc ggtgaagctc cgtccccgta   480
caattcaagg tttgaatcgg ttgcttggtc agcaagtgca tgtcatgatg gagtgggctg   540
gctaacaatc ggaatttctg gtccagatga tgagcagtg gctgtattaa aatacaaccg   600
cataataact gaaaccataa aaagttggag gaagaatata ttgagaacac aagagtctga   660
atgtacctgt gtaaatggtt catgttttac cataatgacc gatggcccaa gtgatgggct   720
ggcctcgtac aaaattttca agatcgagaa ggggaaggtt actaaatcaa tagagttgaa   780
tgcacctaat tctcactacg aggaatgttc ctgttaccct gataccggca aagtgatgtg   840
tgtgtgcaga gacaattggc acggttcgaa ccgaccatgg gtgtccttcg accaaaacct   900
agattataaa ataggataca tctgcagtgg ggttttcggt gacaacccgc gtcccaaaga   960
tggaacaggc agctgtggcc cagtgtctgc tgatggagca aacggagtaa agggattttc  1020
atataagtat ggcaatggtg tttggatagg aaggactaaa agtgacagtt ccagacatgg  1080
gtttgagatg atttgggatc ctaatggatg acagagact gatagtaggt tctctatgag   1140
acaagatgtt gtggcaataa ctaatcggtc agggtacagc ggaagtttcg ttcaacatcc  1200
tgagctaaca gggctagact gtatgaggcc ttgcttctgg gttgaattaa tcagggggct  1260
acctgaggag gacgcaatct ggactagtgg gagcatcatt tcttttgtg gtgtgaatag  1320
tgatactgta gattggtctt ggccagacgg tgctgagttg ccgttcacca ttgacaagta  1380
gtttgttcaa aaaactcctt gtttctact                                    1409
```

<210> SEQ ID NO 89
<211> LENGTH: 25
<212> TYPE: DNA
<213> ORGANISM: Influenza virus A/WSN/33
<220> FEATURE:
<223> OTHER INFORMATION: 3 prime NCR of Influenza virus A/WSN/33 M gene segment

<400> SEQUENCE: 89

```
agcaaaagca ggtagatatt gaaag                                          25
```

<210> SEQ ID NO 90
<211> LENGTH: 982
<212> TYPE: DNA
<213> ORGANISM: Influenza virus A/WSN/33
<220> FEATURE:
<223> OTHER INFORMATION: ORF of Influenza virus A/WSN/33 M gene segment

<400> SEQUENCE: 90

```
atgagtcttc taaccgaggt cgaaacgtac gttctctcta tcgtcccgtc aggccccctc    60
```

```
aaagccgaga tcgcacagag acttgaagat gtctttgcag ggaagaacac cgatcttgag      120
gttctcatgg aatggctaaa gacaagacca atcctgtcac ctctgactaa ggggatttta      180
ggatttgtgt tcacgctcac cgtgcccagt gagcgggac tgcagcgtag acgctttgtc       240
caaaatgctc ttaatgggaa cggagatcca ataacatgg acaaagcagt taaactgtat       300
aggaagctta agagggagat aacattccat ggggccaaag aaatagcact cagttattct      360
gctggtgcac ttgccagttg tatgggcctc atatacaaca ggatggggc tgtggccact       420 gaagtggcat ttggcctggt atgcgcaacc tgtgaacaga ttgctgactc ccagcatcgg      480
tctcataggc aaatggtgac aacaaccaat ccactaatca gacatgagaa cagaatggtt      540
ctagccagca ctacagctaa ggctatggag caaatggctg gatcgagtga gcaagcagca     600
gaggccatgg atattgctag tcaggccagg caaatggtgc aggcgatgag aaccattggg      660
actcatccta gctccagtac tggtctaaaa gatgatcttc ttgaaaattt gcaggcctat     720
cagaaacgaa tggggtgca gatgcaacga ttcaagtgat cctctcgtta ttgcagcaaa      780
tatcattggg atcttgcact tgatattgtg gattcttgat cgtcttttt tcaaatgcat      840 ttatcgtcgc tttaaatacg gtttgaaaag agggccttct acggaaggag tgccagagtc      900
tatgagggaa gaatatcgaa aggaacagca gaatgctgtg gatgttgacg atggtcattt      960
tgtcaacata gagctggagt aa                                              982
```

<210> SEQ ID NO 91
<211> LENGTH: 20
<212> TYPE: DNA
<213> ORGANISM: Influenza virus A/WSN/33
<220> FEATURE:
<223> OTHER INFORMATION: 5 prime NCR of Influenza virus A/WSN/33 M gene
      segment

<400> SEQUENCE: 91

```
aaaactacct tgtttctact                                                  20
```

<210> SEQ ID NO 92
<211> LENGTH: 1027
<212> TYPE: DNA
<213> ORGANISM: Influenza virus A/WSN/33
<220> FEATURE:
<223> OTHER INFORMATION: Influenza virus A/WSN/33 M gene segment

<400> SEQUENCE: 92

```
agcaaaagca ggtagatatt gaaagatgag tcttctaacc gaggtcgaaa cgtacgttct      60
ctctatcgtc ccgtcaggcc ccctcaaagc cgagatcgca cagagacttg aagatgtctt     120
tgcagggaag aacaccgatc ttgaggttct catggaatgg ctaaagacaa gaccaatcct    180
gtcacctctg actaagggga ttttaggatt tgtgttcacg ctcaccgtgc ccagtgagcg      240
gggactgcag cgtagacgct ttgtccaaaa tgctcttaat gggaacggag atccaaataa      300
catggacaaa gcagttaaac tgtataggaa gcttaagagg gagataacat ccatggggc      360 caaagaaata gcactcagtt attctgctgg tgcacttgcc agttgtatgg gcctcatata      420
caacaggatg ggggctgtgg ccactgaagt ggcatttggc ctggtatgcg caacctgtga     480
acagattgct gactcccagc atcggtctca taggcaaatg gtgacaacaa ccaatccact      540
aatcagacat gagaacagaa tggttctagc cagcactaca gctaaggcta tggagcaaat      600
ggctggatcg agtgagcaag cagcagaggc catggatatt gctagtcagg ccaggcaaat     660
ggtgcaggcg atgagaacca ttgggactca tcctagctcc agtactggtc taaaagatga     720
```

```
tcttcttgaa aatttgcagg cctatcagaa acgaatgggg gtgcagatgc aacgattcaa      780
gtgatcctct cgttattgca gcaaatatca ttgggatctt gcacttgata ttgtggattc      840
ttgatcgtct tttttcaaa tgcatttatc gtcgctttaa atacggtttg aaaagagggc      900
cttctacgga aggagtgcca gagtctatga gggaagaata tcgaaggaa cagcagaatg       960 ctgtggatgt tgacgatggt cattttgtca acatagagct ggagtaaaaa actaccttgt     1020
ttctact                                                               1027
```

<210> SEQ ID NO 93
<211> LENGTH: 26
<212> TYPE: DNA
<213> ORGANISM: Influenza virus A/WSN/33
<220> FEATURE:
<223> OTHER INFORMATION: 3 prime NCR of Influenza virus A/WSN/33 NS gene segment

<400> SEQUENCE: 93

```
agcaaaagca gggtgacaaa gacata                                            26
```

<210> SEQ ID NO 94
<211> LENGTH: 838
<212> TYPE: DNA
<213> ORGANISM: Influenza virus A/WSN/33
<220> FEATURE:
<223> OTHER INFORMATION: ORF of Influenza virus A/WSN/33 NS gene segment

<400> SEQUENCE: 94

```
atggatccaa acactgtgtc aagctttcag gtagattgct ttctttggca tgtccgcaaa       60
agagttgcag accaagaact aggtgattcc ccattccttg atcggcttcg ccgagatcag      120
aagtccctaa gaggaagagg cagcactctc ggtctggaca tcgaaacagc cacccgtgct      180
ggaaagcaaa tagtggagcg gattctgaag gaagaatccg atgaggcact taaaatgacc      240
atggcctctg tacctgcatc gcgctaccta actgacatga ctcttgagga aatgtcaagg      300
cactggttca tgctcatgcc caagcagaaa gtggcaggcc ctctttgtat cagaatggac      360
caggcgatca tggataagaa catcatactg aaagcgaact cagtgtgat ttttgaccgg       420 ctggagactc taatattact aagggccttc accgaagagg gaacaattgt tggcgaaatt      480
tcaccactgc cttctcttcc aggacatact gatgaggatg tcaaaaatgc agttggggtc      540
ctcatcggag gacttgaatg gaataataac acagttcgag tctctgaaac tctacagaga      600
ttcgcttgga gaagcagtaa tgagaatggg agacctccac tcactccaaa acagaaacga      660
aaaatggcgg gaacaattag gtcagaagtt tgaagaaata agatggttga ttgaagaagt      720
gagacacaga ctgaagataa cagagaatag ttttgagcaa ataacattta tgcaagcctt      780
acaactattg cttgaagtgg agcaagagat aagaactttc tcgtttcagc ttatttaa       838
```

<210> SEQ ID NO 95
<211> LENGTH: 26
<212> TYPE: DNA
<213> ORGANISM: Influenza virus A/WSN/33
<220> FEATURE:
<223> OTHER INFORMATION: 5 prime NCR of Influenza virus A/WSN/33 NS gene segment

<400> SEQUENCE: 95

```
taataaaaaa caccettgtt tctact                                            26
```

<210> SEQ ID NO 96

```
<211> LENGTH: 890
<212> TYPE: DNA
<213> ORGANISM: Influenza virus A/WSN/33
<220> FEATURE:
<223> OTHER INFORMATION: Influenza virus A/WSN/33 NS gene segment

<400> SEQUENCE: 96
agcaaaagca gggtgacaaa gacataatgg atccaaacac tgtgtcaagc tttcaggtag      60
attgctttct ttggcatgtc cgcaaaagag ttgcagacca agaactaggt gattccccat     120
tccttgatcg gcttcgccga gatcagaagt ccctaagagg aagaggcagc actctcggtc     180
tggacatcga acagccacc cgtgctggaa agcaaatagt ggagcggatt ctgaaggaag      240
aatccgatga ggcacttaaa atgaccatgg cctctgtacc tgcatcgcgc tacctaactg     300
acatgactct tgaggaaatg tcaaggcact ggttcatgct catgcccaag cagaaagtgg     360
caggccctct ttgtatcaga atggaccagg cgatcatgga taagaacatc atactgaaag     420
cgaacttcag tgtgattttt gaccggctgg agactctaat attactaagg gccttcaccg     480
aagagggaac aattgttggc gaaatttcac cactgccttc tcttccagga catactgatg     540
aggatgtcaa aaatgcagtt ggggtcctca tcggaggact tgaatggaat aataacacag     600
ttcgagtctc tgaaactcta cagagattcg cttggagaag cagtaatgag aatgggagac     660
ctccactcac tccaaaacag aaacgaaaaa tggcgggaac aattaggtca gaagtttgaa     720
gaaataagat ggttgattga agaagtgaga cacagactga gataacaga aatagtttt      780 gagcaaataa catttatgca agccttacaa ctattgcttg aagtggagca agagataaga     840
actttctcgt tcagcttat ttaataataa aaaacacccct tgtttctact                890

<210> SEQ ID NO 97
<211> LENGTH: 24
<212> TYPE: DNA
<213> ORGANISM: Influenza virus A/WSN/33
<220> FEATURE:
<223> OTHER INFORMATION: 3 prime NCR of Influenza virus A/WSN/33 PA gene
      segment

<400> SEQUENCE: 97
agcgaaagca ggtactgatt caaa                                             24

<210> SEQ ID NO 98
<211> LENGTH: 2151
<212> TYPE: DNA
<213> ORGANISM: Influenza virus A/WSN/33
<220> FEATURE:
<223> OTHER INFORMATION: ORF of Influenza virus A/WSN/33 PA gene segment

<400> SEQUENCE: 98
atggaagatt ttgtgcgaca atgcttcaat ccgatgattg tcgagcttgc ggaaaaggca      60
atgaaagagt atggagagga cctgaaaatc gaaacaaaca atttgcagc aatatgcact     120 cacttggaag tgtgcttcat gtattcagat tttcacttca tcgatgagca aggcgagtca     180
atagtcgtag aacttggcga tccaaatgca cttttgaagc acagatttga ataatcgag     240 ggaagagatc gcacaatagc ctggacagta ataaacagta tttgcaacac tacaggggct     300
gagaaaccaa agtttctacc agatttgtat gattacaaga gaatagatt catcgaaatt     360 ggagtaacaa ggagagaagt tcacatatac tatctggaaa aggccaataa aattaaatct     420
gagaagacac acatccacat tttctcattc actggggagg aaatggccac aaaggccgac     480
tacactctcg atgaagaaag cagggctagg atcaaaacca ggctattcac cataagacaa     540
```

| | |
|---|---|
| gaaatggcta gcagaggcct ctgggattcc tttcgtcagt ccgagagagg cgaagagaca | 600 |
| attgaagaaa gatttgaaat cacaggaaca atgcgcaagc ttgccgacca aagtctcccg | 660 |
| ccaaacttct ccagccttga aaattttaga gcctatgtgg atggattcga accgaacggc | 720 |
| tacattgagg gcaagctttc tcaaatgtcc aaagaagtaa atgctagaat tgaaccttttc | 780 |
| ttgaaatcaa caccacgacc acttagactt ccggatgggc ctccctgttc tcagcggtcc | 840 |
| aaattcctgc tgatggatgc cttaaaatta agcattgagg acccaagtca tgagggagag | 900 |
| gggataccgc tatatgatgc aatcaaatgc atgagaacat tctttggatg gaaggaaccc | 960 |
| aatgttgtta aaccacacga aagggaata aatccaaatt atcttctgtc atggaagcaa | 1020 |
| gtactggcag aactgcagga cattgagaat gaggagaaaa ttccaaggac taaaaatatg | 1080 |
| aagaaaacga gtcagttaaa gtgggcactt ggtgagaaca tggcaccaga aaaggtagac | 1140 |
| tttgacgatt gtaaagatgt aggcgatttg aagcaatatg atagtgatga accagaattg | 1200 |
| aggtcgcttg caagttggat tcagaatgag ttcaacaagg catgtgaact gaccgattca | 1260 |
| agctggatag agctcgatga gattggagaa atgcggctc caattgaaca cattgcaagc | 1320 |
| atgagaagga attatttcac agcagaggtg tctcattgca gagccacaga atacataatg | 1380 |
| aaggggtgt acatcaatac tgccttgctt aatgcatcct gtgcagcaat ggatgatttc | 1440 |
| caattaattc caatgataag caagtgtaga actaaggagg aaggcgaaa gaccaatttg | 1500 |
| tacggtttca tcataaaagg aagatcccac ttaaggaatg acaccgatgt ggtaaacttt | 1560 |
| gtgagcatgg agttttccct cactgaccca agacttgaac cacacaaatg ggagaagtac | 1620 |
| tgtgttcttg aggtaggaga tatgcttcta agaagtgcca taggccatgt gtcaaggcct | 1680 |
| atgttcttgt atgtgaggac aaatggaacc tcaaaaatta aatgaaatg ggggatggaa | 1740 |
| atgaggcgtt gcctccttca gtcacttcaa caaatcgaga gtatgattga agctgagtcc | 1800 |
| tctgtcaagg agaaagacat gaccaaagag ttctttgaaa acaaatcaga aacatggccc | 1860 |
| gttggagagt cccccaaagg agtggaggaa ggttccattg ggaaggtctg cagaactttta | 1920 |
| ttggcaaagt cggtattcaa cagcttgtat gcatctccac aactggaagg attttcagct | 1980 |
| gaatcaagaa aactgcttct tatcgttcag gctcttaggg acaacctgga acctgggacc | 2040 |
| tttgatcttg gggggctata tgaagcaatt gaggagtgcc tgattaatga tccctgggtt | 2100 |
| ttgcttaatg cttcttggtt caactccttc ctcacacatg cattgagata g | 2151 |

<210> SEQ ID NO 99
<211> LENGTH: 58
<212> TYPE: DNA
<213> ORGANISM: Influenza virus A/WSN/33
<220> FEATURE:
<223> OTHER INFORMATION: 5 prime NCR of Influenza virus A/WSN/33 PA gene segment

<400> SEQUENCE: 99

| | |
|---|---|
| ttgtggcaat gctactattt gctatccata ctgtccaaaa aagtaccttg tttctact | 58 |

<210> SEQ ID NO 100
<211> LENGTH: 2233
<212> TYPE: DNA
<213> ORGANISM: Influenza virus A/WSN/33
<220> FEATURE:
<223> OTHER INFORMATION: Influenza virus A/WSN/33 PA gene segment

<400> SEQUENCE: 100

| | |
|---|---|
| agcgaaagca ggtactgatt caaaatggaa gattttgtgc gacaatgctt caatccgatg | 60 |

| | |
|---|---|
| attgtcgagc ttgcggaaaa ggcaatgaaa gagtatggag aggacctgaa aatcgaaaca | 120 |
| aacaaatttg cagcaatatg cactcacttg gaagtgtgct tcatgtattc agattttcac | 180 |
| ttcatcgatg agcaaggcga gtcaatagtc gtagaacttg gcgatccaaa tgcacttttg | 240 |
| aagcacagat ttgaaataat cgagggaaga gatcgcacaa tagcctggac agtaataaac | 300 |
| agtatttgca cactacagg ggctgagaaa ccaaagtttc taccagattt gtatgattac | 360 |
| aagaagaata gattcatcga aattggagta acaaggagag aagttcacat atactatctg | 420 |
| gaaaaggcca ataaaattaa atctgagaag acacacatcc acattttctc attcactggg | 480 |
| gaggaaatgg ccacaaaggc cgactacact ctcgatgaag aaagcagggc taggatcaaa | 540 |
| accaggctat tcaccataag acaagaaatg gctagcagag gcctctggga ttcctttcgt | 600 |
| cagtccgaga gaggcgaaga gacaattgaa gaaagatttg aaatcacagg aacaatgcgc | 660 |
| aagcttgccg accaaagtct cccgccaaac ttctccagcc ttgaaaattt tagagcctat | 720 |
| gtggatggat tcgaaccgaa cggctacatt gagggcaagc tttctcaaat gtccaaagaa | 780 |
| gtaaatgcta gaattgaacc ttttttgaaa tcaacaccac gaccacttag acttccggat | 840 |
| gggcctccct gttctcagcg gtccaaattc ctgctgatgg atgccttaaa attaagcatt | 900 |
| gaggacccaa gtcatgaggg agaggggata ccgctatatg atgcaatcaa atgcatgaga | 960 |
| acattctttg gatggaagga acccaatgtt gttaaaccac acgaaaaggg aataaatcca | 1020 |
| aattatcttc tgtcatggaa gcaagtactg gcagaactgc aggacattga gaatgaggag | 1080 |
| aaaattccaa ggactaaaaa tatgaagaaa acgagtcagt taaagtgggc acttggtgag | 1140 |
| aacatggcac cagaaaaggt agactttgac gattgtaaag atgtaggcga tttgaagcaa | 1200 |
| tatgatagtg atgaaccaga attgaggtcg cttgcaagtt ggattcagaa tgagttcaac | 1260 |
| aaggcatgtg aactgaccga ttcaagctgg atagagctcg atgagattgg agaagatgcg | 1320 |
| gctccaattg aacacattgc aagcatgaga aggaattatt tcacagcaga ggtgtctcat | 1380 |
| tgcagagcca cagaatacat aatgaagggg gtgtacatca atactgcctt gcttaatgca | 1440 |
| tcctgtgcag caatggatga tttccaatta attccaatga taagcaagtg tagaactaag | 1500 |
| gagggaaggc gaaagaccaa tttgtacggt ttcatcataa aaggaagatc ccacttaagg | 1560 |
| aatgacaccg atgtggtaaa cttttgtgagc atggagtttt ccctcactga cccaagactt | 1620 |
| gaaccacaca aatgggagaa gtactgtgtt cttgaggtag gagatatgct tctaagaagt | 1680 |
| gccataggcc atgtgtcaag gcctatgttc ttgtatgtga ggacaaatgg aacctcaaaa | 1740 |
| attaaaatga aatgggggat ggaaatgagg cgttgcctcc ttcagtcact tcaacaaatc | 1800 |
| gagagtatga ttgaagctga gtcctctgtc aaggagaaag acatgaccaa agagttcttt | 1860 |
| gaaaacaaat cagaaacatg gcccgttgga gagtccccca aaggagtgga ggaaggttcc | 1920 |
| attgggaagg tctgcagaac tttattggca aagtcggtat tcaacagctt gtatgcatct | 1980 |
| ccacaactgg aaggattttc agctgaatca agaaaactgc ttcttatcgt tcaggctctt | 2040 |
| agggacaacc tggaacctgg gacctttgat cttgggggc tatatgaagc aattgaggag | 2100 |
| tgcctgatta atgatccctg ggttttgctt aatgcttctt ggttcaactc cttcctcaca | 2160 |
| catgcattga gatagttgtg gcaatgctac tatttgctat ccatactgtc caaaaaagta | 2220 |
| ccttgtttct act | 2233 |

<210> SEQ ID NO 101
<211> LENGTH: 24
<212> TYPE: DNA
<213> ORGANISM: Influenza virus A/WSN/33

```
<220> FEATURE:
<223> OTHER INFORMATION: 3 prime NCR of Influenza virus A/WSN/33 PB1
      gene segment

<400> SEQUENCE: 101
agcgaaagca ggcaaaccat ttga                                             24

<210> SEQ ID NO 102
<211> LENGTH: 2274
<212> TYPE: DNA
<213> ORGANISM: Influenza virus A/WSN/33
<220> FEATURE:
<223> OTHER INFORMATION: ORF of Influenza virus A/WSN/33 PB1 gene
      segment

<400> SEQUENCE: 102
atggatgtca atccgacttt acttttctta aaagtgccag cacaaaatgc tataagcaca      60
actttccctt atactggaga ccctccttac agccatggga caggaacagg atacaccatg     120
gatactgtca acaggacaca tcagtactca gaaaggggaa gatggacaac aaacaccgaa     180
actggagcac cgcaactcaa cccgattgat gggccactgc cagaagacaa tgaaccaagt     240
ggttatgccc aaacagattg tgtattggaa gcaatggcct ccttgaggga tcccatcct      300 ggtatctttg agacctcgtg tcttgaaacg atggaggttg ttcagcaaac acgagtggac     360
aagctgacac aaggccgaca gacctatgac tggactctaa ataggaacca gcctgctgca     420
acagcattgg ccaacacaat agaagtgttc agatcaaatg gcctcacggc caatgaatcc     480
ggaaggctca tagacttcct taaggatgta atggagtcaa tgaacaaaga agaaatggag     540
atcacaactc attttcagag aaagagacga gtgagagaca atatgactaa gaaaatggtg     600
acacagagaa caataggtaa aaggaagcag agattgaaca aaaggagtta tctaattagg     660
gcattgaccc tgaacacaat gaccaaagat gctgagagag gaagctaaa acggagagca     720 attgcaaccc cagggatgca ataagggggg tttgtatact ttgttgagac actagcaagg     780
agtatatgtg agaaacttga caatcagga ttgccagttg gaggcaatga agaaaagca      840 aagttggcaa atgttgtaag gaagatgatg accaattctc aggacactga aatttctttc     900
accatcactg gagataacac caaatggaac gaaaatcaga ccctcggat gtttttggcc      960 atgatcacat ataaccag aaatcagccc gaatggttca gaaatgttct aagtattgct    1020
ccaataatgt tctcaaacaa aatggcgaga ctggaaaagg ggtacatgtt tgagagcaag    1080
agtattaaaa ttagaactca ataccctgca gaaatgctag caagcatcga tttgaaatac    1140
ttcaatgatt caactagaaa gaagattgaa aaaatccggc cgctcttaat agatgggact    1200
gcatcattga gcctggaat gatgatgggc atgttcaata tgttaagtac tgtattaggc    1260
gtctccatcc tgaatcttgg acaaaagaga cacaccaaga ctacttactg gtgggatggt    1320
cttcaatctt ctgatgattt tgctctgatt gtgaatgcac ccaatcatga agggattcaa    1380
gccggagtca acaggtttta tcgaacctgt aagctacttg gaattaatat gagcaagaaa    1440
aagtcttaca taaacagaac aggtacattt gaattcacaa gttttttcta tcgttatggg    1500
tttgttgcca atttcagcat ggagcttccc agctttgggg tgtctgggat caacgagtct    1560
gcggacatga gtattggagt tactgtcatc aaaaacaata tgataaacaa tgatcttggt    1620
ccagcaaccg ctcaaatggc ccttcagctg ttcatcaaag attacaggta cacgtaccgg    1680
tgccatagag gtgacacaca aatacaaacc cgaagatcat ttgaaataaa gaactgtgg    1740 gagcaaaccc attccaaagc tggactgctg gtctccgacg gaggcccaaa tttatacaac    1800
```

-continued

```
attagaaatc tccacattcc tgaagtctgc ttgaaatggg aattaatgga tgaggattac    1860 cagggggcgtt tatgcaaccc actgaaccca tttgtcaacc ataaagacat tgaatcagtg   1920
aacaatgcag tgataatgcc agcacatggt ccagccaaaa acatggagta tgatgctgtt   1980
gcaacaacac actcctggat ccccaaaaga aatcgatcca tcttgaatac aagccaaaga   2040
ggaatacttg aagatgaaca aatgtaccaa aagtgctgca acttatttga aaaattcttc   2100
cccagcagtt catacagaag accagtcggg atatccagta tggtggaggc tatggttttcc  2160 agagcccgaa ttgatgcacg aattgatttc gaatctggaa ggataaagaa agaggagttc   2220
actgagatca tgaagatctg ttccaccatt gaagagctca gacggcaaaa atag         2274
```

<210> SEQ ID NO 103
<211> LENGTH: 43
<212> TYPE: DNA
<213> ORGANISM: Influenza virus A/WSN/33
<220> FEATURE:
<223> OTHER INFORMATION: 5 prime NCR of Influenza virus A/WSN/33 PB1
      gene segment

<400> SEQUENCE: 103

```
tgaatttagc ttgtccttca tgaaaaaatg ccttgtttct act                      43
```

<210> SEQ ID NO 104
<211> LENGTH: 2341
<212> TYPE: DNA
<213> ORGANISM: Influenza virus A/WSN/33
<220> FEATURE:
<223> OTHER INFORMATION: Influenza virus A/WSN/33 PB1 gene segment

<400> SEQUENCE: 104

```
agcgaaagca ggcaaaccat ttgaatggat gtcaatccga ctttactttt cttaaaagtg    60
ccagcacaaa atgctataag cacaactttc ccttatactg gagaccctcc ttacagccat   120
gggacaggaa caggatacac catggatact gtcaacagga cacatcagta ctcagaaagg   180
ggaagatgga caacaaacac cgaaactgga gcaccgcaac tcaacccgat tgatgggcca   240
ctgccagaag acaatgaacc aagtggttat gcccaaacag attgtgtatt ggaagcaatg   300
gccttccttg aggaatccca tcctggtatc tttgagacct cgtgtcttga acgatggag    360 gttgttcagc aaaacacgag tggacaagctg acacaaggcc gacagaccta tgactggact   420
ctaaatagga ccagcctgc tgcaacagca ttggccaaca caatagaagt gttcagatca   480
aatggcctca cggccaatga atccggaagg ctcatagact tccttaagga tgtaatggag   540
tcaatgaaca agaagaaat ggagatcaca actcattttc agagaaagag acgagtgaga   600
gacaatatga ctaagaaaat ggtgacacag agaacaatag gtaaaaggaa gcagagattg   660
aacaaaagga gttatctaat tagggcattg accctgaaca caatgaccaa agatgctgag   720
agagggaagc taaaacggag agcaattgca ccccaggga tgcaaataag ggggtttgta   780
tactttgttg acactagc aaggagtata tgtgagaaac ttgaacaatc aggattgcca   840
gttggaggca atgagaagaa agcaaagttg gcaaatgttg taaggaagat gatgaccaat   900
tctcaggaca ctgaaattcc tttccaccatc actggagata caccaaaatg aacgaaaat   960 cagaaccctc ggatgttttt ggccatgatc acatatataa ccagaaatca gcccgaatgg  1020
ttcagaaatg ttctaagtat tgctccaata atgttctcaa acaaaatggc gagactggga  1080 aagggggtaca tgtttgagag caagagtatt aaaattagaa ctcaaatacc tgcagaaatg  1140
ctagcaagca tcgatttgaa atacttcaat gattcaacta gaaagaagat tgaaaaaatc  1200
```

```
cggccgctct taatagatgg gactgcatca ttgagccctg aatgatgat  gggcatgttc   1260 aatatgttaa gtactgtatt aggcgtctcc atcctgaatc ttggacaaaa gagacacacc   1320
aagactactt actggtggga tggtcttcaa tcttctgatg attttgctct gattgtgaat   1380
gcacccaatc atgaagggat tcaagccgga gtcaacaggt tttatcgaac ctgtaagcta   1440
cttggaatta atatgagcaa gaaaaagtct tacataaaca gaacaggtac atttgaattc   1500
acaagttttt tctatcgtta tgggtttgtt gccaatttca gcatggagct tcccagcttt   1560
ggggtgtctg ggatcaacga gtctgcggac atgagtattg gagttactgt catcaaaaac   1620
aatatgataa acaatgatct tggtccagca accgctcaaa tggcccttca gctgttcatc   1680
aaagattaca ggtacacgta ccggtgccat agaggtgaca cacaaataca aacccgaaga   1740
tcatttgaaa taagaaact  gtgggagcaa acccattcca aagctggact gctggtctcc   1800
gacggaggcc caaatttata caacattaga aatctccaca ttcctgaagt ctgcttgaaa   1860
tgggaattaa tggatgagga ttaccagggg cgtttatgca acccactgaa cccatttgtc   1920
aaccataaag acattgaatc agtgaacaat gcagtgataa tgccagcaca tggtccagcc   1980
aaaaacatgg agtatgatgc tgttgcaaca acacactcct ggatcccca  agaaatcga   2040 tccatcttga atacaagcca aagaggaata cttgaagatg aacaaatgta ccaaaagtgc   2100
tgcaacttat ttgaaaaatt cttccccagc agttcataca aagaccagt  cgggatatcc   2160 agtatggtgg aggctatggt ttccagagcc cgaattgatg cacgaattga tttcgaatct   2220
ggaaggataa agaaagagga gttcactgag atcatgaaga tctgttccac cattgaagag   2280
ctcagacggc aaaaatagtg aatttagctt gtccttcatg aaaaaatgcc ttgtttctac   2340
t                                                                  2341

<210> SEQ ID NO 105
<211> LENGTH: 27
<212> TYPE: DNA
<213> ORGANISM: Influenza virus A/WSN/33
<220> FEATURE:
<223> OTHER INFORMATION: 3 prime NCR of Influenza virus A/WSN/33 PB2
      gene segment

<400> SEQUENCE: 105
agcgaaagca ggtcaattat attcaat                                       27

<210> SEQ ID NO 106
<211> LENGTH: 2280
<212> TYPE: DNA
<213> ORGANISM: Influenza virus A/WSN/33
<220> FEATURE:
<223> OTHER INFORMATION: ORF of Influenza virus A/WSN/33 PB2 gene
      segment

<400> SEQUENCE: 106
atggaaagaa taaagaaact aaggaatcta atgtcgcagt ctcgcactcg cgagatactc     60
acaaaaacca ccgtggacca tatggccata atcaagaagt acacatcagg aagacaggag   120
aagaacccag cacttaggat gaaatggatg atggcaatga aatatccaat tacagcagac   180
aagaggataa cggaaatgat tcctgagaga atgagcagg  acaaacttt  atggagtaaa   240 atgaatgacg ccggatcaga ccgagtgatg gtatcacctc tggctgtgac atggtggaat   300
aggaatggac cagtgacaag tacagttcat tatccaaaaa tctacaaaac ttattttgaa   360
aaagtcgaaa ggttaaaaca tggaaccttt ggccctgtcc attttagaaa ccaagtcaaa   420
atacgtcgaa gagttgacat aaatcctggt catgcagatc tcagtgccaa agaggcacag   480
```

-continued

```
gatgtaatca tggaagttgt tttccctaac gaagtgggag ccaggatact aacatcggaa      540
tcgcaactaa cgacaaccaa agagaagaaa gaagaactcc agggttgcaa aatttctcct      600
ctgatggtgg catacatgtt ggagagagaa ctggtccgca aaacgagatt cctcccagtg      660
gctggtggaa caagcagtgt gtacattgaa gtgttgcatt tgacccaagg aacatgctgg      720
gaacagatgt acactccagg aggggaggcg aggaatgatg atgttgatca aagcttaatt      780
attgctgcta gaaacatagt aagaagagcc acagtgtcag cagatccact agcatcttta      840
ttggagatgt gccacagcac gcagattggt ggaataagga tggtaaacat ccttaggcag      900
aacccaacag aagagcaagc cgtggatatt tgcaaggctg caatgggact gagaattagc      960
tcatccttca gttttggtgg attcacattt aagagaacaa gcggatcatc agtcaagaga     1020
gaggaagagg tgcttacggg caatcttcag acattgaaga taagagtgca tgagggatat     1080
gaagagttca caatggttgg gagaagagca acagctatac tcagaaaagc aaccaggaga     1140
ttgattcagc tgatagtgag tgggagggac gaacagtcga ttgccgaagc aataattgtg     1200
gccatggtat tttcacaaga ggattgtatg ataaaagcag ttagaggtga cctgaatttc     1260
gtcaataggg cgaatcagcg attgaacccc atgcaccaac ttttgagaca ttttcagaag     1320
gatgcaaagg cgctctttca aaattgggga attgaatcca tcgacaatgt gatgggaatg     1380
atcgggatat tgcccgacat gactccaagc accgagatgt caatgagagg agtgagaatc     1440
agcaaaatgg gggtagatga gtattccagc gcggagaaga tagtggtgag cattgaccgt     1500
tttttgagag ttagggacca acgtgggaat gtactactgt ctcccgagga ggtcagtgaa     1560
acacagggaa cagagaaact gacaataact tactcatcgt caatgatgtg ggagattaat     1620
ggtcctgaat cagtgttggt caataccat cagtggatca tcagaaactg ggaaactgtt     1680
aaaattcagt ggtcccagaa tcctacaatg ctgtacaata aatggaatt tgagccattt     1740 cagtctttag ttccaaaggc cgttagaggc aatacagtg ggtttgtgag aactctgttc     1800
caacaaatga gggatgtgct tgggacattt gataccgctc agataataaa acttcttccc     1860
ttcgcagccg ctccaccaaa gcaaagtgga atgcagttct cctcattgac tataaatgtg     1920
aggggatcag aatgagaat acttgtaagg gcaattctc aatattcaa ctacaacaag     1980 accactaaaa gactcacagt tctcggaaag gatgctggcc ctttaactga agacccagat     2040
gaaggcacag ctggagttga gtccgcagtt ctgagaggat tcctcattct gggcaaagaa     2100
gacaggagat atggaccagc attaagcata aatgaactga gcaaccttgc gaaaggagag     2160
aaggctaatg tgctaattgg gcaaggagac gtggtgttgg taatgaaacg gaaacggaac     2220
tctagcatac ttactgacag ccagacagcg accaaaagaa ttcggatggc catcaattag     2280
```

<210> SEQ ID NO 107
<211> LENGTH: 34
<212> TYPE: DNA
<213> ORGANISM: Influenza virus A/WSN/33
<220> FEATURE:
<223> OTHER INFORMATION: 5 prime NCR of Influenza virus A/WSN/33 PB2
      gene segment

<400> SEQUENCE: 107

```
tgtcgaatag tttaaaaacg accttgtttc tact                                   34
```

<210> SEQ ID NO 108
<211> LENGTH: 2341
<212> TYPE: DNA
<213> ORGANISM: Influenza virus A/WSN/33

-continued

<220> FEATURE:
<223> OTHER INFORMATION: Influenza virus A/WSN/33 PB2 gene segment

<400> SEQUENCE: 108

```
agcgaaagca ggtcaattat attcaatatg gaaagaataa aagaactaag gaatctaatg     60
tcgcagtctc gcactcgcga gatactcaca aaaaccaccg tggaccatat ggccataatc    120
aagaagtaca catcaggaag acaggagaag aacccagcac ttaggatgaa atggatgatg    180
gcaatgaaat atccaattac agcagacaag aggataacgg aaatgattcc tgagagaaat    240
gagcagggac aaactttatg gagtaaaatg aatgacgccg gatcagaccg agtgatggta    300
tcacctctgg ctgtgacatg gtggaatagg aatggaccag tgacaagtac agttcattat    360
ccaaaaatct acaaaactta ttttgaaaaa gtcgaaaggt taaaacatgg aacctttggc    420
cctgtccatt ttagaaacca agtcaaaata cgtcgaagag ttgacataaa tcctggtcat    480
gcagatctca gtgccaaaga ggcacaggat gtaatcatgg aagttgtttt ccctaacgaa    540
gtgggagcca ggatactaac atcggaatcg caactaacga caaccaaaga gaagaaagaa    600
gaactccagg gttgcaaaat ttctcctctg atggtggcat acatgttgga gagagaactg    660
gtccgcaaaa cgagattcct cccagtggct ggtggaacaa gcagtgtgta cattgaagtg    720
ttgcatttga cccaaggaac atgctgggaa cagatgtaca ctccaggagg ggaggcgagg    780
aatgatgatg ttgatcaaag cttaattatt gctgctagaa acatagtaag aagagccaca    840
gtgtcagcag atccactagc atctttattg gagatgtgcc acagcacgca gattggtgga    900
ataaggatgg taaacatcct taggcagaac ccaacagaag agcaagccgt ggatatttgc    960
aaggctgcaa tgggactgag aattagctca tccttcagtt ttggtggatt cacatttaag   1020
agaacaagcg gatcatcagt caagagagag gaagaggtgc ttacgggcaa tcttcagaca   1080
ttgaagataa gagtgcatga gggatatgaa gagttcacaa tggttgggag aagagcaaca   1140
gctatactca gaaaagcaac caggagattg attcagctga tagtgagtgg gagggacgaa   1200
cagtcgattg ccgaagcaat aattgtggcc atggtatttt cacaagagga ttgtatgata   1260
aaagcagtta gaggtgacct gaatttcgtc aatagggcga atcagcgatt gaaccccatg   1320
caccaacttt tgagacattt tcagaaggat gcaaaggcgc tctttcaaaa ttggggaatt   1380
gaatccatcg acaatgtgat gggaatgatc gggatattgc ccgacatgac tccaagcacc   1440
gagatgtcaa tgagaggagt gagaatcagc aaaatggggg tagatgagta ttccagcgcg   1500
gagaagatag tggtgagcat tgaccgtttt ttgagagtta gggaccaacg tgggaatgta   1560
ctactgtctc ccgaggaggt cagtgaaaca cagggaacag agaaactgac aataacttac   1620
tcatcgtcaa tgatgtggga gattaatggt cctgaatcag tgttggtcaa tacctatcag   1680
tggatcatca gaaactggga aactgttaaa attcagtggt cccagaatcc tacaatgctg   1740
tacaataaaa tggaatttga gccatttcag tctttagttc caaaggccgt tagaggccaa   1800
tacagtgggt ttgtgagaac tctgttccaa caaatgaggg atgtgcttgg gacatttgat   1860
accgctcaga taataaaact tcttcccttc gcagccgctc caccaaagca aagtggaatg   1920
cagttctcct cattgactat aaatgtgagg ggatcaggaa tgagaatact tgtaaggggc   1980
aattctccaa tattcaacta caacaagacc actaaaagac tcacagttct cggaaaggat   2040
gctggccctt taactgaaga cccagatgaa ggcacagctg gagttgagtc cgcagttctg   2100
agaggattcc tcattctggg caaagaagac aggagatatg gaccagcatt aagcataaat   2160
gaactgagca accttgcgaa aggagagaag gctaatgtgc taattgggca aggagacgtg   2220
```

```
gtgttggtaa tgaaacggaa acggaactct agcatactta ctgacagcca gacagcgacc    2280
aaaagaattc ggatggccat caattagtgt cgaatagttt aaaaacgacc ttgtttctac    2340
t                                                                    2341

<210> SEQ ID NO 109
<211> LENGTH: 45
<212> TYPE: DNA
<213> ORGANISM: Influenza virus A/WSN/33
<220> FEATURE:
<223> OTHER INFORMATION: 3 prime NCR of Influenza virus A/WSN/33 NP
      gene segment

<400> SEQUENCE: 109
agcaaaagca gggtagataa tcactcacag agtgacatcg aaatc                      45

<210> SEQ ID NO 110
<211> LENGTH: 1497
<212> TYPE: DNA
<213> ORGANISM: Influenza virus A/WSN/33
<220> FEATURE:
<223> OTHER INFORMATION: ORF of Influenza virus A/WSN/33 NP gene segment

<400> SEQUENCE: 110
atggcgacca aaggcaccaa acgatcttac gaacagatgg agactgatgg agaacgccag      60
aatgccactg aaatcagagc atctgtcgga aaaatgattg gtggaattgg acgattctac     120
atccaaatgt gcaccgaact aaactcagtg gattatgagg acggctgat tcagaacagc     180 ttaacaatag agagaatggt gctctctgct tttgacgaga ggaggaataa atatctagaa     240
gaacatccca gtgcggggaa agatcctaag aaaactggag gacctatata caggagagta     300 gatgaaagt ggatgagaga actcatcctt tatgacaaag aagaaataag acgaatctgg     360
cgccaagcta ataatggtga cgatgcaacg gctggtctga ctcacatgat gatctggcac     420
tccaatttga atgatgcaac ttaccagagg acaagagctc ttgttcgcac aggaatggat     480
cccaggatgt gctcactgat gcagggttca accctccta ggaggtctgg ggccgcaggt     540
gctgcagtca aggagttgg aacaatggtg atggaattga tcagaatgat caaacgtggg     600
atcaatgatc ggaacttctg gaggggtgag aatggacgga gaacaaggat tgcttatgaa     660
agaatgtgca acattctcaa agggaaattt caaacagctg cacaaagagc aatggtggat     720
caagtgagag agagccggaa tccaggaaat gctgagttcg aagatctcat ctttctagca     780
cggtctgcac tcatattgag agggtcagtt gctcacaagt cctgcctgcc tgcctgtgtg     840 tatgacctg ccgtagccag tggatacgac tttgaaagag ggatactc tctagtcgga     900 atagaccctt tcagactgct tcaaaacagc caagtataca gcctaatcag accaaatgag     960
aatccagcac acaagagtca actggtgtgg atggcatgcc attctgctgc atttgaagat    1020
ctaagagtat caagcttcat cagagggacg aaagtggtcc caagagggaa gctttccact    1080
agaggagttc aaattgcttc caatgaaaac atggagacta ggaatcaag tacccttgaa    1140 ctgagaagca gatactggc cataaggacc agaagtggag gaacaccaa tcaacagagg    1200 gcttcctcgg gccaaatcag catacaacct acgttctcag tacagagaaa tctcccttt    1260 gacagaccaa ccattatggc agcattcact gggaatacag aggggagaac atctgacatg    1320
agaaccgaaa tcataaggct gatggaaagt gcaagaccag aagatgtgtc tttccagggg    1380
cggggagtct tcgagctctc ggacgaaaag gcagcgagcc cgatcgtgcc ctcctttgac    1440
atgagtaatg aaggatctta tttcttcgga gacaatgcag aggagtacga caattaa      1497
```

<210> SEQ ID NO 111
<211> LENGTH: 23
<212> TYPE: DNA
<213> ORGANISM: Influenza virus A/WSN/33
<220> FEATURE:
<223> OTHER INFORMATION: 5 prime NCR of Influenza virus A/WSN/33 NP gene segment

<400> SEQUENCE: 111
agaaaaatac ccttgtttct act                                              23

<210> SEQ ID NO 112
<211> LENGTH: 1565
<212> TYPE: DNA
<213> ORGANISM: Influenza virus A/WSN/33
<220> FEATURE:
<223> OTHER INFORMATION: Influenza virus A/WSN/33 NP gene segment

<400> SEQUENCE: 112
agcaaaagca gggtagataa tcactcacag agtgacatcg aaatcatggc gaccaaaggc      60
accaaacgat cttacgaaca gatggagact gatggagaac gccagaatgc cactgaaatc     120
agagcatctg tcggaaaaat gattggtgga attggacgat ctacatcca aatgtgcacc      180 gaacttaaac tcagtgatta tgagggacgg ctgattcaga acagcttaac aatagagaga     240
atggtgctct ctgcttttga cgagaggagg aataaatatc tagaagaaca tcccagtgcg     300
gggaaagatc ctaagaaaac tggaggacct atatacagga gagtagatgg aaagtggatg     360
agagaactca tcctttatga caaagaagaa ataagacgaa tctggcgcca agctaataat     420
ggtgacgatg caacggctgg tctgactcac atgatgatct ggcactccaa tttgaatgat     480
gcaacttacc agaggacaag agctcttgtt cgcacaggaa tggatcccag gatgtgctca     540
ctgatgcagg gttcaaccct ccctaggagg tctgggccg caggtgctgc agtcaaagga     600
gttggaacaa tggtgatgga attgatcaga atgatcaaac gtgggatcaa tgatcggaac     660
ttctggaggg gtgagaatgg acggagaaca aggattgctt atgaaagaat gtgcaacatt     720
ctcaaaggga aatttcaaac agctgcacaa agagcaatgg tggatcaagt gagagagagc     780
cggaatccag gaaatgctga gttcgaagat ctcatctttc tagcacggtc tgcactcata     840
ttgagagggt cagttgctca caagtcctgc ctgcctgcct gtgtgtatgg acctgccgta     900
gccagtggat acgactttga agagaggga tactctctag tcggaataga ccctttcaga     960
ctgcttcaaa acagccaagt atacagccta atcagaccaa atgagaatcc agcacacaag    1020
agtcaactgg tgtggatggc atgccattct gctgcatttg aagatctaag agtatcaagc    1080
ttcatcagag ggacgaaagt ggtcccaaga gggaagcttt ccactagagg agttcaaatt    1140
gcttccaatg aaaacatgga gactatgaa tcaagtaccc ttgaactgag aagcagatac    1200
tgggccataa ggaccagaag tggagggaac accaatcaac agagggcttc ctcgggccaa    1260
atcagcatac aacctacgtt ctcagtacag agaaatctcc cttttgacag accaccatt    1320 atggcagcat tcactgggaa tacagagggg agaacatctg acatgagaac cgaaatcata    1380
aggctgatgg aaagtgcaag accagaagat gtgtctttcc aggggcgggg agtcttcgag    1440
ctctcggacg aaaaggcagc gagcccgatc gtgccctcct tgacatgag taatgaagga    1500 tcttatttct tcggagacaa tgcagaggag tacgacaatt aaagaaaaat acccttgttt    1560
ctact                                                               1565

<210> SEQ ID NO 113

<211> LENGTH: 131
<212> TYPE: RNA
<213> ORGANISM: Artificial Sequence
<220> FEATURE:
<223> OTHER INFORMATION: 3 prime end 130 nt of the NS-HAmut-NS RNA

<400> SEQUENCE: 113

```
rucguuuucg ucccacuguu ucuguaugac cuagguuugu gacacaguuc gggagucgau 60
cuaacgggag aaaccgaaca ggcguuugcu caacgucugg uucucggucg uacuuucgcu 120
uggacaauca a 131

<210> SEQ ID NO 114
<211> LENGTH: 81
<212> TYPE: DNA
<213> ORGANISM: Artificial Sequence
<220> FEATURE:
<223> OTHER INFORMATION: forward primer used to amplify the HA ORF
carried synonymous mutations
<400> SEQUENCE: 114
cagctagcat gaaagcgaat ttgttagttt tactgtccgc gttggcggcc gcggacgcag 60
acacaatatg tataggctac c 81

<210> SEQ ID NO 115
<211> LENGTH: 67
<212> TYPE: DNA
<213> ORGANISM: Artificial Sequence
<220> FEATURE:
<223> OTHER INFORMATION: reverse primer used to amplify the HA ORF
carried synonymous mutations
<400> SEQUENCE: 115
ccaaaaggaa atcgctccta aactaactag caatactaag ctggaagcga cagttgagta 60
gatcgcc 67

<210> SEQ ID NO 116
<211> LENGTH: 73
<212> TYPE: DNA
<213> ORGANISM: Artificial Sequence
<220> FEATURE:
<223> OTHER INFORMATION: reverse primer used to amplify the HA ORF
carried synonymous mutations
<400> SEQUENCE: 116
gtctcgagtc aaatacaaat ccgacattgt aggctcccgt tgctgcacat ccaaaaggaa 60
atcgctccta aac 73

<210> SEQ ID NO 117
<211> LENGTH: 63
<212> TYPE: DNA
<213> ORGANISM: Artificial Sequence
<220> FEATURE:
<223> OTHER INFORMATION: forward primer used to introduced synonymous
mutations into the NS ORF
<400> SEQUENCE: 117
cagctagcat ggacccgaat accgtaagtt cttttcaggt agactgcttt ctttggcatg 60
tcc 63

<210> SEQ ID NO 118
<211> LENGTH: 57
<212> TYPE: DNA
<213> ORGANISM: Artificial Sequence

```
<220> FEATURE:
<223> OTHER INFORMATION: reverse primer used to introduced synonymous
      mutations into the NS ORF

<400> SEQUENCE: 118
gtctcgagtt agatcaattg aagctaaag gtccggattt cctgctccac ttcaagc         57

<210> SEQ ID NO 119
<211> LENGTH: 2668
<212> TYPE: DNA
<213> ORGANISM: Artificial Sequence
<220> FEATURE:
<223> OTHER INFORMATION: Chimeric influenza virus gene

<400> SEQUENCE: 119
agcgaaagca ggggtttaaa ttgaatccaa atcagaaaat aacaaccatt ggatcaatct      60
gtctggtagt cggactaatt agcctaatat tgcaaatagg gaatataatc tcaatttgga     120
ttagccattc aattcaaact ggaagtcaaa accatactgg aatttgcaac caagctagca     180
tggacgttaa cccaactctg ttatttctga aggtaccggc gcagaacgcc atcagtacga     240
cctttcctta tactggagac cctccttaca gccatgggac aggaacagga tacaccatgg     300
atactgtcaa caggacacat cagtactcag aaaaggaag atggacaaca acaccgaaa      360 ctggagcacc gcaactcaac ccgattgatg gccactgcc agaagacaat gaaccaagtg     420
gttatgccca acagattgt gtattggaag caatggcttt ccttgaggaa tcccatcctg     480 gtattttga aaactcgtgt attgaaacga tggaggttgt tcagcaaaca cgagtagaca     540
agctgacaca aggccgacag acctatgact ggactctaaa tagaaaccaa cctgctgcaa     600
cagcattggc caacacaata gaagtgttca gatcaaatgg cctcacggcc aatgagtctg     660
gaaggctcat agcttccctt aaggatgtaa tggagtcaat gaaaaagaa gaaatgggga     720 tcacaactca ttttcagaga agagacgggg tgagagacaa tatgactaag aaaatgataa     780
cacagagaac aataggtaaa agaagcagag gattgaacaa aaggagttat ctaattagag     840 cattgacccct gaacacaatg accaaagatg ctgagagagg gaagctaaaa cggagagcaa     900
ttgcaacccc agggatgcaa ataagggggt tgtatactt tgttgagaca ctggcaagga     960
gtatatgtga gaaacttgaa caatcagggt tgccagttgg aggcaatgag aagaaagcaa    1020
agttggcaaa tgttgtaagg aagatgatga ccaattctca ggacaccgaa cttttcttca    1080
ccatcactgg agataacacc aaatggaacg aaaatcagaa tcctcggatg tttttggcca    1140
tgatcacata tatgacaaga aatcagcccg aatggttcag aaatgttcta agtattgctc    1200
caataatgtt ctcaaacaaa atggcgagac tgggaaaagg gtatatgttt gagagcaaga    1260
gtatgaaact tagaactcaa ataccctgcag aaatgctagc aagcatcgat ttgaaatatt    1320
tcaatgattc aacaagaaag aagattgaaa aaatccgacc gctcttaata gagggggactg    1380 catcattgag ccctggaatg atgatgggca tgttcaatat gttaagcact gtattaggcg    1440
tctccatcct gaatcttgga caaaagagat acaccaagac tacttactgg tgggatggtc    1500
ttcaatcctc tgacgatttt gctctgattg tgaatgcacc caatcatgaa gggattcaag    1560
ccggagtcga caggttttat cgaacctgta gctacttgg aatcaatatg agcaagaaaa    1620
agtcttacat aaacagaaca ggtacatttg aattcacaag ttttttctat cgttatgggt    1680
ttgttgccaa tttcagcatg gagctcccca gttttgggggt gtctgggatc aacgagtcag    1740
cggacatgag tattggagtt actgtcatca aaaacaatat gataaacaat gatcttggtc    1800
cagcaacagc tcaaatggcc cttcagttgt tcatcaaaga ttacaggtac acgtaccgat    1860
```

```
gccatagagg tgacacacaa atacaaaccc gaagatcatt tgaaataaag aaactgtggg      1920
agcaaacccg ttccaaagct ggactgctgg tctccgacgg aggcccaaat ttatacaaca      1980
ttagaaatct ccacattcct gaagtctgcc taaaatggga attgatggat gaggattacc      2040
aggggcgttt atgcaaccca ctgaacccat ttgtcagcca taaagaaatt gaatcaatga      2100
acaatgcagt gatgatgcca gcacatggtc cagccaaaaa catggagtat gatgctgttg      2160
caacaacaca ctcctggatc cccaaaagaa atcgatccat cttgaataca agtcaaagag      2220
gagtacttga agatgaacaa atgtaccaaa ggtgctgcaa tttatttgaa aaattcttcc      2280
ccagcagttc atacagaaga ccagtcggga tatccagtat ggtggaggct atggtttcca      2340
gagcccgaat tgatgcacgg attgatttcg aatctggaag gataaagaaa gaagagttca      2400
ctgagatcat gaaaatttgc agtacaatcg aggaacttcg gagacagaag tagctcgagt      2460
gagctaacag ggctagactg tatgaggccg tgcttctggg ttgaattaat caggggacga      2520
cctaaagaaa aaacaatctg gactagtgcg agcagcattt cttttttgtgg cgtgaatagt      2580 gatactgtag attggtcttg gccagacggt gctgagttgc cattcagcat tgacaagtag      2640
tctgttcaaa aaactccttg tttctact                                         2668

<210> SEQ ID NO 120
<211> LENGTH: 2674
<212> TYPE: DNA
<213> ORGANISM: Artificial Sequence
<220> FEATURE:
<223> OTHER INFORMATION: Chimeric influenza virus gene

<400> SEQUENCE: 120
agcgaaagca ggggtttaaa ttgaatccaa atcagaaaat aacaaccatt ggatcaatct        60
gtctggtagt cggactaatt agcctaatat tgcaaatagg aatataatc tcaatttgga       120 ttagccattc aattcaaact ggaagtcaaa accatactgg aatttgcaac caagctagca       180
tggagcggat caaggagttg cggaacttga tgtcgcagtc tcgcacccgc gagatactca       240
caaaaaccac cgtggaccat atggccataa tcaagaagta cacatcagga agacaggaga       300
agaacccagc acttaggatg aaatggatga tggcaatgaa atatccaatt acagcagaca       360
agaggataac ggaaatgatt cctgagagaa atgagcaagg acaaacttta tggagtaaaa       420
tgaatgatgc aggatcagac cgagtgatgg tatcacctct ggctgtgaca tggtggaata       480
ggaatggacc aataacaaat acagttcatt atccaaaaat ctacaaaact tattttgaaa       540
gagtcgaaag gctaaagcat ggaaccttg gccctgtcca ttttagaaac caagtcaaaa       600
tacgtcggag agttgacata aatcctggtc atgcagatct cagtgccaag gaggcacagg       660
atgtaatcat ggaagttgtt tccctaacg aagtgggagc caggatacta acatcggaat       720
cgcaactaac gataaccaaa gagaagaaag aagaactcca ggattgcaaa atttctcctt       780
tgatggttgc atacatgttg agagagaac tggtccgcaa aacgagattc ctcccagtgg       840
ctggtggaac aagcagtgtg tacattgaag tgttgcattt gactcaagga acatgctggg       900
aacagatgta tactccagga ggggaagtga ggaatgatga tgttgatcaa gcttgatta       960 ttgctgctag gaacatagtg agaagagctg cagtatcagc agatccacta gcatctttat      1020
tggagatgtg ccacagcaca cagattggtg gaattaggat ggtagacatc cttaggcaga      1080
acccaacaga agagcaagcc gtggatatat gcaggctgc aatgggactg agaattagct      1140
catccttcag ttttggtgga ttcacattta agagaacaag cggatcatca gtcaagagag      1200
```

| | |
|---|---|
| aggaagaggt gcttacgggc aatcttcaaa cattgaagat aagagtgcat gagggatatg | 1260 |
| aagagttcac aatggttggg agaagagcaa cagccatact cagaaaagca accaggagat | 1320 |
| tgattcagct gatagtgagt gggagagacg aacagtcgat tgccgaagca ataattgtgg | 1380 |
| ccatggtatt ttcacaagag gattgtatga taaaagcagt cagaggtgat ctgaatttcg | 1440 |
| tcaatagggc gaatcagcga ttgaatccta tgcatcaact tttaagacat tttcagaagg | 1500 |
| atgcgaaagt gcttttcaa aattggggag ttgaacctat cgacaatgtg atgggaatga | 1560 |
| ttgggatatt gccagacatg actccaagca tcgagatgtc aatgagagga gtgagaatca | 1620 |
| gcaaaatggg tgtagatgag tactccagca cggagagggt agtggtgagc attgaccgtt | 1680 |
| ttttgagaat ccgggaccaa cgaggaaatg tactactgtc tcccgaggag gtcagtgaaa | 1740 |
| cacagggaac agagaaactg acaataactt actcatcgtc aatgatgtgg gagattaatg | 1800 |
| gtcctgaatc agtgttggtc aatacctatc aatggatcat cagaaactgg gaaactgtta | 1860 |
| aaattcagtg gtcccagaac cctacaatgc tatacaataa aatggaattt gaaccatttc | 1920 |
| agtctttagt acctaaggcc attagaggcc aatacagtgg gtttgtaaga actctgttcc | 1980 |
| aacaaatgag ggatgtgctt ggacatttg ataccgcaca gataataaaa cttcttccct | 2040 |
| tcgcagccgc tccaccaaag caagtagaa tgcagttctc ctcatttact gtgaatgtga | 2100 |
| ggggatcagg aatgagaata cttgtaaggg gcaattctcc tgtattcaac tataacaagg | 2160 |
| ccacgaagag actcacagtt ctcggaaagg atgctggcac tttaactgaa gacccagatg | 2220 |
| aaggcacagc tggagtggag tccgctgttc tgaggggatt cctcattctg ggcaaagaag | 2280 |
| acaagagata tgggccagca ctaagcatca atgaactgag caaccttgcg aaaggagaga | 2340 |
| aggctaatgt gctaattggg caaggagacg tggtactagt gatgaagaga aagagagata | 2400 |
| gctctatctt gacggattca caaacggcaa ctaaggaggat ccgtatggct attaactagc | 2460 |
| tcgagtgagc taacagggct agactgtatg aggccgtgct tctgggttga attaatcagg | 2520 |
| ggacgaccta aagaaaaaac aatctggact agtgcgagca gcatttcttt ttgtggcgtg | 2580 |
| aatagtgata ctgtagattg gtcttggcca gacggtgctg agttgccatt cagcattgac | 2640 |
| aagtagtctg ttcaaaaaac tccttgtttc tact | 2674 |

<210> SEQ ID NO 121
<211> LENGTH: 2545
<212> TYPE: DNA
<213> ORGANISM: Artificial Sequence
<220> FEATURE:
<223> OTHER INFORMATION: Chimeric influenza virus gene

<400> SEQUENCE: 121

| | |
|---|---|
| agcgaaagca ggggtttaaa ttgaatccaa atcagaaaat aacaaccatt ggatcaatct | 60 |
| gtctggtagt cggactaatt agcctaatat tgcaaatagg gaatataatc tcaatttgga | 120 |
| ttagccattc aattcaaact ggaagtcaaa accatactgg aatttgcaac caagctagca | 180 |
| tggaggactt cgtaaggcag tgttttaacc caatgatcgt tgaactcgca gagaagacga | 240 |
| tgaaggagta tgggaggac ctgaaaatcg aaacaaacaa atttgcagca atatgcactc | 300 |
| acttggaagt atgcttcatg tattcagatt ttcacttcat caatgagcaa ggcgagtcaa | 360 |
| taatcgtaga acttggtgat ccaaatgcac ttttgaagca cagatttgaa ataatcgagg | 420 |
| gaagagatcg cacaatggcc tggacagtag taaacagtat ttgcaacact acaggggctg | 480 |
| agaaaccaaa gtttctacca gatttgtatg attacaagga aatagattc atcgaaattg | 540 |
| gagtaacaag gagagaagtt cacatatact atctggaaaa ggccaataaa attaaatctg | 600 | agaaaacaca catccacatt ttctcgttca ctggggaaga aatggccaca aaggcagact      660 acactctcga tgaagaaagc agggctagga tcaaaaccag actattcacc ataagacaag      720 aaatggccag cagaggcctc tgggattcct ttcgtcagtc cgagagagga gaagagacaa      780 ttgaagaaag gtttgaaatc acaggaacaa tgcgcaagct tgccgaccaa agtctcccgc      840 cgaacttctc cagccttgaa aattttagag cctatgtgga tggattcgaa ccgaacggct      900 acattgaggg caagctgtct caaatgtcca agaagtaaa tgctagaatt gaaccttttt      960 tgaaaacaac accacgacca cttagacttc cgaatgggcc tccctgttct cagcggtcca     1020 aattcctgct gatggatgcc ttaaaattaa gcattgagga cccaagtcat gaaggagagg     1080 gaataccgct atatgatgca atcaaatgca tgagaacatt ctttggatgg aaggaaccca     1140 atgttgttaa accacacgaa aagggaataa atccaaatta tcttctgtca tggaagcaag     1200 tactggcaga actgcaggac attgagaatg aggagaaaat tccaaagact aaaaatatga     1260 agaaaacaag tcagctaaag tgggcacttg gtgagaacat ggcaccagaa aaggtagact     1320 ttgacgactg taaagatgta ggtgatttga agcaatatga tagtgatgaa ccagaattga     1380 ggtcgctagc aagttggatt cagaatgagt ttaacaaggc atgcgaactg acagattcaa     1440 gctggataga gctcgatgag attggagaag atgtggctcc aattgaacac attgcaagca     1500 tgagaaggaa ttatttcaca tcagaggtgt ctcactgcag agccacgaaa tacataatga     1560 agggggtgta catcaatact gccttgctta atgcatcttg tgcagcaatg gatgatttcc     1620 aattaattcc aatgataagc aagtgtgaaa ctaaggaggg aaggcgaaag accaacttgt     1680 atggtttcat cataaaagga agatcccact taaggaatga caccgacgtg gtaaactttg     1740 tgagcatgga gttttctctc actgacccaa gacttgaacc acataaatgg gagaagtact     1800 gtgttcttga gataggagat atgcttataa gaagtgccat aggccaggtt tcaaggccca     1860 tgttcttgta tgtgagaaca aatggaacct caaaaattaa aatgaaatgg ggaatggaga     1920 tgaggcgttg cctcctccag tcacttcaac aaattgagag tatgattgaa gctgagtcct     1980 ctgtcaaaga gaaagacatg accaaagagt tctttgagaa caaatcagaa acatggccca     2040 ttggagagtc ccccaaagga gtggaggaaa gttccattgg gaaggtctgc aggactttat     2100 tagcaaagtc ggtattcaac agcttgtatg catctccaca actagaagga ttttcagctg     2160 aatcaagaaa actgcttctt atcgttcagg ctcttaggga caaccttgaa cctgggacct     2220 ttgatcttgg ggggctatat gaagcaattg aggagtgcct gattaatgat ccctgggttt     2280 tgcttaacgc cagctggttt aattcttttt tgacgcacgc gctatcatag ctcgagtgag     2340 ctaacagggc tagactgtat gaggccgtgc ttctgggttg aattaatcag gggacgacct     2400 aaagaaaaaa caatctggac tagtgcgagc agcatttctt tttgtggcgt gaatagtgat     2460 actgtagatt ggtcttggcc agacggtgct gagttgccat tcagcattga caagtagtct     2520 gttcaaaaaa ctccttgttt ctact                                           2545

<210> SEQ ID NO 122
<211> LENGTH: 1032
<212> TYPE: DNA
<213> ORGANISM: Artificial Sequence
<220> FEATURE:
<223> OTHER INFORMATION: Chimeric influenza virus gene

<400> SEQUENCE: 122
agcgaaagca ggcaaaccat ttgattggtt gtcaatccga ccttactttt cttaaaagtg       60

```
ccagcacaaa ttgctataag cacaactttc ccttatactg gagaccctcc ttacagcctt      120
gggacaggaa caggatacac cttggttgct agcatggtga gcaagggcga ggagctgttc      180
accggggtgg tgcccatcct ggtcgagctg gacggcgacg taaacggcca caagttcagc      240
gtgtccggcg agggcgaggg cgatgccacc tacggcaagc tgaccctgaa gttcatctgc      300
accaccggca agctgcccgt gccctggccc accctcgtga ccaccctgac ctacggcgtg      360
cagtgcttca gccgctaccc cgaccacatg aagcagcacg acttcttcaa gtccgccatg      420
cccgaaggct acgtccagga gcgcaccatc ttcttcaagg acgacggcaa ctacaagacc      480
cgcgccgagg tgaagttcga gggcgacacc ctggtgaacc gcatcgagct gaagggcatc      540
gacttcaagg aggacggcaa catcctgggg cacaagctgg agtacaacta caacagccac      600
aacgtctata tcatggccga caagcagaag aacggcatca aggtgaactt caagatccgc      660
cacaacatcg aggacggcag cgtgcagctc gccgaccact accagcagaa cacccccatc      720
ggcgacggcc ccgtgctgct gcccgacaac cactacctga gcacccagtc cgccctgagc      780
aaagacccca acgagaagcg cgatcacatg gtcctgctgg agttcgtgac cgccgccggg      840
atcactctcg gcatggacga gctgtacaag taactcgagc ccgaattgat gcacggattg      900
atttcgaatc tggaaggata agaaagaag agttcactga gatcatgaag atctgttcca      960
ccattgaaga gctcagacgg caaaaatagt gaatttagct tgtccttcat gaaaaaatgc     1020
cttgtttcta ct                                                        1032
```

<210> SEQ ID NO 123
<211> LENGTH: 1047
<212> TYPE: DNA
<213> ORGANISM: Artificial Sequence
<220> FEATURE:
<223> OTHER INFORMATION: Chimeric influenza virus gene

<400> SEQUENCE: 123

```
agcgaaagca ggtcaattat attcaatttg gaaagaataa agaactaag aaatctattg        60
tcgcagtctc gcacccgcga gatactcaca aaaaccaccg tggaccattt ggccataatc      120
aagaagtaca catcaggaag acaggagaag aagctagcat ggtgagcaag ggcgaggagc      180
tgttcaccgg ggtggtgccc atcctggtcg agctggacgg cgacgtaaac ggccacaagt      240
tcagcgtgtc cggcgagggc gagggcgatg ccacctacgg caagctgacc ctgaagttca      300
tctgcaccac cggcaagctg cccgtgccct ggcccaccct cgtgaccacc ctgacctacg      360
gcgtgcagtg cttcagccgc taccccgacc acatgaagca gcacgacttc ttcaagtccg      420
ccatgcccga aggctacgtc caggagcgca ccatcttctt caaggacgac ggcaactaca      480
agacccgcgc cgaggtgaag ttcgagggcg acaccctggt gaaccgcatc gagctgaagg      540
gcatcgactt caaggaggac ggcaacatcc tggggcacaa gctggagtac aactacaaca      600
gccacaacgt ctatatcatg gccgacaagc agaagaacgg catcaaggtg aacttcaaga      660
tccgccacaa catcgaggac ggcagcgtgc agctcgccga ccactaccag cagaacaccc      720
ccatcggcga cggccccgtg ctgctgcccg acaaccacta cctgagcacc cagtccgccc      780
tgagcaaaga ccccaacgag aagcgcgatc acatggtcct gctggagttc gtgaccgccg      840
ccgggatcac tctcggcatg gacgagctgt acaagtaact cgagaaagga gaaggcta       900
atgtgctaat tgggcaagga gacgtggtgt tggtaatgaa acggaaacgg gactctagca      960
tacttactga cagccagaca gcgaccaaaa gaattcggag gccatcaat tagtgtcgaa     1020
tagtttaaaa acgaccttgt ttctact                                         1047
```

<210> SEQ ID NO 124
<211> LENGTH: 1049
<212> TYPE: DNA
<213> ORGANISM: Artificial Sequence
<220> FEATURE:
<223> OTHER INFORMATION: Chimeric influenza virus gene

<400> SEQUENCE: 124

```
agcgaaagca ggtactgatc caaattggaa gattttgtgc gacattgctt caatccgttg      60
attgtcgagc ttgcggaaaa acattgaaa gagtttgggg aggacctgaa atcgaaaca      120
aacaaatttg cagcaatttg ctagcatggt gagcaagggc gaggagctgt tcaccggggt     180
ggtgcccatc ctggtcgagc tggacggcga cgtaaacggc cacaagttca gcgtgtccgg     240
cgagggcgag ggcgatgcca cctacggcaa gctgaccctg aagttcatct gcaccaccgg     300
caagctgccc gtgccctggc ccaccctcgt gaccaccctg acctacggcg tgcagtgctt     360
cagccgctac cccgaccaca tgaagcagca cgacttcttc aagtccgcca tgcccgaagg     420
ctacgtccag gagcgcacca tcttcttcaa ggacgacggc aactacaaga cccgcgccga     480
ggtgaagttc gagggcgaca ccctggtgaa ccgcatcgag ctgaagggca tcgacttcaa     540
ggaggacggc aacatcctgg ggcacaagct ggagtacaac tacaacagcc acaacgtcta     600
tatcatggcc gacaagcaga agaacggcat caaggtgaac ttcaagatcc gccacaacat     660
cgaggacggc agcgtgcagc tcgccgacca ctaccagcag aacacccca tcggcgacgg     720
ccccgtgctg ctgcccgaca ccactacct gagcacccag tccgccctga gcaaagaccc     780
caacgagaag cgcgatcaca tggtcctgct ggagttcgtg accgccgccg ggatcactct     840
cggcatggac gagctgtaca gtaactcga gcctgggacc tttgatcttg gggggctata     900
tgaagcaatt gaggagtgcc tgattaatga tccctgggtt ttgcttaatg cttcttggtt     960
caactccttc cttacacatg cattgagtta gttgtggcag tgctactatt tgctatccat    1020
actgtccaaa aaagtacctt gtttctact                                      1049
```

<210> SEQ ID NO 125
<211> LENGTH: 2013
<212> TYPE: DNA
<213> ORGANISM: Artificial Sequence
<220> FEATURE:
<223> OTHER INFORMATION: Chimeric influenza virus gene

<400> SEQUENCE: 125

```
agcgaaagca ggcaaaccat ttgattggtt gtcaatccga ccttactttt cttaaaagtg      60
ccagcacaaa ttgctataag cacaactttc ccttatactg agaccctcc ttacagcctt     120
gggacaggaa caggatacac cttggttgct agcatgaaga ccatcattgc tttgagctac     180
attttctgtc tggctctcgg ccaagacctt ccaggaaatg acaacagcac agcaacgctg     240
tgcctgggac atcatgcggt gccaaacgga acactagtga aaacaatcac agatgatcag     300
attgaagtga ctaatgctac tgagctagtt cagagctcct caacggggaa aatatgcaac     360
aatcctcatc gaatccttga tggaatagac tgcacactga tagatgctct attggggac     420
cctcattgtg atgttttca aaatgagaca tgggaccttt cgttgaacg cagcaaagct     480
ttcagcaact gttacccctta tgatgtgcca gattatgcct cccttaggtc actagttgcc     540
tcgtcaggca ctctggagtt tatcactgag ggtttcactt ggactggggt cactcagaat     600
gggggaagca atgcttgcaa aaggggacct ggtagcggtt ttttcagtag actgaactgg     660
```

```
ttgaccaaat caggaagcac atatccagtg ctgaacgtga ctatgccaaa caatgacaat    720
tttgacaaac tatacatttg gggggttcac cacccgagca cgaaccaaga acaaaccagc    780
ctgtatgttc aagcatcagg gagagtcaca gtctctacca ggagaagcca gcaaactata    840
atcccgaata tcgggtccag accctgggta aggggtctgt ctagtagaat aagcatctat    900
tggacaatag ttaagccggg agacgtactg gtaattaata gtaatgggaa cctaatcgct    960
cctcggggtt atttcaaaat gcgcactggg aaaagctcaa taatgaggtc agatgcacct   1020
attgatacct gtatttctga atgcatcact ccaaatggaa gcattcccaa tgacaagccc   1080
tttcaaaacg taaacaagat cacatatgga gcatgcccca gtatgttaa gcaaaacacc    1140
ctgaagttgg caacagggat gcggaatgta ccagagaaac aaactagagg cctattcggc   1200
gcaatagcag gtttcataga aaatggttgg gagggaatga tagacggttg gtacggtttc   1260
aggcatcaaa attctgaggg cacaggacaa gcagcagatc ttaaaagcac tcaagcagcc   1320
atcgaccaaa tcaatgggaa attgaacagg gtaatcgaga agacaacga gaaattccat    1380
caaatcgaaa aggaattctc agaagtagaa gggagaattc aggacctcga gaaatacgtt   1440
gaagacacta aaatagatct ctggtcttac aatgcggagc ttcttgtcgc tctggagaat   1500
caacatacaa ttgacctgac tgactcggaa atgaacaagc tgtttgaaaa acagggagg    1560
caactgaggg aaaatgctga agacatgggc aatggttgct tcaaaatata ccacaaatgt   1620
gacaacgctt gcatagagtc aatcagaaat gggacttatg accatgatgt atacagagac   1680
gaagcattaa acaaccggtt tcagatcaaa ggtgttgaac tgaagtctgg atacaaagac   1740
tggatcctgt ggatttcctt tgccatatca tgcttttgc tttgtgttgt tttgctgggg    1800
ttcatcatgt gggcctgcca gagaggcaac attaggtgca acatttgcat ttgactcgag   1860
cccgaattga tgcacggatt gatttcgaat ctggaaggat aaagaaagaa gagttcactg   1920
agatcatgaa gatctgttcc accattgaag agctcagacg gcaaaaatag tgaatttagc   1980
ttgtccttca tgaaaaaatg ccttgtttct act                                2013

<210> SEQ ID NO 126
<211> LENGTH: 2028
<212> TYPE: DNA
<213> ORGANISM: Artificial Sequence
<220> FEATURE:
<223> OTHER INFORMATION: Chimeric influenza virus gene

<400> SEQUENCE: 126
agcgaaagca ggtcaattat attcaatttg gaaagaataa agaactaag aaatctattg     60
tcgcagtctc gcacccgcga gatactcaca aaaaccaccg tggaccattt ggccataatc    120
aagaagtaca catcaggaag acaggagaag aagctagcat gaagaccatc attgctttga    180
gctacatttt ctgtctggct ctcggccaag accttccagg aaatgacaac agcacagcaa    240
cgctgtgcct gggacatcat gcggtgccaa acggaacact agtgaaaaca atcacagatg    300
atcagattga agtgactaat gctactgagc tagttcagag ctcctcaacg ggaaaatat    360
gcaacaatcc tcatcgaatc cttgatggaa tagactgcac actgatagat gctctattgg    420
gggaccctca ttgtgatgtt tttcaaaatg agacatggga ccttttcgtt gaacgcagca    480
aagctttcag caactgttac ccttatgatg tgccagatta tgcctccctt aggtcactag    540
ttgcctcgtc aggcactctg gagtttatca ctgagggttt cacttggact ggggtcactc    600
agaatggggg aagcaatgct tgcaaaaggg gacctggtag cggttttttc agtgactga    660
actggttgac caaatcagga agcacatatc cagtgctgaa cgtgactatg ccaaacaatg    720
```

```
acaattttga caaactatac atttgggggg ttcaccaccc gagcacgaac caagaacaaa      780
ccagcctgta tgttcaagca tcagggagag tcacagtctc taccaggaga agccagcaaa      840
ctataatccc gaatatcggg tccagaccct gggtaagggg tctgtctagt agaataagca      900
tctattggac aatagttaag ccgggagacg tactggtaat taatagtaat gggaacctaa      960
tcgctcctcg gggttatttc aaaatgcgca ctgggaaaag ctcaataatg aggtcagatg     1020
cacctattga tacctgtatt tctgaatgca tcactccaaa tggaagcatt cccaatgaca     1080
agccctttca aaacgtaaac aagatcacat atggagcatg ccccaagtat gttaagcaaa     1140
acaccctgaa gttggcaaca gggatgcgga atgtaccaga gaaacaaact agaggcctat     1200
tcggcgcaat agcaggtttc atagaaaatg gttgggaggg aatgatagac ggttggtacg     1260
gtttcaggca tcaaaattct gagggcacag acaagcagc agatcttaaa agcactcaag     1320
cagccatcga ccaaatcaat gggaaattga cagggtaat cgagaagacg aacgagaaat     1380
tccatcaaat cgaaaggaa ttctcagaag tagaagggga aattcaggac ctcgagaaat     1440
acgttgaaga cactaaaata gatctctggt cttacaatgc ggagcttctt gtcgctctgg     1500
agaatcaaca tacaattgac ctgactgact cggaaatgaa caagctgttt gaaaaaacag     1560
ggaggcaact gagggaaaat gctgaagaca tgggcaatgg ttgcttcaaa ataccaca     1620 aatgtgacaa cgcttgcata gagtcaatca gaaatgggac ttatgaccat gatgtataca     1680
gagacgaagc attaaacaac cggtttcaga tcaaaggtgt tgaactgaag tctggataca     1740
aagactggat cctgtggatt tcctttgcca tatcatgctt tttgctttgt gttgttttgc     1800
tggggttcat catgtgggcc tgccagagag gcaacattag gtgcaacatt tgcatttgac     1860
tcgagaaagg agagaaggct aatgtgctaa ttgggcaagg agacgtggtg ttggtaatga     1920
aacggaaacg ggactctagc atacttactg acagccagac agcgaccaaa agaattcgga     1980
tggccatcaa ttagtgtcga atagtttaaa aacgaccttg tttctact                 2028
```

<210> SEQ ID NO 127
<211> LENGTH: 1248
<212> TYPE: DNA
<213> ORGANISM: Artificial Sequence
<220> FEATURE:
<223> OTHER INFORMATION: Chimeric influenza virus gene

<400> SEQUENCE: 127

```
agcgaaagca ggcaaaccat ttgattggtt gtcaatccga ccttactttt cttaaaagtg       60
ccagcacaaa ttgctataag cacaactttc ccttatactg agaccctcc ttacagcctt      120 gggacaggaa caggatacac cttggttgct agcatgactt cgaaagttta tgatccagaa      180
caaaggaaac ggatgataac tggtccgcag tggtgggcca gatgtaaaca atgaatgtt      240 cttgattcat ttattaatta ttatgattca gaaaaacatg cagaaaatgc tgttattttt      300
ttacatggta acgcggcctc ttcttattta tggcgacatg ttgtgccaca tattgagcca      360
gtagcgcggt gtattatacc agaccttatt ggtatgggca aatcaggcaa atctggtaat      420
ggttcttata ggttacttga tcattacaaa tatcttactg catggtttga acttcttaat      480
ttaccaaaga agatcatttt tgtcggccat gattggggtg cttgtttggc atttcattat      540
agctatgagc atcaagataa gatcaaagca atagttcacg ctgaaagtgt agtagatgtg      600
attgaatcat gggatgaatg gcctgatatt gaagaagata ttgcgttgat caaatctgaa      660
gaaggagaaa aatggttttt ggagaataac ttcttcgtgg aaaccatgtt gccatcaaaa      720
```

-continued

| | |
|---|---|
| atcatgagaa agttagaacc agaagaattt gcagcatatc ttgaaccatt caaagagaaa | 780 |
| ggtgaagttc gtcgtccaac attatcatgg cctcgtgaaa tcccgttagt aaaaggtggt | 840 |
| aaacctgacg ttgtacaaat tgttaggaat tataatgctt atctacgtgc aagtgatgat | 900 |
| ttaccaaaaa tgtttattga atcggaccca ggattctttt ccaatgctat tgttgaaggt | 960 |
| gccaagaagt ttcctaatac tgaatttgtc aaagtaaaag gtcttcattt ttcgcaagaa | 1020 |
| gatgcacctg atgaaatggg aaaatatatc aaatcgttcg ttgagcgagt tctcaaaaat | 1080 |
| gaacaataac tcgagcccga attgatgcac ggattgattt cgaatctgga aggataaaga | 1140 |
| aagaagagtt cactgagatc atgaagatct gttccaccat tgaagagctc agacggcaaa | 1200 |
| aatagtgaat ttagcttgtc cttcatgaaa aaatgccttg tttctact | 1248 |

<210> SEQ ID NO 128
<211> LENGTH: 89
<212> TYPE: DNA
<213> ORGANISM: Artificial Sequence
<220> FEATURE:
<223> OTHER INFORMATION: Primer

<400> SEQUENCE: 128

| | |
|---|---|
| cagctagcat ggacgttaac ccaactctgt tatttctgaa ggtaccggcg cagaacgcca | 60 |
| tcagtacgac ctttccttat actggagac | 89 |

<210> SEQ ID NO 129
<211> LENGTH: 66
<212> TYPE: DNA
<213> ORGANISM: Artificial Sequence
<220> FEATURE:
<223> OTHER INFORMATION: Primer

<400> SEQUENCE: 129

| | |
|---|---|
| gtctcgagct acttctgtct ccgaagttcc tcgattgtac tgcaaatttt catgatctca | 60 |
| gtgaac | 66 |

<210> SEQ ID NO 130
<211> LENGTH: 55
<212> TYPE: DNA
<213> ORGANISM: Artificial Sequence
<220> FEATURE:
<223> OTHER INFORMATION: Primer

<400> SEQUENCE: 130

| | |
|---|---|
| cagctagcat ggagcggatc aaggagttgc ggaacttgat gtcgcagtct cgcac | 55 |

<210> SEQ ID NO 131
<211> LENGTH: 65
<212> TYPE: DNA
<213> ORGANISM: Artificial Sequence
<220> FEATURE:
<223> OTHER INFORMATION: Primer

<400> SEQUENCE: 131

| | |
|---|---|
| tgtgaatccg tcaagataga gctatctctc tttctcttca tcactagtac cacgtctcct | 60 |
| tgccc | 65 |

<210> SEQ ID NO 132
<211> LENGTH: 60
<212> TYPE: DNA
<213> ORGANISM: Artificial Sequence
<220> FEATURE:
<223> OTHER INFORMATION: Primer

```
<400> SEQUENCE: 132
gactcgagct agttaatagc catacggatc ctcttagttg ccgtttgtga atccgtcaag        60

<210> SEQ ID NO 133
<211> LENGTH: 87
<212> TYPE: DNA
<213> ORGANISM: Artificial Sequence
<220> FEATURE:
<223> OTHER INFORMATION: Primer

<400> SEQUENCE: 133
cagctagcat ggaggacttc gtaaggcagt gttttaaccc aatgatcgtt gaactcgcag        60
agaagacgat gaaggagtat ggggagg                                           87

<210> SEQ ID NO 134
<211> LENGTH: 66
<212> TYPE: DNA
<213> ORGANISM: Artificial Sequence
<220> FEATURE:
<223> OTHER INFORMATION: Primer

<400> SEQUENCE: 134
gtctcgagct atgatagcgc gtgcgtcaaa aaagaattaa accagctggc gttaagcaaa        60
acccag                                                                  66

<210> SEQ ID NO 135
<211> LENGTH: 41
<212> TYPE: DNA
<213> ORGANISM: Artificial Sequence
<220> FEATURE:
<223> OTHER INFORMATION: Primer

<400> SEQUENCE: 135
cagctagcat gaagaccatc attgctttga gctacatttt c                           41

<210> SEQ ID NO 136
<211> LENGTH: 42
<212> TYPE: DNA
<213> ORGANISM: Artificial Sequence
<220> FEATURE:
<223> OTHER INFORMATION: Primer

<400> SEQUENCE: 136
gtctcgagtc aaatgcaaat gttgcaccta atgttgcctc tc                          42
```